US010694693B2

(12) United States Patent
Bourdoncle et al.

(10) Patent No.: US 10,694,693 B2
(45) Date of Patent: Jun. 30, 2020

(54) METHODS FOR PRODUCING CORN PLANTS WITH NORTHERN LEAF BLIGHT RESISTANCE AND COMPOSITIONS THEREOF

(71) Applicant: Monsanto Technology LLC, St. Louis, MO (US)

(72) Inventors: William J. Bourdoncle, Borken (DE); Franck J. Chopin, Boucau (FR); Romain Fouquet, Saint-Palais (FR); Marcelo P. Giovanini, Londrina (BR); Peter V. Maloney, Galena, MD (US); Yule Pan, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/382,229

(22) Filed: Dec. 16, 2016

(65) Prior Publication Data

US 2017/0172098 A1    Jun. 22, 2017

Related U.S. Application Data

(60) Provisional application No. 62/269,635, filed on Dec. 18, 2015.

(51) Int. Cl.
*A01H 5/10* (2018.01)
*C12Q 1/68* (2018.01)
*A01H 1/02* (2006.01)
*A01H 1/04* (2006.01)
*C12Q 1/6895* (2018.01)

(52) U.S. Cl.
CPC .............. *A01H 5/10* (2013.01); *A01H 1/02* (2013.01); *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. |
| 5,217,863 A | 6/1993 | Cotton et al. |
| 5,468,613 A | 11/1995 | Erlich et al. |
| 5,563,055 A | 10/1996 | Townsend et al. |
| 5,595,890 A | 1/1997 | Newton et al. |
| 5,595,891 A | 1/1997 | Rose et al. |
| 5,616,464 A | 4/1997 | Albagli et al. |
| 5,762,876 A | 6/1998 | Lincoln et al. |
| 5,800,944 A | 9/1998 | Blonsky et al. |
| 5,876,930 A | 3/1999 | Livak et al. |
| 5,945,283 A | 8/1999 | Kwok et al. |
| 6,004,744 A | 12/1999 | Goelet et al. |
| 6,013,431 A | 1/2000 | Söderlund et al. |
| 6,030,787 A | 2/2000 | Livak et al. |
| 6,090,558 A | 7/2000 | Butler et al. |
| 6,503,710 B2 | 1/2003 | Gut et al. |
| 6,613,509 B1 | 9/2003 | Chen |
| 6,799,122 B2 | 9/2004 | Benson |
| 6,913,879 B1 | 7/2005 | Schena |
| 6,996,476 B2 | 2/2006 | Najarian |
| 7,238,476 B2 | 7/2007 | McKeown et al. |
| 7,250,252 B2 | 7/2007 | Katz et al. |
| 7,270,981 B2 | 9/2007 | Armes et al. |
| 7,282,355 B2 | 10/2007 | Shi |
| 7,297,485 B2 | 11/2007 | Bornarth et al. |
| 7,312,039 B2 | 12/2007 | Barany et al. |
| 2008/0319927 A1 | 12/2008 | Dallmier et al. |
| 2010/0095395 A1 | 4/2010 | Wilson et al. |
| 2015/0218660 A1 | 8/2015 | Li et al. |

FOREIGN PATENT DOCUMENTS

| | | | |
|---|---|---|---|
| WO | WO 2008/021225 A2 | | 2/2008 |
| WO | WO 2008/143993 A2 | | 11/2008 |
| WO | WO 2009/002924 A1 | * | 12/2008 |
| WO | WO 2009/029771 A2 | | 3/2009 |

OTHER PUBLICATIONS

Arús et al., "Marker-assisted selection," *Plant Breeding*, Part of the series Plant Breeding Series, pp. 314-331 (1993).
Borevitz et al. "Large-Scale Identification of Single-Feature Polymorphisms in Complex Genomes," *Genome Research*, 13:512-523 (2003).
Churchill et al., "Empirical Threshold Values for Quantitative Trait Mapping," *Genetics*, 138(3):963-971 (1994).
Cui et al., "Detecting single-feature polymorphisms using oligonucleotide arrays and robustified projection pursuit," *Bioinformatics*, 21(20):3852-3858 (2005).
Flint-Garcia et al., "Structure of linkage disequilirium in plants," *Annual Review of Plant Biology*, 54:357-374 (2003).
Gaj et al., "ZFN, TALEN, and CRISPR/Cas-based methods for genome engineering," *Trends in Biotechnology*, 31(7):397-405 (2013).
Gianola et al., "Bayesian Methods in Animal Breeding Theory," *Journal of Animal Science*, 63:217-244 (1986).
Gruber et al., "Vectors for Plant Transformation," *Methods in Plant Molecular Biology and Biotechnology*, Glick B.R. and Thompson, J.E. Eds. (CRC Press, Inc., Boca Raton, pp. 89-119 (1993).
Hedrick, "Gametic Disequilibrium Measures: Proceed With Caution," *Genetics*, 117:331-341 (1987).
Heffner et al., "Genomic Selection for Crop Improvement," *Crop Science*, 49:1-12 (2009).

(Continued)

*Primary Examiner* — Bratislav Stankovic
(74) *Attorney, Agent, or Firm* — Arnold & Porter Kaye Scholer; Matthew Madsen; David R. Marsh

(57) ABSTRACT

The present disclosure is in the field of plant breeding and disease resistance. The disclosure provides methods for breeding corn plants having northern leaf blight (NLB) resistance using marker-assisted selection. The disclosure further provides corn germplasm resistant to NLB. The disclosure also provides markers associated with NLB resistance loci for introgressing these loci into elite germplasm in a breeding program, thus producing novel NLB resistant germplasm.

23 Claims, No Drawings
Specification includes a Sequence Listing.

(56) References Cited

OTHER PUBLICATIONS

Henderson, "Best Linear Unbiased Estimation and Prediction Under a Selection Model," *Biometrics*, 31:423-447 (1975).
Horsch et al., "A Simple and General Method for Transferring Genes into Plants," *Science*, 227(4691):1229-1231 (1985).
Jannink et al., "Assocation Mapping in Plant Populations," *Quantitative Genetics, Genomics and Plant Breeding*, (ed. M.S. Kang) CAB International, pp. 59-68 (2002).
Jansen et al., "High resolution of quantitative traits into multiple loci via interval mapping," *Genetics*, 136(4):1447-1455 (1994).
Jansen et al., "Genotype-by-environment interaction in genetic mapping of multiple quantitative trait loci," *Theoretical and Applied Genetics*, 91(1):33-37 (1995).
Jansen, "Biometrics in Plant Breeding: applications of molecular markers," Proceedings of the Ninth Meeting of the EUCARPIA Section Biometrics in Plant Breeding, Jul. 6-8, 1994, Wageningen, The Netherlands, CPRO-DLA, pp. 195-204 (1994).
Kruglyak et al., "A nonparametric approach for mapping quantitative trait loci.," *Genetics*, 139(3):1421-1428 (1995).
Lander et al., "Mapping Mendelian Factors Underlying Quantitative Traits Using RFLP Linkage Maps," *Genetics*, 121:185-199 (1989).
Lincoln et al., "Mapping Genes Controlling Quantitative Traits Using MAPMAKER/QTL," Whitehead Institute for Biomedical Research, Massachusetts (1990).
Mueller, "Corn Disease Loss Estimates From the United Sates and Ontario, Canada—2012," *Purdue Extension Publication BP-96-12--W* (2014).
Nakaya et al., "Will genomic selection be a practical method for plant breeding?" *Annals of Botany*, 110:1303-1316 (2012).
Openshaw et al., Marker-assisted selection in backcross breeding, in *ASHS/CSSA Joint Plant Breeding Symposium on Analysis of Molecular Marker Data*, pp. 41-43, (1994).
Pataky, "Relationships between yield of sweet corn and northern leaf blight caused by *Exserohilum turcicum*," *Phytopathology*, 82(3), 370-375 (1992).
Perkins et al., "Disease Development and Yield Losses Associated with Northern Leaf Blight on Corn," *Plant Disease*, 71:940-943.

Ragot et al., "Marker-assisted backcrossing: a practical example,". *Techniques et utilisations des markers moléculaires*, Montpellier, France, Paris 1995, Les Colloques, No. 72, pp. 45-56.
Reich et al., "Linkage disequilibrium in the human genome," *Nature* (411):199-204 (2001).
Service, "The Race for the $1000 Genome," *Science*, 17(5767):1544-1546.
Simcox et al., "The Use of Molecular Markers to Study *Setosphaeria turcica* Resistance in Maize," *Phytopathology*, 83(12):1326-1330 (1993).
Utz et al., "Comparison of different approaches to interval mapping of quantitative trait loci," Proceedings of the Ninth Meeting of the EUCARPIA Section Biometrics in Plant Breeding, Jul. 6-8, 1994, Wageningen, The Netherlands, CPRO-DLA, pp. 195-204 (1994).
Van Staden et al., SCAR markers for the Ht1, Ht2, Ht3, and Htn1 resistance genes in maize, $43^{rd}$ Annual Maize Genetics Conference, Program and Abstracts, Mar. 14-18, 2001, Grand Geneva Resort, Lake Beneva, Wisconsin, Abstract P134.
Van Vleck et al., "Estimated Breeding Values for Meat Characteristics of Crossbred Cattle with an Animal Mode 1," *Journal of Animal Science*, 70:363-371 (1992).
Zaitlin et al., "Linkage of a second gene for NCLB resistance to molecular markers in maize," *Maize Genetics Cooperative Newsletter*, 66:69-80 (1992).
Zeng, "Precision mapping of quantitative trait loci.," *Genetics*, 136(4):1457-1468 (1994).
Ding et al., "Genome-wide associate mapping reveals novel sources of resistance to northern corn leaf blight in maize," *BMC Plant Biology*, 15:206 (2015).
Partial European Search Report dated Apr. 10, 2019, in European Patent Application No. 16876822.4.
Poland et al., "Genome-wide nested association mapping of quantitative resistance to northern leaf blight in maize," *PNAS*, 108(17):6893-6898 (2011).
Balint-Kurti et al. "Use of a Maize Advances Intercross Line for Mapping of QTL for Northern Leaf Blight Resistance and Multiple Disease Resistance," *Crop Science*, 50(2):458-466 (2010).
Chung et al. "Resistance loci affecting distinct stages of fungal pathogenesis: use of introgression lines for QTL mapping and characterization in the maize—Setosphaeria turcica pathosystem," BMC Plan Biology, Biomed Central, 10(1):103 (2010).
Extended European Search Report dated Jul. 10, 2019, in EP Appln. No. 16876822.4.

* cited by examiner

METHODS FOR PRODUCING CORN PLANTS WITH NORTHERN LEAF BLIGHT RESISTANCE AND COMPOSITIONS THEREOF

CROSS REFERENCE TO RELATED APPLICATIONS

This application claims the benefit and priority of U.S. Provisional Application No. 62/269,635 filed Dec. 18, 2015, which is incorporated by reference in its entirety.

FIELD

The present disclosure relates to the field of agricultural biotechnology. More specifically, this disclosure relates to methods for producing corn plants, seeds, or cells with improved northern leaf blight resistance.

INCORPORATION OF SEQUENCE LISTING

A sequence listing contained in the file named P34361US01_SEQ.txt, which is 221,184 bytes (measure in MS-Windows®) and created on Dec. 16, 2016, comprising 630 nucleotide sequences, is filed electronically herewith and incorporated by reference in its entirety.

BACKGROUND

Corn (*Zea mays* L.) is one of the most important commercial crops in the world. Like many commercial crops, corn is subjected to numerous potentially detrimental environmental conditions (e.g., moisture availability, temperature stresses, soil conditions, pests, disease) that can reduce, or entirely eliminate, crop yield. Crop disease alone accounted for the loss of more than 1.3 billion bushels of corn in the United States and Ontario, Canada in 2012. See Mueller, Corn Disease Loss Estimates from the United States and Ontario, Canada—2012. *Purdue Extension Publication* BP-96-12--W (2014).

Northern leaf blight (NLB) is a crop disease caused by the fungal pathogen *Exserohilum turcicum* (also referred to as *Helminthosporium turcicum* or *Setosphaeria turcica* in some literature). NLB can infect corn in tropical and temperate climates. Infected corn plants can exhibit a range of symptoms from cigar-shaped lesions on lower leaves to complete destruction of multiple leaves. Corn infected with NLB is also highly susceptible to stem rot and root rot caused by secondary infections. NLB is particularly problematic in tropical highlands, where environmental conditions favor disease development. However, NLB infection can cause yield losses of 30%-50% in temperate environments, including the United States and Europe.

*E. turcicum* overwinters as mycelia and conidia on corn plant parts left on the soil surface. The conidia are transformed into spores, and during warm, wet weather, new conidia are produced and carried by wind or rain onto the lower leaves of corn plants. Infection requires the presence of water on the leaf surface for at least 6 hours and a temperature of between 65° F. and 80° F. If infection occurs, lesions develop within 12 days and produce new conidia which can spread the infection to additional leaves and plants. NLB management strategies include crop rotation, destruction of over-wintering corn plant parts, and fungicide application. However, fungicide application alone is not an efficient mechanism of control, especially in Brazil.

There is a need in corn breeding to identify corn germplasm that provides resistance to NLB infection. There is also a need to develop polymorphic markers for monitoring and introgressing NLB resistance alleles, and further develop agronomically elite corn lines comprising NLB resistance for enhancing plant productivity.

SUMMARY

The present disclosure identifies genetic loci conferring NLB resistance in corn, and provides molecular markers linked to these resistance loci. This disclosure further provides methods for introgressing resistance alleles of genetic loci conferring NLB resistance into plant varieties previously lacking such alleles, thereby providing plants with NLB resistance. The genetic loci, markers, and methods provided herein therefore allow for production of new varieties with enhanced NLB resistance.

In one aspect, this disclosure provides a method of creating a population of corn plants, seeds, or cells comprising genotyping a first population of corn plants, seeds, or cells at one or more marker loci associated with and within about 10 cM of one or more NLB resistance quantitative trait loci (QTLs) selected from the group consisting of NLB resistance QTLs NLB_2.01, NLB_3.01, NLB_4.01, NLB_4.02, NLB_5.01, NLB_6.01, NLB_7.01, and NLB_9.01; selecting from the first population one or more corn plants, seeds, or cells comprising one or more NLB resistance alleles of the one or more marker loci; and producing from the selected one or more corn plants, seeds, or cells a second population of corn plants, seeds, or cells comprising the one or more NLB QTLs.

In one aspect, this disclosure provides a method of introgressing an NLB resistance QTL comprising crossing a first corn plant comprising an NLB resistance QTL with a second corn plant of a different genotype to produce one or more progeny plants or seeds; and selecting a progeny plant or seed comprising an NLB resistance allele of a polymorphic locus linked to the NLB resistance QTL, where the polymorphic locus is in a chromosomal segment flanked by: any two of marker loci SEQ ID NOs: 1 to 18, any two of marker loci SEQ ID NOs: 19 to 31, any two of marker loci SEQ ID NOs: 32 to 52 and 471-475, any two of marker loci SEQ ID NOs: 53 to 65 and 446 to 468, any two of marker loci SEQ ID NOs: 66 to 84, any two of marker loci SEQ ID NOs: 85 to 89, marker loci SEQ ID NOs: 469 and 470, or any two of marker loci SEQ ID NOs: 476-482.

In one aspect, this disclosure provides an NLB resistant corn plant, seed, or cell comprising a combination of two or more, three or more, four or more, five or more, six or more, or seven or more introgressed NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01.

In one aspect, this disclosure provides a method for selecting a corn plant, seed, or cell comprising isolating nucleic acids from a corn plant, seed, or cell; analyzing the nucleic acids to detect a polymorphic marker associated with and within 10 cM of an NLB resistance QTL selected from the group consisting of NLB resistance QTLs NLB_2.01, NLB_3.01, NLB_4.01, NLB_4.02, NLB_5.01, NLB_6.01, NLB_7.01, and NLB_9.01; and selecting a corn plant, seed, or cell comprising the NLB resistance QTL.

In one aspect, this disclosure provides a method comprising providing a set of corn seeds comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01, to a person desirous of planting said set of corn seeds in a field plot.

In one aspect, this disclosure provides a method of growing a population of corn plants in a field plot, said method comprising planting a population of corn seeds comprising one or more, two or more, three or more, four or more, five or more, six or more, or seven or more introgressed NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 in said field plot.

BRIEF DESCRIPTION OF THE SEQUENCES

SEQ ID NOs: 1-89 and 446-482 list sequences of exemplary SNP marker loci associated with an NLB resistance QTL. Example resistant and susceptible alleles of these marker loci are listed in Table 5. SEQ ID NOs: 90-445 and 483-630 list the sequences of exemplary primers and probes which can be used to detect the SNP marker loci of SEQ ID NOs: 1-89 and 446-482.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant and/or progeny of the same. A progeny plant can be from any filial generation, e.g., $F_1$, $F_2$, $F_3$, $F_4$, $F_5$, $F_6$, $F_7$, etc. A "plant part" refers to any part of a plant, comprising a cell or tissue culture derived from a plant, plant components or organs (e.g., leaves, stems, roots, etc.), plant tissues, seeds, and plant cells. A plant cell is a biological cell of a plant, taken from a plant or derived through culture from a cell taken from a plant.

As used herein, a "corn plant" or "maize plant" refers to a plant of species *Zea mays* L and includes all plant varieties that can be bred with corn, including wild maize species.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed, or tissues from which new plants can be grown, or plant parts, such as leaves, stems, pollen, or cells that can be cultured into a whole plant.

As used herein, the phrase "associated with" or "linked to" refers to a recognizable and/or assayable relationship between two entities. For example, the phrase "associated with NLB resistance" refers to a trait, locus, gene, allele, marker, phenotype, etc., or the expression thereof, the presence or absence of which can influence an extent, degree, and/or rate at which a plant or a part of interest thereof that has an NLB resistance trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with a resistance allele" refers to a marker whose presence or absence can be used to predict whether and to what extent a plant will display an NLB resistance phenotype.

As used herein, a "centimorgan" (cM) is a unit of measure of recombination frequency and genetic distance between two loci. One cM is equal to a 1% chance that a marker at one genetic locus will be separated from a marker at a second locus due to crossing over in a single generation.

As used herein, "closely linked" means that the marker or locus is within about 20 cM, 15 cM, 10 cM, 5 cM, 4 cM, 3 cM, 2 cM, 1 cM, 0.5 cM, or less than 0.5 cM of another marker or locus. For example, 20 cM means that recombination occurs between the marker and the locus with a frequency of equal to or less than about 20%.

As used herein, "locus" is a chromosome region or chromosomal region where a polymorphic nucleic acid, trait determinant, gene, or marker is located. A locus can represent a single nucleotide, a few nucleotides or a large number of nucleotides in a genomic region. The loci of this disclosure comprise one or more polymorphisms in a population (e.g., alternative alleles are present in some individuals).

As used herein, "allele" refers to an alternative nucleic acid sequence at a particular locus. The length of an allele can be as small as one nucleotide base. For example, a first allele can occur on one chromosome, while a second allele occurs on a second homologous chromosome, e.g., as occurs for different chromosomes of a heterozygous individual, or between different homozygous or heterozygous individuals in a population.

As used herein, "crossed," "cross," or "crossing" means to produce progeny via fertilization (e.g., cells, seeds, or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot et al., Marker-assisted Backcrossing: A Practical Example, in *Techniques Et Utilisation Des Marqueurs Moleculaires Les Colloques,* 72:45-56 (1995); and Openshaw et al., Marker-assisted Selection in Backcross Breeding, in Proceedings Of The Symposium "Analysis Of Molecular Marker Data," pp. 41-43 (1994). The initial cross gives rise to the $F_1$ generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "agronomically elite background" means any line that has resulted from breeding and selection for superior agronomic performance. Similarly, an "elite germplasm" or elite strain of germplasm is an agronomically superior germplasm. Numerous elite lines are available and known to those of skill in the art of corn breeding.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. The term "genotype" can also refer to determining the genetic constitution of an individual (or group of individuals) at one or more genetic loci.

As used herein, a "haplotype" is the genotype of an individual at a plurality of genetic loci. Typically, the genetic loci described by a haplotype are physically and genetically linked, e.g., in the same chromosome interval. A haplotype can also refer to a combination of SNP alleles located within a single gene.

As used herein, "marker assay" means a method for detecting a polymorphism at a particular locus using a particular method, e.g. measurement of at least one phenotype (such as seed color, flower color, or other visually detectable traits), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism can manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation can comprise, but is not limited to, one or more nucleotide base changes, the insertion of one or more nucleotides or the deletion of one or more nucleotides. A polymorphism can arise from random processes in nucleic acid replication, through mutagenesis, as a result of mobile genomic elements, from copy number variation and during the process of meiosis, such as unequal crossing over, genome duplication, and chromosome breaks and fusions. The variation can be commonly found or can exist at low frequency within a population, the former having greater utility in general plant breeding and the latter can be associated with rare but important phenotypic variation. Useful polymorphisms can include a single nucleotide polymorphisms (SNP), an insertion or deletion in DNA sequence (indel), a simple sequence repeats of DNA sequence (SSR), a restriction fragment length polymorphism (RFLP), and a tag SNP. A genetic marker, a gene, a DNA-derived sequence, a RNA-derived sequence, a promoter, a 5' untranslated region of a gene, a 3' untranslated region of a gene, microRNA, small interfering RNA, a tolerance locus, a satellite marker, a transgene, mRNA, double-stranded RNA, a transcriptional profile, and a methylation pattern can also comprise a polymorphism. In addition, the presence, absence, or variation in copy number of the preceding can comprise a polymorphism.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker," "molecular marker," or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of markers and integrated genetic maps have been developed for corn (e.g., the UMC 98 map, the Nested Association Mapping (NAM) map, the Intermated B73/Mo17 (IBM2) Neighbors 2008 genetic map, and the LHRF Gnp2004 map. See maizegdb.org/data_center/map for more). All markers are used to define a specific locus in corn genomes. Large numbers of these markers have been mapped. See maizegdb.org/data_center/marker. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in corn. In an aspect, markers used herein exhibit LOD scores of 2 or greater, 3 or greater, 4 or greater, 5 or greater, 6 or greater, 7 or greater, 8 or greater, or 9 or greater with an associated trait of interest (e.g., NLB resistance), measuring using a method known in the art such as Qgene Version 2.23 (1996) and default parameters. Without being limiting, examples of molecular markers and molecular marker systems include SNPs, indels, RFLPs, SSRs, restriction site-associated DNA (RAD), diversity array technology (DArT), and genotyping by sequencing (GBS).

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. Linkage disequilibrium can be measured using any one of the methods provided in Hedrick, Gametic disequilibrium measures: proceed with caution. *Genetics,* 117:331-41(1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

As used herein, a "genetic map" is the relationship of genetic linkage among loci on one or more chromosomes (or linkage groups) within a given species, generally depicted in a diagrammatic or tabular form. Genetic mapping is the process of defining the linkage relationships of loci through the use of genetic markers, populations segregating for the markers, and standard genetic principles of recombination frequency. A genetic map location is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that can occur between populations, genetic map and marker information derived from one population generally remains useful across multiple populations in identification of plants with desired traits, counter-selection of plants with undesirable traits and in MAS breeding. As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that this disclosure be limited to any particular mapping populations, use of any particular software, or any particular set of software parameters to determine linkage of a particular marker or haplotypes with a desired phenotype. It is well within the ability of one of ordinary skill in the art to extrapolate the novel features described herein to any gene pool or population of interest, and using any particular software and software parameters. Indeed, observations regarding genetic markers and haplotypes in populations in addition to those described herein are readily made using the teaching of the present disclosure.

As used herein, "selecting" or "selection" in the context of marker-assisted selection or breeding refer to the act of picking or choosing desired individuals, normally from a population, based on certain pre-determined criteria.

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers can be provided in double-stranded form, though the single-stranded form is more typically used. A primer can further contain a detectable label (e.g., a 5' end label).

As used herein, "probe" refers to an oligonucleotide (synthetic or occurring naturally) that is complementary (though not necessarily fully complementary) to a polynucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, a "population of plants" or a "population of seeds" means a set comprising any number, at least two, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants or seeds. The population members need not be identical to the population members selected for use in subsequent cycles of analyses or those ultimately selected to obtain final progeny plants or seeds. Often, a population of plants or seeds is derived from a single biparental cross, but can also derive from two or more crosses between the same or different parents. Although a population of plants or seeds can comprise any number of individuals, those of skill in the art will recognize that plant breeders commonly use population sizes ranging from one or two hundred individuals to several thousand, and that the highest performing 5% to 20% of a population is what is commonly selected to be used in subsequent crosses in order to improve the performance of subsequent generations of the population.

As used herein, "cultivar" and "variety" are used synonymously and mean a group of plants within a species (e.g., *Z. mays* L.) that share certain genetic traits that separate them from other possible varieties within that species. Corn cultivars can be inbreds or hybrids, though commercial corn cultivars are mostly hybrids to take advantage of hybrid vigor. Individuals within a corn hybrid cultivar are homogeneous, nearly genetically identical, with most loci in the heterozygous state.

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, "introgression" refers to the transmission of a desired allele of a genetic locus from one genetic background to another.

As used herein, the term "chromosome interval" or "chromosomal interval" designates a contiguous linear span of genomic DNA that resides on a single chromosome.

As used herein, "flanked by," when used to describe a chromosomal interval, refers to two loci physically surrounding the chromosomal interval, with one locus on each side of the chromosomal interval. As referenced herein, a chromosomal interval flanked by two marker loci includes the two marker loci.

As used herein, a "resistant allele" or "resistance allele" is an allele at a particular locus that confers, or contributes to, NLB resistance, or alternatively, is an allele that allows the identification of plants that comprise NLB resistance. A resistant allele of a marker is a marker allele that segregates with NLB resistance, or alternatively, segregates with NLB susceptibility, therefore providing the benefit of identifying plants having NLB susceptibility. A resistant allelic form of a chromosome interval is a chromosome interval that includes a nucleotide sequence that contributes to NLB resistance at one or more genetic loci physically located in the chromosome interval.

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence.

As used herein, the terms "phenotype," or "phenotypic trait," or "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "resistance" and "enhanced resistance" are used interchangeably herein and refer to any type of increase in resistance, or any type of decrease in susceptibility. A plant or plant variety exhibiting resistance need not possess absolute or complete resistance. Instead, a plant or plant variety with "enhanced resistance" will have a level of resistance which is higher than that of a comparable susceptible plant or variety. The level of NLB resistance can be determined based on disease ratings as determined in Example 1. Briefly, resistance to NLB infection of corn plants is scored using an NLB resistance scale, wherein NLB resistance is measured by rating the percentage of leaf area infected on a scale of 1 to 9. An NLB resistance scale comprises ratings of: 1 (highly resistant; 0% of leaf area infected, no visible lesions), 2 (highly resistant; less than 1% leaf area infected, few lesions dispersed through lower leaves), 3 (resistant; 1% to less than 20% leaf area infected), 4 (resistant; 20% to less than 40% leaf area infected), 5 (mildly resistant; 40% to less than 50% leaf area infected, lesions reaching ear leaf with sparse lesions in leaves above the ear), 6 (mildly susceptible; 50% to less than 60% leaf area infected, lesions reaching the leaves above the ears), 7 (susceptible; 60% to less than 75% leaf area infected), 8 (susceptible; 75% to less than 90% leaf area infected), and 9 (susceptible; greater than 90% of leaf area infected, with premature death of the plant).

As used herein, "quantitative trait locus" (QTL) or "quantitative trait loci" (QTLs) refer to a genetic domain that effects a phenotype that can be described in quantitative terms and can be assigned a "phenotypic value" which corresponds to a quantitative value for the phenotypic trait.

As used herein, "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "northern leaf blight" or "NLB" refers to a plant disease caused by the fungal pathogen *Exserohilum turcicum*, which is also referred to as *Helminthosporium turcicum* or *Setosphaeria turcica*.

As used herein, "field plot" refers to a location that is suitable for growing corn. The location can be indoors (e.g., a greenhouse or a growth chamber) or outdoors; irrigated or non-irrigated; in the ground or in a container that holds soil.

As used herein, a "planting season" is the length of time, typically about 90-120 days, in which corn can be grown from seed to maturity. One skilled in the art would recognize that a "planting season" could be significantly shorter or longer than about 90-120 days depending on the corn variety being grown and environmental conditions.

As used herein, "transgenic" means a plant or seed whose genome has been altered by the stable integration of recombinant DNA. A transgenic line includes a plant regenerated from an originally-transformed plant cell and progeny transgenic plants from later generations or crosses of a transformed plant.

As used herein, "haploid" means a line that has had its normal chromosome complement reduced by half, typically by pollinating an ear with pollen from a haploid inducing line. In corn, haploid refers to an individual plant or seed that has a haploid chromosome complement where n=10, instead of the normal diploid chromosome complement where 2n=20. A "doubled haploid" refers to a haploid line (n=10) that has been induced, typically via chemical means, to double its chromosome complement and return to a diploid state (2n=20) that is homozygous at all loci within the genome.

As used herein, "yield penalty" refers to a reduction of seed yield in a line correlated with or caused by the presence of an NLB resistance allele or NLB resistance QTL as compared to a line that does not contain that NLB resistance allele or NLB resistance QTL.

As used herein, "seed yield" can refer to a measure of crop production such as test weight, seed number per plant, seed weight, seed number per unit area (i.e. seeds, or weight of seeds, per acre), bushels per acre, tons per acre, kilograms per hectare, or quintals per hectare.

Northern leaf blight is a plant disease caused by the fungal pathogen *Exserohilum turcicum* (also referred to as *Helminthosporium turcicum* or *Setosphaeria turcica* by some researchers). NLB afflicts corn in temperate and tropical regions worldwide. NLB is endemic to the United States. Yield losses of over 30% are reported in susceptible hybrids, and yield loss can reach 70% if the onset of NLB infection occurs 2-3 weeks after silking. See Perkins and Pedersen, Disease development and yield losses associated with northern leaf blight on corn, *Plant Disease*, 71: 940-943 (1987); and Pataky, Relationships between yield of sweet corn and northern leaf blight caused by *Exserohilum turcicum*, *Phytopathology*, 82: 370-375 (1992).

Corn plants in tropical regions are especially at risk to NLB infection due to environmental conditions that are conducive to NLB growth. *E. turcicum* thrives in humid environments with heavy dews, frequent rain showers, and moderate temperatures. However, *E. turcicum* also overwinters in areas that see hard freezes as mycelia and conidia on corn plant parts left on the soil surface and NLB is also a major corn disease in temperate regions. NLB conidia are transformed into resting spores during warm, wet weather in spring and early summer. New conidia are then produced and carried by wind or rain onto the lower leaves of young corn plants. Infection requires the presence of water on the leaf surface for 6-18 hours and a temperature of between 65° F. and 80° F. If infection occurs, lesions develop within 12 days and produce new conidia which can spread the infection to additional leaves and plants via new spores carried by wind or rain. NLB lesions can begin producing spores in as little as 7 days under ideal conditions. Generally, NLB infections begin on lower leaves and progress upwards to younger leaves. However, during high spore loads infections can begin at the top of the plant, including the tassel and flag leaf.

The first sign of NLB infection is an elliptical, or cigar-shaped, gray-green lesion. Lesions typically, but not always, occur on lower leaves before upper leaves. As lesions enlarge they can reach over 6 inches in length and turn a pale gray to brown in color. NLB lesions are not restricted by leaf veins, and the entire leaf can be covered by one or a few lesions in an advanced infection as individual lesions grow and merge. Leaves from highly susceptible plants often appear gray or burned, with little or no healthy, green, photosynthetic tissue remaining. The reduction in tissue capable of photosynthesis leads to a lack of carbohydrates needed for grain fill, which can reduce seed yield. During moist conditions lesions, especially on a lower leaf surface, can produce numerous dark gray spores. Plants infected with NLB are also susceptible to secondary infections from fungi, bacteria, and/or viruses that can cause stem rot and/or root rot.

Several fungicides, including picoxystrobin, cyproconazole, tetraconazole, pyraclostrobin, metconazole, azoxystrobin, propiconazole, prothioconazole, trifloxystrobin, and combinations thereof are used to treat NLB. However, reliance on chemical agents to reduce NLB incidence is unreliable because NLB can develop resistance to the chemical agents.

Four NLB resistance loci conferring incomplete, race-specific, NLB resistance have been reported in corn: Ht1, Ht2, Ht3, and Htn1. Resistance conferred by these loci appears dependent on environmental conditions (e.g., light, temperature), and the loci tend to confer delayed leaf lesion development or delayed sporulation rather than complete disease resistance.

Ht1 maps to the long arm of chromosome 1. See Bentolila et al., Identification of an RFLP marker tightly linked to the Ht1 gene in maize. *Theoretical and Applied Genetics.* 82: 393-398 (1991). Ht2 maps to the long arm of chromosome 8, and Htn1 maps approximately 10 centimorgans distal to Ht2 on chromosome 8. See Zaitlin et al., Linkage of a second gene for NCLB resistance to molecular markers in maize. *Maize Genetics Cooperative Newsletter.* 66: 69-70 (1992); Simcox and Bennetzen, The use of molecular markers to study *Setosphaeria turcica* resistance in maize. *Phytopathology.* 83: 1326-1330 (1993); Yin et al., Fine mapping of the Ht2 (*Helminthosporium turcicum* resistance 2) gene in maize. *Chinese Science Bulletin.* 48: 165-169 (2003); and Chung et al., Characterization and fine-mapping of a resistance locus for northern leaf blight in maize bin 8.06. *Theoretical and Applied Genetics.* 121: 205-227 (2010). Ht3 maps to chromosome 7. See Van Staden et al., SCAR markers for the Ht1, Ht2, Ht3, and Htn1 resistance genes in maize. *Maize Genetics Conference Abstract.* 43: P134 (2001).

A corn plant, seed, or cell provided herein possesses one or more NLB resistance QTLs and/or one or more NLB resistance alleles that confer enhanced resistance to NLB compared to a corn plant, seed, or cell that lacks the one or more NLB resistance QTLs and/or one or more NLB resistance alleles. Further, a corn plant, seed, or cell provided herein provided herein does not suffer a yield penalty when grown in the absence of NLB spores, conidia, and/or mycelia.

In an aspect, a corn plant, seed, or cell provided herein is a *Zea mays* L. corn plant, seed, or cell. In another aspect, a corn plant, seed, or cell provided herein is a *Zea mays* ssp. *mays* corn plant, seed, or cell. In yet another aspect, a corn plant or seed provided herein is a domesticated line, cultivar, or variety of corn plant or seed. In another aspect, a corn plant, seed, or cell provided herein is a sweet corn plant, sweet corn seed, or sweet corn cell.

In an aspect, this disclosure provides quantitative trait loci (QTLs) that exhibit significant co-segregation with NLB resistance. The QTLs of this disclosure can be tracked during plant breeding or introgressed into a desired genetic background in order to provide plants exhibiting enhanced NLB resistance and one or more other beneficial traits. As an example, this disclosure identifies QTL intervals that are associated with NLB resistance in corn varieties CV114258, CV115214, CV099829, CV102084, CV095508, CV103141, CV105893, CV595358, CV593417, CV117407, CV592505, and CV592420.

In an aspect, this disclosure provides molecular markers closely linked to one or more NLB resistance QTLs and methods of using these markers for detection of and selection for NLB resistance. An aspect of this disclosure includes specific markers and their resistance alleles, chromosome intervals comprising the markers, and methods of detecting markers genetically linked to NLB resistance to identify plant lines with enhanced NLB resistance. For example, one aspect of this disclosure provides a chromosome interval associated with NLB resistance which is flanked by any two of marker loci SEQ ID NOs: 12 to 15. Another example of this disclosure provides a chromosome interval associated with NLB resistance, where the interval is flanked by any two of marker loci SEQ ID NOs: 22 to 25. Another example of this disclosure provides a chromosome interval associated with NLB resistance which is flanked by any two of marker loci SEQ ID NOs: 37 to 42 and 474. Another example of this disclosure provides a chromosome interval associated with NLB resistance which is flanked by any two of marker loci SEQ ID NOs: 44 to 49. Another example of this disclosure provides a chromosome interval associated with NLB resistance which is flanked by any two of marker loci SEQ ID NOs: 57 to 62 and 458 to 466. Another example of this disclosure provides a chromosome interval associated with NLB resistance which is flanked by any two of marker loci SEQ ID NOs: 79 to 81. Another example of this disclosure provides a chromosome interval associated with NLB resistance which is flanked by any two of marker loci SEQ ID NOs: 87 to 89 and 477 to 480. Another example of this disclosure provides a chromosome interval associated with NLB resistance which is flanked by marker loci SEQ ID NOs: 469 and 470.

One aspect of this disclosure provides a chromosome interval associated with NLB resistance which is flanked by any two of marker loci SEQ ID NOs: 8 to 18. Another aspect of this disclosure provides a chromosome interval associated with NLB resistance, where the interval is flanked by any two of marker loci SEQ ID NOs: 21 to 29. Another aspect of this disclosure provides a chromosome interval associated with NLB resistance which is flanked by any two of marker loci SEQ ID NOs: 33 to 42, 473, and 474. Another aspect of this disclosure provides a chromosome interval associated with NLB resistance which is flanked by any two of marker loci SEQ ID NOs: 43 to 49 and 475. Another aspect of this disclosure provides a chromosome interval associated with NLB resistance which is flanked by any two of marker loci SEQ ID NOs: 57 to 64 and 458 to 468. Another aspect of this disclosure provides a chromosome interval associated with NLB resistance which is flanked by any two of marker loci SEQ ID NOs: 74 to 82. Another aspect of this disclosure provides a chromosome interval associated with NLB resistance which is flanked by any two of marker loci SEQ ID NOs: 86 to 89 and 476, 477, 479, and 480. Also provided herein are markers, e.g., SEQ ID NOs: 1-89 and 446-482, that are useful for tracking NLB resistant alleles and can be used in MAS breeding programs to produce plants with enhanced NLB resistance.

This disclosure further provides methods of using the markers identified herein to introgress loci associated with NLB resistance into NLB susceptible plants. As an example, one skilled in the art can use this disclosure to create a novel corn plant, seed, or cell with NLB resistance by crossing a donor line comprising a QTL provided herein with any desired recipient line, with or without MAS.

In another aspect, this disclosure further provides methods for introgressing multiple NLB resistance QTLs identified herein to generate an enhanced NLB resistant population of corn plants, seeds, or cells.

In an aspect, this disclosure provides a method of creating a population of corn plants, seeds, or cells, where the method comprises the steps of: (a) genotyping a first population of corn plants, seeds, or cells at one or more marker loci associated with one or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01; (b) selecting from the first population one or more corn plants, seeds, or cells comprising one or more NLB resistance alleles of the one or more marker loci; and (c) producing from the selected one or more corn plants, seeds, or cells a second population of corn plants, seeds, or cells comprising one or more NLB QTLs.

In an aspect, this disclosure provides a corn plant, seed, or cell as described in any of paragraphs [00175] to [00183], where the corn seed further comprises one or more NLB resistance loci selected from the group consisting of Ht1, Ht2, Ht3, and Htn1. In another aspect, this disclosure provides a corn plant, seed, or cell as described in any of paragraphs [00175] to [00183], where the corn seed further comprises two or more NLB resistance loci selected from the group consisting of Ht1, Ht2, Ht2, and Htn1. In another aspect, this disclosure provides a corn plant, seed, or cell as described in any of paragraphs [00175] to [00183], where the corn seed further comprises three or more NLB resistance loci selected from the group consisting of Ht1, Ht2, Ht2, and Htn1. In another aspect, this disclosure provides a corn plant, seed, or cell as described in any of paragraphs [00175] to [00183], where the corn seed further comprises NLB resistance loci Ht1, Ht2, Ht2, and Htn1.

In another aspect, this disclosure provides a corn plant, seed, or cell comprising a first NLB resistance locus selected from the group consisting of NLB resistance QTLs NLB_2.01, NLB_3.01, NLB_4.01, NLB_4.02, NLB_5.01, NLB_6.01, NLB_7.01, and NLB_9.01 and a second NLB resistance locus Ht1. In another aspect, this disclosure provides a corn plant, seed, or cell comprising a first NLB resistance locus selected from the group consisting of NLB resistance QTLs NLB_2.01, NLB_3.01, NLB_4.01, NLB_4.02, NLB_5.01, NLB_6.01, NLB_7.01, and NLB_9.01 and a second NLB resistance locus Ht2. In another aspect, this disclosure provides a corn plant, seed, or cell comprising a first NLB resistance locus selected from the group consisting of NLB resistance QTLs NLB_2.01, NLB_3.01, NLB_4.01, NLB_4.02, NLB_5.01, NLB_6.01, NLB_7.01, and NLB_9.01 and a second NLB resistance locus Ht3. In another aspect, this disclosure provides a corn plant, seed, or cell comprising a first NLB resistance locus selected from the group consisting of NLB resistance QTLs NLB_2.01, NLB_3.01, NLB_4.01, NLB_4.02, NLB_5.01, NLB_6.01, NLB_7.01, and NLB_9.01 and a second NLB resistance locus Htn1.

In another aspect, this disclosure provides a corn plant, seed, or cell comprising a first NLB resistance locus selected from the group consisting of NLB resistance QTLs NLB_4.01 and NLB_4.02 and a second NLB resistance locus selected from the group consisting of Ht1, Ht2, Ht3, and Htn1. In another aspect, this disclosure provides a corn plant, seed, or cell comprising a first NLB resistance locus selected from the group consisting of NLB resistance QTLs NLB_4.01 and NLB_4.02 and a second NLB resistance locus Ht1. In another aspect, this disclosure provides a corn plant, seed, or cell comprising a first NLB resistance locus selected from the group consisting of NLB resistance QTLs NLB_4.01 and NLB_4.02 and a second NLB resistance locus Ht2. In another aspect, this disclosure provides a corn plant, seed, or cell comprising a first NLB resistance locus selected from the group consisting of NLB resistance QTLs NLB_4.01 and NLB_4.02 and a second NLB resistance locus Ht3. In another aspect, this disclosure provides a corn plant, seed, or cell comprising a first NLB resistance locus selected from the group consisting of NLB resistance QTLs NLB_4.01 and NLB_4.02 and a second NLB resistance locus Htn1.

In an aspect, this disclosure provides a method of creating a population of corn plants, seeds, or cells, which method comprising the steps of: (a) genotyping a first population of corn plants, the population comprising at least one allele associated with NLB resistance, wherein the NLB resistance allele is associated with a marker selected from the group consisting of SEQ ID NOs: 1-89 and 446-482; (b) selecting from the first population one or more corn plants, seeds, or cells comprising the NLB resistance allele; and (c) producing from the selected corn plants, seeds, or cells a second population of corn plants, seeds, or cells comprising the at least one NLB resistance allele.

In an aspect, this disclosure provides a method for introgressing a resistance allele of a locus conferring NLB resistance, which method comprising the steps of: (a) crossing a first corn plant with a second corn plant, wherein the first corn plant comprises the resistance allele, wherein the NLB resistance allele is associated with a marker selected from the group consisting of SEQ ID NOs: 1-89 and 446-482; (b) genotyping a progeny corn plant or seed from the cross using a marker associated with the resistance allele; and (c) selecting a progeny plant or seed comprising the resistance allele.

In an aspect, this disclosure provides a method for introgressing an NLB resistance QTL, which method comprising the steps of: (a) crossing a first corn plant comprising an NLB resistance QTL selected from the group consisting of NLB resistance QTLs NLB_2.01, NLB_3.01, NLB_4.01, NLB_4.02, NLB_5.01, NLB_6.01, NLB_7.01, and NLB_9.01, with a second corn plant of a different genotype to produce one or more progeny plants or seeds; (b) assaying the one or more progeny plants or seeds at a marker locus associated with the NLB resistance QTL; and (c) selecting a progeny plant or seed comprising the NLB resistance QTL.

In an aspect, this disclosure provides a method for creating a population of corn plants, seeds, or cells with NLB resistance, which method comprising the steps of: (a) concurrently detecting in a first population of corn plants, seeds, or cells the presence of a combination of two or more, three or more, four or more, five or more, six or more, or seven or more introgressed NLB resistance loci selected from the group consisting of NLB resistance QTLs NLB_2.01, NLB_3.01, NLB_4.01, NLB_4.02, NLB_5.01, NLB_6.01, NLB_7.01, and NLB_9.01; (b) selecting from the first population one or more corn plants or seed comprising the one or more, two or more, three or more, four or more, five or more, six or more, or seven or more introgressed NLB resistance QTLs; and (c) producing a population of offspring from the selected one or more corn plants, seeds, or cells. In an aspect, a method comprises concurrent detection of one or more molecular markers located in at least one chromosome interval flanked by any two of marker loci SEQ ID NOs: 1 to 18, any two of marker loci SEQ ID NOs: 19 to 31, any two of marker loci SEQ ID NOs: 32 to 52 and 471 to 475, any two of marker loci SEQ ID NOs: 53 to 65 and 446 to 468, any two of marker loci SEQ ID NOs: 66 to 84, any two of marker loci SEQ ID NOs: 85 to 89 and 476 to 482, or marker loci SEQ ID NOs: 469 and 470. In another aspect, a method comprises concurrent detection of one or more molecular markers located in at least one chromosome interval flanked by any two of marker loci SEQ ID NOs: 12 to 15, any two of marker loci SEQ ID NOs: 22 to 25, any two of marker loci SEQ ID NOs: 37 to 42 and 474, any two of marker loci SEQ ID NOs: 44 to 49, any two of marker loci SEQ ID NOs: 57 to 62 and 458 to 466, any two of marker loci SEQ ID NOs: 79 to 81, or any two of marker loci SEQ ID NOs: 87 to 89 and 477 to 480. In another aspect, a method comprises concurrent detection of one or more molecular markers located in at least one chromosome interval flanked by any two of marker loci SEQ ID NOs: 8 to 18, any two of marker loci SEQ ID NOs: 21 to 29, any two of marker loci SEQ ID NOs: 33 to 42, 473, and 474, any two of marker loci SEQ ID NOs: 43 to 49 and 475, any two of marker loci SEQ ID NOs: 57 to 64 and 458 to 468, any two of marker loci SEQ ID NOs: 74 to 82, or any two of marker loci SEQ ID NOs: 86 to 89 and 476, 477, 479, and 480.

In an aspect, a method comprises concurrently detecting NLB resistance QTLs NLB_4.01, and NLB_4.02. In another aspect, a method comprises concurrently detecting NLB resistance QTLs NLB_4.01 and NLB_4.02 and at least one or more NLB resistance QTLs selected from the group consisting of NLB_2.01, NLB_3.01, NLB_5.01, NLB_6.01, NLB_7.01, and NLB_9.01. In another aspect, a method comprises concurrently detecting NLB resistance QTLs NLB_4.01 and NLB_4.02 and at least two or more NLB resistance QTLs selected from the group consisting of NLB_2.01, NLB_3.01, NLB_5.01, NLB_6.01, NLB_7.01, and NLB_9.01. In another aspect, a method comprises concurrently detecting NLB resistance QTLs NLB_4.01 and NLB_4.02 and at least three or more NLB resistance QTLs selected from the group consisting of NLB_2.01, NLB_3.01, NLB_5.01, NLB_6.01, NLB_7.01, and NLB_9.01. In another aspect, a method comprises concurrently detecting NLB resistance QTLs NLB_4.01 and NLB_4.02 and at least four or more NLB resistance QTLs selected from the group consisting of NLB_2.01, NLB_3.01, NLB_5.01, NLB_6.01, NLB_7.01, and NLB_9.01. In another aspect, a method comprises concurrently detecting NLB resistance QTLs NLB_4.01 and NLB_4.02 and at least five or more NLB resistance QTLs selected from the group consisting of NLB_2.01, NLB_3.01, NLB_5.01, NLB_6.01, NLB_7.01, and NLB_9.01.

In another aspect, a method comprises concurrently detecting NLB resistance QTLs NLB_3.01, NLB_4.01, and NLB_4.02. In another aspect, a method comprises concurrently detecting NLB resistance QTLs NLB_3.01, NLB_4.01, and NLB_4.02 and at least one or more NLB resistance QTLs selected from the group consisting of NLB_2.01, NLB_5.01, NLB_6.01, NLB_7.01, and NLB_9.01. In another aspect, a method comprises concurrently detecting NLB resistance QTLs NLB_3.01, NLB_4.01, and NLB_4.02 and at least two or more NLB resistance QTLs selected from the group consisting of NLB_2.01, NLB_5.01, NLB_6.01, NLB_7.01, and NLB_9.01. In another aspect, a method comprises concurrently detecting NLB resistance QTLs NLB_3.01, NLB_4.01, and NLB_4.02 and at least three or more NLB resistance QTLs selected from the group consisting of NLB_2.01, NLB_5.01, NLB_6.01, NLB_7.01, and NLB_9.01. In another aspect, a method comprises concurrently detecting NLB resistance QTLs NLB_3.01, NLB_4.01, and NLB_4.02 and at least four or more NLB resistance QTLs selected from the group consisting of NLB_2.01, NLB_5.01, NLB_6.01, NLB_7.01, and NLB_9.01.

In another aspect, a method comprises concurrently detecting NLB resistance QTLs NLB_3.01 and NLB_4.01. In another aspect, a method comprises concurrently detecting NLB resistance QTLs NLB_3.01 and NLB_4.01 and at least one or more NLB resistance QTLs selected from the group consisting of NLB_2.01, NLB_4.02, NLB_5.01, NLB_6.01, NLB_7.01, and NLB_9.01. In another aspect, a method comprises concurrently detecting NLB resistance QTLs NLB_3.01 and NLB_4.01 and at least two or more NLB resistance QTLs selected from the group consisting of NLB_2.01, NLB_4.02, NLB_5.01, NLB_6.01, NLB_7.01, and NLB_9.01. In another aspect, a method comprises concurrently detecting NLB resistance QTLs NLB_3.01 and NLB_4.01 and at least three or more NLB resistance QTLs selected from the group consisting of NLB_2.01, NLB_4.02, NLB_5.01, NLB_6.01, NLB_7.01, and NLB_9.01. In another aspect, a method comprises concurrently detecting NLB resistance QTLs NLB_3.01 and NLB_4.01 and at least four or more NLB resistance QTLs selected from the group consisting of NLB_2.01, NLB_4.02, NLB_5.01, NLB_6.01, NLB_7.01, and NLB_9.01. In another aspect, a method comprises concurrently detecting NLB resistance QTLs NLB_3.01 and NLB_4.01 and at least five or more NLB resistance QTLs selected from the group consisting of NLB_2.01, NLB_4.02, NLB_5.01, NLB_6.01, NLB_7.01, and NLB_9.01.

In another aspect, a method comprises concurrently detecting NLB resistance QTLs NLB_3.01 and NLB_4.02. In another aspect, a method comprises concurrently detecting NLB resistance QTLs NLB_3.01 and NLB_4.02 and at least one or more NLB resistance QTLs selected from the group consisting of NLB_2.01, NLB_4.01, NLB_5.01, NLB_6.01, NLB_7.01, and NLB_9.01. In another aspect, a method comprises concurrently detecting NLB resistance QTLs NLB_3.01 and NLB_4.02 and at least two or more NLB resistance QTLs selected from the group consisting of NLB_2.01, NLB_4.01, NLB_5.01, NLB_6.01, NLB_7.01, and NLB_9.01. In another aspect, a method comprises concurrently detecting NLB resistance QTLs NLB_3.01 and NLB_4.02 and at least three or more NLB resistance QTLs selected from the group consisting of NLB_2.01, NLB_4.01, NLB_5.01, NLB_6.01, NLB_7.01, and NLB_9.01. In another aspect, a method comprises concurrently detecting NLB resistance QTLs NLB_3.01 and NLB_4.02 and at least four or more NLB resistance QTLs selected from the group consisting of NLB_2.01, NLB_4.01, NLB_5.01, NLB_6.01, NLB_7.01, and NLB_9.01. In another aspect, a method comprises concurrently detecting NLB resistance QTLs NLB_3.01 and NLB_4.02 and at least five or more NLB resistance QTLs selected from the group consisting of NLB_2.01, NLB_4.01, NLB_5.01, NLB_6.01, NLB_7.01, and NLB_9.01.

In an aspect, a method comprises concurrently detecting NLB resistance QTLs NLB_2.01, NLB_4.01, and NLB_4.02. In another aspect, a method comprises concurrently detecting NLB resistance QTLs NLB_2.01, NLB_4.01, and NLB_4.02 and at least one or more NLB resistance QTLs selected from the group consisting of NLB_3.01, NLB_5.01, NLB_6.01, NLB_7.01, and NLB_9.01. In another aspect, a method comprises concurrently detecting NLB resistance QTLs NLB_2.01, NLB_4.01, and NLB_4.02 and at least two or more NLB resistance QTLs selected from the group consisting of NLB_3.01, NLB_5.01, NLB_6.01, NLB_7.01, and NLB_9.01. In another aspect, a method comprises concurrently detecting NLB resistance QTLs NLB_2.01, NLB_4.01, and NLB_4.02 and at least three or more NLB resistance QTLs selected from the group consisting of NLB_3.01, NLB_5.01, NLB_6.01, NLB_7.01, and NLB_9.01. In another aspect, a method comprises concurrently detecting NLB resistance QTLs NLB_2.01, NLB_4.01, and NLB_4.02 and at least four or more NLB resistance QTLs selected from the group consisting of NLB_3.01, NLB_5.01, NLB_6.01, NLB_7.01, and NLB_9.01.

In an aspect, a method comprises concurrently detecting NLB resistance QTLs NLB_2.01 and NLB_4.01. In another aspect, a method comprises concurrently detecting NLB resistance QTLs NLB_2.01 and NLB_4.01 and at least one or more NLB resistance QTLs selected from the group consisting of NLB_3.01, NLB_4.02, NLB_5.01, NLB_6.01, NLB_7.01, and NLB_9.01. In another aspect, a method comprises concurrently detecting NLB resistance QTLs NLB_2.01 and NLB_4.01 and at least two or more NLB resistance QTLs selected from the group consisting of NLB_3.01, NLB_4.02, NLB_5.01, NLB_6.01, NLB_7.01, and NLB_9.01. In another aspect, a method comprises concurrently detecting NLB resistance QTLs NLB_2.01 and NLB_4.01 and at least three or more NLB resistance QTLs selected from the group consisting of NLB_3.01, NLB_4.02, NLB_5.01, NLB_6.01, NLB_7.01, and NLB_9.01. In another aspect, a method comprises concurrently detecting NLB resistance QTLs NLB_2.01 and NLB_4.01 and at least four or more NLB resistance QTLs selected from the group consisting of NLB_3.01, NLB_4.02, NLB_5.01, NLB_6.01, NLB_7.01, and NLB_9.01. In another aspect, a method comprises concurrently detecting NLB resistance QTLs NLB_2.01 and NLB_4.01 and at least five or more NLB resistance QTLs selected from the group consisting of NLB_3.01, NLB_4.02, NLB_5.01, NLB_6.01, NLB_7.01, and NLB_9.01.

In an aspect, a method comprises concurrently detecting NLB resistance QTLs NLB_2.01 and NLB_4.02. In another aspect, a method comprises concurrently detecting NLB resistance QTLs NLB_2.01 and NLB_4.02 and at least one or more NLB resistance QTLs selected from the group consisting of NLB_3.01, NLB_4.01, NLB_5.01, NLB_6.01, NLB_7.01, and NLB_9.01. In another aspect, a method comprises concurrently detecting NLB resistance QTLs NLB_2.01 and NLB_4.02 and at least two or more NLB resistance QTLs selected from the group consisting of NLB_3.01, NLB_4.01, NLB_5.01, NLB_6.01, NLB_7.01, and NLB_9.01. In another aspect, a method comprises concurrently detecting NLB resistance QTLs NLB_2.01 and NLB_4.02 and at least three or more NLB resistance QTLs selected from the group consisting of NLB_3.01, NLB_4.01, NLB_5.01, NLB_6.01, NLB_7.01, and NLB_9.01. In another aspect, a method comprises concurrently detecting NLB resistance QTLs NLB_2.01 and NLB_4.02 and at least four or more NLB resistance QTLs selected from the group consisting of NLB_3.01, NLB_4.01, NLB_5.01, NLB_6.01, NLB_7.01, and NLB_9.01. In another aspect, a method comprises concurrently detecting NLB resistance QTLs NLB_2.01 and NLB_4.02 and at least five or more NLB resistance QTLs selected from the group consisting of NLB_3.01, NLB_4.01, NLB_5.01, NLB_6.01, NLB_7.01, and NLB_9.01.

In another aspect, a method comprises concurrently detecting NLB resistance QTL NLB_4.01 and at least one or more NLB resistance loci selected from the group consisting of Ht1, Ht2, Ht3, and Htn1. In another aspect, a method comprises concurrently detecting NLB resistance QTL NLB_4.01 and at least two or more NLB resistance loci selected from the group consisting of Ht1, Ht2, Ht3, and Htn1. In another aspect, a method comprises concurrently detecting NLB resistance QTL NLB_4.01 and at least three or more NLB resistance loci selected from the group consisting of Ht1, Ht2, Ht3, and Htn1. In another aspect, a method comprises concurrently detecting NLB resistance QTL NLB_4.02 and at least one or more NLB resistance loci selected from the group consisting of Ht1, Ht2, Ht3, and Htn1. In another aspect, a method comprises concurrently detecting NLB resistance QTL NLB_4.02 and at least two or more NLB resistance loci selected from the group consisting of Ht1, Ht2, Ht3, and Htn1. In another aspect, a method comprises concurrently detecting NLB resistance QTL NLB_4.02 and at least three or more NLB resistance loci selected from the group consisting of Ht1, Ht2, Ht3, and Htn1. In another aspect, a method comprises concurrently detecting NLB resistance QTLs NLB_4.01 and NLB_4.02 and at least one or more NLB resistance loci selected from the group consisting of Ht1, Ht2, Ht3, and Htn1. In another aspect, a method comprises concurrently detecting NLB resistance QTLs NLB_4.01 and NLB_4.02 and at least two or more NLB resistance loci selected from the group consisting of Ht1, Ht2, Ht3, and Htn1. In another aspect, a method comprises concurrently detecting NLB resistance QTLs NLB_4.01 and NLB_4.02 and at least three or more NLB resistance loci selected from the group consisting of Ht1, Ht2, Ht3, and Htn1.

In another aspect, a method comprises concurrently detecting NLB resistance QTL NLB_2.01 and one or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a method comprises concurrently detecting NLB resistance QTL NLB_2.01 and two or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a method comprises concurrently detecting NLB resistance QTL NLB_2.01 and three or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a method comprises concurrently detecting NLB resistance QTL NLB_2.01 and four or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a method comprises concurrently detecting NLB resistance QTL NLB_2.01 and five or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a method comprises concurrently detecting NLB resistance QTL NLB_2.01 and or six or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a method comprises concurrently detecting NLB resistance QTL NLB_2.01 and NLB resistance QTLs NLB_3.01, NLB_4.01, NLB_4.02, NLB_5.01, NLB_6.01, NLB_7.01, and NLB_9.01.

In another aspect, a method comprises concurrently detecting NLB resistance QTL NLB_3.01 and one or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a method comprises concurrently detecting NLB resistance QTL NLB_3.01 and two or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a method comprises concurrently detecting NLB resistance QTL NLB_3.01 and three or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a method comprises concurrently detecting NLB resistance QTL NLB_3.01 and four or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a method comprises concurrently detecting NLB resistance QTL NLB_3.01 and five or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a method comprises concurrently detecting NLB resistance QTL NLB_3.01 and or six or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a method comprises concurrently detecting NLB resistance QTL NLB_3.01 and NLB resistance QTLs NLB_2.01, NLB_4.01, NLB_4.02, NLB_5.01, NLB_6.01, NLB_7.01, and NLB_9.01.

In another aspect, a method comprises concurrently detecting NLB resistance QTL NLB_4.01 and one or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a method comprises concurrently detecting NLB resistance QTL NLB_4.01 and two or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a method comprises concurrently detecting NLB resistance QTL NLB_4.01 and three or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a method comprises concurrently detecting NLB resistance QTL NLB_4.01 and four or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a method comprises concurrently detecting NLB resistance QTL NLB_4.01 and five or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a method comprises concurrently detecting NLB resistance QTL NLB_4.01 and or six or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a method comprises concurrently detecting NLB resistance QTL NLB_4.01 and NLB resistance QTLs NLB_2.01, NLB_3.01, NLB_4.02, NLB_5.01, NLB_6.01, NLB_7.01, and NLB_9.01.

In another aspect, a method comprises concurrently detecting NLB resistance QTL NLB_4.02 and one or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a method comprises concurrently detecting NLB resistance QTL NLB_4.02 and two or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a method comprises concurrently detecting NLB resistance QTL NLB_4.02 and three or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a method comprises concurrently detecting NLB resistance QTL NLB_4.02 and four or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a method comprises concurrently detecting NLB resistance QTL NLB_4.02 and five or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a method comprises concurrently detecting NLB resistance QTL NLB_4.02 and or six or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a method comprises concurrently detecting NLB resistance QTL NLB_4.02 and NLB resistance QTLs NLB_2.01, NLB_3.01, NLB_4.01, NLB_5.01, NLB_6.01, NLB_7.01, and NLB_9.01.

In another aspect, a method comprises concurrently detecting NLB resistance QTL NLB_5.01 and one or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a method comprises concurrently detecting NLB resistance QTL NLB_5.01 and two or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a method comprises concurrently detecting NLB resistance QTL NLB_5.01 and three or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a method comprises concurrently detecting NLB resistance QTL NLB_5.01 and four or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a method comprises concurrently detecting NLB resistance QTL NLB_5.01 and five or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a method comprises concurrently detecting NLB resistance QTL NLB_5.01 and or six or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a method comprises concurrently detecting NLB resistance QTL NLB_5.01 and NLB resistance QTLs NLB_2.01, NLB_3.01, NLB_4.01, NLB_4.02, NLB_6.01, NLB_7.01, and NLB_9.01.

In another aspect, a method comprises concurrently detecting NLB resistance QTL NLB_6.01 and one or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a method comprises concurrently detecting NLB resistance QTL NLB_6.01 and two or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a method comprises concurrently detecting NLB resistance QTL NLB_6.01 and three or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a method comprises concurrently detecting NLB resistance QTL NLB_6.01 and four or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a method comprises concurrently detecting NLB resistance QTL NLB_6.01 and five or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a method comprises concurrently detecting NLB resistance QTL NLB_6.01 and or six or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a method comprises concurrently detecting NLB resistance QTL NLB_6.01 and NLB resistance QTLs NLB_2.01, NLB_3.01, NLB_4.01, NLB_4.02, NLB_5.01, NLB_7.01, and NLB_9.01.

In another aspect, a method comprises concurrently detecting NLB resistance QTL NLB_7.01 and one or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a method comprises concurrently detecting NLB resistance QTL NLB_7.01 and two or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a method comprises concurrently detecting NLB resistance QTL NLB_7.01 and three or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a method comprises concurrently detecting NLB resistance QTL NLB_7.01 and four or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a method comprises concurrently detecting NLB resistance QTL NLB_7.01 and five or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a method comprises concurrently detecting NLB resistance QTL NLB_7.01 and or six or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a method comprises concurrently detecting NLB resistance QTL NLB_7.01 and NLB resistance QTLs NLB_2.01, NLB_3.01, NLB_4.01, NLB_4.02, NLB_5.01, NLB_6.01, and NLB_9.01.

In another aspect, a method comprises concurrently detecting NLB resistance QTL NLB_9.01 and one or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a method comprises concurrently detecting NLB resistance QTL NLB_9.01 and two or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a method comprises concurrently detecting NLB resistance QTL NLB_9.01 and three or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a method comprises concurrently detecting NLB resistance QTL NLB_9.01 and four or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a method comprises concurrently detecting NLB resistance QTL NLB_9.01 and five or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a method comprises concurrently detecting NLB resistance QTL NLB_9.01 and or six or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a method comprises concurrently detecting NLB resistance QTL NLB_9.01 and NLB resistance QTLs NLB_2.01, NLB_3.01, NLB_4.01, NLB_4.02, NLB_5.01, NLB_6.01, and NLB_7.01.

In an aspect, this disclosure provides a method of producing a corn plant with enhanced NLB resistance, which method comprising the steps of: (a) crossing a first corn plant comprising an NLB resistance QTL with a second corn plant of a different genotype to produce one or more progeny plants or seeds; (b) selecting a progeny plant or seed comprising an NLB resistance allele of a polymorphic locus linked to an NLB resistance QTL, wherein a polymorphic locus is in a chromosomal segment flanked by any two of marker loci SEQ ID NOs: 1 to 18, any two of marker loci SEQ ID NOs: 19 to 31, any two of marker loci SEQ ID NOs: 32 to 52 and 471 to 475, any two of marker loci SEQ ID NOs: 53 to 65 and 446 to 468, any two of marker loci SEQ ID NOs: 66 to 84, any two of marker loci SEQ ID NOs: 85 to 89 and 476 to 482, or marker loci SEQ ID NOs: 469 and 470; (c) crossing the selected progeny plant with itself or the second corn plant to produce one or more further progeny plants or seeds; and (d) selecting a further progeny plant or seed comprising the NLB resistance allele. In an aspect, the further progeny plant in step (d) is an $F_2$ to $F_7$ progeny plant. In another aspect, the further progeny plant in step (d) comprises 2 to 7 generations of backcrossing. In yet another aspect, a method comprises using marker-assisted selection to select an NLB resistance allele in at least one polymorphic locus selected from the group consisting of SEQ ID NOs: 1-89 and 446-482.

In an aspect, this disclosure provides a method of obtaining a corn plant, seed, or cell with enhanced NLB resistance, which method comprises the steps of: (a) detecting in a population of corn plants, seeds, or cells a plant or seed comprising an NLB resistance allele at a polymorphic locus in a chromosomal segment flanked by SEQ ID NOs: 1 to 18, any two of marker loci SEQ ID NOs: 19 to 31, any two of marker loci SEQ ID NOs: 32 to 52 and 471 to 475, any two of marker loci SEQ ID NOs: 53 to 65 and 446 to 468, any two of marker loci SEQ ID NOs: 66 to 84, any two of marker loci SEQ ID NOs: 85 to 89 and 476 to 482, or marker loci SEQ ID NOs: 469 and 470; and (b) selecting the corn plant, seed, or cell from the population based on the presence of the NLB resistance allele.

In an aspect, this disclosure provides a method of producing a corn plant with enhanced NLB resistance, which method comprising the steps of: (a) crossing a first corn plant comprising an NLB resistance haplotype with a second corn plant of a different genotype to produce one or more progeny plants or seeds; (b) selecting a progeny plant or seed based on the presence of the NLB resistance haplotype, wherein the haplotype comprises resistance alleles of two or more polymorphic loci in a chromosomal interval flanked by: any two marker loci selected from the group consisting of SEQ ID NOs: 1 to 18, any two of marker loci SEQ ID NOs: 19 to 31, any two of marker loci SEQ ID NOs: 32 to 52 and 471 to 475, any two of marker loci SEQ ID NOs: 53 to 65 and 446 to 468, any two of marker loci SEQ ID NOs: 66 to 84, any two of marker loci SEQ ID NOs: 85 to 89 and 476 to 482, or marker loci SEQ ID NOs: 469 and 470.

In an aspect, this disclosure provides a method of obtaining a corn plant, seed, or cell with enhanced NLB resistance, which method comprising the steps of: (a) detecting in a population of corn plants, seeds, or cells a plant or seed comprising an NLB resistance haplotype, wherein the haplotype comprises resistance alleles of two or more polymorphic loci in a chromosomal interval flanked by: any two marker loci selected from the group consisting of SEQ ID NOs: 12 to 15; any two marker loci selected from the group consisting of SEQ ID NOs: 22 to 25; any two marker loci selected from the group consisting of SEQ ID NOs: 37 to 42 and 474; any two marker loci selected from the group consisting of SEQ ID NOs: 44 to 49; any two marker loci selected from the group consisting of SEQ ID NOs: 57 to 62 and 458 to 466; any two marker loci selected from the group consisting of SEQ ID NOs: 79 to 81; any two marker loci selected from the group consisting of SEQ ID NOs: 87 to 89 and 477 to 480; and marker loci SEQ ID NOs: 469 and 470; and (b) selecting a corn plant, seed, or cell from the population based on the presence of the NLB resistance haplotype. In another aspect, an NLB resistance haplotype comprises resistance alleles of two or more polymorphic loci selected from the group consisting of SEQ ID NOs: 12-15; 22-24; 37-41 and 474; 44-46; 60-62 and 464-466; 79-81; 87-89, 477, and 480; and 469-470.

In an aspect, this disclosure provides a method of obtaining a corn plant, seed, or cell with enhanced NLB resistance, which method comprising the steps of: (a) detecting in a population of corn plants, seeds, or cells a corn plant, seed, or cell comprising an NLB resistance haplotype, wherein the haplotype comprises resistance alleles of two or more polymorphic loci in a chromosomal interval flanked by: any two marker loci selected from the group consisting of SEQ ID NOs: 8 to 18; any two marker loci selected from the group consisting of SEQ ID NOs: 21 to 29; any two marker loci selected from the group consisting of SEQ ID NOs: 33 to 42, 473, and 474; any two marker loci selected from the group consisting of SEQ ID NOs: 43 to 49 and 475; any two marker loci selected from the group consisting of SEQ ID NOs: 57 to 64 and 458 to 468; any two marker loci selected from the group consisting of SEQ ID NOs: 74 to 82; any two marker loci selected from the group consisting of SEQ ID NOs: 86 to 89, 476, 477, 479, and 480; and marker loci SEQ ID NOs: 469 and 470; and (b) selecting a corn plant, seed, or cell from the population based on the presence of the NLB resistance haplotype. In yet another aspect, an NLB resistance haplotype comprises resistance alleles of two or more polymorphic loci selected from the group consisting of SEQ ID NOs: 8-18; 21-29; 33-42, 473, and 474; 43-49 and 475; 57-64 and 458-468; 74-82; 86-89, 476, 477, 479, and 480; and 469-470.

In an aspect, this disclosure provides a method for selecting a corn plant, seed, or cell, which method comprising the steps of: (a) isolating nucleic acids from a corn plant, seed, or cell; (b) analyzing the nucleic acids to detect a polymorphic marker associated with an NLB resistance QTL selected from the group consisting of NLB resistance QTLs NLB_2.01, NLB_3.01, NLB_4.01, NLB_4.02, NLB_5.01, NLB_6.01, NLB_7.01, and NLB_9.01; and (c) selecting a corn plant, seed, or cell comprising the NLB resistance QTL.

In an aspect, this disclosure provides a method for selecting a corn plant, seed, or cell, which method comprising the steps of: (a) detecting in a population of corn plants, seeds, or cells a corn plant, seed, or cell comprising an NLB resistance allele of a marker locus associated with an NLB resistance QTL selected from the group consisting of NLB resistance QTLs NLB_2.01, NLB_3.01, NLB_4.01, NLB_4.02, NLB_5.01, NLB_6.01, NLB_7.01, and NLB_9.01; and (b) selecting a corn plant, seed, or cell comprising the NLB resistance allele.

In an aspect, this disclosure provides a method for evaluating a collection of corn germplasm, which method comprising the steps of: (a) obtaining a collection of corn germplasm; (b) isolating nucleic acids from each germplasm; (c) assaying the nucleic acids for one or more markers linked to an NLB resistance QTL selected from the group consisting of NLB resistance QTLs NLB_2.01, NLB_3.01, NLB_4.01, NLB_4.02, NLB_5.01, NLB_6.01, NLB_7.01, and NLB_9.01; and (d) selecting germplasm comprising an NLB resistance QTL based on the marker assay.

In an aspect, a method provided herein comprises genotyping by a marker assay. As an example, a method provided herein comprises marker-assisted selection. As another example, a method provided herein comprises assaying a SNP marker. In yet another example, a method provided herein comprises the use of an oligonucleotide probe. In a further example, a method provided herein comprises using an oligonucleotide probe adjacent to a polymorphic nucleotide position in a marker locus being genotyped.

As an example, a corn plant or seed provided herein can be an inbred, a hybrid, a transgenic, a haploid, a doubled haploid, or in an agronomically elite background. These groups are not mutually exclusive, and a corn plant or seed could be in two or more groups (e.g., a plant could be a transgenic hybrid, another plant could be an inbred doubled haploid, etc.).

In an aspect, a method provided herein comprises genotyping a corn plant, seed, or cell at a polymorphic marker locus within about 20 cM of any one of marker loci SEQ ID NOs: 1-89 and 446-482. In an aspect, a method provided herein comprises genotyping a corn plant, seed, or cell at a polymorphic marker locus within about 15 cM of any one of marker loci SEQ ID NOs: 1-89 and 446-482. In an aspect, a method provided herein comprises genotyping a corn plant, seed, or cell at a polymorphic marker locus within about 10 cM of any one of marker loci SEQ ID NOs: 1-89 and 446-482. In an aspect, a method provided herein comprises genotyping a corn plant, seed, or cell at a polymorphic marker locus within about 5 cM of any one of marker loci SEQ ID NOs: 1-89 and 446-482. In an aspect, a method provided herein comprises genotyping a corn plant, seed, or cell at a polymorphic marker locus within about 4 cM of any one of marker loci SEQ ID NOs: 1-89 and 446-482. In an aspect, a method provided herein comprises genotyping a corn plant, seed, or cell at a polymorphic marker locus within about 3 cM of any one of marker loci SEQ ID NOs: 1-89 and 446-482. In an aspect, a method provided herein comprises genotyping a corn plant, seed, or cell at a polymorphic marker locus within about 2 cM of any one of marker loci SEQ ID NOs: 1-89 and 446-482. In an aspect, a method provided herein comprises genotyping a corn plant, seed, or cell at a polymorphic marker locus within about 1 cM of any one of marker loci SEQ ID NOs: 1-89 and 446-482. In an aspect, a method provided herein comprises genotyping a corn plant, seed, or cell at a polymorphic marker locus within about 0.5 cM of any one of marker loci SEQ ID NOs: 1-89 and 446-482. In an aspect, a method provided herein comprises genotyping a corn plant, seed, or cell at a polymorphic marker locus within less than about 0.5 cM of any one of marker loci SEQ ID NOs: 1-89 and 446-482. In an aspect, this disclosure provides a method comprising genotyping a polymorphic locus selected from the group consisting of SEQ ID NOs: 1-89 and 446-482.

In an aspect, a method provided herein comprises genotyping a corn plant, seed, or cell at a marker locus associated with NLB resistance QTL NLB_2.01, which NLB resistance QTL NLB_2.01 is located in a chromosomal interval flanked by any two of the marker loci selected from the group consisting of SEQ ID NOs: 1 to 18. In another aspect, a method provided herein comprises genotyping a corn plant, seed, or cell at a marker locus associated with NLB resistance QTL NLB_2.01, which NLB resistance QTL NLB_2.01 is located in a chromosomal interval flanked by any two of the marker loci selected from the group consisting of SEQ ID NOs: 12 to 15. In another aspect, a method provided herein comprises genotyping a corn plant, seed, or cell at a marker locus associated with NLB resistance QTL NLB_2.01, which NLB resistance QTL NLB_2.01 is located in a chromosomal interval flanked by any two of the marker loci selected from the group consisting of SEQ ID NOs: 8 to 18.

In an aspect, a method provided herein comprises genotyping a corn plant, seed, or cell at a marker locus within about 20 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 15 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 10 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 5 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 4 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 3 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 2 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 1 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within about 0.5 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus within less than about 0.5 cM of NLB resistance QTL NLB_2.01, which NLB resistance QTL NLB_2.01 is located in a chromosomal interval flanked by any two of the marker loci selected from the group consisting of SEQ ID NOs: 1 to 18. In an aspect, a method provided herein comprises genotyping a corn plant, seed, or cell at a marker locus associated with NLB resistance QTL NLB_3.01, which NLB resistance QTL NLB_3.01 is located in a chromosomal interval flanked by any two of the marker loci selected from the group consisting of SEQ ID NOs: 19 to 31. In another aspect, a method provided herein comprises genotyping a corn plant, seed, or cell at a marker locus associated with NLB resistance QTL NLB_3.01, which NLB resistance QTL NLB_3.01 is located in a chromosomal interval flanked by any two of the marker loci selected from the group consisting of SEQ ID NOs: 22 to 25. In another aspect, a method provided herein comprises genotyping a corn plant, seed, or cell at a marker locus associated with NLB resistance QTL NLB_3.01, which NLB resistance QTL NLB_3.01 is located in a chromosomal interval flanked by any two of the marker loci selected from the group consisting of SEQ ID NOs: 21 to 29.

In an aspect, a method provided herein comprises genotyping a corn plant, seed, or cell at a marker locus associated with and within about 20 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 15 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 10 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 5 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 4 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 3 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 2 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 1 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus associated with and within about 0.5 cM of NLB resistance QTL NLB_3.01, which NLB resistance QTL NLB_3.01 is located in a chromosomal interval flanked by any two of the marker loci selected from the group consisting of SEQ ID NOs: 19 to 31. In an aspect, a method provided herein comprises genotyping a corn plant, seed, or cell at a marker locus within less than about 0.5 cM of NLB resistance QTL NLB_3.01, which NLB resistance QTL NLB_3.01 is located in a chromosomal interval flanked by any two of the marker loci selected from the group consisting of SEQ ID NOs: 19 to 31.

In an aspect, a method provided herein comprises genotyping a corn plant, seed, or cell at a marker locus associated with NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In another aspect, a method provided herein comprises genotyping a corn plant, seed, or cell at a marker locus associated with NLB resistance QTL NLB_4.01, which NLB resistance QTL NLB_4.01 is located in a chromosomal interval flanked by any two of the marker loci selected from the group consisting of SEQ ID NOs: 37 to 42 and 474. In another aspect, a method provided herein comprises genotyping a corn plant, seed, or cell at a marker locus associated with NLB resistance QTL NLB_4.01, which NLB resistance QTL NLB_4.01 is located in a chromosomal interval flanked by any two of the marker loci selected from the group consisting of SEQ ID NOs: 33 to 42, 473, and 474.

In an aspect, a method provided herein comprises genotyping a corn plant, seed, or cell at a marker locus associated with and within about 20 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 15 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 10 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 5 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 4 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 3 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 2 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 1 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 0.5 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus within less than about 0.5 cM of NLB resistance QTL NLB_4.01, which NLB resistance QTL NLB_4.01 is located in a chromosomal interval flanked by any two of the marker loci selected from the group consisting of SEQ ID NOs: 32 to 52 and 471 to 475.

In an aspect, a method provided herein comprises genotyping a corn plant, seed, or cell at a marker locus associated with NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In another aspect, a method provided herein comprises genotyping a corn plant, seed, or cell at a marker locus associated with NLB resistance QTL NLB_4.02, which NLB resistance QTL NLB_4.02 is located in a chromosomal interval flanked by any two of the marker loci selected from the group consisting of SEQ ID NOs: 44 to 49. In another aspect, a method provided herein comprises genotyping a corn plant, seed, or cell at a marker locus associated with NLB resistance QTL NLB_4.02, which NLB resistance QTL NLB_4.02 is located in a chromosomal interval flanked by any two of the marker loci selected from the group consisting of SEQ ID NOs: 43 to 49 and 475.

In an aspect, a method provided herein comprises genotyping a corn plant, seed, or cell at a marker locus associated with and within about 20 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 15 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 10 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 5 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 4 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 3 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 2 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 1 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus associated with and within about 0.5 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475. In an aspect, a method provided herein comprises genotyping a corn plant, seed, or cell at a marker locus within less than about 0.5 cM of NLB resistance QTL NLB_4.02, which NLB resistance QTL NLB_4.02 is located in a chromosomal interval flanked by any two of the marker loci selected from the group consisting of SEQ ID NOs: 32 to 52 and 471 to 475.

In an aspect, a method provided herein comprises genotyping a corn plant, seed, or cell at a marker locus associated with NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In another aspect, a method provided herein comprises genotyping a corn plant, seed, or cell at a marker locus associated with NLB resistance QTL NLB_5.01, which NLB resistance QTL NLB_5.01 is located in a chromosomal interval flanked by any two of the marker loci selected from the group consisting of SEQ ID NOs: 57 to 62 and 458 to 466. In another aspect, a method provided herein comprises genotyping a corn plant, seed, or cell at a marker locus associated with NLB resistance QTL NLB_5.01, which NLB resistance QTL NLB_5.01 is located in a chromosomal interval flanked by any two of the marker loci selected from the group consisting of SEQ ID NOs: 57 to 64 and 458 to 468.

In an aspect, a method provided herein comprises genotyping a corn plant, seed, or cell at a marker locus associated with and within about 20 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 15 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 10 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 5 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 4 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 3 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 2 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 1 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus associated with and within about 0.5 cM of NLB resistance QTL NLB_5.01, which NLB resistance QTL NLB_5.01 is located in a chromosomal interval flanked by any two of the marker loci selected from the group consisting of SEQ ID NOs: 53 to 65 and 446 to 468. In an aspect, a method provided herein comprises genotyping a corn plant, seed, or cell at a marker locus within less than about 0.5 cM of NLB resistance QTL NLB_5.01, which NLB resistance QTL NLB_3.01 is located in a chromosomal interval flanked by any two of the marker loci selected from the group consisting of SEQ ID NOs: 53 to 65 and 446 to 468.

In an aspect, a method provided herein comprises genotyping a corn plant, seed, or cell at a marker locus associated with NLB resistance QTL NLB_6.01, which NLB resistance QTL NLB_6.01 is located in a chromosomal interval flanked by any two of the marker loci selected from the group consisting of SEQ ID NOs: 66 to 84. In another aspect, a method provided herein comprises genotyping a corn plant, seed, or cell at a marker locus associated with NLB resistance QTL NLB_6.01, which NLB resistance QTL NLB_6.01 is located in a chromosomal interval flanked by any two of the marker loci selected from the group consisting of SEQ ID NOs: 79 to 81. In another aspect, a method provided herein comprises genotyping a corn plant, seed, or cell at a marker locus associated with NLB resistance QTL NLB_6.01, which NLB resistance QTL NLB_6.01 is located in a chromosomal interval flanked by any two of the marker loci selected from the group consisting of SEQ ID NOs: 74 to 82.

In an aspect, a method provided herein comprises genotyping a corn plant, seed, or cell at a marker locus associated with and within about 20 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 15 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 10 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 5 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 4 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 3 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 2 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 1 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus associated with and within about 0.5 cM of NLB resistance QTL NLB_6.01, which NLB resistance QTL NLB_6.01 is located in a chromosomal interval flanked by any two of the marker loci selected from the group consisting of SEQ ID NOs: 74 to 82. In an aspect, a method provided herein comprises genotyping a corn plant, seed, or cell at a marker locus within less than about 0.5 cM of NLB resistance QTL NLB_6.01, which NLB resistance QTL NLB_3.01 is located in a chromosomal interval flanked by any two of the marker loci selected from the group consisting of SEQ ID NOs: 74 to 82.

In an aspect, a method provided herein comprises genotyping a corn plant, seed, or cell at a marker locus associated with NLB resistance QTL NLB_7.01, which NLB resistance QTL NLB_7.01 is located in a chromosomal interval flanked by the marker loci SEQ ID NOs: 469 and 470.

In an aspect, a method provided herein comprises genotyping a corn plant, seed, or cell at a marker locus associated with and within about 20 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 15 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 10 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 5 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 4 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 3 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 2 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 1 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus associated with and within about 0.5 cM of NLB resistance QTL NLB_7.01, which NLB resistance QTL NLB_7.01 is located in a chromosomal interval flanked by any two of the marker loci selected from the group consisting of SEQ ID NOs: 469 and 470. In an aspect, a method provided herein comprises genotyping a corn plant, seed, or cell at a marker locus within less than about 0.5 cM of NLB resistance QTL NLB_7.01, which NLB resistance QTL NLB_3.01 is located in a chromosomal interval flanked by any two of the marker loci selected from the group consisting of SEQ ID NOs: 469 and 470.

In an aspect, a method provided herein comprises genotyping a corn plant, seed, or cell at a marker locus associated with NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In another aspect, a method provided herein comprises genotyping a corn plant, seed, or cell at a marker locus associated with NLB resistance QTL NLB_9.01, which NLB resistance QTL NLB_9.01 is located in a chromosomal interval flanked by any two of the marker loci selected from the group consisting of SEQ ID NOs: 86 to 89, 476, 477, 479, and 480. In another aspect, a method provided herein comprises genotyping a corn plant, seed, or cell at a marker locus associated with NLB resistance QTL NLB_9.01, which NLB resistance QTL NLB_9.01 is located in a chromosomal interval flanked by any two of the marker loci selected from the group consisting of SEQ ID NOs: 87 to 89, 477, and 480.

In an aspect, a method provided herein comprises genotyping a corn plant, seed, or cell at a marker locus associated with and within about 20 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 15 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 10 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 5 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 4 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 3 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 2 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 1 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus associated with and within about 0.5 cM of NLB resistance QTL NLB_9.01, which NLB resistance QTL NLB_9.01 is located in a chromosomal interval flanked by any two of the marker loci selected from the group consisting of SEQ ID NOs: 85 to 89 and 476 to 482. In an aspect, a method provided herein comprises genotyping a corn plant, seed, or cell at a marker locus within less than about 0.5 cM of NLB resistance QTL NLB_9.01, which NLB resistance QTL NLB_3.01 is located in a chromosomal interval flanked by any two of the marker loci selected from the group consisting of SEQ ID NOs: 85 to 89 and 476 to 482.

In a further aspect, a method provided herein comprises genotyping a corn plant, seed, or cell at a marker locus located in a chromosomal interval flanked by any two of marker loci SEQ ID NOs: 1 to 18. In another aspect, a method provided herein comprises genotyping a corn plant, seed, or cell at a marker locus located in a chromosomal interval flanked by any two of marker loci SEQ ID NOs: 12 to 15. In another aspect, a method provided herein comprises genotyping a corn plant, seed, or cell at a marker locus located in a chromosomal interval flanked by any two of marker loci SEQ ID NOs: 8 to 18.

In a further aspect, a method provided herein comprises genotyping a corn plant, seed, or cell at a marker locus located in a chromosomal interval flanked by any two of marker loci SEQ ID NOs: 19 to 31. In another aspect, a method provided herein comprises genotyping a corn plant, seed, or cell at a marker locus located in a chromosomal interval flanked by any two of marker loci SEQ ID NOs: 22 to 25. In another aspect, a method provided herein comprises genotyping a corn plant, seed, or cell at a marker locus located in a chromosomal interval flanked by any two of marker loci SEQ ID NOs: 21 to 29.

In a further aspect, a method provided herein comprises genotyping a corn plant, seed, or cell at a marker locus located in a chromosomal interval flanked by any two of marker loci SEQ ID NOs: 32 to 52 and 471 to 475. In another aspect, a method provided herein comprises genotyping a corn plant, seed, or cell at a marker locus located in a chromosomal interval flanked by any two of marker loci SEQ ID NOs: 37 to 42 and 474. In yet another aspect, a method provided herein comprises genotyping a corn plant, seed, or cell at a marker locus located in a chromosomal interval flanked by any two of marker loci SEQ ID NOs: 44 to 49. In yet another aspect, a method provided herein comprises genotyping a corn plant, seed, or cell at a marker locus located in a chromosomal interval flanked by any two of marker loci SEQ ID NOs: 33 to 42, 473, and 474. In yet another aspect, a method provided herein comprises genotyping a corn plant, seed, or cell at a marker locus located in a chromosomal interval flanked by any two of marker loci SEQ ID NOs: 43 to 49 and 475.

In a further aspect, a method provided herein comprises genotyping a corn plant, seed, or cell at a marker locus located in a chromosomal interval flanked by any two of marker loci SEQ ID NOs: 53 to 65 and 446 to 468. In another aspect, a method provided herein comprises genotyping a corn plant, seed, or cell at a marker locus located in a chromosomal interval flanked by any two of marker loci SEQ ID NOs: 57 to 62 and 458 to 466. In another aspect, a method provided herein comprises genotyping a corn plant, seed, or cell at a marker locus located in a chromosomal interval flanked by any two of marker loci SEQ ID NOs: 57 to 64 and 458 to 468.

In a further aspect, a method provided herein comprises genotyping a corn plant, seed, or cell at a marker locus located in a chromosomal interval flanked by any two of marker loci SEQ ID NOs: 66 to 84. In another aspect, a method provided herein comprises genotyping a corn plant, seed, or cell at a marker locus located in a chromosomal interval flanked by any two of marker loci SEQ ID NOs: 79 to 81. In another aspect, a method provided herein comprises genotyping a corn plant, seed, or cell at a marker locus located in a chromosomal interval flanked by any two of marker loci SEQ ID NOs: 74 to 82.

In a further aspect, a method provided herein comprises genotyping a corn plant, seed, or cell at a marker locus located in a chromosomal interval flanked by marker loci SEQ ID NOs: 469 and 470.

In a further aspect, a method provided herein comprises genotyping a corn plant, seed, or cell at a marker locus located in a chromosomal interval flanked by any two of marker loci SEQ ID NOs: 85 to 89 and 476 to 482. In another aspect, a method provided herein comprises genotyping a corn plant, seed, or cell at a marker locus located in a chromosomal interval flanked by any two of marker loci SEQ ID NOs: 86 to 89, 476, 477, 479, and 480. In another aspect, a method provided herein comprises genotyping a corn plant, seed, or cell at a marker locus located in a chromosomal interval flanked by any two of marker loci SEQ ID NOs: 87 to 89, 477, and 480.

In another aspect, a method provided herein comprises genotyping a corn plant, seed, or cell by detecting a haplotype. In an aspect, a haplotype comprises an NLB resistance allele at one or more, two or more, three or more, four or more, or five or more of marker loci SEQ ID NOs: 1 to 18. In an aspect, a haplotype comprises an NLB resistance allele at two or more of marker loci SEQ ID NOs: 1 to 18. In an aspect, a haplotype comprises an NLB resistance allele at three or more of marker loci SEQ ID NOs: 1 to 18. In an aspect, a haplotype comprises an NLB resistance allele at four or more of marker loci SEQ ID NOs: 1 to 18. In an aspect, a haplotype comprises an NLB resistance allele at five or more of marker loci SEQ ID NOs: 1 to 18. In an aspect, a haplotype comprises an NLB resistance allele at one or more of marker loci SEQ ID NOs: 12 to 15. In an aspect, a haplotype comprises an NLB resistance allele at two or more of marker loci SEQ ID NOs: 12 to 15. In an aspect, a haplotype comprises an NLB resistance allele at three or more of marker loci SEQ ID NOs: 12 to 15. In an aspect, a haplotype comprises an NLB resistance allele at marker loci SEQ ID NOs: 12 to 15. In an aspect, a haplotype comprises an NLB resistance allele at one or more of marker loci SEQ ID NO: 8 to 18. In an aspect, a haplotype comprises an NLB resistance allele at two or more of marker loci SEQ ID NOs: 8 to 18. In an aspect, a haplotype comprises an NLB resistance allele at three or more of marker loci SEQ ID NOs: 8 to 18. In an aspect, a haplotype comprises an NLB resistance allele at four or more of marker loci SEQ ID NOs: 8 to 18. In an aspect, a haplotype comprises an NLB resistance allele at five or more of marker loci SEQ ID NOs: 8 to 18.

In an aspect, a haplotype comprises an NLB resistance allele at one or more, two or more, three or more, four or more, or five or more of marker loci SEQ ID NOs: 19 to 31. In an aspect, a haplotype comprises an NLB resistance allele at two or more of marker loci SEQ ID NOs: 19 to 31. In an aspect, a haplotype comprises an NLB resistance allele at three or more of marker loci SEQ ID NOs: 19 to 31. In an aspect, a haplotype comprises an NLB resistance allele at four or more of marker loci SEQ ID NOs: 19 to 31. In an aspect, a haplotype comprises an NLB resistance allele at five or more of marker loci SEQ ID NOs: 19 to 31. In an aspect, a haplotype comprises an NLB resistance allele at one or more of marker loci SEQ ID NO: 22 to 25. In an aspect, a haplotype comprises an NLB resistance allele at two or more of marker loci SEQ ID NOs: 22 to 25. In an aspect, a haplotype comprises an NLB resistance allele at three or more of marker loci SEQ ID NOs: 22 to 25. In an aspect, a haplotype comprises an NLB resistance allele at marker loci SEQ ID NOs: 22 to 25. In an aspect, a haplotype comprises an NLB resistance allele at one or more of marker loci SEQ ID NO: 21 to 29. In an aspect, a haplotype comprises an NLB resistance allele at two or more of marker loci SEQ ID NOs: 21 to 29. In an aspect, a haplotype comprises an NLB resistance allele at three or more of marker loci SEQ ID NOs: 21 to 29. In an aspect, a haplotype comprises an NLB resistance allele at four or more of marker loci SEQ ID NOs: 21 to 29. In an aspect, a haplotype comprises an NLB resistance allele at five or more of marker loci SEQ ID NOs: 21 to 29.

In an aspect, a haplotype comprises an NLB resistance allele at one or more of marker loci SEQ ID NO: 32 to 52 and 471 to 475. In an aspect, a haplotype comprises an NLB resistance allele at two or more of marker loci SEQ ID NOs: 32 to 52 and 471 to 475. In an aspect, a haplotype comprises an NLB resistance allele at three or more of marker loci SEQ ID NOs: 32 to 52 and 471 to 475. In an aspect, a haplotype comprises an NLB resistance allele at four or more of marker loci SEQ ID NOs: 32 to 52 and 471 to 475. In an aspect, a haplotype comprises an NLB resistance allele at five or more of marker loci SEQ ID NOs: 32 to 52 and 471 to 475. In an aspect, a haplotype comprises an NLB resistance allele at one or more of marker loci SEQ ID NO: 37 to 42 and 474. In an aspect, a haplotype comprises an NLB resistance allele at two or more of marker loci SEQ ID NOs: 37 to 42 and 474. In an aspect, a haplotype comprises an NLB resistance allele at three or more of marker loci SEQ ID NOs: 37 to 42 and 474. In an aspect, a haplotype comprises an NLB resistance allele at four or more of marker loci SEQ ID NOs: 37 to 42 and 474. In an aspect, a haplotype comprises an NLB resistance allele at five or more of marker loci SEQ ID NOs: 37 to 42 and 474. In an aspect, a haplotype comprises an NLB resistance allele at one or more of marker loci SEQ ID NO: 33 to 42, 473 and 474. In an aspect, a haplotype comprises an NLB resistance allele at two or more of marker loci SEQ ID NOs: 33 to 42, 473 and 474. In an aspect, a haplotype comprises an NLB resistance allele at three or more of marker loci SEQ ID NOs: 33 to 42, 473 and 474. In an aspect, a haplotype comprises an NLB resistance allele at four or more of marker loci SEQ ID NOs: 33 to 42, 473 and 474. In an aspect, a haplotype comprises an NLB resistance allele at five or more of marker loci SEQ ID NOs: 33 to 42, 473 and 474. In an aspect, a haplotype comprises an NLB resistance allele at one or more of marker loci SEQ ID NO: 43 to 49 and 475. In an aspect, a haplotype comprises an NLB resistance allele at two or more of marker loci SEQ ID NOs: 43 to 49 and 475. In an aspect, a haplotype comprises an NLB resistance allele at three or more of marker loci SEQ ID NOs: 43 to 49 and 475. In an aspect, a haplotype comprises an NLB resistance allele at four or more of marker loci SEQ ID NOs: 43 to 49 and 475. In an aspect, a haplotype comprises an NLB resistance allele at five or more of marker loci SEQ ID NOs: 43 to 49 and 475. In an aspect, a haplotype comprises an NLB resistance allele at one or more of marker loci SEQ ID NO: 44 to 49. In an aspect, a haplotype comprises an NLB resistance allele at two or more of marker loci SEQ ID NOs: 44 to 49. In an aspect, a haplotype comprises an NLB resistance allele at three or more of marker loci SEQ ID NOs: 44 to 49. In an aspect, a haplotype comprises an NLB resistance allele at four or more of marker loci SEQ ID NOs: 44 to 49. In an aspect, a haplotype comprises an NLB resistance allele at five or more of marker loci SEQ ID NOs: 44 to 49.

In an aspect, a haplotype comprises an NLB resistance allele at one or more of marker loci SEQ ID NO: 53 to 65 and 446 to 468. In an aspect, a haplotype comprises an NLB resistance allele at two or more of marker loci SEQ ID NOs: 53 to 65 and 446 to 468. In an aspect, a haplotype comprises an NLB resistance allele at three or more of marker loci SEQ ID NOs: 53 to 65 and 446 to 468. In an aspect, a haplotype comprises an NLB resistance allele at four or more of marker loci SEQ ID NOs: 53 to 65 and 446 to 468. In an aspect, a haplotype comprises an NLB resistance allele at five or more of marker loci SEQ ID NOs: 53 to 65 and 446 to 468. In an aspect, a haplotype comprises an NLB resistance allele at one or more of marker loci SEQ ID NO: 57 to 64 and 458 to 468. In an aspect, a haplotype comprises an NLB resistance allele at two or more of marker loci SEQ ID NOs: 57 to 64 and 458 to 468. In an aspect, a haplotype comprises an NLB resistance allele at three or more of marker loci SEQ ID NOs: 57 to 64 and 458 to 468. In an aspect, a haplotype comprises an NLB resistance allele at four or more of marker loci SEQ ID NOs: 57 to 64 and 458 to 468. In an aspect, a haplotype comprises an NLB resistance allele at five or more of marker loci SEQ ID NOs: 57 to 64 and 458 to 468. In an aspect, a haplotype comprises an NLB resistance allele at one or more of marker loci SEQ ID NO: 57 to 62 and 458 to 466. In an aspect, a haplotype comprises an NLB resistance allele at two or more of marker loci SEQ ID NOs: 57 to 62 and 458 to 466. In an aspect, a haplotype comprises an NLB resistance allele at three or more of marker loci SEQ ID NOs: 57 to 62 and 458 to 466. In an aspect, a haplotype comprises an NLB resistance allele at four or more of marker loci SEQ ID NOs: 57 to 62 and 458 to 466. In an aspect, a haplotype comprises an NLB resistance allele at five or more of marker loci SEQ ID NOs: 57 to 62 and 458 to 466.

In an aspect, a haplotype comprises an NLB resistance allele at one or more of marker loci SEQ ID NO: 66 to 84. In an aspect, a haplotype comprises an NLB resistance allele at two or more of marker loci SEQ ID NOs: 66 to 84. In an aspect, a haplotype comprises an NLB resistance allele at three or more of marker loci SEQ ID NOs: 66 to 84. In an aspect, a haplotype comprises an NLB resistance allele at four or more of marker loci SEQ ID NOs: 66 to 84. In an aspect, a haplotype comprises an NLB resistance allele at five or more of marker loci SEQ ID NOs: 66 to 84. In an aspect, a haplotype comprises an NLB resistance allele at one or more of marker loci SEQ ID NO: 79 to 81. In an aspect, a haplotype comprises an NLB resistance allele at two or more of marker loci SEQ ID NOs: 79 to 81. In an aspect, a haplotype comprises an NLB resistance allele at marker loci SEQ ID NOs: 79 to 81. In an aspect, a haplotype comprises an NLB resistance allele at one or more of marker loci SEQ ID NO: 74 to 82. In an aspect, a haplotype comprises an NLB resistance allele at two or more of marker loci SEQ ID NOs: 74 to 82. In an aspect, a haplotype comprises an NLB resistance allele at three or more of marker loci SEQ ID NOs: 74 to 82. In an aspect, a haplotype comprises an NLB resistance allele at four or more of marker loci SEQ ID NOs: 74 to 82. In an aspect, a haplotype comprises an NLB resistance allele at five or more of marker loci SEQ ID NOs: 74 to 82.

In an aspect, a haplotype comprises an NLB resistance allele at one or more of marker loci SEQ ID NO: 85 to 89 and 476 to 482. In an aspect, a haplotype comprises an NLB resistance allele at two or more of marker loci SEQ ID NOs: 85 to 89 and 476 to 482. In an aspect, a haplotype comprises an NLB resistance allele at three or more of marker loci SEQ ID NOs: 85 to 89 and 476 to 482. In an aspect, a haplotype comprises an NLB resistance allele at four or more of marker loci SEQ ID NOs: 85 to 89 and 476 to 482. In an aspect, a haplotype comprises an NLB resistance allele at five or more of marker loci SEQ ID NOs: 85 to 89 and 476 to 482. In an aspect, a haplotype comprises an NLB resistance allele at one or more of marker loci SEQ ID NO: 86 to 89, 476, 477, 479, and 480. In an aspect, a haplotype comprises an NLB resistance allele at two or more of marker loci SEQ ID NOs: 86 to 89, 476, 477, 479, and 480. In an aspect, a haplotype comprises an NLB resistance allele at three or more of marker loci SEQ ID NOs: 86 to 89, 476, 477, 479, and 480. In an aspect, a haplotype comprises an NLB resistance allele at four or more of marker loci SEQ ID NOs: 86 to 89, 476, 477, 479, and 480. In an aspect, a haplotype comprises an NLB resistance allele at five or more of marker loci SEQ ID NOs: 86 to 89, 476, 477, 479, and 480. In an aspect, a haplotype comprises an NLB resistance allele at one or more, or two or more of marker loci SEQ ID NO: 87 to 89, 477 and 480. In an aspect, a haplotype comprises an NLB resistance allele at two or more of marker loci SEQ ID NOs: 87 to 89, 477 and 480. In an aspect, a haplotype comprises an NLB resistance allele at three or more of marker loci SEQ ID NOs: 87 to 89, 477 and 480. In an aspect, a haplotype comprises an NLB resistance allele at four or more of marker loci SEQ ID NOs: 87 to 89, 477 and 480. In an aspect, a haplotype comprises an NLB resistance allele at five or more of marker loci SEQ ID NOs: 87 to 89, 477 and 480.

In an aspect, a haplotype comprises an NLB resistance allele at one or more of marker loci SEQ ID NO: 469 and 470. In an aspect, a haplotype comprises an NLB resistance allele at marker loci SEQ ID NO: 469 and 470.

In an aspect, a corn plant, seed, or cell comprising NLB resistance QTLs or NLB resistant alleles provided herein exhibits intermediate resistance to NLB infection from *Exserohilum turcicum* (also referred to as *Helminthosporium turcicum* or *Setosphaeria turcica*). In another aspect, a corn plant, seed, or cell comprising NLB resistance QTLs or NLB resistant alleles provided herein exhibits at least mild resistance (e.g., NLB resistance score of ≤5; see Table 1) to NLB infection from *Exserohilum turcicum* (also referred to as *Helminthosporium turcicum* or *Setosphaeria turcica*). In a further aspect, a corn plant, seed, or cell comprising NLB resistance QTLs or NLB resistant alleles provided herein exhibits resistance (e.g., NLB resistance score of ≤4; see Table 1) to NLB infection from *Exserohilum turcicum* (also referred to as *Helminthosporium turcicum* or *Setosphaeria turcica*). In an aspect, NLB infection is caused by *Exserohilum turcicum* (also referred to as *Helminthosporium turcicum* or *Setosphaeria turcica*).

As used herein, a "low NLB stress condition" refers to a condition where very few to no NLB susceptible corn plants in a field plot (e.g., less than 10%) exhibit signs of NLB infection. Signs of NLB infection can include: leaf lesions, foliage destruction, root rot, or stalk rot.

As used herein, a "high NLB stress condition" refers to a condition where a plurality of NLB susceptible corn plants in a field plot (e.g., more than 30%) exhibit signs of NLB infection.

As an example, an NLB resistance QTL or NLB resistance allele provided herein does not confer a yield penalty under a low NLB stress condition. In another example, a combination of two or more, three or more, four or more, five or more, or six or more NLB resistance QTLs provided herein does not confer a yield penalty under a low NLB stress condition. In an aspect, presence of NLB resistance QTL NLB_2.01 in a corn plant, seed, or cell genome does not confer a yield penalty under a low NLB stress condition. In an aspect, presence of NLB resistance QTL NLB_3.01 in a corn plant, seed, or cell genome does not confer a yield penalty under a low NLB stress condition. In an aspect, presence of NLB resistance QTL NLB_4.01 in a corn plant, seed, or cell genome does not confer a yield penalty under a low NLB stress condition. In an aspect, presence of NLB resistance QTL NLB_4.02 in a corn plant, seed, or cell genome does not confer a yield penalty under a low NLB stress condition. In an aspect, presence of NLB resistance QTL NLB_5.01 in a corn plant, seed, or cell genome does not confer a yield penalty under a low NLB stress condition. In an aspect, presence of NLB resistance QTL NLB_6.01 in a corn plant, seed, or cell genome does not confer a yield penalty under a low NLB stress condition. In an aspect, presence of NLB resistance QTL NLB_7.01 in a corn plant, seed, or cell genome does not confer a yield penalty under a low NLB stress condition. In an aspect, presence of NLB resistance QTL NLB_9.01 in a corn plant, seed, or cell genome does not confer a yield penalty under a low NLB stress condition.

In another aspect, a corn plant or seed provided herein comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 exhibits a reduction of NLB rating score of about 0.25 or more, 0.5 or more, 0.75 or more, 1 or more, 1.5 or more, 2 or more, 2.5 or more, 3 or more, 3.5 or more, 4 or more, 4.5 or more, 5 or more, 5.5 or more, 6 or more, 6.5 or more, 7 or more, or 7.5 or more compared to a corn plant or seed without the one or more, two or more, three or more, four or more, five or more, or six or more NLB resistance QTLs under a high NLB stress condition.

In an aspect, a corn plant or seed provided herein as described in any of paragraphs [00175] to [00183] exhibits a reduction of NLB rating score of about 0.25 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 0.5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 0.75 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 1 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 1.5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 2 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 2.5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 3 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 3.5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 4 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 4.5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 5.5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 6 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 6.5 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 7 or more compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of about 7.5 or more compared to a corn plant without the one or more, two or more, three or more, four or more, five or more, six or more, or seven or more NLB resistance QTLs under a high NLB stress condition.

In another aspect, a corn plant or seed provided herein comprising one or more, two or more, three or more, four or more, five or more, six or more, or seven or more NLB resistance QTLs or NLB resistance alleles provided herein exhibits a reduction of NLB rating score of about 0.25 or more, 0.5 or more, 0.75 or more, 1 or more, 1.5 or more, 2 or more, 2.5 or more, 3 or more, 3.5 or more, 4 or more, 4.5 or more, 5 or more, 5.5 or more, 6 or more, 6.5 or more, 7 or more, or 7.5 or more compared to a corn plant or seed without the one or more, two or more, three or more, four or more, five or more, or six or more NLB resistance QTLs or NLB resistance alleles under a high NLB stress condition.

In another aspect, a corn plant or seed provided herein comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 exhibits a reduction of NLB rating score of between 0.25 and 8, between 0.25 and 7.5, between 0.25 and 7, between 0.25 and 6.5, between 0.25 and 6, between 0.25 and 5.5, between 0.25 and 5, between 0.25 and 4.5, between 0.25 and 4, between 0.25 and 3.5, between 0.25 and 3, between 0.25 and 2.5, between 0.25 and 2, between 0.25 and 1.5, between 0.25 and 1, between 1 and 8, between 1 and 7, between 1 and 6, between 1 and 5, between 1 and 4, between 1 and 3, or between 1 and 2 compared to a corn plant or seed without the one or more, two or more, three or more, four or more, five or more, six or more, or seven or more NLB resistance QTLs under a high NLB stress condition.

In an aspect, a corn plant or seed provided herein as described in any of paragraphs [00175] to [00183] exhibits a reduction of NLB rating score of between 0.25 and 8 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 7.5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 7 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 6.5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 6 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 5.5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 4.5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 4 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 3.5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 3 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 2.5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 2 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 1.5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 0.25 and 1 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 1 and 8 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 1 and 7 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 1 and 6 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 1 and 5 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 1 and 4 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 1 and 3 compared to a corn plant without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a reduction of NLB rating score of between 1 and 2 compared to a corn plant without the one or more, two or more, three or more, four or more, five or more, six or more, or seven or more NLB resistance QTLs under a high NLB stress condition.

In another aspect, a corn plant or seed provided herein comprising one or more, two or more, three or more, four or more, five or more, six or more, or seven or more NLB resistance QTLs or NLB resistance alleles provided herein exhibits a reduction of NLB rating score of between 0.25 and 8, between 0.25 and 7.5, between 0.25 and 7, between 0.25 and 6.5, between 0.25 and 6, between 0.25 and 5.5, between 0.25 and 5, between 0.25 and 4.5, between 0.25 and 4, between 0.25 and 3.5, between 0.25 and 3, between 0.25 and 2.5, between 0.25 and 2, between 0.25 and 1.5, between 0.25 and 1, between 1 and 8, between 1 and 7, between 1 and 6, between 1 and 5, between 1 and 4, between 1 and 3, or between 1 and 2 compared to a corn plant or seed without the one or more, two or more, three or more, four or more, five or more, six or more, or seven or more NLB resistance QTLs or NLB resistance alleles under a high NLB stress condition.

In another aspect, a corn plant or seed provided herein comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 exhibits a reduction of NLB rating score of between 5% and 90%, 5% and 80%, between 5% and 70%, between 5% and 60%, between 5% and 50%, between 5% and 40%, between 5% and 30%, between 5% and 20%, between 5% and 15%, or between 5% and 10%, compared to a corn plant or seed without the one or more, two or more, three or more, four or more, five or more, six or more, or seven or more NLB resistance QTLs under a high NLB stress condition.

In an aspect, a corn plant or seed provided herein comprising one or more, two or more, three or more, four or more, five or more, six or more, seven or more, eight or more, nine or more, ten or more, or eleven or more NLB resistance QTLs or NLB resistance alleles provided herein exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the one or more, two or more, three or more, four or more, five or more, six or more, seven or more, eight or more, nine or more, ten or more, or eleven or more NLB resistance QTLs or NLB resistance alleles under a high NLB stress condition.

In an aspect, a corn plant or seed provided herein as described in any of paragraphs [00175] to [00183] exhibits a seed yield increase of about 1% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 1% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 2% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 2% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 3% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 3% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 4% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 4% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 5% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 5% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 10% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 10% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 15% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 15% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 20% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 20% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 25% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 25% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 30% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 30% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 40% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 40% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 50% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 50% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 60% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 60% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 70% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 70% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 80% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 80% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 90% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 90% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein as described in any of paragraphs [00175] to [00183] exhibits a seed yield increase of about 100% or more than seed yield of a corn plant or seed without the NLB resistance QTLs under a high NLB stress condition. In an aspect, a corn plant or seed provided herein comprising one or more, two or more, three or more, four or more, five or more, six or more, seven or more, eight or more, nine or more, ten or more, or eleven or more NLB resistance alleles provided herein exhibits a seed yield increase of about 100% or more than seed yield of a corn plant or seed without the one or more, two or more, three or more, four or more, five or more, six or more, seven or more, eight or more, nine or more, ten or more, or eleven or more NLB resistance alleles under a high NLB stress condition.

In an aspect, a corn plant or seed provided herein comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the one or more, two or more, three or more, four or more, five or more, six or more, or seven or more NLB resistance QTLs under a high NLB stress condition.

In another aspect, a corn plant or seed provided herein comprising one or more, two or more, three or more, four or more, five or more, six or more, or seven or more NLB resistance QTLs or NLB resistance alleles provided herein exhibits a seed yield increase of between 1% and 100%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the one or more, two or more, three or more, four or more, five or more, six or more, or seven or more NLB resistance QTLs or NLB resistance alleles under a high NLB stress condition.

In an aspect, a corn plant or seed provided herein comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 exhibits a seed yield increase of between 1% and 100%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a seed yield increase of between 1% and 100% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 90% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 80% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 70% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 60% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 50% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 40% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 30% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 25% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 20% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 15% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 10% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 5% compared to the seed yield of a corn plant or seed without the NLB resistance QTLs under a high NLB stress condition. In an aspect, a corn plant or seed provided herein as described in any of paragraphs [00175] to [00183]

exhibits a seed yield increase of between 1% and 4% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 3% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 1% and 2% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 2% and 90% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 3% and 80% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 4% and 70% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 5% and 60% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 10% and 50% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 15% and 40% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 20% and 30% compared to the seed yield of a corn plant or seed without the NLB resistance QTLs under a high NLB stress condition. In an aspect, a corn plant or seed provided herein as described in any of paragraphs [00175] to [00183] exhibits a seed yield increase of between 5% and 25% compared to the seed yield of a corn plant or seed without the NLB resistance QTLs under a high NLB stress condition.

In an aspect, a corn plant or seed provided herein comprising one or more, two or more, three or more, four or more, five or more, six or more, or seven or more NLB resistance QTLs or NLB resistance alleles provided herein exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the one or more, two or more, three or more, four or more, five or more, six or more, or seven or more NLB resistance QTLs or NLB resistance alleles under a high NLB stress condition.

In an aspect, a corn plant or seed provided herein comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the one or more, two or more, three or more, four or more, five or more, six or more, or seven or more NLB resistance QTLs under a high NLB stress condition. In an aspect, a corn plant or seed provided herein as described in any of paragraphs [00175] to [00183] exhibits a seed yield increase of about 0.1 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 0.25 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 0.5 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 0.75 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 1 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 1.5 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 2 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 2.5 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 3 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 0.1 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 4 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 4.5 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 5 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 6 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 7 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 8 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 9 quintal/hectare or more than seed yield of a corn plant or seed without the NLB resistance QTLs under a high NLB stress condition. In an aspect, a corn plant or seed provided herein as described in any of paragraphs [00175] to [00183] exhibits a seed yield increase of about 10 quintal/hectare or more than seed yield of a corn plant or seed without the NLB resistance QTLs under a high NLB stress condition.

In another aspect, a corn plant or seed provided herein comprising one or more, two or more, three or more, four or more, five or more, six or more, or seven or more NLB resistance QTLs or NLB resistance alleles provided herein exhibits a seed yield between 0.1 and 10 quintal/hectare, between 0.1 and 9 quintal/hectare, between 0.1 and 8 quintal/hectare, between 0.1 and 7 quintal/hectare, between 0.1 and 6 quintal/hectare, between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the one or more, two or more, three or more, four or more, five or more, six or more, or seven or more NLB resistance QTLs or NLB resistance alleles under a high NLB stress condition. In an aspect, a corn plant or seed provided herein as described in any of paragraphs [00175] to [00183] exhibits a seed yield between 0.1 and 10 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 9 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 8 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 7 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 6 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 5 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 4.5 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 4 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 3.5 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 3 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 2.5 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 2 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 1.5 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 1 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 0.75 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 0.5 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.1 and 0.25 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.25 and 9 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.5 and 8 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 0.75 and 7 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 1 and 6 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 1.5 and 5 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 2 and 4 quintal/hectare higher than seed yield of a corn plant or seed without the NLB resistance QTLs under a high NLB stress condition. In an aspect, a corn plant or seed provided herein as described in any of paragraphs [00175] to [00183] exhibits a seed yield between 3 and 3.5 quintal/hectare higher than seed yield of a corn plant or seed without the NLB resistance QTLs under a high NLB stress condition.

In an aspect, a corn plant or seed provided herein comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_7.01, NLB_6.01, and NLB_9.01 exhibits a seed yield between 0.1 and 10 quintal/hectare, between 0.1 and 9 quintal/hectare, between 0.1 and 8 quintal/hectare, between 0.1 and 7 quintal/hectare, between 0.1 and 6 quintal/hectare, between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the one or more, two or more, three or more, four or more, five or more, six or more, or seven or more NLB resistance QTLs under a high NLB stress condition.

In an aspect, this disclosure provides an NLB resistant corn plant or seed comprising one or more, two or more, three or more, four or more, five or more, six or more, or seven or more introgressed NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01. In an aspect, a corn plant or seed provided herein comprises NLB resistance QTLs NLB_2.01, NLB_3.01, NLB_4.01, NLB_4.02, NLB_5.01, NLB_6.01, NLB_7.01, and NLB_9.01 obtainable, obtained, or introgressed from any one of corn lines CV114258, CV115214, CV099829, CV102084, CV095508, CV103141, CV105893, CV595358, CV593417, CV117407, CV592505, and CV592420.

In an aspect, a corn plant, seed, or cell provided herein comprises NLB resistance QTLs NLB_4.01, and NLB_4.02. In another aspect, a corn plant, seed, or cell provided herein comprises NLB resistance QTLs NLB_2.01, NLB_4.01, and NLB_4.02. In an aspect, a corn plant, seed, or cell provided herein comprises NLB resistance QTLs NLB_2.01 and NLB_4.01. In an aspect, a corn plant, seed, or cell provided herein comprises NLB resistance QTLs NLB_2.01 and NLB_4.02.

In another aspect, a corn plant, seed, or cell provided herein comprises NLB resistance QTL NLB_2.01 and one or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_2.01 and two or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_2.01 and three or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_2.01 and four or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_2.01 and five or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_2.01 and or six or more NLB resistance QTLs selected from the group consisting of NLB resistance QTLs NLB_3.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_2.01 and NLB resistance QTLs NLB_3.01, NLB_4.01, NLB_4.02, NLB_5.01, NLB_6.01, NLB_7.01, and NLB_9.01.

In another aspect, a corn plant, seed, or cell provided herein comprises NLB resistance QTL NLB_3.01 and one or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_3.01 and two or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_3.01 and three or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_3.01 and four or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_3.01 and five or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_3.01 and or six or more NLB resistance QTLs selected from the group consisting of NLB resistance QTLs NLB_2.01, NLB_4.01, NLB_4.02, NLB_5.01, NLB_6.01, NLB_7.01, and NLB_9.01. In another aspect, a corn plant, seed, or cell provided herein comprises NLB resistance QTL NLB_3.01 and NLB resistance QTLs NLB_2.01, NLB_4.01, NLB_4.02, NLB_5.01, NLB_6.01, NLB_7.01, and NLB_9.01.

In another aspect, a corn plant, seed, or cell provided herein comprises NLB resistance QTL NLB_4.01 and one or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a corn plant, seed, or cell provided herein comprises NLB resistance QTL NLB_4.01 and two or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a corn plant, seed, or cell provided herein comprises NLB resistance QTL NLB_4.01 and three or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a corn plant, seed, or cell provided herein comprises NLB resistance QTL NLB_4.01 and four or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a corn plant, seed, or cell provided herein comprises NLB resistance QTL NLB_4.01 and five or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a corn plant, seed, or cell provided herein comprises NLB resistance QTL NLB_4.01 and or six or more NLB resistance QTLs selected from the group consisting of NLB resistance QTLs NLB_2.01, NLB_3.01, NLB_4.02, NLB_5.01, NLB_6.01, NLB_7.01, and NLB_9.01. In another aspect, a corn plant, seed, or cell provided herein comprises NLB resistance QTL NLB_4.01 and NLB resistance QTLs NLB_2.01, NLB_3.01, NLB_4.02, NLB_5.01, NLB_6.01, NLB_7.01, and NLB_9.01.

In another aspect, a corn plant, seed, or cell provided herein comprises NLB resistance QTL NLB_4.02 and one or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a corn plant, seed, or cell provided herein comprises NLB resistance QTL NLB_4.02 and two or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a corn plant, seed, or cell provided herein comprises NLB resistance QTL NLB_4.02 and three or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a corn plant, seed, or cell provided herein comprises NLB resistance QTL NLB_4.02 and four or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a corn plant, seed, or cell provided herein comprises NLB resistance QTL NLB_4.02 and five or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a corn plant, seed, or cell provided herein comprises NLB resistance QTL NLB_4.02 and or six or more NLB resistance QTLs selected from the group consisting of NLB resistance QTLs NLB_2.01, NLB_3.01, NLB_4.01, NLB_5.01, NLB_6.01, NLB_7.01, and NLB_9.01. In another aspect, a corn plant, seed, or cell provided herein comprises NLB resistance QTL NLB_4.02 and NLB resistance QTLs NLB_2.01, NLB_3.01, NLB_4.01, NLB_5.01, NLB_6.01, NLB_7.01, and NLB_9.01.

In another aspect, a corn plant, seed, or cell provided herein comprises NLB resistance QTL NLB_5.01 and one or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a corn plant, seed, or cell provided herein comprises NLB resistance QTL NLB_5.01 and two or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a corn plant, seed, or cell provided herein comprises NLB resistance QTL NLB_5.01 and three or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a corn plant, seed, or cell provided herein comprises NLB resistance QTL NLB_5.01 and four or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a corn plant, seed, or cell provided herein comprises NLB resistance QTL NLB_5.01 and five or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a corn plant, seed, or cell provided herein comprises NLB resistance QTL NLB_5.01 and or six or more NLB resistance QTLs selected from the group consisting of NLB resistance QTLs NLB_2.01, NLB_3.01, NLB_4.01, NLB_4.02, NLB_6.01, NLB_7.01, and NLB_9.01. In another aspect, a corn plant, seed, or cell provided herein comprises NLB resistance QTL NLB_5.01 and NLB resistance QTLs NLB_2.01, NLB_3.01, NLB_4.01, NLB_4.02, NLB_6.01, NLB_7.01, and NLB_9.01.

In another aspect, a corn plant, seed, or cell provided herein comprises NLB resistance QTL NLB_6.01 and one or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a corn plant, seed, or cell provided herein comprises NLB resistance QTL NLB_6.01 and two or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a corn plant, seed, or cell provided herein comprises NLB resistance QTL NLB_6.01 and three or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a corn plant, seed, or cell provided herein comprises NLB resistance QTL NLB_6.01 and four or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a corn plant, seed, or cell provided herein comprises NLB resistance QTL NLB_6.01 and five or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a corn plant, seed, or cell provided herein comprises NLB resistance QTL NLB_6.01 and or six or more NLB resistance QTLs selected from the group consisting of NLB resistance QTLs NLB_2.01, NLB_3.01, NLB_4.01, NLB_4.02, NLB_5.01, NLB_7.01, and NLB_9.01. In another aspect, a corn plant, seed, or cell provided herein comprises NLB resistance QTL NLB_6.01 and NLB resistance QTLs NLB_2.01, NLB_3.01, NLB_4.01, NLB_4.02, NLB_5.01, NLB_7.01, and NLB_9.01.

In another aspect, a corn plant, seed, or cell provided herein comprises NLB resistance QTL NLB_7.01 and one or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a corn plant, seed, or cell provided herein comprises NLB resistance QTL NLB_7.01 and two or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a corn plant, seed, or cell provided herein comprises NLB resistance QTL NLB_7.01 and three or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a corn plant, seed, or cell provided herein comprises NLB resistance QTL NLB_7.01 and four or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a corn plant, seed, or cell provided herein comprises NLB resistance QTL NLB_7.01 and five or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a corn plant, seed, or cell provided herein comprises NLB resistance QTL NLB_7.01 and or six or more NLB resistance QTLs selected from the group consisting of NLB resistance QTLs NLB_2.01, NLB_3.01, NLB_4.01, NLB_4.02, NLB_5.01, NLB_6.01, and NLB_9.01. In another aspect, a corn plant, seed, or cell provided herein comprises NLB resistance QTL NLB_7.01 and NLB resistance QTLs NLB_2.01, NLB_3.01, NLB_4.01, NLB_4.02, NLB_5.01, NLB_6.01, and NLB_9.01.

In another aspect, a corn plant, seed, or cell provided herein comprises NLB resistance QTL NLB_9.01 and one or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a corn plant, seed, or cell provided herein comprises NLB resistance QTL NLB_9.01 and two or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a corn plant, seed, or cell provided herein comprises NLB resistance QTL NLB_9.01 and three or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a corn plant, seed, or cell provided herein comprises NLB resistance QTL NLB_9.01 and four or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a corn plant, seed, or cell provided herein comprises NLB resistance QTL NLB_9.01 and five or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a corn plant, seed, or cell provided herein comprises NLB resistance QTL NLB_9.01 and or six or more NLB resistance QTLs selected from the group consisting of NLB resistance QTLs NLB_2.01, NLB_3.01, NLB_4.01, NLB_4.02, NLB_5.01, NLB_6.01, and NLB_7.01. In another aspect, a corn plant, seed, or cell provided herein comprises NLB resistance QTL NLB_9.01 and NLB resistance QTLs NLB_2.01, NLB_3.01, NLB_4.01, NLB_4.02, NLB_5.01, NLB_6.01, and NLB_7.01.

As an example, a corn plant or seed comprising one or more NLB resistance QTLs provided herein exhibits smaller leaf lesions compared to a corn plant or seed lacking the one or more NLB resistance QTLs under a high NLB stress condition. In an aspect, a corn plant or seed comprising one or more NLB resistance QTLs provided herein exhibits fewer leaf lesions compared to a corn plant or seed lacking the one or more NLB resistance QTLs under a high NLB stress condition. In an aspect, a corn plant or seed comprising one or more NLB resistance QTLs provided herein exhibits less leaf area covered by leaf lesions compared to a corn plant or seed lacking the one or more NLB resistance QTLs under a high NLB stress condition. In an aspect, a corn plant or seed comprising one or more NLB resistance QTLs provided herein exhibits reduced stem rot compared to a corn plant or seed lacking the one or more NLB resistance QTLs under a high NLB stress condition. In an aspect, a corn plant or seed comprising one or more NLB resistance QTLs provided herein exhibits reduced root rot compared to a corn plant or seed lacking the one or more NLB resistance QTLs under a high NLB stress condition. In an aspect, a corn plant or seed comprising one or more NLB resistance QTLs provided herein exhibits less foliage destruction compared to a corn plant or seed lacking the one or more NLB resistance QTLs under a high NLB stress condition.

In an aspect, this disclosure provides a method comprising providing a set of corn seeds described in any one of paragraphs [00175] to [00183] to a person desirous of planting the set of corn seeds in a field plot. In an aspect, a method comprising a field plot that exhibits NLB infection in any one of the previous one or more, two or more, three or more, four or more, five or more, six or more, seven or more, eight or more, nine or more, or ten or more planting seasons.

In an aspect, a method, a corn plant, or a corn seed provided herein is used in combination with one or more pesticides including, but not limited to, herbicides, fungicides (e.g., picoxystrobin, cyproconazole, tetraconazole, pyraclostrobin, metconazole, azoxystrobin, propiconazole, prothioconazole, trifloxystrobin), insecticides, microbiocides, nematicides, insect repellents, bactericides, and other substances used to control pests. In another aspect, a method, a corn plant, or a corn seed provided herein is used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which can be applied as a seed treatment, a foliar treatment, a drench treatment, or a drip treatment.

In an aspect, corn seeds provided herein are untreated. In another aspect, corn seeds provided herein can be subjected to various and multiple treatments. For example, without being limiting, the seeds can be treated to improve germination by priming the seeds, by disinfection to protect against seed borne pathogens, or both priming and disinfection. In another example, seeds can be coated with any available coating to improve, for example, plantability, seed emergence, and protection against seed borne pathogens. Seed coating can be any form of seed coating including, but not limited to, pelleting, film coating, and encrustments.

In a further example, the disclosure provides methods to enhance NLB resistance by combining two or more, three or more, five or more, six or more, or seven or more NLB resistance QTLs provided herein. In an aspect, the combined NLB resistance QTLs have additive effects in providing NLB resistance. In another aspect, the combined NLB resistance QTLs have synergistic effects in providing NLB resistance. In a further aspect, the combination of two or more, three or more, four or more, five or more, six or more, or seven or more NLB resistance QTLs provided herein has no negative effects over corn physiology, resistance, yield, or performance in general.

In an aspect, this disclosure provides corn plant cells, tissues, and organs that are not reproductive material and do not mediate the natural reproduction of the plant. In one aspect, this disclosure provides a non-reproductive corn cell. In another aspect, this disclosure also provides corn plant cells, tissues, and organs that are reproductive material and mediate the natural reproduction of the plant. In another aspect, this disclosure provides corn plant cells, tissues, and organs that cannot maintain themselves via photosynthesis. In another aspect, this disclosure provides somatic corn plant cells. Somatic cells, contrary to germline cells, do not mediate plant reproduction.

As an example, the provided cells, tissues and organs can be from seed, fruit, leaf, leaf blade, leaf sheath, auricle, ligule, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, bud, or vascular tissue. In another example, this disclosure provides a corn plant chloroplast or mitochondria. In a further example, this disclosure provides epidermal cells, stomata cell, trichomes, root hairs, a storage root, or a tuber. In another example, this disclosure provides a corn protoplast.

Skilled artisans understand that corn plants naturally reproduce via seeds, not via asexual reproduction or vegetative propagation. In an example, this disclosure provides corn endosperm. In another example, this disclosure provides corn endosperm cells. In a further example, this disclosure provides a male or female sterile corn plant, which cannot reproduce without human intervention.

In a further aspect, this disclosure provides processed products made from a provided corn plant, seed, or cell. As an example, such products include, but are not limited to, meal, oil, plant extract, starch, fermentation products, or digestion products. In another example, this disclosure also provides a corn meal, which is substantially oil free and which is produced using the oilseed of any of the plants provided herein. In another example, this disclosure also provides a method of providing a corn meal by crushing oilseed of any of the plants provided herein.

A corn plant, seed, or cell provided herein can also be genetically engineered to express various phenotypes of agronomic interest. Exemplary genes implicated in this regard include, but are not limited to, genes that confer resistance to pests or disease, genes that confer resistance or tolerance to an herbicide, genes that control male sterility, genes that affect abiotic stress resistance, and other genes and transcription factors that affect plant growth and agronomic traits such as yield, flowering, plant growth, or plant architecture.

Corn Transformation

A corn plant, seed, or cell provided herein can be genetically transformed. Numerous methods for plant transformation have been developed including biological and physical plant transformation protocols. See, for example, Mild et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

One method for introducing an expression vector into plants is based on the natural transformation system of *Agrobacterium*. See, e.g., Horsch et al., A Simple and General Method for Transferring Genes into Plants. *Science*, 227:1229-1231 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055, incorporated herein by reference in its entirety.

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of corn target tissues, expression of the above-described selectable marker genes allows for preferential selection of transformed cells, tissues, and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular corn line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

A corn plant, seed, or cell provided herein can also be produced by one or more genome engineering techniques or subject to further genomic editing. For example, one or more NLB resistance alleles can be introduced into an NLB susceptible background. Exemplary genome engineering techniques include meganucleases, zinc-finger nucleases, TALENs, and CRISPR/Cas9 systems. See, e.g., Gaj et al., ZFN, TALEN, and CRISPR/Cas-based methods for genome engineering. *Trends in Biotechnology*, 31:397-405 (2013). Additional genome engineering techniques known to those of ordinary skill in the art are also envisioned.

Additional Breeding

A corn plant or seed provided herein can also be subject to additional breeding using one or more known methods in the art, e.g., pedigree breeding, recurrent selection, mass selection, and mutation breeding. Pedigree breeding starts with the crossing of two genotypes, such as a corn variety comprising an NLB resistance QTL or NLB resistance allele provided herein and another corn variety lacking such a locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-fertilization and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety can comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a corn variety can be crossed with another variety to produce a first generation progeny plant. The first generation progeny plant can then be backcrossed to one of its parent varieties to create a BC1 or BC2. Progenies are selfed and selected so that the newly developed variety has many of the attributes of the recurrent parent and yet several of the desired attributes of the non-recurrent parent. This approach leverages the value and strengths of the recurrent parent for use in new corn varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into a corn plant or seed provided herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, gamma rays (e.g., cobalt-60 or cesium-137), neutrons (product of nuclear fission by uranium-235 in an atomic reactor), beta radiation (emitted from radioisotopes such as phosphorus-32 or carbon-14), or ultraviolet radiation (from 2500 to 2900 nm)), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait can then be incorporated into existing germplasm by traditional breeding techniques.

In an aspect, the disclosure provides a doubled haploid corn plant and seed that comprise an NLB resistance QTL or NLB resistance marker alleles provided herein. The doubled haploid approach achieves isogenic plants in a shorter time frame, and is particularly useful for generating inbred lines and quantitative genetics studies. Doubled haploid plants can be produced according to methods known in the art. For example, the initial step involves the haploidization of the plant which results in the production of a population comprising haploid seed. Non-homozygous lines are crossed with an inducer parent, resulting in the production of haploid seeds. Seeds that have haploid embryos, but normal triploid endosperm, advance to the second stage. After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This doubled haploid seed is cultivated and subsequently evaluated and used in hybrid testcross production.

In an aspect, this disclosure also provides methods for making a substantially homozygous corn plant by producing or obtaining a seed from a cross of a corn plant comprising an NLB resistance allele and another corn plant and applying doubled haploid methods to the $F_1$ seed or $F_1$ plant or to any successive filial generation.

Hybrid Production

In an aspect, this disclosure provides a hybrid corn plant or seed, and their production. The development of a corn hybrid in a corn plant breeding program generally involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in corn, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line, is a factor in the selection of improved corn lines that can be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. A pollination control system and effective transfer of pollen from one parent to the other offers improved plant breeding and an effective method for producing hybrid corn seed and plants. For example, a male sterility system can be used to produce corn hybrids.

Male sterility genes can increase the efficiency with which hybrids are made, in that they eliminate the need to physically emasculate the plant used as a female in a given cross. Where one desires to employ male-sterility systems, it can be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

Marker Detection

In an aspect, the present disclosure provides markers that are in linkage disequilibrium with at least one NLB resistance QTL or NLB resistance allele and can be used to select for NLB resistance. Exemplary markers comprise SEQ ID NOs: 1-89 and 446-482 with their NLB resistance alleles shown in Table 4. Markers within approximately 20 cM, 15 cM, 10 cM, 5 cM, 4 cM, 3 cM, 2 cM, 1 cM, 0.5 cM or less than 0.5 cM of these exemplary markers can also be identified from the known art.

Genetic markers are distinguishable from each other (as well as from the plurality of alleles of any one particular marker) on the basis of polynucleotide length and/or sequence. In general, any differentially inherited polymorphic trait (including a nucleic acid polymorphism) that segregates among progeny is a potential genetic marker.

As a set, polymorphic markers serve as a useful tool for fingerprinting plants to inform the degree of identity of lines or varieties. These markers can form a basis for determining associations with phenotype and can be used to drive genetic gain. The implementation of marker-assisted selection is dependent on the ability to detect and analyze underlying genetic differences between individuals.

As an example, nucleic acid analysis methods include, but are not limited to, PCR-based detection methods, microarray methods, mass spectrometry-based methods, and/or nucleic acid sequencing methods. In an aspect, the detection of polymorphic sites in a sample of DNA, RNA, or cDNA can be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) using primer pairs that are capable of hybridizing to the proximal sequences that define a polymorphism in its double-stranded form. Methods for typing DNA based on mass spectrometry have been provided in U.S. Pat. Nos. 6,613,509 and 6,503,710, and references found therein.

Polymorphisms in DNA sequences can be detected or typed by a variety of effective methods well known in the art including, but not limited to, those provided in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981; and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as provided in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as provided in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Large-scale identification of single-feature polymorphisms in complex genomes. *Genome Research,* 13:513-523 (2003); Cui et al., Detecting single-feature polymorphisms using oligonucleotide array and robustified projection pursuit. *Bioinformatics,* 21:3852-3858 (2005)). On any one microarray, it is expected there will be a plurality of target sequences, which can represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is provided in U.S. Pat. Nos. 6,799,122; 6,913,879; and 6,996,476.

Target nucleic acid sequence can also be detected by probe linking methods as provided in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other exemplary methods for detecting SNPs and Indels include single base extension (SBE) methods. Examples of SBE methods include, but are not limited, to those provided in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In an aspect, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another exemplary method for detecting polymorphisms, SNPs and indels can be detected by methods provided in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g., by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

As an example, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), Pac-Bio (Menlo Park, Calif.) and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by Service, Gene sequencing: the race for the $1000 genome. *Science,* 311:1544-46 (2006).

As an example, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST®, or even simple word processors.

In an aspect, any of the aforementioned marker types can be employed in the context of this disclosure to identify chromosome intervals encompassing a genetic element that contributes to superior agronomic performance (e.g., corn NLB resistance).

The markers to be used in the methods of the present disclosure should preferably be diagnostic of origin in order for inferences to be made about subsequent populations. Experience to date suggests that SNP markers can be ideal for mapping because the likelihood that a particular SNP allele is derived from independent origins in the extant populations of a particular species is very low. As such, SNP markers appear to be useful for tracking and assisting introgression of QTL, particularly in the case of genotypes.

Association Mapping

In an aspect, the present disclosure also provides chromosome intervals, marker loci, germplasm for conducting genome-wide association mapping for NLB resistance. Exemplary chromosome intervals and marker loci are provided in Tables 4 and 6. Genome-wide association mapping is conducted to find signals of association for various complex traits by surveying genetic variation in the whole genome.

Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding,* Kang, Ed. CAB International, pp. 59-68 (2002)).

An approach used to link phenotypic variation with genetic loci is marker-trait association (MTA) mapping, also known as linkage disequilibrium (LD) mapping. LD mapping emerged as an important gene mapping tool in the early 1990's with the advent of high-throughput genotyping technology, and has been widely used in human genetics to identify genes affecting human diseases. This approach was introduced and began to be adopted in plant gene mapping studies in early 2000's (Flint-Garcia et al., Structure of linkage disequilibrium in plants. *Annual Review of Plant Biology,* 54:357-374 (2003)).

LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al., Linkage disequilibrium in the human genome. *Nature,* 411:199-204 (2001)). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., $F_2$, BC, doubled haploid, recombinant inbred line, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Identification of QTLs

As an example, markers, alleles, and haplotypes provided herein can be used for identifying QTLs associated with NLB resistance. The statistical principles of QTL identification include penalized regression analysis, ridge regression, single marker analysis, complex pedigree analysis, Bayesian MCMC, identity-by-descent analysis, interval mapping, composite interval mapping (CIM), joint linkage mapping, and Haseman-Elston regression.

A QTL can act through a single gene mechanism or by a polygenic mechanism. In an aspect, the present disclosure provides an NLB resistance QTL interval, where an NLB resistance QTL (or multiple NLB resistance QTLs) that segregates with an NLB resistance trait is contained in the chromosomal interval. As used herein, when a QTL (or multiple QTLs) segregates with the NLB resistance trait, it is referred to herein as an "NLB resistance locus" (or "NLB resistance loci").

In an aspect of this disclosure, the boundaries of an NLB resistance QTL interval are drawn to encompass markers that will be closely linked to or associated with one or more NLB resistance QTLs. In other words, an NLB resistance QTL interval is drawn such that any marker that lies within that interval (including the terminal markers that define the boundaries of the interval) is genetically linked to or associated with the NLB resistance QTL. Each interval comprises at least one NLB resistance QTL, and furthermore, can indeed comprise more than one NLB resistance QTL. Close proximity of multiple QTLs in the same interval can obfuscate the correlation of a particular marker with a particular QTL, as one marker can demonstrate linkage to more than one QTL. Conversely, e.g., if two markers in close proximity show co-segregation with the desired phenotypic trait, it is sometimes unclear if each of those markers identifying the same QTL or two different QTLs. Regardless, knowledge of how many QTLs are in a particular interval is not necessary to make or practice the claimed subject matter.

As an example, the present disclosure also provides the mapping of additional SNP markers associated with or closely linked to one or more NLB resistance QTLs provided herein. SNP markers are ideal for mapping because the likelihood that a particular SNP allele is derived from independent origins in the extant populations of a particular species is very low. As such, SNP markers are useful for tracking and assisting introgression of NLB resistance QTLs, particularly in the case of haplotypes. In an aspect, a SNP marker is selected for mapping an NLB resistance QTL based on the marker's genetic map position. In another aspect, a SNP marker is selected for mapping an NLB resistance QTL based on the marker's physical map position.

The genetic linkage of additional marker molecules can be established by a gene mapping model such as, without limitation, the flanking marker model reported by Lander and Botstein, (Lander and Botstein, Mapping Mendelian Factors Underlying Quantitative Traits Using RFLP Linkage Maps. *Genetics,* 121:185-199 (1989)), and the interval mapping, based on maximum likelihood methods described by Lander and Botstein (supra), and implemented in the software package MAPMAKER/QTL (Lincoln and Lander, *Mapping Genes Controlling Quantitative Traits Using MAPMAKER/QTL,* Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, (Lander and Botstein, Mapping Mendelian Factors Underlying Quantitative Traits Using RFLP Linkage Maps.

*Genetics,* 121:185-199 (1989), and further described by Arús and Moreno-González, *Plant Breeding,* Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, A Nonparametric Approach for Mapping Quantitative Trait Loci. *Genetics,* 139:1421-1428 (1995), the entirety of which is herein incorporated by reference). Multiple regression methods or models can be also be used, in which the trait is regressed on a large number of markers (Jansen, *Biometrics in Plant Breed,* van Oij en, Jansen (eds.) Proceedings of the Ninth Meeting of the Eucarpia Section Biometrics in Plant Breeding, The Netherlands, pp. 116-124 (1994); Weber and Wricke, *Advances in Plant Breeding,* Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, High Resolution of Quantitative Traits Into Multiple Loci via Interval Mapping. *Genetics,* 136:1447-1455 (1994) and Zeng, Precision Mapping of Quantitative Trait Loci. *Genetics,* 136:1457-1468 (1994). Generally, the use of cofactors reduces the bias and sampling error of the estimated QTL positions (Utz and Melchinger, *Biometrics in Plant Breeding,* van Oijen, Jansen (eds.) Proceedings of the Ninth Meeting of the Eucarpia Section Biometrics in Plant Breeding, The Netherlands, pp. 195-204 (1994)), thereby improving the precision and efficiency of QTL mapping (Zeng, Precision Mapping of Quantitative Trait Loci. *Genetics,* 136:1457-1468 (1994)). These models can be extended to multi-environment experiments to analyze genotype-environment interactions (Jansen et al., Genotype-by-environment interaction in genetic mapping of multiple quantitative trait loci. *Theoretical and Applied Genetics,* 91:33-37 (1995)).

In an aspect, this disclosure provides chromosomal intervals comprising QTL associated with NLB resistance. In an aspect, the chromosome intervals of this disclosure are characterized by genomic regions including and flanked by any two of marker loci SEQ ID NOs: 12 to 15. In another aspect, the chromosome intervals of this disclosure are characterized by genomic regions including and flanked by any two of marker loci SEQ ID NOs: 22 to 25. In another aspect, the chromosome intervals of this disclosure are characterized by genomic regions including and flanked by any two of marker loci SEQ ID NOs: 37 to 42 and 474. In another aspect, the chromosome intervals of this disclosure are characterized by genomic regions including and flanked by any two of marker loci SEQ ID NOs: 44 to 49. In another aspect, the chromosome intervals of this disclosure are characterized by genomic regions including and flanked by any two of marker loci SEQ ID NOs: 57 to 62 and 458 to 466. In another aspect, the chromosome intervals of this disclosure are characterized by genomic regions including and flanked by any two of marker loci SEQ ID NOs: 79 to 81. In another aspect, the chromosome intervals of this disclosure are characterized by genomic regions including and flanked by any two of marker loci SEQ ID NOs: 87 to 89, 477, and 480. In another aspect, the chromosome intervals of this disclosure are characterized by genomic regions including and flanked by the marker loci SEQ ID NOs: 469 and 470.

In an aspect, this disclosure provides chromosomal intervals comprising QTL associated with NLB resistance. In an aspect, the chromosome intervals of this disclosure are characterized by genomic regions including and flanked by any two of marker loci SEQ ID NOs: 8 to 18. In another aspect, the chromosome intervals of this disclosure are characterized by genomic regions including and flanked by any two of marker loci SEQ ID NOs: 21 to 29. In another aspect, the chromosome intervals of this disclosure are characterized by genomic regions including and flanked by any two of marker loci SEQ ID NOs: 33 to 42, 473, and 474. In another aspect, the chromosome intervals of this disclosure are characterized by genomic regions including and flanked by any two of marker loci SEQ ID NOs: 43 to 49 and 475. In another aspect, the chromosome intervals of this disclosure are characterized by genomic regions including and flanked by any two of marker loci SEQ ID NOs: 57 to 64 and 458 to 468. In another aspect, the chromosome intervals of this disclosure are characterized by genomic regions including and flanked by any two of marker loci SEQ ID NOs: 74 to 82. In another aspect, the chromosome intervals of this disclosure are characterized by genomic regions including and flanked by any two of marker loci SEQ ID NOs: 86 to 89, 476, 477, 479, and 480.

This disclosure also provides multiple markers linked to or associated with an NLB resistance QTL, for example, the markers having the sequence selected from SEQ ID NOs: 1-89 and 446-482. This disclosure therefore provides plants comprising a nucleic acid molecule selected from the group consisting of SEQ ID NOs: 1-89 and 446-482, fragments thereof, or complements thereof. The present disclosure further provides a plant comprising alleles of the chromosome interval linked to or associated with NLB resistance or fragments and complements thereof as well as any plant comprising any combination of two or more NLB resistance alleles of marker loci selected from the group consisting of SEQ ID NOs: 1-89 and 446-482. Plants provided by this disclosure can be homozygous or heterozygous for such alleles.

The compositions and methods of the present disclosure can be utilized to guide MAS or breeding corn varieties with a desired complement (set) of allelic forms of chromosome intervals associated with superior agronomic performance (e.g., NLB resistance). Any of the provided marker alleles can be introduced into a corn line via introgression, by traditional breeding (or introduced via transformation, or both) to yield a corn plant with superior agronomic performance. The number of alleles associated with NLB resistance that can be introduced or be present in a corn plant of the present disclosure ranges from 1 to the number of alleles provided herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this disclosure.

These marker loci can be introgressed into any desired genomic background, germplasm, plant, line, variety, etc., as part of an overall MAS breeding program designed to enhance NLB resistance. This disclosure also provides QTL intervals that can be used in MAS to select plants that demonstrate NLB resistance. Similarly, QTL intervals can also be used to counter-select plants that are lacking NLB resistance. By identifying plants lacking a desired marker locus, plants lacking NLB resistance can be identified and selected or eliminated from subsequent crosses.

The present disclosure also extends to a method of making a progeny corn plant and the resulting progeny corn plants. In an aspect, the method comprises crossing a first parent corn plant with a second corn plant and growing the corn plant parent under plant growth conditions to yield corn plant progeny. Methods of crossing and growing a corn plant are well within the ability of those of ordinary skill in the art. Such corn plant progeny can be assayed for alleles associated with NLB resistance as provided herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants can be a corn plant of the present disclosure in that it comprises at least one of the allelic forms of the markers of the present disclosure, such that the progeny are capable of inheriting the allele.

By providing the positions in the corn genome of QTL intervals and the associated markers within those intervals, this disclosure also allows one skilled in the art to identify and use other markers within the intervals provided herein or linked to or associated with the intervals provided herein. Having identified such markers, these intervals can be readily identified from public linkage maps.

Closely linked markers flanking the locus of interest that have alleles in linkage disequilibrium (LD) with an NLB resistance allele at that locus can be effectively used to select for progeny plants with NLB resistance. Thus, the markers described herein, such as those listed in Table 4, as well as other markers genetically linked to or associated with the same chromosome interval, can be used to select for a corn plant, seed, or cell with NLB resistance. Often, a set of these markers will be used, (e.g., 2 or more, 3 or more, 4 or more, 5 or more) in the flanking regions of the locus. Optionally, as described above, a marker flanking or within the actual locus can also be used. The parents and their progeny can be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice this disclosure is not limited and can be any marker that is genetically linked to or associated with the QTL intervals as described in Table 6, including markers within approximately 20 cM, 15 cM, 10 cM, 5 cM, 4 cM, 3 cM, 2 cM, 1 cM, 0.5 cM or less than 0.5 cM of the intervals provided herein. Examples include, but are not limited to, any marker selected from SEQ ID NOs: 1-89 and 446-482. In an aspect, a marker locus selected from SEQ ID NOs: 1-89 and 446-482 can be amplified using an appropriate pair of primers as indicated in Table 5. Furthermore, since there are many different types of marker detection assays known in the art, it is not intended that the type of marker detection assay used to practice this disclosure be limited in any way.

Marker Assisted Selection (MAS) Breeding

Marker loci and their NLB resistance alleles provided herein can be used in MAS breeding of NLB resistance. The more tightly linked a marker is with a DNA locus influencing a phenotype (e.g., NLB resistance), the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype. However, markers do not need to contain or correspond to causal mutations in order to be effective in MAS. In fact, most MAS breeding only uses markers linked to or associated with a causal mutation.

Developing molecular markers in crop species can increase efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that exhibit NLB resistance by identifying chromosomal intervals and genetic markers associated with NLB resistance.

In general, MAS uses polymorphic markers that have been identified as having a significant likelihood of co-segregation with a desired trait. Such markers are presumed to map near a gene or genes that give the plant its desired phenotype, and are considered indicators for the desired trait.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In an aspect, it is contemplated that a plurality of markers for desired traits are sequentially or simultaneous selected and/or introgressed. The combinations of markers that are selected for in a single plant is not limited, and can include any combination of markers provided herein or any marker linked to the markers provided herein, or any markers located within the QTL intervals defined herein.

In an aspect, a first corn plant or germplasm exhibiting a desired trait (the donor, e.g., an NLB resistant corn plant) can be crossed with a second corn plant or germplasm (the recipient; e.g., an elite or exotic corn, depending on characteristics that are desired in the progeny) to create an introgressed corn plant or germplasm as part of a breeding program. In an aspect, the recipient plant can also contain one or more loci associated with one or more desired traits, which can be qualitative or quantitative trait loci. In another aspect, the recipient plant can contain a transgene.

In an aspect, the recipient corn plant or germplasm will typically lack desired traits as compared to the first corn plant or germplasm, while the introgressed corn plant or germplasm will display improved traits as compared to the second plant or germplasm. An introgressed corn plant or germplasm produced by these methods are also a feature of this disclosure.

MAS is a powerful shortcut to select for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than cultivating and observing plants for visible traits.

Genomic Selection

Genomic selection (GS), also known as genome wide selection (GWS), is a form of MAS that estimates all locus, haplotype, and/or marker effects across the entire genome to calculate genomic estimated breeding values (GEBVs). See Nakaya and Isobe, Will genomic selection be a practical method for plant breeding? *Annals of Botany* 110: 1303-1316 (2012); Van Vleck et al., Estimated breeding values for meat characteristics of cross-bred cattle with an animal model. *Journal of Animal Science* 70: 363-371 (1992); and Heffner et al., Genomic selection for crop improvement. *Crop Science* 49: 1-12 (2009). GS utilizes a training phase and a breeding phase. In the training phase, genotypes and phenotypes are analyzed in a subset of a population to generate a GS prediction model that incorporates significant relationships between phenotypes and genotypes. A GS training population must be representative of selection candidates in the breeding program to which GS will be applied. In the breeding phase, genotype data are obtained in a breeding population, then favorable individuals are selected based on GEBVs obtained using the GS prediction model generated during the training phase without the need for phenotypic data.

Larger training populations typically increase the accuracy of GEBV predictions. Increasing the training population to breeding population ratio is helpful for obtaining accurate GEBVs when working with populations having high genetic diversity, small breeding populations, low heritability of traits, or large numbers of QTLs. The number of markers required for GS modeling is determined based on the rate of LD decay across the genome, which must be calculated for each specific population to which GS will be applied. In general, more markers will be necessary with faster raters of LD decay. Ideally, GS comprises at least one marker in LD with each QTL, but in practical terms one of ordinary skill in the art would recognized that this is not necessary.

With genotyping data, favorable individuals from a population can be selected based only on GEBVs. GEBVs are the sum of the estimate of genetic deviation and the weighted sum of estimates of breed effects, which are predicted using phenotypic data. Without being limiting, commonly used statistical models for prediction of GEBVs include best linear unbiased prediction (Henderson, Best linear unbiased estimation and prediction under a selection model. *Biometrics* 31: 423 (1975)) and a Bayesian framework (Gianola and Fernando, Bayesian methods in animal breeding theory. *Journal of Animal Science* 63: 217-244 (1986)).

The compositions and methods of the present disclosure can be utilized for GS or breeding corn varieties with a desired complement (set) of allelic forms of chromosome intervals associated with superior agronomic performance (e.g., NLB resistance). In an aspect, a corn plant, seed, or cell provided herein can be selected using genomic selection. In another aspect, SEQ ID NOs: 1-89 and 446-482 can be used in a method comprising genomic selection. In another aspect, a genomic selection method provided herein comprises phenotyping a population of corn plants for NLB resistance using the NLB rating scale provided in Table 1. In another aspect, a genomic selection method provided herein comprises genotyping a population of corn plants, seeds, or cells with at least one of marker loci SEQ ID NOs: 1-89 and 446-482.

Introgression of NLB Resistance QTLs Using MAS

The disclosure provides methods and markers for introgressing one or more NLB resistance QTLs provided herein into a new corn variety using MAS.

Multiple methods are available to achieve the introgression. For example, introgression of a desired allele at a specified locus can be transmitted to at least one progeny via a cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The introgression of one or more desired loci from a donor line into another line is achieved via repeated backcrossing to a recurrent parent accompanied by selection to retain one or more loci from the donor parent. Markers associated with NLB resistance are assayed in progeny and those progeny with one or more desired markers are selected for advancement. In another aspect, one or more markers can be assayed in the progeny to select for plants with the genotype of the agronomically elite parent.

It is generally anticipated that trait introgression activities will require more than one generation, wherein progeny are crossed to the recurrent (agronomically elite) parent or selfed. Selections are made based on the presence of one or more markers linked to NLB resistance and can also be made based on the recurrent parent genotype, wherein screening is performed on a genetic marker and/or phenotype basis. In another aspect, markers of this disclosure can be used in conjunction with other markers, ideally at least one on each chromosome of the corn genome, to track the introgression of NLB resistance into elite germplasm. In another aspect, QTL intervals associated with NLB resistance will be useful in conjunction with SNP molecular markers of the present disclosure to combine quantitative and qualitative NLB resistance in the same plant. It is within the scope of this disclosure to utilize the methods and compositions for trait integration of NLB resistance. It is contemplated by the inventors that the present disclosure will be useful for developing commercial varieties with NLB resistance and other agronomically elite phenotypes.

The following non-limiting embodiments are envisioned:

1. A method of creating a population of corn plants, seeds, or cells, said method comprising:
    a. genotyping a first population of corn plants, seeds, or cells at one or more marker loci associated with and within about 10 cM of one or more Northern Leaf Blight (NLB) resistance quantitative trait loci (QTLs) selected from the group consisting of NLB resistance QTLs NLB_2.01, NLB_3.01, NLB_4.01, NLB_4.02, NLB_5.01, NLB_6.01, NLB_7.01, and NLB_9.01;
    b. selecting from said first population one or more corn plants, seeds, or cells comprising one or more NLB resistance alleles of said one or more marker loci; and
    c. producing from said selected one or more corn plants, seeds, or cells a second population of corn plants, seeds, or cells comprising said one or more NLB QTLs.

2. The method of embodiment 1, wherein said one or more marker loci are located in a chromosomal interval flanked by:
   any two of marker loci SEQ ID NOs: 1 to 18;
   any two of marker loci SEQ ID NOs: 19 to 31;
   any two of marker loci SEQ ID NOs: 32 to 52 and 471 to 475;
   any two of marker loci SEQ ID NOs: 53 to 65 and 446 to 468;
   any two of marker loci SEQ ID NOs: 66 to 84;
   any two of marker loci SEQ ID NOs: 85 to 89 and 476 to 482; or
   marker loci SEQ ID NOs: 469 and 470.
3. The method of embodiments 1 or 2, wherein said one or more marker loci are located in a chromosomal interval flanked by:
   any two marker loci selected from the group consisting of SEQ ID NOs: 12 to 15;
   any two marker loci selected from the group consisting of SEQ ID NOs: 22 to 25;
   any two marker loci selected from the group consisting of SEQ ID NOs: 37 to 42 and 474;
   any two marker loci selected from the group consisting of SEQ ID NOs: 44 to 49;
   any two marker loci selected from the group consisting of SEQ ID NOs: 57 to 62 and 458 to 466;
   any two marker loci selected from the group consisting of SEQ ID NOs: 79 to 81;
   any two marker loci selected from the group consisting of SEQ ID NOs: 87 to 89, 477, and 480; or
   marker loci SEQ ID NOs: 469 and 470.
4. The method of embodiments 1 or 2, wherein said one or more marker loci are located in a chromosomal interval flanked by:
   any two marker loci selected from the group consisting of SEQ ID NOs: 8 to 18;
   any two marker loci selected from the group consisting of SEQ ID NOs: 21 to 29;
   any two marker loci selected from the group consisting of SEQ ID NOs: 33 to 42, 473, and 474;
   any two marker loci selected from the group consisting of SEQ ID NOs: 43 to 49 and 475;
   any two marker loci selected from the group consisting of SEQ ID NOs: 57 to 64 and 458 to 468;
   any two marker loci selected from the group consisting of SEQ ID NOs: 74 to 82;
   any two marker loci selected from the group consisting of SEQ ID NOs: 86 to 89, 476, 477, 479, and 480; or
   marker loci SEQ ID NOs: 469 and 470.
5. The method of any one of embodiments 1-4, wherein said one or more marker loci are within about 5 cM, 1 cM, 0.5 cM, or less than 0.5 cM of any one of marker loci selected from the group consisting of SEQ ID NOs: 1-89 and 446-482.
6. The method of any one of embodiments 1-5, wherein said one or more NLB resistance QTLs provide mild resistance or resistance to infection by *Exserohilum turcicum*.
7. The method of any one of embodiments 1-6, wherein said second population of corn plants or seeds exhibit reduced root rot, reduced stalk rot, fewer leaf lesions, less foliage destruction, or any combination thereof compared to corn plants or seeds lacking said NLB resistance QTL under a high NLB stress condition.
8. The method of any one of embodiments 1-7, wherein said one or more NLB resistance QTLs confer no yield penalty under a low NLB stress condition.
9. The method of any one of embodiments 1-8, wherein said step (a) comprises assaying a single nucleotide polymorphism marker.
10. The method of any one of embodiments 1-9, wherein said step (a) comprises the use of an oligonucleotide probe.
11. The method of embodiment 10, wherein said oligonucleotide probe is adjacent to a polymorphic nucleotide position in said marker locus.
12. The method of any one of embodiments 1-11, wherein said step (a) comprises detecting a haplotype.
13. A method of introgressing an NLB resistance QTL, said method comprising:
    a. crossing a first corn plant comprising an NLB resistance QTL with a second corn plant of a different genotype to produce one or more progeny plants or seeds; and
    b. selecting a progeny plant or seed comprising an NLB resistance allele of a polymorphic locus linked to said NLB resistance QTL, wherein said polymorphic locus is in a chromosomal segment flanked by:
       any two of marker loci SEQ ID NOs: 1 to 18;
       any two of marker loci SEQ ID NOs: 19 to 31;
       any two of marker loci SEQ ID NOs: 32 to 52 and 471 to 475;
       any two of marker loci SEQ ID NOs: 53 to 65 and 446 to 468;
       any two of marker loci SEQ ID NOs: 66 to 84;
       any two of marker loci SEQ ID NOs: 85 to 89 and 476 to 482; or
       marker loci SEQ ID NOs: 469 and 470.
14. The method of embodiment 13, wherein said polymorphic locus is within about 10 cM, 5 cM, 1 cM, 0.5 cM, or less than 0.5 cM of any one of marker loci selected from the group consisting of SEQ ID NOs: 1-89 and 446-482.
15. The method of embodiment 13 or 14, further comprising:
    c. crossing said progeny plant with itself or said second plant to produce one or more further progeny plants or seeds; and
    d. selecting a further progeny plant or seed comprising said NLB resistance allele.
16. An NLB resistant corn plant, seed, or cell comprising a combination of two or more, three or more, four or more, five or more, six or more, or seven or more introgressed NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01.
17. The corn plant, seed, or cell of embodiment 16, wherein seed yield of said corn plant is about 1% or more, 3% or more, 5% or more, 10% or more, 20% or more, 30% or more, 40% or more, 50% or more, 60% or more, 70% or more, 80% or more, 90% or more, or 100% or more higher than seed yield of a corn plant without said combination of introgressed NLB resistance QTLs under a high NLB stress condition.
18. The corn plant, seed, or cell of embodiment 16 or 17, wherein said corn plant, seed, or cell is in an agronomically elite background.
19. The corn plant, seed, or cell of any one of embodiments 16-18, wherein said corn plant or seed is a transgenic hybrid plant, seed, or cell.

20. The corn plant, seed, or cell of any one of embodiments 16-19, wherein said combination of introgressed NLB resistance QTLs comprises one or more QTLs selected from the group consisting of NLB resistance QTLs NLB_4.01 and NLB_4.02.

21. The corn plant, seed, or cell of any one of embodiments 16-19, wherein said combination of introgressed NLB resistance QTLs comprises NLB resistance QTL NLB_4.01 and at least one NLB resistance QTL selected from the group consisting of NLB_2.01, NLB_3.01, NLB_4.02, NLB_5.01, NLB_6.01, NLB_7.01, and NLB_9.01.

22. The corn plant, seed, or cell of any one of embodiments 16-19, wherein said combination of introgressed NLB resistance QTLs comprises NLB resistance QTL NLB_4.02 and at least one NLB resistance QTL selected from the group consisting of NLB_2.01, NLB_3.01, NLB_4.01, NLB_5.01, NLB_6.01, NLB_7.01, and NLB_9.01.

23. The corn plant, seed, or cell of any one of embodiments 16-19, wherein said combination of introgressed NLB resistance QTLs comprises NLB resistance QTLs NLB_4.01 and NLB_4.02, and at least one NLB resistance QTL selected from the group consisting of NLB_2.01, NLB_3.01, NLB_5.01, NLB_6.01, NLB_7.01, and NLB_9.01.

24. A method for selecting a corn plant, seed, or cell, said method comprising:
   a. isolating nucleic acids from a corn plant, seed, or cell;
   b. analyzing said nucleic acids to detect a polymorphic marker associated with and within 10 cM of an NLB resistance QTL selected from the group consisting of NLB resistance QTLs NLB_2.01, NLB_3.01, NLB_4.01, NLB_4.02, NLB_5.01, NLB_6.01, NLB_7.01, and NLB_9.01; and
   c. selecting a corn plant, seed, or cell comprising said NLB resistance QTL.

25. A method comprising providing a set of corn seeds comprising one or more, two or more, three or more, four or more, five or more, six or more, or seven or more NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01, to a person desirous of planting said set of corn seeds in a field plot.

26. A method of growing a population of corn plants in a field plot, said method comprising planting a population of corn seeds comprising one or more, two or more, three or more, four or more, five or more, six or more, or seven or more introgressed NLB resistance QTLs selected from the group consisting of NLB resistance QTLs NLB_2.01, NLB_3.01, NLB_4.01, NLB_4.02, NLB_5.01, NLB_6.01, NLB_7.01, and NLB_9.01 in said field plot.

Having now generally described the invention, the same will be more readily understood through reference to the following examples that are provided by way of illustration, and are not intended to be limiting of the present invention, unless specified.

Each periodical, patent, and other document or reference cited herein is herein incorporated by reference in its entirety.

EXAMPLES

Example 1. Identification of QTLs Associated with Northern Leaf Blight Resistance in Biparental Mapping Populations Biparental mapping populations are constructed to investigate the genetic basis of northern leaf blight (NLB) disease resistance in corn. Plant phenotyping is performed in field plots. About 30-40 plots per mapping population, each plot comprising 10 to 12 individual plants, are inoculated with *E. turcicum* by placing a sorghum seed carrying *E. turcicum* spores in the whorl of each plant between V6 (six leaf collars visible) stage and V8 stage. NLB disease resistance is measured 14-21 days after inoculation by rating the percentage of leaf area infected on a scale of 1 (highly resistant) to 9 (susceptible) as shown in Table 1.

TABLE 1

Description of NLB rating scale, ILA = infected leaf area.

| Symptoms | Score | Rating |
| --- | --- | --- |
| 0% of leaf area infected; no visible lesions | 1 | Highly Resistant |
| ILA <1%; few lesions, dispersed through lower leaves | 2 | Highly Resistant |
| 1% ≤ ILA < 20% | 3 | Resistant |
| 20% ≤ ILA < 40% | 4 | Resistant |
| 40% ≤ ILA < 50%; lesions reaching ear leaf, with sparse lesions in the leaves above the ear | 5 | Mildly Resistant |
| 50% ≤ ILA < 60%; lesions reaching the leaves above the ear | 6 | Mildly Susceptible |
| 60% ≤ ILA < 75% | 7 | Susceptible |
| 75% ≤ ILA < 90% | 8 | Susceptible |
| >90% of foliar area infected, with premature death of the plant before forming black layer | 9 | Susceptible |

Sixteen mapping populations are shown in Table 2. These populations include twelve NLB resistant parents (CV114258, CV115214, CV099829, CV102084, CV095508, CV103141, CV105893, CV595358, CV593417, CV117407, CV592505, and CV592420). Each mapping population is scored for NLB resistance and individual plant scores from rows of 20 plants each are averaged and reported as a final score for the row.

Plants from all mapping populations are genotyped using SNP markers that collectively span each chromosome in the maize genome. Marker-trait association studies are performed to identify NLB disease resistance QTLs and their associated markers using composite interval mapping (CIM) and single marker analysis (SMA).

TABLE 2

Mapping populations.

| Mapping Population | Cross | NLB Resistant Line | NLB Susceptible Line | Population Type |
| --- | --- | --- | --- | --- |
| A | CV113018/CV114258 | CV114258 | CV113018 | Double-haploid |
| B | CV115214/CV236864 | CV115214 | CV236864 | $F_4$ |
| C | CV108503/CV099829 | CV099829 | CV108503 | Double-haploid |
| D | CV102084/CV108986 | CV102084 | CV108986 | Double-haploid |
| E | CV102084/CV109562 | CV102084 | CV109562 | Double-haploid |
| F | CV102084/CV112706 | CV102084 | CV112706 | Double-haploid |
| G | CV095508/CV095869 | CV095508 | CV095869 | Double-haploid |

TABLE 2-continued

Mapping populations.

| Mapping Population | Cross | NLB Resistant Line | NLB Susceptible Line | Population Type |
|---|---|---|---|---|
| H | CV095508/CV097202 | CV095508 | CV097202 | $F_3$ |
| I | CV112894/CV103141 | CV103141 | CV112894 | $F_3$ |
| J | CV105893/CV112894 | CV105893 | CV112894 | $F_3$ |
| K | CV595358/CV589205 | CV595358 | CV589205 | Double-haploid |
| L | CV582063/CV593417 | CV593417 | CV582063 | Double-haploid |
| M | CV625558/CV593417 | CV593417 | CV625558 | Double-haploid | tests (Churchill and Doerg, *Genetics*, 138(3):963-71 (1994)). The composite interval mapping (CIM) analysis reveals several strong QTLs associated with NLB resistance. The QTLs are confirmed in multiple genetic backgrounds and summarized in Table 3.

In Table 3, genetic positions are represented in cM with position zero being the first (most distal) marker known at the beginning of the chromosome on Monsanto's internal consensus genetic map. Each row of Table 3 provides mapping population ID, number of SNP markers genotyped, resistant parent, chromosome position, the peak of the likelihood ratio corresponding to NLB resistance, left and right flanking positions, p-value, additive effect, and the phenotypic variance ($R^2$) of individual QTL or Total QTLs.

TABLE 3

CIM results from all mapping populations.

| Mapping population | Number of Markers Genotyped | Resistant Parent | Chr | QTL Positions (cM) Peak | Left Flank | Right Flank | p-value* | Additive | Individual QTL $R^2$ | Total $R^2$ |
|---|---|---|---|---|---|---|---|---|---|---|
| A | 112 | CV114258 | 4 | 168.3 | 152.3 | 175.5 | 0.01 | 0.53 | 0.21 | 0.58 |
| B | 90 | CV115214 | 4 | 155 | 152 | 158 | 0.01 | 0.7 | 0.19 | 0.54 |
| C | 158 | CV099829 | 3 | 113.21 | 104.2 | 118.5 | 0.01 | 0.41 | 0.09 | 0.67 |
| C | 158 | CV099829 | 4 | 166.31 | 161.3 | 179.5 | 0.01 | 0.36 | 0.08 | 0.65 |
| C | 158 | CV099829 | 5 | 80.01 | 71.9 | 89.4 | 0.01 | 0.44 | 0.11 | 0.67 |
| C | 158 | CV099829 | 4 | 72.31 | 62.8 | 79.3 | 0.01 | 0.86 | 0.17 | 0.57 |
| D | 169 | CV102084 | 2 | 107.51 | 100.5 | 118.3 | 0.01 | 1.04 | 0.23 | 0.76 |
| E | 173 | CV102084 | 2 | 115.6 | 107.5 | 119.6 | 0.01 | 0.51 | 0.08 | 0.52 |
| E | 173 | CV102084 | 2 | 114.61 | 108.6 | 118.7 | 0.05 | 0.64 | 0.09 | 0.50 |
| F | 171 | CV102084 | 2 | 113.9 | 102.9 | 122.9 | 0.01 | 0.78 | 0.14 | 0.50 |
| E | 173 | CV102084 | 4 | 174.31 | 166.3 | 184.4 | 0.01 | 0.47 | 0.07 | 0.51 |
| F | 171 | CV102084 | 4 | 172.8 | 165.8 | 183.4 | 0.01 | 0.51 | 0.07 | 0.51 |
| F | 171 | CV102084 | 4 | 172.8 | 165.8 | 183.4 | 0.01 | 0.81 | 0.15 | 0.48 |
| E | 173 | CV102084 | 6 | 74.31 | 64.3 | 84.1 | 0.01 | 0.65 | 0.13 | 0.50 |
| E | 173 | CV102084 | 6 | 78.31 | 65.3 | 85.3 | 0.01 | 0.93 | 0.19 | 0.52 |
| G | 111 | CV095869 | 5 | 93.6 | 84.9 | 100.6 | 0.01 | −0.58 | 0.23 | 0.49 |
| H | 156 | CV097202 | 5 | 98.1 | 90.1 | 108.6 | 0.01 | −0.65 | 0.2 | 0.38 |
| I | 158 | CV103141 | 9 | 69.9 | 60.9 | 74.9 | 0.01 | 0.65 | 0.18 | 0.64 |
| J | 153 | CV105893 | 5 | 89.61 | 85.6 | 100.4 | 0.01 | 0.53 | 0.17 | 0.52 |
| K | 182 | CV595358 | 5 | 90.3 | 86 | 93.2 | 0.01 | 1.43 | 0.12 | 0.92 |
| K | 182 | CV595358 | 7 | 109.3 | 106.1 | 121.3 | 0.05 | 0.92 | 0.08 | 0.94 |
| L | 173 | CV593417 | 5 | 90.3 | 85.1 | 98.8 | 0.01 | 1.97 | 0.67 | 0.88 |
| M | 174 | CV593417 | 5 | 90.3 | 80.6 | 95.6 | 0.01 | 1.7 | 0.51 | 0.69 |
| O | 142 | CV117407 | 9 | 69.3 | 63.6 | 75.3 | 0.01 | 0.41 | 0.12 | 0.54 |
| P | 150 | CV592505 | 4 | 165.8 | 161.2 | 171.9 | 0.01 | 0.45 | 0.13 | 0.54 |
| Q | 146 | CV592420 | 9 | 72.9 | 67.5 | 83.9 | 0.01 | 0.54 | 0.13 | 0.53 |

*p-value is based on 1,000 permutation tests;
† Based on Monsanto's internal consensus genetic map.

TABLE 2-continued

Mapping populations.

| Mapping Population | Cross | NLB Resistant Line | NLB Susceptible Line | Population Type |
|---|---|---|---|---|
| O | CV603347/CV117407 | CV117407 | CV603347 | Double-haploid |
| P | CV592505/CV031573 | CV592505 | CV031573 | Double-haploid |
| Q | CV112894/CV592420 | CV592420 | CV112894 | $F_3$ |

Example 2. Identification of NLB Disease Resistance QTLs Via Composite Interval Mapping A composite interval mapping (CIM) approach is taken to identify NLB resistance QTL intervals based on the phenotyping and genotyping data collected in Example 1. For each marker, the thresholds of likelihood ratio between full and null models for CIM are based on 1000 random permutation tests (Churchill and Doerg, *Genetics*, 138(3):963-71 (1994)).

Example 3. Identification of Molecular Markers Associated with NLB Disease Resistance Via Single-Marker Analysis (SMA)

Single-marker analysis (SMA) is performed to identify markers associated with NLB resistance using the genotypic data from Example 1. For each marker, the thresholds (p-value) for SMA are based on 10,000 random permutation tests (Churchill and Doerg, *Genetics*, 138(3):963-71 (1994)).

In total, 126 SNP markers are identified to be linked to NLB disease resistance (Table 4). Table 4 also provides the effect estimates on NLB rating score for each marker linked to NLB disease resistance. Further provided are the SEQ ID NO of the marker, chromosome position, marker position on Monsanto's internal consensus genetic map, corresponding marker position on the Neighbors 2008 maize genetic map (publicly available at the MaizeGDB website, maizegdb.org/data_center/map), genetic source of favorable allele, resistant allele SNP, susceptible allele SNP, the estimated effect that the marker polymorphism has on the NLB rating score, and p-value based on 10,000 random permutation tests. For example, SEQ ID NO: 1 is associated with a 0.47% reduction in NLB rating score by one copy of the resistant allele. However, one of skill in the art recognizes that a "resistant" allele at one locus can be a "susceptible" allele in a different genetic background. Thus, this disclosure is not limited to the "resistant" and "susceptible" alleles exemplified herein.

The primer sequences for amplifying exemplary SNP marker loci linked to NLB disease resistance and the probes used to genotype the corresponding SNP sequences are provided in Table 5. In an illustrative example, SNP marker SEQ ID NO: 1 can be amplified using the primers described in Table 5 as SEQ ID NO: 90 (forward primer) and SEQ ID NO: 179 (reverse primer), and detected with probes indicated as SEQ ID NO: 268 (Probe 1) and SEQ ID NO: 357 (Probe 2).

TABLE 4

Estimate effects of markers linked to NLB disease resistance from all mapping populations by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability |
|---|---|---|---|---|---|---|---|---|
| 1 | 2 | 102.8 | 342.0 | CV112894 | A | G | 0.47 | 0.001 |
| 2 | 2 | 105.6 | 347.4 | CV102084 | G | C | 0.44 | 0.001 |
| 3 | 2 | 106.5 | 370.8 | CV112894 | A | G | 0.47 | 0.001 |
| 4 | 2 | 106.7 | 349.9 | CV102084 | A | G | 0.49 | 0.001 |
| 5 | 2 | 107.3 | 351.2 | CV102084 | T | C | 0.43 | 0.001 |
| 6 | 2 | 108.3 | 353.5 | CV102084 | G | A | 0.60 | 0.001 |
| 7 | 2 | 108.3 | 370.8 | CV102084 | T | G | 0.50 | 0.001 |
| 8 | 2 | 109.1 | 355.6 | CV102084 | A | G | 0.56 | 0.001 |
| 9 | 2 | 109.9 | 358.3 | CV112894 | T | A | 0.54 | 0.001 |
| 10 | 2 | 110.0 | 361.2 | CV102084 | G | A | 0.62 | 0.001 |
| 11 | 2 | 111.4 | 370.0 | CV102084 | A | C | 0.41 | 0.001 |
| 12 | 2 | 113.2 | 374.0 | CV112894 | A | G | 0.56 | 0.001 |
| 13 | 2 | 113.6 | 374.5 | CV102084 | G | A | 0.61 | 0.001 |
| 14 | 2 | 117.3 | 380.7 | CV102084 | G | A | 0.83 | 0.001 |
| 15 | 2 | 117.4 | 380.8 | CV102084 | C | T | 0.37 | 0.001 |
| 16 | 2 | 120.2 | 388.9 | CV102084 | T | C | 0.56 | 0.001 |
| 17 | 2 | 120.7 | 390.5 | CV102084 | A | C | 0.64 | 0.001 |
| 18 | 2 | 120.9 | 391.2 | CV112894 | C | T | 0.66 | 0.001 |
| 19 | 3 | 100.8 | 348.1 | CV117407 | T | C | 0.57 | 0.001 |
| 19 | 3 | 100.8 | 348.1 | CV099829 | T | C | 0.57 | 0.001 |
| 20 | 3 | 102.2 | 352.2 | CV117407 | G | T | 0.55 | 0.001 |
| 20 | 3 | 102.2 | 352.2 | CV099829 | G | T | 0.55 | 0.001 |
| 21 | 3 | 104.2 | 358.1 | CV117407 | G | A | 0.56 | 0.001 |
| 21 | 3 | 104.2 | 358.1 | CV099829 | G | A | 0.56 | 0.001 |
| 22 | 3 | 110.9 | 382.6 | CV117407 | A | G | 0.58 | 0.001 |
| 22 | 3 | 110.9 | 382.6 | CV099829 | A | G | 0.58 | 0.001 |
| 23 | 3 | 111.6 | 387.5 | CV118913 | G | A | 0.59 | 0.001 |
| 23 | 3 | 111.6 | 387.5 | CV095508 | G | A | 0.59 | 0.001 |
| 24 | 3 | 112.2 | 390.8 | CV117407 | T | C | 0.58 | 0.001 |
| 24 | 3 | 112.2 | 390.8 | CV099829 | T | C | 0.58 | 0.001 |
| 25 | 3 | 114.9 | 398.4 | CV095508 | C | T | 0.43 | 0.001 |
| 26 | 3 | 115.9 | 401.2 | CV118913 | T | A | 0.34 | 0.001 |
| 27 | 3 | 115.9 | 401.2 | CV095508 | T | C | 0.43 | 0.001 |
| 28 | 3 | 116.5 | 403.0 | CV117407 | T | C | 0.46 | 0.001 |
| 28 | 3 | 116.5 | 403.0 | CV099829 | T | C | 0.46 | 0.001 |
| 29 | 3 | 118.0 | 408.4 | CV117407 | C | T | 0.44 | 0.001 |
| 29 | 3 | 118.0 | 408.4 | CV099829 | C | T | 0.44 | 0.001 |
| 30 | 3 | 119.2 | 412.5 | CV117407 | G | A | 0.44 | 0.001 |
| 30 | 3 | 119.2 | 412.5 | CV099829 | G | A | 0.44 | 0.001 |
| 31 | 3 | 123.4 | 429.3 | CV095508 | T | C | 0.40 | 0.001 |
| 32 | 4 | 155.0 | 531.5 | CV095508 | A | C | 0.33 | 0.001 |
| 33 | 4 | 162.8 | 573.4 | CV099829 | G | A | 0.30 | 0.001 |
| 34 | 4 | 164.3 | 576.6 | CV102084 | G | A | 0.53 | 0.001 |
| 35 | 4 | 165.2 | 578.4 | CV102084 | G | A | 0.61 | 0.001 |
| 36 | 4 | 165.4 | 578.8 | CV102084 | A | C | 0.60 | 0.001 |
| 37 | 4 | 165.8 | 579.6 | CV102084 | A | T | 0.60 | 0.001 |
| 37 | 4 | 165.8 | 579.6 | CV102084 | A | T | 0.60 | 0.001 |
| 37 | 4 | 165.8 | 579.6 | CV102084 | A | T | 0.60 | 0.001 |
| 38 | 4 | 166.3 | 581.8 | CV102084 | G | A | 0.58 | 0.001 |
| 39 | 4 | 166.3 | 581.8 | CV102084 | T | C | 0.58 | 0.001 |
| 39 | 4 | 166.3 | 581.8 | CV102084 | T | C | 0.58 | 0.001 |
| 39 | 4 | 166.3 | 581.8 | CV114258 | T | C | 0.58 | 0.001 |
| 40 | 4 | 167.2 | 583.8 | CV095508 | C | T | 0.32 | 0.001 |
| 41 | 4 | 168.4 | 586.4 | CV105893 | G | A | 0.34 | 0.001 |
| 42 | 4 | 169.3 | 588.3 | CV102084 | T | A | 0.43 | 0.001 |
| 43 | 4 | 170.5 | 590.9 | CV102084 | T | A | 0.44 | 0.001 |
| 44 | 4 | 171.9 | 594.0 | CV102084 | G | T | 0.64 | 0.001 |
| 45 | 4 | 172.8 | 601.6 | CULU085 | A | G | 0.49 | 0.001 |
| 46 | 4 | 173.3 | 601.4 | CV102084 | T | G | 0.74 | 0.001 |
| 47 | 4 | 175.5 | 610.2 | CV114258 | C | A | 0.59 | 0.001 |
| 48 | 4 | 176.4 | 614.4 | CV102084 | C | T | 0.61 | 0.001 |
| 48 | 4 | 176.4 | 614.4 | CV102084 | C | T | 0.61 | 0.001 |

TABLE 4-continued

Estimate effects of markers linked to NLB disease resistance from all mapping populations by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability |
|---|---|---|---|---|---|---|---|---|
| 48 | 4 | 176.4 | 614.4 | CV102084 | C | T | 0.61 | 0.001 |
| 48 | 4 | 176.4 | 614.4 | CV102084 | C | T | 0.61 | 0.001 |
| 49 | 4 | 176.9 | 616.7 | CV105893 | A | G | 0.39 | 0.001 |
| 50 | 4 | 183.4 | 647.2 | CV099829 | A | T | 0.34 | 0.001 |
| 50 | 4 | 183.4 | 647.2 | CV105893 | A | T | 0.34 | 0.001 |
| 51 | 4 | 185.2 | 655.6 | CV102084 | A | G | 0.59 | 0.001 |
| 51 | 4 | 185.2 | 655.6 | CV102084 | A | G | 0.59 | 0.001 |
| 52 | 4 | 185.7 | 656.5 | CV102084 | C | T | 0.52 | 0.001 |
| 52 | 4 | 185.7 | 656.5 | CV102084 | C | T | 0.52 | 0.001 |
| 52 | 4 | 185.7 | 656.5 | CV102084 | C | T | 0.52 | 0.001 |
| 53 | 5 | 83.7 | 295.8 | CV097202 | C | A | 0.39 | 0.001 |
| 54 | 5 | 83.9 | 296.7 | CV095869 | T | C | 0.49 | 0.001 |
| 55 | 5 | 86.6 | 310.8 | CV097202 | C | G | 0.47 | 0.001 |
| 55 | 5 | 86.6 | 310.8 | CV105893 | C | G | 0.47 | 0.001 |
| 56 | 5 | 87.2 | 313.9 | CV097202 | C | T | 0.38 | 0.001 |
| 57 | 5 | 89.0 | 321.3 | CV097202 | C | A | 0.40 | 0.001 |
| 58 | 5 | 89.7 | 321.3 | CV105893 | A | G | 0.56 | 0.001 |
| 59 | 5 | 93.2 | 325.0 | CV105893 | T | C | 0.55 | 0.001 |
| 60 | 5 | 93.6 | 328.5 | CV095869 | A | C | 0.58 | 0.001 |
| 61 | 5 | 96.7 | 333.8 | CV105893 | A | G | 0.53 | 0.001 |
| 62 | 5 | 99.4 | 336.7 | CV105893 | T | C | 0.55 | 0.001 |
| 63 | 5 | 102.6 | 340.0 | CV097202 | T | C | 0.41 | 0.001 |
| 64 | 5 | 103.3 | 342.5 | CV105893 | C | T | 0.54 | 0.001 |
| 65 | 5 | 105.2 | 347.6 | CV095869 | G | T | 0.41 | 0.001 |
| 66 | 6 | 63.9 | 302.0 | CV102084 | G | A | 0.53 | 0.001 |
| 67 | 6 | 64.1 | 302.7 | CV102084 | C | T | 0.48 | 0.001 |
| 68 | 6 | 64.2 | 303.1 | CV102084 | T | C | 0.53 | 0.001 |
| 69 | 6 | 64.2 | 303.1 | CV102084 | G | T | 0.50 | 0.001 |
| 70 | 6 | 64.5 | 304.1 | CV102084 | T | G | 0.50 | 0.001 |
| 71 | 6 | 65.3 | 306.9 | CV102084 | T | A | 0.48 | 0.001 |
| 72 | 6 | 66.0 | 312.3 | CV102084 | G | A | 0.45 | 0.001 |
| 73 | 6 | 66.4 | 313.4 | CV102084 | G | A | 0.45 | 0.001 |
| 74 | 6 | 68.1 | 318.2 | CV102084 | T | C | 0.51 | 0.001 |
| 75 | 6 | 68.1 | 318.2 | CV102084 | C | T | 0.52 | 0.001 |
| 76 | 6 | 68.3 | 318.7 | CV102084 | C | G | 0.46 | 0.001 |
| 77 | 6 | 70.0 | 324.0 | CV102084 | G | A | 0.48 | 0.001 |
| 78 | 6 | 71.3 | 329.9 | CV102084 | T | C | 0.46 | 0.001 |
| 79 | 6 | 73.2 | 337.5 | CV102084 | A | T | 0.36 | 0.001 |
| 80 | 6 | 74.3 | 341.9 | CV102084 | A | G | 0.50 | 0.001 |
| 81 | 6 | 74.7 | 343.2 | CV102084 | A | G | 0.26 | 0.001 |
| 82 | 6 | 77.7 | 350.2 | CV102084 | T | C | 0.35 | 0.001 |
| 83 | 6 | 83.8 | 369.0 | CV102084 | C | T | 0.36 | 0.001 |
| 84 | 6 | 85.0 | 373.8 | CV102084 | G | A | 0.31 | 0.001 |
| 85 | 9 | 58.1 | 164.3 | CV103141 | T | C | 0.27 | 0.001 |
| 86 | 9 | 61.4 | 188.5 | CV103141 | C | T | 0.30 | 0.001 |
| 87 | 9 | 63.3 | 199.4 | CV103141 | C | T | 0.46 | 0.001 |
| 88 | 9 | 68.6 | 227.2 | CV103141 | G | C | 0.46 | 0.001 |
| 89 | 9 | 69.9 | 240.5 | CV103141 | A | G | 0.38 | 0.001 |
| 446 | 5 | 80.0 | 282.6 | CV595358 | T | C | 1.64 | 0.001 |
| 447 | 5 | 80.0 | 282.6 | CV595358 | T | G | 1.64 | 0.001 |
| 448 | 5 | 80.3 | 283.9 | CV595358 | C | T | 1.65 | 0.001 |
| 449 | 5 | 80.6 | 286.7 | CV595358 | T | C | 1.65 | 0.001 |
| 450 | 5 | 80.6 | 286.7 | CV595358 | C | T | 1.65 | 0.001 |
| 451 | 5 | 82.4 | 291.2 | CV595358 | G | A | 1.82 | 0.001 |
| 53 | 5 | 83.7 | 295.8 | CV595358 | A | C | 1.66 | 0.001 |
| 452 | 5 | 84.0 | 297.1 | CV595358 | G | A | 1.88 | 0.001 |
| 453 | 5 | 84.1 | 297.5 | CV595358 | A | C | 1.88 | 0.001 |
| 454 | 5 | 85.9 | 306.9 | CV595358 | T | C | 1.88 | 0.001 |
| 455 | 5 | 86.0 | 307.3 | CV595358 | T | C | 1.88 | 0.001 |
| 456 | 5 | 86.0 | 307.3 | CV595358 | C | T | 1.88 | 0.001 |
| 457 | 5 | 88.4 | 311.8 | CV595358 | G | A | 2.00 | 0.001 |
| 57 | 5 | 89.0 | 321.3 | CV595358 | A | C | 1.93 | 0.001 |
| 458 | 5 | 89.2 | 310.4 | CV595358 | G | T | 1.93 | 0.001 |
| 459 | 5 | 90.3 | 316.9 | CV595358 | T | C | 2.00 | 0.001 |
| 460 | 5 | 90.3 | 316.9 | CV595358 | G | C | 2.00 | 0.001 |
| 461 | 5 | 90.8 | 320.6 | CV595358 | G | A | 2.00 | 0.001 |
| 462 | 5 | 91.4 | 321.9 | CV595358 | A | G | 1.93 | 0.001 |
| 463 | 5 | 92.0 | 322.9 | CV595358 | G | C | 1.93 | 0.001 |
| 59 | 5 | 93.2 | 327.6 | CV595358 | C | T | 1.93 | 0.001 |
| 464 | 5 | 93.6 | 328.5 | CV595358 | T | C | 1.87 | 0.001 |
| 465 | 5 | 95.3 | 332.3 | CV595358 | G | T | 1.87 | 0.001 |
| 466 | 5 | 97.8 | 335.0 | CV595358 | C | A | 1.79 | 0.001 |
| 62 | 5 | 99.4 | 336.7 | CV595358 | T | C | 1.79 | 0.001 |
| 467 | 5 | 101.8 | 339.3 | CV595358 | A | G | 1.80 | 0.001 |

TABLE 4-continued

Estimate effects of markers linked to NLB disease resistance from all mapping populations by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability |
|---|---|---|---|---|---|---|---|---|
| 446 | 5 | 80.0 | 282.6 | CV593417 | T | C | 1.83 | 0.001 |
| 447 | 5 | 80.0 | 282.6 | CV593417 | T | G | 1.83 | 0.001 |
| 448 | 5 | 80.3 | 283.9 | CV593417 | C | T | 1.83 | 0.001 |
| 449 | 5 | 80.6 | 286.7 | CV593417 | T | C | 1.83 | 0.001 |
| 450 | 5 | 80.6 | 286.7 | CV593417 | C | T | 1.83 | 0.001 |
| 451 | 5 | 82.4 | 291.2 | CV593417 | G | A | 1.83 | 0.001 |
| 53 | 5 | 83.7 | 295.8 | CV593417 | A | C | 1.83 | 0.001 |
| 452 | 5 | 84.0 | 297.1 | CV593417 | G | A | 1.87 | 0.001 |
| 453 | 5 | 84.1 | 297.5 | CV593417 | A | C | 1.87 | 0.001 |
| 454 | 5 | 85.9 | 306.9 | CV593417 | T | C | 1.91 | 0.001 |
| 455 | 5 | 86.0 | 403.0 | CV593417 | T | C | 1.91 | 0.001 |
| 456 | 5 | 86.0 | 403.0 | CV593417 | C | T | 1.91 | 0.001 |
| 457 | 5 | 88.4 | 311.8 | CV593417 | G | A | 1.93 | 0.001 |
| 57 | 5 | 89.0 | 321.3 | CV593417 | A | C | 1.91 | 0.001 |
| 458 | 5 | 89.2 | 310.4 | CV593417 | G | T | 1.91 | 0.001 |
| 459 | 5 | 90.3 | 316.9 | CV593417 | T | C | 1.93 | 0.001 |
| 460 | 5 | 90.3 | 316.9 | CV593417 | G | C | 1.93 | 0.001 |
| 461 | 5 | 90.8 | 320.6 | CV593417 | G | A | 1.94 | 0.001 |
| 462 | 5 | 91.4 | 321.9 | CV593417 | A | G | 1.92 | 0.001 |
| 463 | 5 | 92.0 | 322.9 | CV593417 | G | C | 1.92 | 0.001 |
| 464 | 5 | 93.6 | 328.5 | CV593417 | T | C | 1.92 | 0.001 |
| 466 | 5 | 97.8 | 335.0 | CV593417 | C | A | 1.87 | 0.001 |
| 467 | 5 | 101.8 | 339.3 | CV593417 | A | G | 1.72 | 0.001 |
| 468 | 5 | 102.3 | 340.3 | CV593417 | C | A | 1.68 | 0.001 |
| 64 | 5 | 103.3 | 342.5 | CV593417 | T | C | 1.61 | 0.001 |
| 446 | 5 | 80.0 | 282.6 | CV593417 | T | C | 1.61 | 0.001 |
| 448 | 5 | 80.3 | 283.9 | CV593417 | C | T | 1.61 | 0.001 |
| 449 | 5 | 80.6 | 286.7 | CV593417 | T | C | 1.61 | 0.001 |
| 450 | 5 | 80.6 | 286.7 | CV593417 | C | T | 1.61 | 0.001 |
| 451 | 5 | 82.4 | 291.2 | CV593417 | G | A | 1.62 | 0.001 |
| 409 | 5 | 83.7 | 295.8 | CV593417 | A | C | 1.62 | 0.001 |
| 452 | 5 | 84.0 | 297.1 | CV593417 | G | A | 1.70 | 0.001 |
| 453 | 5 | 84.1 | 297.5 | CV593417 | A | C | 1.70 | 0.001 |
| 454 | 5 | 85.9 | 306.9 | CV593417 | T | C | 1.68 | 0.001 |
| 455 | 5 | 86.0 | 307.3 | CV593417 | T | C | 1.68 | 0.001 |
| 456 | 5 | 86.0 | 307.3 | CV593417 | C | T | 1.68 | 0.001 |
| 457 | 5 | 88.4 | 311.8 | CV593417 | G | A | 1.67 | 0.001 |
| 57 | 5 | 89.0 | 321.3 | CV593417 | A | C | 1.67 | 0.001 |
| 458 | 5 | 89.2 | 310.4 | CV593417 | G | T | 1.67 | 0.001 |
| 459 | 5 | 90.3 | 316.9 | CV593417 | T | C | 1.67 | 0.001 |
| 460 | 5 | 90.3 | 316.9 | CV593417 | G | C | 1.67 | 0.001 |
| 462 | 5 | 91.4 | 321.9 | CV593417 | A | G | 1.62 | 0.001 |
| 463 | 5 | 92.0 | 322.9 | CV593417 | G | C | 1.59 | 0.001 |
| 464 | 5 | 93.6 | 328.5 | CV593417 | T | C | 1.45 | 0.001 |
| 466 | 5 | 97.8 | 335.0 | CV593417 | C | A | 1.25 | 0.001 |
| 467 | 5 | 101.8 | 339.3 | CV593417 | A | G | 1.03 | 0.001 |
| 469 | 7 | 103.3 | 381.2 | CV595358 | T | C | 1.03 | 0.001 |
| 470 | 7 | 110.0 | 409.4 | CV595358 | G | A | 1.45 | 0.001 |
| 471 | 4 | 159.2 | 564.4 | CV592505 | G | A | 0.25 | 0.001 |
| 472 | 4 | 161.4 | 570.3 | CV592505 | T | C | 0.28 | 0.001 |
| 473 | 4 | 163.7 | 575.4 | CV592505 | G | C | 0.35 | 0.001 |
| 474 | 4 | 165.8 | 579.6 | CV592505 | G | T | 0.39 | 0.001 |
| 40 | 4 | 167.2 | 583.8 | CV592505 | C | T | 0.40 | 0.001 |
| 475 | 4 | 170.1 | 590.1 | CV592505 | A | G | 0.30 | 0.001 |
| 44 | 4 | 171.9 | 594.0 | CV592505 | T | G | 0.29 | 0.001 |
| 47 | 4 | 175.5 | 610.2 | CV592505 | C | A | 0.13 | 0.001 |
| 476 | 9 | 61.6 | 325.0 | CV117407 | G | A | 0.18 | 0.001 |
| 477 | 9 | 69.3 | 232.8 | CV117407 | C | T | 0.34 | 0.001 |
| 478 | 9 | 79.2 | 295.7 | CV117407 | G | A | 0.22 | 0.001 |
| 479 | 9 | 61.5 | 189.3 | CV592420 | C | G | 0.44 | 0.001 |
| 480 | 9 | 67.6 | 340.0 | CV592420 | C | G | 0.54 | 0.001 |
| 481 | 9 | 70.4 | 243.6 | CV592420 | A | G | 0.50 | 0.001 |
| 482 | 9 | 72.9 | 254.5 | CV592420 | C | T | 0.56 | 0.001 | cM = centimorgans, IcM = map units of the IBM2 2008 Neighbors Genetic Map.

In Table 4, "IcM" refers to the map units of the IBM2 2008 Neighbors Genetic Map, which was generated with an intermated recombinant inbred population (syn 4) that resulted in approximately a four-fold increase in the number of meiosies as compared to the typical recombination experiment that is used to generate cM distances (Lee et al., 2002, *Plant Mol Biol* 48:453 and the Maize Genetics and Genomics Database). "cM" refers to the classical definition of a centimorgan wherein one cM is equal to a 1% chance that a trait at one genetic locus will be separated from a trait at another locus due to crossing over in a single generation (meaning the traits co-segregate 99% of the time during meiosis), and this definition is used herein to delineate map locations pertaining to this invention.

TABLE 5

Exemplary primers and probes used for genotyping representative SNP markers associated with NLB disease resistance.

| SEQ ID NO. | SNP Position | Forward Primer | Reverse Primer | Probe 1 | Probe 2 |
|---|---|---|---|---|---|
| 1 | 101 | 90 | 179 | 268 | 357 |
| 2 | 101 | 91 | 180 | 269 | 358 |
| 3 | 101 | 92 | 181 | 270 | 359 |
| 4 | 77 | 93 | 182 | 271 | 360 |
| 5 | 101 | 94 | 183 | 272 | 361 |
| 6 | 136 | 95 | 184 | 273 | 362 |
| 7 | 104 | 96 | 185 | 274 | 363 |
| 8 | 112 | 97 | 186 | 275 | 364 |
| 9 | 902 | 98 | 187 | 276 | 365 |
| 10 | 101 | 99 | 188 | 277 | 366 |
| 11 | 205 | 100 | 189 | 278 | 367 |
| 12 | 245 | 101 | 190 | 279 | 368 |
| 13 | 43 | 102 | 191 | 280 | 369 |
| 14 | 144 | 103 | 192 | 281 | 370 |
| 15 | 101 | 104 | 193 | 282 | 371 |
| 16 | 247 | 105 | 194 | 283 | 372 |
| 17 | 341 | 106 | 195 | 284 | 373 |
| 18 | 91 | 107 | 196 | 285 | 374 |
| 19 | 216 | 108 | 197 | 286 | 375 |
| 20 | 81 | 109 | 198 | 287 | 376 |
| 21 | 194 | 110 | 199 | 288 | 377 |
| 22 | 46 | 111 | 200 | 289 | 378 |
| 23 | 859 | 112 | 201 | 290 | 379 |
| 24 | 200 | 113 | 202 | 291 | 380 |
| 25 | 73 | 114 | 203 | 292 | 381 |
| 26 | 352 | 115 | 204 | 293 | 382 |
| 27 | 162 | 116 | 205 | 294 | 383 |
| 28 | 106 | 117 | 206 | 295 | 384 |
| 29 | 319 | 118 | 207 | 296 | 385 |
| 30 | 127 | 119 | 208 | 297 | 386 |
| 31 | 101 | 120 | 209 | 298 | 387 |
| 33 | 319 | 122 | 211 | 300 | 389 |
| 35 | 101 | 124 | 213 | 302 | 391 |
| 36 | 373 | 125 | 214 | 303 | 392 |
| 37 | 115 | 126 | 215 | 304 | 393 |
| 38 | 171 | 127 | 216 | 305 | 394 |
| 39 | 37 | 128 | 217 | 306 | 395 |
| 40 | 101 | 129 | 218 | 307 | 396 |
| 41 | 101 | 130 | 219 | 308 | 397 |
| 42 | 101 | 131 | 220 | 309 | 398 |
| 43 | 101 | 132 | 221 | 310 | 399 |
| 44 | 2239 | 133 | 222 | 311 | 400 |
| 45 | 569 | 134 | 223 | 312 | 401 |
| 46 | 101 | 135 | 224 | 313 | 402 |
| 47 | 240 | 136 | 225 | 314 | 403 |
| 48 | 247 | 137 | 226 | 315 | 404 |
| 49 | 719 | 138 | 227 | 316 | 405 |
| 50 | 429 | 139 | 228 | 317 | 406 |
| 51 | 101 | 140 | 229 | 318 | 407 |
| 52 | 81 | 141 | 230 | 319 | 408 |
| 53 | 62 | 142 | 231 | 320 | 409 |
| 54 | 167 | 143 | 232 | 321 | 410 |
| 55 | 99 | 144 | 233 | 322 | 411 |
| 56 | 390 | 145 | 234 | 323 | 412 |
| 57 | 279 | 146 | 235 | 324 | 413 |
| 58 | 101 | 147 | 236 | 325 | 414 |
| 59 | 61 | 148 | 237 | 326 | 415 |
| 60 | 339 | 149 | 238 | 327 | 416 |
| 61 | 125 | 150 | 239 | 328 | 417 |
| 62 | 101 | 151 | 240 | 329 | 418 |
| 63 | 369 | 152 | 241 | 330 | 419 |
| 64 | 101 | 153 | 242 | 331 | 420 |
| 65 | 101 | 154 | 243 | 332 | 421 |
| 66 | 101 | 155 | 244 | 333 | 422 |
| 67 | 101 | 156 | 245 | 334 | 423 |
| 68 | 101 | 157 | 246 | 335 | 424 |
| 69 | 101 | 158 | 247 | 336 | 425 |
| 70 | | | | | |
| 71 | 101 | 160 | 249 | 338 | 427 |
| 72 | 279 | 161 | 250 | 339 | 428 |
| 73 | 265 | 162 | 251 | 340 | 429 |
| 74 | 101 | 163 | 252 | 341 | 430 |
| 75 | 101 | 164 | 253 | 342 | 431 |
| 76 | 209 | 165 | 254 | 343 | 432 |
| 77 | 256 | 166 | 255 | 344 | 433 |
| 78 | 101 | 167 | 256 | 345 | 434 |
| 79 | 101 | 168 | 257 | 346 | 435 |
| 80 | 91 | 169 | 258 | 347 | 436 |
| 81 | 47 | 170 | 259 | 348 | 437 |
| 82 | 321 | 171 | 260 | 349 | 438 |
| 83 | 101 | 172 | 261 | 350 | 439 |
| 84 | 474 | 173 | 262 | 351 | 440 |
| 85 | 101 | 174 | 263 | 352 | 441 |
| 86 | 101 | 175 | 264 | 353 | 442 |
| 87 | 101 | 176 | 265 | 354 | 443 |
| 88 | 49 | 177 | 266 | 355 | 444 |
| 89 | 223 | 178 | 267 | 356 | 445 |
| 446 | 101 | 483 | 520 | 557 | 594 |
| 447 | 101 | 484 | 521 | 558 | 595 |
| 448 | 216 | 485 | 522 | 559 | 596 |
| 449 | 184 | 486 | 523 | 560 | 597 |
| 450 | 101 | 487 | 524 | 561 | 598 |
| 451 | 101 | 488 | 525 | 562 | 599 |
| 452 | 265 | 489 | 526 | 563 | 600 |
| 453 | 101 | 490 | 527 | 564 | 601 |
| 454 | 105 | 491 | 528 | 565 | 602 |
| 455 | 254 | 492 | 529 | 566 | 603 |
| 456 | 322 | 493 | 530 | 567 | 604 |
| 457 | 345 | 494 | 531 | 568 | 605 |
| 458 | 58 | 495 | 532 | 569 | 606 |
| 459 | 342 | 496 | 533 | 570 | 607 |
| 460 | 542 | 497 | 534 | 571 | 608 |
| 461 | 101 | 498 | 535 | 572 | 609 |
| 462 | 73 | 499 | 536 | 573 | 610 |
| 463 | 129 | 500 | 537 | 574 | 611 |
| 464 | 101 | 501 | 538 | 575 | 612 |
| 465 | 101 | 502 | 539 | 576 | 613 |
| 466 | 234 | 503 | 540 | 577 | 614 |
| 467 | 101 | 504 | 541 | 578 | 615 |
| 468 | 486 | 505 | 542 | 579 | 616 |
| 469 | 191 | 506 | 543 | 580 | 617 |
| 470 | 426 | 507 | 544 | 581 | 618 |
| 471 | 173 | 508 | 545 | 582 | 619 |
| 472 | 101 | 509 | 546 | 583 | 620 |
| 473 | 101 | 510 | 547 | 584 | 621 |
| 474 | 101 | 511 | 548 | 585 | 622 |
| 475 | 101 | 512 | 549 | 586 | 623 |
| 476 | 101 | 513 | 550 | 587 | 624 |
| 477 | 101 | 514 | 551 | 588 | 625 |
| 478 | 412 | 515 | 552 | 589 | 626 |
| 479 | 444 | 516 | 553 | 590 | 627 |
| 480 | 101 | 517 | 554 | 591 | 628 |
| 481 | 101 | 518 | 555 | 592 | 629 |
| 482 | 101 | 519 | 556 | 593 | 630 |

One of skill in the art recognizes that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, this disclosure is not limited to the primers, probes, or marker sequences specifically listed in the tables.

In summary, the QTLs are designated as NLB_2.01, NLB_3.01, NLB_4.01, NLB_4.02, NLB_5.01, NLB_6.01, NLB_7.01, and NLB_9.01 (Table 6).

TABLE 6

Summary of NLB QTLs.

| Chromosome | Interval of QTL Peak | | QTL Designation |
|---|---|---|---|
| | MON Map (cM) | IBM2008 Map (IcM) | |
| 2 | 114-117 | 375-380 | NLB_2.01 |
| 3 | 109-114 | 370-396 | NLB_3.01 |
| 4 | 166-169 | 580-588 | NLB_4.01 |
| 4 | 172-177 | 594-617 | NLB_4.02 |
| 5 | 89-98 | 321-335 | NLB_5.01 |
| 6 | 73-75 | 336-344 | NLB_6.01 |
| 7 | 109 | 405 | NLB_7.01 |
| 9 | 63-73 | 196-255 | NLB_9.01 | cM = centimorgans; IcM = map units of the IBM2 2008 Neighbors Genetic Map.

Example 4. Validation of NLB QTLs

Plants with or without resistant NLB QTL are derived. Plants carrying the resistant allele of NLB-2.01, NLB-3.01 or NLB-4.02 show significant reductions in NLB rating score when compared to plants carrying the susceptible allele (Table 7).

TABLE 7

Validation of NLB QTLs.

| QTL interval | Resistance QTL Profile | NLB Infection Score | p-value |
|---|---|---|---|
| NLB_2.01 | Absent | 5.88 | 2.74E−58 |
| | Present | 2.47 | |
| NLB_3.01 | Absent | 5.3 | 1.70E−37 |
| | Present | 3.5 | |
| NLB_4.02 | Absent | 5.34 | 7.23E−27 |
| | Present | 2.92 | |
| NLB_6.01 | Absent | 3.78 | 0.15 |
| | Present | 4.26 | |

Example 5: Introgression of NLB Resistance QTLs into Additional Maize Lines

A maize plant comprising one or more, two or more, or three or more NLB resistance QTLs is crossed with an elite maize line comprising a desirable trait (e.g., improved yield under water, temperature, or pest stress conditions), but susceptible to NLB. $F_1$ progeny plants from this cross are assayed for one or more SNP markers exemplified in Tables 4 and 5 or molecular markers linked to those SNP markers to select for NLB resistance QTLs. A selected $F_1$ progeny plant is then backcrossed with the parent elite maize line comprising the desirable trait (recurrent parent). Plants from the BC1 generation are also genotyped using SNP markers exemplified in Table 5, or a linked marker, to select for NLB resistance QTLs. After multiple rounds of backcrossing (e.g., 5-7 generations) with the recurrent parent line, a new elite maize line is obtained comprising both NLB resistance and the desirable trait in the recurrent parent line. Using the above introgression and marker-assisted selection strategy, the pyramiding or stacking of multiple NLB resistance QTLs can be achieved.

As various modifications could be made in the constructions and methods herein described and illustrated without departing from the scope of this disclosure, it is intended that the foregoing description shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method of creating a population of Northern Leaf Blight (NLB) resistant corn plants, corn seeds, or corn cells, said method comprising:
   a) crossing a first NLB resistant corn plant comprising NLB resistance quantitative trait locus (QTL) NLB_4.01 with a second corn plant to generate a first population of corn plants, corn seeds, or corn cells;

b) genotyping said first population of corn plants, corn seeds, or corn cells at one or more marker loci linked to, and within 10 centimorgans (cM) of, said NLB resistance QTL NLB_4.01; and c) selecting from said first population one or more corn plants, corn seeds, or corn cells having resistance to NLB comprising said one or more of said marker loci linked to said NLB resistance QTL NLB_4.01 linked to an NLB resistance allele selected from the group consisting of:

SEQ ID NO: 33 comprising a G, at position number 319;
SEQ ID NO: 35 comprising a G, at position number 101;
SEQ ID NO: 36 comprising an A, at position number 373;
SEQ ID NO: 37 comprising an A, at position number 115;
SEQ ID NO: 38 comprising a G, at position number 171;
SEQ ID NO: 39 comprising a T, at position number 37;
SEQ ID NO: 40 comprising a C, at position number 101;
SEQ ID NO: 41 comprising a G, at position number 101;
SEQ ID NO: 42 comprising a T, at position number 101;
SEQ ID NO: 43 comprising a T, at position number 101;
SEQ ID NO: 44 comprising a G or a T, at position number 2239;
SEQ ID NO: 45 comprising an A, at position number 569;
SEQ ID NO: 46 comprising a T, at position number 101;
SEQ ID NO: 47 comprising a C, at position number 240;
SEQ ID NO: 48 comprising a C, at position number 247;
SEQ ID NO: 49 comprising an A, at position number 719;
SEQ ID NO: 50 comprising an A, at position number 429;
SEQ ID NO: 51 comprising an A, at position number 101;
SEQ ID NO: 52 comprising a C, at position number 81;
SEQ ID NO: 471 comprising a G, at position number 173;
SEQ ID NO: 472 comprising a T, at position number 101;
SEQ ID NO: 473 comprising a G, at position number 101;
SEQ ID NO: 474 comprising a G, at position number 101; and
SEQ ID NO: 475 comprising an A, at position number 101.

2. The method of claim 1, wherein said one or more marker loci are located in a chromosomal interval flanked by any two of SEQ ID NOs: 32 to 52 and 471 to 475, and said NLB resistance allele is at said QTL NLB_4.01.

3. The method of claim 1, wherein said one or more marker loci are located in a chromosomal interval flanked by any two of SEQ ID NOs: 37 to 42 and 474, and said NLB resistance allele is at said QTL NLB_4.01.

4. The method of claim 1, wherein said one or more marker loci are located in a chromosomal interval flanked by any two of SEQ ID NOs: 33 to 42, 473, and 474, and said NLB resistance allele is at said QTL NLB_4.01.

5. The method of claim 1, wherein said one or more marker loci are linked to, and within 5 cM of, any one of the marker loci selected from the group consisting of SEQ ID NOs: 32 to 52 and 471 to 475.

6. The method of claim 1, wherein said NLB resistance QTL NLB_4.01 provides mild resistance or resistance to infection by *Exserohilum turcicum*.

7. The method of claim 1, wherein a second population of corn plants comprising said one or more of said marker loci exhibit reduced root rot, reduced stalk rot, fewer leaf lesions, less foliage destruction, or any combination thereof, compared to corn plants lacking said NLB resistance QTL NLB_4.01 when grown under a high NLB stress condition.

8. The method of claim 1, wherein said NLB resistance QTL NLB_4.01 does not confer a yield penalty when grown under a low NLB stress condition.

9. The method of claim 1, wherein said method further comprises:
producing from said one or more corn plants, corn seeds, or corn cells selected in step c) a second population of corn plants, corn seeds, or corn cells comprising said NLB resistance QTL NLB_4.01.

10. The method of claim 9, wherein said second population of corn plants or seeds exhibits a reduction of NLB rating score of 1 or more as compared to corn plants or seeds lacking said NLB resistance QTL NLB_4.01 when grown under a high NLB stress condition.

11. The method of claim 9, wherein said second population of corn plants or seeds exhibits a reduction of NLB rating score of 2 or more as compared to corn plants or seeds lacking said NLB resistance QTL NLB_4.01 when grown under a high NLB stress condition.

12. The method of claim 1, wherein said one or more marker loci is selected from the group consisting of:
SEQ ID NO: 33 comprising a G, at position number 319;
SEQ ID NO: 35 comprising a G, at position number 101;
SEQ ID NO: 36 comprising an A, at position number 373;
SEQ ID NO: 37 comprising an A, at position number 115;
SEQ ID NO: 38 comprising a G, at position number 171;
SEQ ID NO: 39 comprising a T, at position number 37;
SEQ ID NO: 40 comprising a C, at position number 101;
SEQ ID NO: 41 comprising a G, at position number 101;
SEQ ID NO: 42 comprising a T, at position number 101;
SEQ ID NO: 43 comprising a T, at position number 101;
SEQ ID NO: 44 comprising a G or a T, at position number 2239;
SEQ ID NO: 45 comprising an A, at position number 569;
SEQ ID NO: 46 comprising a T, at position number 101;
SEQ ID NO: 47 comprising a C, at position number 240;
SEQ ID NO: 48 comprising a C, at position number 247;
SEQ ID NO: 49 comprising an A, at position number 719;
SEQ ID NO: 50 comprising an A, at position number 429;
SEQ ID NO: 51 comprising an A, at position number 101;
SEQ ID NO: 52 comprising a C, at position number 81;
SEQ ID NO: 471 comprising a G, at position number 173;
SEQ ID NO: 472 comprising a T, at position number 101;
SEQ ID NO: 473 comprising a G, at position number 101;
SEQ ID NO: 474 comprising a G, at position number 101; and
SEQ ID NO: 475 comprising an A, at position number 101.

13. A method of creating a population of Northern Leaf Blight (NLB) resistant corn plants, corn seeds, or corn cells, said method comprising:
a) crossing a first NLB resistant corn plant comprising an NLB resistance quantitative trait loci (QTL) with a second corn plant to generate a first population of corn plants, corn seeds, or corn cells;
b) genotyping said first population of corn plants, corn seeds, or corn cells at one or more marker loci linked to, and within 10 centimorgans (cM) of, any one of the marker loci selected from the group consisting of SEQ ID NOs: 32 to 52 and 471 to 475, wherein said marker is associated with said NLB resistance QTL NLB_4.01; and
c) selecting from said first population one or more corn plants, corn seeds, or corn cells having resistance to NLB comprising said one or more of said marker loci linked to said NLB resistance QTL NLB_4.01 linked to an NLB resistance allele selected from the group consisting of:
SEQ ID NO: 33 comprising a G, at position number 319;
SEQ ID NO: 35 comprising a G, at position number 101;
SEQ ID NO: 36 comprising an A, at position number 373;
SEQ ID NO: 37 comprising an A, at position number 115;
SEQ ID NO: 38 comprising a G, at position number 171;
SEQ ID NO: 39 comprising a T, at position number 37;
SEQ ID NO: 40 comprising a C, at position number 101;
SEQ ID NO: 41 comprising a G, at position number 101;
SEQ ID NO: 42 comprising a T, at position number 101;
SEQ ID NO: 43 comprising a T, at position number 101;
SEQ ID NO: 44 comprising a G or a T, at position number 2239;
SEQ ID NO: 45 comprising an A, at position number 569;
SEQ ID NO: 46 comprising a T, at position number 101;
SEQ ID NO: 47 comprising a C, at position number 240;
SEQ ID NO: 48 comprising a C, at position number 247;
SEQ ID NO: 49 comprising an A, at position number 719;
SEQ ID NO: 50 comprising an A, at position number 429;
SEQ ID NO: 51 comprising an A, at position number 101;
SEQ ID NO: 52 comprising a C, at position number 81;
SEQ ID NO: 471 comprising a G, at position number 173;
SEQ ID NO: 472 comprising a T, at position number 101;
SEQ ID NO: 473 comprising a G, at position number 101;
SEQ ID NO: 474 comprising a G, at position number 101; and
SEQ ID NO: 475 comprising an A, at position number 101.

14. The method of claim 1, wherein said first or second corn plant comprises an NLB resistance QTL selected from NLB_2.01, NLB_3.01, NLB_4.02, NLB_5.01, NLB_6.01, NLB_7.01, or NLB_9.01, wherein said NLB resistance QTL is linked to a second NLB resistance allele from the group consisting of:
SEQ ID NO: 1 comprising an A, at position number 101;
SEQ ID NO: 2 comprising a G, at position number 101;
SEQ ID NO: 3 comprising an A, at position number 101;
SEQ ID NO: 4 comprising an A, at position number 77;
SEQ ID NO: 5 comprising a T, at position number 101;
SEQ ID NO: 6 comprising a G, at position number 136;
SEQ ID NO: 7 comprising a T, at position number 104;
SEQ ID NO: 8 comprising an A, at position number 112;
SEQ ID NO: 9 comprising a T, at position number 902;
SEQ ID NO: 10 comprising a G, at position number 101;
SEQ ID NO: 11 comprising an A, at position number 205;

SEQ ID NO: 12 comprising an A, at position number 245;
SEQ ID NO: 13 comprising a G, at position number 43;
SEQ ID NO: 14 comprising a G, at position number 144;
SEQ ID NO: 15 comprising a C, at position number 101;
SEQ ID NO: 16 comprising a T, at position number 247;
SEQ ID NO: 17 comprising an A, at position number 341;
SEQ ID NO: 18 comprising a C, at position number 91;
SEQ ID NO: 19 comprising a T, at position number 216;
SEQ ID NO: 20 comprising a G, at position number 81;
SEQ ID NO: 21 comprising a G, at position number 194;
SEQ ID NO: 22 comprising an A, at position number 46;
SEQ ID NO: 23 comprising a G, at position number 859;
SEQ ID NO: 24 comprising a T, at position number 200;
SEQ ID NO: 25 comprising a C, at position number 73;
SEQ ID NO: 26 comprising a T, at position number 352;
SEQ ID NO: 27 comprising a T, at position number 162;
SEQ ID NO: 28 comprising a T, at position number 106;
SEQ ID NO: 29 comprising a C, at position number 319;
SEQ ID NO: 30 comprising a G, at position number 127;
SEQ ID NO: 31 comprising a T, at position number 101;
SEQ ID NO: 53 comprising a C or an A, at position number 62;
SEQ ID NO: 54 comprising a T, at position number 167;
SEQ ID NO: 55 comprising a C, at position number 99;
SEQ ID NO: 56 comprising a C, at position number 390;
SEQ ID NO: 57 comprising a C or an A, at position number 279;
SEQ ID NO: 58 comprising an A, at position number 101;
SEQ ID NO: 59 comprising a T or a C, at position number 61;
SEQ ID NO: 60 comprising an A, at position number 339;
SEQ ID NO: 61 comprising an A, at position number 125;
SEQ ID NO: 62 comprising a T, at position number 101;
SEQ ID NO: 63 comprising a T, at position number 369;
SEQ ID NO: 64 comprising a C or a T, at position number 101;
SEQ ID NO: 65 comprising a G, at position number 101;
SEQ ID NO: 66 comprising a G, at position number 101;
SEQ ID NO: 67 comprising a C, at position number 101;
SEQ ID NO: 68 comprising a T, at position number 101;
SEQ ID NO: 69 comprising a G, at position number 101;
SEQ ID NO: 70 comprising a T, at position number 101;
SEQ ID NO: 71 comprising a T, at position number 101;
SEQ ID NO: 72 comprising a G, at position number 279;
SEQ ID NO: 73 comprising a G, at position number 265;
SEQ ID NO: 74 comprising a T, at position number 101;
SEQ ID NO: 75 comprising a C, at position number 101;
SEQ ID NO: 76 comprising a C, at position number 209;
SEQ ID NO: 77 comprising a G, at position number 256;
SEQ ID NO: 78 comprising a T, at position number 101;
SEQ ID NO: 79 comprising an A, at position number 101;
SEQ ID NO: 80 comprising an A, at position number 91;
SEQ ID NO: 81 comprising an A, at position number 47;
SEQ ID NO: 82 comprising a T, at position number 321;
SEQ ID NO: 83 comprising a C, at position number 101;
SEQ ID NO: 84 comprising a G, at position number 474;
SEQ ID NO: 85 comprising a T, at position number 101;
SEQ ID NO: 86 comprising a C, at position number 101;
SEQ ID NO: 87 comprising a C, at position number 101;
SEQ ID NO: 88 comprising a G, at position number 49;
SEQ ID NO: 89 comprising an A, at position number 223;
SEQ ID NO: 446 comprising a T, at position number 101;
SEQ ID NO: 447 comprising a T, at position number 101;
SEQ ID NO: 448 comprising a C, at position number 216;
SEQ ID NO: 449 comprising a T, at position number 184;
SEQ ID NO: 450 comprising a C, at position number 101;
SEQ ID NO: 451 comprising a G, at position number 101;
SEQ ID NO: 452 comprising a G, at position number 265;
SEQ ID NO: 453 comprising an A, at position number 101;
SEQ ID NO: 454 comprising a T, at position number 105;
SEQ ID NO: 455 comprising a T, at position number 254;
SEQ ID NO: 456 comprising a C, at position number 322;
SEQ ID NO: 457 comprising a G, at position number 345;
SEQ ID NO: 458 comprising a G, at position number 58;
SEQ ID NO: 459 comprising a T, at position number 342;
SEQ ID NO: 460 comprising a G, at position number 542;
SEQ ID NO: 461 comprising a G, at position number 101;
SEQ ID NO: 462 comprising an A, at position number 73;
SEQ ID NO: 463 comprising a G, at position number 129;
SEQ ID NO: 464 comprising a T, at position number 101;
SEQ ID NO: 465 comprising a G, at position number 101;
SEQ ID NO: 466 comprising a C, at position number 234;
SEQ ID NO: 467 comprising an A, at position number 101;
SEQ ID NO: 468 comprising a C, at position number 486;
SEQ ID NO: 469 comprising a T, at position number 191;
SEQ ID NO: 470 comprising a G, at position number 426;
SEQ ID NO: 476 comprising a G, at position number 101;
SEQ ID NO: 477 comprising a C, at position number 101;
SEQ ID NO: 478 comprising a G, at position number 412;
SEQ ID NO: 479 comprising a C, at position number 444;
SEQ ID NO: 480 comprising a C, at position number 101;
SEQ ID NO: 481 comprising an A, at position number 101; and
SEQ ID NO: 482 comprising a C, at position number 101.

15. The method of claim 1, wherein said selecting of step c) further comprises selecting an NLB resistance QTL from the group consisting of NLB_2.01, NLB_3.01, NLB_4.02, NLB_5.01, NLB_6.01, NLB_7.01, or NLB_9.01.

16. The method of claim 15, wherein said NLB resistance QTL is NLB_2.01.

17. The method of claim 15, wherein said NLB resistance QTL is NLB_3.01.

18. The method of claim 15, wherein said NLB resistance QTL is NLB_4.02.

19. The method of claim 15, wherein said NLB resistance QTL is NLB_5.01.

20. The method of claim 15, wherein said NLB resistance QTL is NLB_6.01.

21. The method of claim 15, wherein said NLB resistance QTL is NLB_7.01.

22. The method of claim 15, wherein said NLB resistance QTL is NLB_9.01.

23. The method of claim 13, wherein said first population further comprises a second NLB resistance allele at an NLB resistance QTL selected from NLB_2.01, NLB_3.01, NLB_4.02, NLB_5.01, NLB_6.01, NLB_7.01, or NLB_9.01.

* * * * *

SEQUENCE LISTING

```
<160> NUMBER OF SEQ ID NOS: 630

<210> SEQ ID NO 1
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 1
agccttatgt ctgatggcct ccgctaaacc gtcagacata agggacatgg gccctgccaa      60
cagttgttaa gaccgttatc gaggataaac gtcgacaacc naaaggttcc atcggacata     120
gcttatttcc gatggccgcc gttggaaata aggttatttt tgaccctta cggccgaggg     180 acaagtaccg tcggacataa g                                               201

<210> SEQ ID NO 2
<211> LENGTH: 201
<212> TYPE: DNA
<213> ORGANISM: Zea mays
<220> FEATURE:
```

```
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 2
atacatgggc atcaacgagt ccnaaaaaaa caagagcgga aaaaaaacaa gagcggaaac      60
tggaaatgag tccgtgtgtt atttatgacg cccgcaaggc ngcaacgcca gtttggtgga     120
agccccagta ccgtctgact ttgctggact gtacgtaatg cacgtaccat cctcctaatc    180
ccatcctaac ccccgcaatt a                                                201

<210> SEQ ID NO 3
<211> LENGTH: 201
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 3
tgctattcan accattaaat ttcgaggcna aattcagggt cgaaaagttt tggttcttgt      60
ggattccgat agttntcatt catttctcag tttgcgggtg ncgtctaaat tagagggtgt    120
gtcagagatg ccatggccag tgatggtgca agtagctgat ggtggtagat tgttatgtga    180
caaacagttt ttgggggcca c                                                201

<210> SEQ ID NO 4
<211> LENGTH: 1186
<212> TYPE: DNA
<213> ORGANISM: Zea mays
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1172)..(1176)
<223> OTHER INFORMATION: n is a, c, g, or t

<400> SEQUENCE: 4
tggcgtgatt ctaggtaaaa gtttatgttt acataataat cagagatgta tttcgagtaa      60
ctgaattatt gtatatncct tcgtccttttt cctttcttgg aaactagctt tgtaaactat   120
tgctttacta tactaagttg ggaaacctac ttctgttagt agtctccttt tgcaagtgtt    180
tttctggtta atctttcata acgagactgg agtgaatagg ttaaatggat tatgatccct    240
atcgcatgca gccttttttg tatgcacaac agcattttt tgttgctgca agccttctac      300
```

```
ctttgagaat atatttgctc ttacgtagtt atgtattttg acaacatagt tttggtcatt        360
gtttagtact cctataagct cccgcgtatc ctatcaggtg catttccttt tagcttataa        420
aattttccct taatccttta tatatgctga ttttacatgt tccatcccat tgggaattaa        480
aactgtaata cctaaaatat atgttagttt acttctcact gtttcatgag gatgtctttt        540
caagttttca gcaaatttgg tgatatcttt gacgaagatc acttcattga gtcacttaga        600
aaatatgtaa gggttgtaaa agatcttcct gaagatgttt ttctgcgatt caaccataat        660
atcagcataa taccaaacat gagaaccaaa gctttctcac ccccaagtta ctacttacaa        720
catgtgcttc caaagctgtt ggagctaggg tacgtgctcc ctcttttttc tccttgacat        780
gaagtagagt ctgatatttg cactgagcat cacatagcac catgtcttca cttatttctt        840
gttctatgac acagggctgt gcgtattgcc cctttctcaa atagactggc tcattcagtt        900
cctatgaata tccaggcatt gagatgtttg acaaactata aggcattaag attttctgaa        960
ccaataagaa ttcttgcaga taatatggtt gaccgaatga tcaagaggag ttttttaagt       1020
ggcgggaagt acgtctcggt tcatcttcgc tttgaagagg ttttactaaa gtttatcttg       1080
tgtggactaa tattactact tttctcaagt tgtgatgagt tatatgtcta ggacatggta       1140 gcttttcat gctgtaatta tganngtggc tnnnnngaga ataatg                      1186

<210> SEQ ID NO 5
<211> LENGTH: 201
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 5
tttggccatg tcagggaaaa aaaggtagga tgaattgaat gcattnttgc cagtttcacg         60
caacactaga taagcaactg caatgagaga ttataagaag naacaagctc acttttgtat        120
ccgtcttcag cctttttgct ggttcattgt cgcagcagtt ctcgggactg ccatctgaat        180
ctggcttggt tattgaaatc g                                                 201

<210> SEQ ID NO 6
<211> LENGTH: 355
<212> TYPE: DNA
<213> ORGANISM: Zea mays
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t

<400> SEQUENCE: 6
tgatggcggg ggatcagggt ctgggtccgg nnccggatcc ggtgatagta gtccttatgg         60
tacccatgca agtgctggag ggggtggtgc aggtggtgga gctagccaat acggtgggtc        120
tggatatggt tcaggntcag ggtctggttc agggtctagt acatatagtc aaggagggta        180
ttattcgggt tatggagaat cttctaatgc tggtggttct ggtggaggtg ggggtggagg        240
```

```
acaagctgga ggttatggga attccaatgc tcaaggatct ggtagtggca ccggttctgg    300
ctctagctat gctaacaggt attgggatgg atcaagtgga ggtgcaaatg ctaat         355

<210> SEQ ID NO 7
<211> LENGTH: 355
<212> TYPE: DNA
<213> ORGANISM: Zea mays
<220> FEATURE:
<221> NAME/KEY: misc_feature
<222> LOCATION: (104)..(104)
<223> OTHER INFORMATION: n is a, c, g, or t

<400> SEQUENCE: 7
aagagaacgt gactcctgcc tctaaggtga agaccgttgt taggggagtt cttggtacaa    60
ggatggataa ttcagtgtca gcagcaaatg cttcaaataa gaanaaagtt cttgggtcaa   120
gggtagataa ttcagtgtca acagagaata gctcaaataa gaagcaatgt gaattatcat   180
cgaagtccaa aaaagtccac acagtagatt ttgatgtttt ctattcggat aaggagaact   240
tgactcctat atcttcagga ggcatgaaag caaggaagtt ttttcccaag gacctctcag   300
tcgacttaga ccaagatctg gaagcattct gctcagacaa ggagaacttg acacc        355

<210> SEQ ID NO 8
<211> LENGTH: 273
<212> TYPE: DNA
<213> ORGANISM: Zea mays
<220> FEATURE:
<221> NAME/KEY: misc_feature
<222> LOCATION: (112)..(112)
<223> OTHER INFORMATION: n is a, c, g, or t

<400> SEQUENCE: 8
aaaaggaacc attgcatgca ggagaaaaga aatgatgaga taaagggaaa aaaaggagg    60 gagagagaga gaggaaccaa tgcaagaagg tgatccgatc aacaggcaga gncatggcca   120
ttggtcgatc tagccacggt ctctactcgc tgccgggggg cttgtaggcg atgaagctga   180
cgcactgcgt ctgcctgacg ttgtcgaagc cgatgacgcg gtggaaggcg tccgggtacg   240
cggcgatggc ctcctgcagc tccttgtacc acc                                273

<210> SEQ ID NO 9
<211> LENGTH: 1024
<212> TYPE: DNA
<213> ORGANISM: Zea mays
<220> FEATURE:
<221> NAME/KEY: misc_feature
<222> LOCATION: (902)..(902)
<223> OTHER INFORMATION: n is a, c, g, or t

<400> SEQUENCE: 9
ctctaggtct gttttctttt ggcttcttgt acgcagttct atcacctaag ttttatttc    60 ctatgttact ggacatattt tctttatttt atgtcttatt actaatcttt acctttggtt   120
ctccagccta gcagttattt ttggtgctgg acttgtaact agtttatctc cttgtacact   180
aagtgttcta ccactaactc taggatatat aggtaactat attgttttgt ttgagatgat   240
tgttggcaaa atgcccaga attgatcatc attaattact ctgattcagt gctttcttca   300
taaacattta ggtgcatttg gctcagggaa aggccgatcc gaggtaattt aagatgagtg   360
aaaaattgta cttctttatg ccatggaaaa acttgaagat attgctattt atctgttagg   420
atatgtatta ccacaaagtt atcttcactg aaggatttac ttgactaatt aaggctatga   480
ataatgttga aacctgatta ttctagctgg gggcttccct tgatacatgc attgacttgg   540
```

-continued

```
cttttctatc aattataggt tgttgggaat tcaattgcat tttcactagg actagcaaca    600
accttagcca ttcttggtgt tgctgcttct tttgctggaa aggcttatgg tcaggtagga    660
caagggctcc cagtggctgc ttccggtttg gccattatca tgggattgaa ccttctggag    720
gtaaatcaca tgaaacagaa actacatata tagactgaag catgccaatc agaatttcct    780
cctaccttgt ttccttaagt tacaagatga ttcaatccct gtatttcttg gtttctcatt    840
ataaatacta ctgtagaagt acaaaccaat tttgtgatag tttgttactt tgttcttatg    900
antttcgtat tcctgcttgc tcctgtaaag tacatgtaac tacgttatca aatgttctgc    960
cctaagctgt ttattatctg tccttaacag gtacttgaat tgcaacttcc ctcattttca   1020
gcga                                                                1024
```

```
<210> SEQ ID NO 10
<211> LENGTH: 201
<212> TYPE: DNA
<213> ORGANISM: Zea mays
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 10
gtaaaggcct catagtgtta ccntgcctcg cttccttggt agaggtgtat gggggtcgta     60
caaccgcatg gcagaaacaa atacatagaa gattactaaa nagatactgg aaggcttatc    120
tgaagatact ggtgacagcg atagctatga tgtggaaagc ggggacgaag attttgagga    180
tcggccctgg aggccaagtc a                                              201
```

```
<210> SEQ ID NO 11
<211> LENGTH: 460
<212> TYPE: DNA
<213> ORGANISM: Zea mays
<220> FEATURE:
<221> NAME/KEY: misc_feature
<222> LOCATION: (205)..(205)
<223> OTHER INFORMATION: n is a, c, g, or t

<400> SEQUENCE: 11
aacagcagca tatgccatat cagccatcca accgctctcg gttcagcctt tcatttcatt     60
tctagggtta atcccgaacc cgccagtttc agcagggctc gctcagtcga aggatacata    120
agaccacagt gaaaattaga gggccttaca aaagcagcag cagcagcaat gcagcacgca    180
gatcaaattt acacatcaaa acgcnggcca aaacccgaga agaaaccgaa accccgccgc    240
cgccaagcac acacatgcac ccacacacac acaccaccgc ccacggccgc aatatacaca    300
acggaaccta ccccggcaac tccaaccgaa acacagcacc catcaccgca ctcggcaagc    360
cgtggccggg acggcagggg agcacttggg gttcgggatg gccctgaagt ggacgctgtt    420
cccggttatc ctgcggcgac ccctatagtc aggaaggcca                          460
```

```
<210> SEQ ID NO 12
<211> LENGTH: 381
<212> TYPE: DNA
<213> ORGANISM: Zea mays
<220> FEATURE:
<221> NAME/KEY: misc_feature
<222> LOCATION: (245)..(245)
```

<223> OTHER INFORMATION: n is a, c, g, or t

<400> SEQUENCE: 12

```
agctgacaca gatatcgagg accaggagaa caatgcaatt ggtgatgatt acaatgatga      60
ccttatggat gaagaagatg acgactttct tgagaaccat gttatagaag taagatggag     120
ggagagctta actcgaatgg attatgatca tcatctgaga ttttccaggg gtcgtgcaga     180
ctccagtggt tttattgata tatcttctga gtcatttcat ggtgtgggga cagttgattc     240
atttnatctg catcgttcgt ttggtcttga acggcggcgc caaatcggaa gtaggtcgct     300
tcttgatcga ccaaggaccg atgggaatgc ctttcttcat ccactgcttg tcaggccagc     360
acagtctagg gagggaacta a                                               381
```

<210> SEQ ID NO 13
<211> LENGTH: 484
<212> TYPE: DNA
<213> ORGANISM: Zea mays
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t

<400> SEQUENCE: 13

```
ttgcctcttg tacaaatctt gtgactcgtc ctgcatcgaa ggncaacaca atttgagatc      60
tggactcaag gtgtgcctgg aaacgcttta cagaaacatt gagtgaaatg catgcataca     120
aggcctgaga actgactgcn aagngggaa aaacactnta cagaaacatt gagtgaaaac      180
aatattaatc gctctcttag ccacaacagg ctaaagctaa gctaagctaa gccaatggca     240
ctcagagatt cggtacggca ttttcttctc tggcttttn aaaanggact acttgcaagt      300
aaatgacaat gtgtataacct tctctataga accaaataat gctcccacaa gtcacggaca    360
aagaggtgat ataatcgagc atgacaatgt atcttaacca ttcggtatca tagtactata    420
gcatccttcg agacaaattt acccatgaac cttggtatgc ccaatttaca tgcacaaaga    480
gaca                                                                  484
```

<210> SEQ ID NO 14
<211> LENGTH: 648
<212> TYPE: DNA
<213> ORGANISM: Zea mays
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature -continued
<222> LOCATION: (203)..(203)
<223> OTHER INFORMATION: n is a, c, g, or t

<400> SEQUENCE: 14

```
gatgggcatt taccgagtgg aacataaccc attgtgacat aaaaaaagaa aaggttagac      60
tctttgctcc cagtaagaaa acatcagtag ctccaattac aacactttta gcagggtatg     120
ttacgcagtg agggattggg aggnttctaa tgtcaactag tgtggaacag tagcgcatat     180
gaactttcca actgaatcct ttnaaatcct agttgctata acacatttag caaacttatg     240
tgaatcctat gagaccctca catcctgtat tattctttct gcattagcct ctccacatac     300
ccactagcta tcactacttc ctgaacacag aactatctgg ctccactact attggacata     360
catcagttac tacctagaat agctagctac actactatat tttcaacaag agtcttatat     420
tcatcctagt atctatctct ctaattactc accccatcac tgttacattt aatcacaatc     480
ttatccttcc cacctcatat caatatgctt tttcacatac ttacctattt ctattacata     540
tcaatcgtac tattcttact tcagtctatc acacctcttt accaatcatg tataacttaa     600
tatacctatc tactacttat ttactatatc tatttcttca tacttatt                   648
```

<210> SEQ ID NO 15
<211> LENGTH: 201
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t

<400> SEQUENCE: 15

```
tccgtgtcca tttcttacag tcttccaact ctccttctca actngtatat acaagcactc      60
actagattgc tattnaagnt gaacaccttc tcaacgagtg nactgtgtac tatgtgatac     120
tagtcctact catacttaac acttgttatg gncttttaat ttttntttnat taattgctag     180
actagttata ggctaagcca a                                                201
```

<210> SEQ ID NO 16
<211> LENGTH: 677
<212> TYPE: DNA
<213> ORGANISM: Zea mays
<220> FEATURE:
<221> NAME/KEY: misc_feature
<222> LOCATION: (247)..(247)

<223> OTHER INFORMATION: n is a, c, g, or t

<400> SEQUENCE: 16

| cgtgcccgtg | cgtttccttg | tcgcatcgca | cgtagccatt | aattcccatg | cacgtaggcc | 60 |
| accgctgcat | gctgcacggc | cacgagaaca | gcacacgccc | ctcgttacgt | tcctggcatg | 120 |
| catatctgat | tgcgtttctt | gctccttgcg | tgttcctcgt | gcatcgtggc | atgtcgatcg | 180 |
| gcggatcgag | caggtgtggg | aggtgccgga | gggcgcggag | gttctggcct | cctccgacaa | 240 |
| gaccggngtc | gagatgttct | gcgtcggcga | gcacgtgctg | ggcatccagg | ggcacccgga | 300 |
| gtacaccaag | gacatcttcc | tcagcctcgt | cgaccgcctc | ctcgccgcgg | gatccatcac | 360 |
| cgtgagtgcc | tgctttcacg | tcaccttaca | gcgactgatt | cctctcacca | aacggacaag | 420 |
| cagccgcgtc | gctctccgca | tctctactct | gattccgctt | tgccactcgc | acacgctgca | 480 |
| gattcccttt | gctgaggccg | tgaacaggca | gctggagacc | actgcgccgg | accgggagtt | 540 |
| ctggctcatg | ctctgcaaga | gcttcctcaa | ggctcgtgaa | gaataagagt | attaattaga | 600 |
| gtttgcacac | tgtgatgtca | ttgtcactta | ccattaaaac | ggttgtaaat | cttctatcac | 660 |
| ttcaacaaat | aaacctc | | | | | 677 |

<210> SEQ ID NO 17
<211> LENGTH: 428
<212> TYPE: DNA
<213> ORGANISM: Zea mays
<220> FEATURE:
<221> NAME/KEY: misc_feature
<222> LOCATION: (341)..(341)
<223> OTHER INFORMATION: n is a, c, g, or t

<400> SEQUENCE: 17

| tgctaatcct | tgtcgtcccc | ttcctcgccg | catcgacgtc | ggcggacggg | aaggccggag | 60 |
| acatgcagcg | gcggcggcgg | cgacaggtcc | tgctgcggga | caaggcgact | ctgctggacc | 120 |
| tgaagcaggg | gctcaggctg | tcatcttcag | cggccctggc | ggactggaac | gagtccaacg | 180 |
| gcgacgtctg | cggcttcacc | ggcgtcacct | gcgactggcg | gcgggagcac | gttgttgggc | 240 |
| tctctctcgc | caacttgggc | atcagtgttg | ctattccacg | ggtcattggc | aatctctcgc | 300 |
| acctccgggg | cctcgacgtg | tccaacaaca | caatctctgg | ncagataccg | acgtccgtcg | 360 |
| gcaacctcac | gcgactggag | cgcctcttca | tgaacaacaa | cgacatctcg | ggcaccatct | 420 |
| cttcaatc | | | | | | 428 |

<210> SEQ ID NO 18
<211> LENGTH: 452
<212> TYPE: DNA
<213> ORGANISM: Zea mays
<220> FEATURE:
<221> NAME/KEY: misc_feature
<222> LOCATION: (91)..(91)
<223> OTHER INFORMATION: n is a, c, g, or t

<400> SEQUENCE: 18

| agagtgctat | ataccattcc | ggattgacgc | ctcggctgat | ggcggggagg | aaaacaaatg | 60 |
| cttgaaaggg | ggtgtttact | tagctgacgg | ngacgaaact | gttccagttc | ttagcgcggg | 120 |
| ctacatgtgt | gcaaaagggt | ggcgtggcaa | aactcgtttc | aaccctgccg | gcagcaagac | 180 |
| ttacgtgaga | gagtacagcc | attcaccacc | ctcaactctc | ctggaaggca | ggggcactca | 240 |
| gagcggtgca | catgttgata | taatgggggaa | cttcgctttg | atcgaggaca | tcatcaggat | 300 |
| agctgccggg | gcaaccggtg | aggaaattgg | tggcgaccag | gtttattcag | atatattcaa | 360 |

```
atggtcagag aaaatcaaat tgaaattgta acccatggga agttaaaaga agtgccccaa    420
cccgttcatt gcgttcctaa atgcttgcct ga                                 452
```

<210> SEQ ID NO 19
<211> LENGTH: 393
<212> TYPE: DNA
<213> ORGANISM: Zea mays
<220> FEATURE:
<221> NAME/KEY: misc_feature
<222> LOCATION: (216)..(216)
<223> OTHER INFORMATION: n is a, c, g, or t

<400> SEQUENCE: 19

```
gcggcggcgg tggaggtggc tgaccatagc gccttcgttg gagcagttgt tgggaaggag    60
gtggaggtgc aggtgcaggt gcaggtgaaa gaagaggagg agcaggagga ggaggaggag   120
gaaggaaacg aggaggagct gcacacgaga gtggaggact tcattgcgag ggtcaagagg   180
caaaggaagc tggagctcaa gagcttcttc gatgtngatc gatgatgact atatgatatg   240
tttggcaggt gcaaaattac agtaaggttg cgggcgccct aaaaaggatc tgtaatggtt   300
tgtgctgcta gctatccttt tgattaattc tgtcacttgt agttgtagta ggttaaaatg   360
tcgaaggtaa aacgataagg agacgaaccc atc                                393
```

<210> SEQ ID NO 20
<211> LENGTH: 686
<212> TYPE: DNA
<213> ORGANISM: Zea mays
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t
<220> FEATURE:
<221> NAME/KEY: misc_feature
<222> LOCATION: (650)..(651)
<223> OTHER INFORMATION: n is a, c, g, or t
<220> FEATURE:
<221> NAME/KEY: misc_feature
<222> LOCATION: (657)..(663)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (673)..(683)

<223> OTHER INFORMATION: n is a, c, g, or t

<400> SEQUENCE: 20

```
ttcccattcc catcaagcaa gcacattctc acttttccag catcaaggca tggagtatgg      60
caacggatga caccttgctg nataatttcc acacatacct taacatcacc aaacagcact     120
tgccatgaac tgtgaggggg attgcaaagg aagtctccta caatgataac ctgcattaca     180
ttttcataag tccccaacca ttgtagttct cggcacaggt ttgtccaaac tgataagttc     240
tttttgttt cnttgggttc tctggactca ggcttcaagc tttcagatca aaatacttaa      300
gtattactcc tcaattctga tttctaaaag taacttgatt ttagattttg ccactcgtat     360
atatatgcag gtcattatag gattctagna acccgtcccc cattttttct tcttatgccc     420
atgctaaaca atctactaat cacagttaaa ggtcatttga atcatttcaa cacttcatta     480
atttntatgc acaagcctaa aacaacttac atttggcatc agagtatgta agtaccacat     540
gaagatatgt tttgttcaat attatgccan tagaaaagaa gaaagaagaa tgcatgttgc     600
agtaatttaa tcaagcctag taactcgtac tcatatcata cctnngtacn ntcatannnn     660
nnngctgntn ctnnnnnnnn nnnatg                                          686
```

<210> SEQ ID NO 21
<211> LENGTH: 417
<212> TYPE: DNA
<213> ORGANISM: Zea mays
<220> FEATURE:
<221> NAME/KEY: misc_feature
<222> LOCATION: (194)..(194)
<223> OTHER INFORMATION: n is a, c, g, or t

<400> SEQUENCE: 21

```
tgatgtttga cgggcaggac gacaagctgt tcgagcactt ctccatggtc gcgcagaggc      60
ttggcgttta caccgccagg gactacgccg acatcctcga gttcctcgtc gacaggtgga     120
aggtggcgaa cctgactggt ctgtcgggtg aagggaacaa ggcgcaggac tacctttgca     180
cccttgcttc aagnatcagg aggctggagg agagggccca gagcagagcc aagaaagcag     240
gcacgctgcc tttcagctgg gtatacggta gggacgtcca actgtgagat cggaaacctg     300
ctgcggactg cttagacaag acctgctgtg ctgtgtctgc gttacatagt tctccaggtt     360
ttgatcagat ggtcccgtgt cgtcttatag agcgatagga gaacgtgttg gtctgtg        417
```

<210> SEQ ID NO 22
<211> LENGTH: 254
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t

<400> SEQUENCE: 22

```
agggtagtat atgtgcattc atcgttttc attagccttg attagnccaa agtgatagtt       60
tatgcttggt catcgagagt ttggtgatca gacgatgaag attgtgagtg gcacaactta     120
agaggtaaac agttgtgtga ttcaacatag tagagtgaca aatgatcgac tcatagagag     180
ccctcgtatg agacgtgagc gacactcctt cataggtgtt ctaataagga ttagttagaa     240
gtgtcaactc ttga                                                      254
```

<210> SEQ ID NO 23
<211> LENGTH: 1041

```
<212> TYPE: DNA
<213> ORGANISM: Zea mays
<220> FEATURE:
<221> NAME/KEY: misc_feature
<222> LOCATION: (859)..(859)
<223> OTHER INFORMATION: n is a, c, g, or t
<220> FEATURE:
<221> NAME/KEY: misc_feature
<222> LOCATION: (985)..(993)
<223> OTHER INFORMATION: n is a, c, g, or t
<220> FEATURE:
<221> NAME/KEY: misc_feature
<222> LOCATION: (1017)..(1021)
<223> OTHER INFORMATION: n is a, c, g, or t

<400> SEQUENCE: 23
ctcccttcgt cgcgctggtc gctgccgcct cccctcgtg ttcacactcc tctaggcgcc      60
tcaggcctca cggtcttcgt cctcgcctcg gcgtctcagc ctcgcgaccc gcgtggagct    120
cacggcggcg accgccattg tagttcccgg aggtacaaag ctcgcctctc tctcctcgcc    180
tggaatgcct agctagcttt cttcgcttct agcgtttctc ggctcccgtg tattgtaatc    240
attatcacgc gcgtttgatt gctttgggct ttggcatcgt cccgtgcagt tccttcagca    300
tttgtgattt aggtgcttgt tcaagtgctg cgattgggtg ggagcctgat ttggtgcgca    360
aggtgcataa aactcgcaca cgtgcacgca cggcgcgctc tgaggttggg atcgggagta    420
gcggcaggtg tttcaggtga tcctgtgttt ccgctcggct agaggtcctg tgattacgac    480
agatttaggg cttaggggg aattggattt agtgagctta ctatgggaag agtactcttt    540
gggctaagtg gagtttctga tcgtcagctt ttgcatgcct tgagtatgat aattcgttgt    600
tttcatgcct aagtttctac atttcaagag ataggaacga agtactccg tatgcgcgat    660
ttaaggtcaa atacattcga caggctatac tggcgatcac tttatgggat gtgcttttat    720
atgggactgt ctatgtttcc ttaagtggag taagacccat aaatggcgtc tgaaatttct    780
ttaagctgta ccactttttt tatggtttgg taagttctgc agctaaaata gagtcttcaa    840
tcttgataca ggtcaatgna ggagtcagtg ccaatgtcag taatcagcag tatttcaaac    900
ttccgcacgc tgtctaccag cagtgtggta gaaactgagc tagttaagag atactgccgg    960
aagatcaatg aaatcctggg tcttnnnnnn nngtcctgg atgaagttct cacccannnn   1020
nagtctggat gataggatgc t                                            1041

<210> SEQ ID NO 24
<211> LENGTH: 748
<212> TYPE: DNA
<213> ORGANISM: Zea mays
<220> FEATURE:
<221> NAME/KEY: misc_feature
<222> LOCATION: (42)..(45)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
```

```
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (635)..(642)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (649)..(651)
<223> OTHER INFORMATION: n is a, c, g, or t
<220> FEATURE:
<221> NAME/KEY: misc_feature
<222> LOCATION: (654)..(656)
<223> OTHER INFORMATION: n is a, c, g, or t
<220> FEATURE:
<221> NAME/KEY: misc_feature
<222> LOCATION: (666)..(667)
<223> OTHER INFORMATION: n is a, c, g, or t
<220> FEATURE:
<221> NAME/KEY: misc_feature
<222> LOCATION: (673)..(679)
<223> OTHER INFORMATION: n is a, c, g, or t
<220> FEATURE:
<221> NAME/KEY: misc_feature
<222> LOCATION: (685)..(693)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (715)..(723)
<223> OTHER INFORMATION: n is a, c, g, or t
<220> FEATURE:
<221> NAME/KEY: misc_feature
<222> LOCATION: (726)..(730)
<223> OTHER INFORMATION: n is a, c, g, or t
<220> FEATURE:
<221> NAME/KEY: misc_feature
<222> LOCATION: (732)..(742)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
```

<400> SEQUENCE: 24

```
cataatgcaa caaacgttaa aaaactacag agatggaaaa annnncagtc accataaaag    60
atgncttgta caacaagttc atgcaaaaaa nttattatta ctattaatga gctaactana   120
aacaaacacc cnaaatataa catcatgaca tcaaaaggaa gacatgtacc ttgagggcac   180
caaagacacg gttcccagtn gtagtcctaa taaggccaac atccaagaga gcacggaaag   240
gcctcctctc atcagctggc tcaacagaga antcctcacc agtggcctga tgaangaaaa   300
gaaacaatat aaatgcccaa ccaatgtgac atcagcaaaa aataagatcn aaatttagcc   360
aaattttacc tcaacattgc cctcatattc cttatctaaa ccacgggtct tgagcacacg   420
gcgagccaac agaaggccag tgcagtaggc tacaagatga gtgtaagcag ttgaactagt   480
gaatatataa attcattaag gtacaatatg caatttacac antatttcca gaaggnaaat   540
taccagctgc atagttggtc agaccaactt caagaccata tcgtggcaac tcatgcgagt   600
aagcagaagc aagnnccata tcacctgcta tactnnnnnn nntgatntnn nctnnnatgt   660
ccttgnnggt ctnnnnnnnt ctagnnnnnn nnacaatat tatgcnactg nagcnnnnnn   720
nnnatnnnnn tnnnnnnnnn nnanatga                                      748
```

<210> SEQ ID NO 25
<211> LENGTH: 714
<212> TYPE: DNA
<213> ORGANISM: Zea mays
<220> FEATURE:
<221> NAME/KEY: misc_feature
<222> LOCATION: (35)..(41)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (651)..(652)
<223> OTHER INFORMATION: n is a, c, g, or t
<220> FEATURE:
<221> NAME/KEY: misc_feature
<222> LOCATION: (668)..(669)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (695)..(696)
<223> OTHER INFORMATION: n is a, c, g, or t
<220> FEATURE:
<221> NAME/KEY: misc_feature
<222> LOCATION: (702)..(709)
<223> OTHER INFORMATION: n is a, c, g, or t

<400> SEQUENCE: 25

```
ctcagcagtt ttaagtttct ctatagttca cactnnnnnn nacaaatccg gctgtgccca    60
aacaactcta ttnaacagag aagcatcgaa actagcatgg agcaaaatct gaattcctta   120
aatctccaac ctaaaacact tagccgacca aaaagcccct gcttcccaaa cgattcgcca   180
```

```
agttcgttaa agattttggg ggaaaacgag gcctaaacaa cgggaagtaa gggaaatcaa    240
tagaaaaaac atggttttgg tgagaacctg tgcctagcng cgctctgggg aagattggct    300
gagggagctg cgttttgggg gagtgcaaga ggagcacggt atccagggaa gatgtgcggg    360
agagagatat atattggata cagctcaaga ggggaggaac gctcctcctt aattgttcaa    420
ggcaacgctc ctgccttctt ccaaaaaaaa gaggggagga tcctgacaaa attccagcaa    480
agataggtgt gagagtttat tgctgccttc cttttctgct tgccttttt atctcctcaa     540 aagagttgtg tttgtgttct atccccgta aaacacaatt tggaaagtgt ttctcaaaaa     600
ttctgatgca tgcattgact ctcttttttt tgtcactatc ctggatttct nngtattctt    660
atttccanng tantgataac taaaaaaatg aancnntagt tnnnnnnnnt atat          714
```

```
<210> SEQ ID NO 26
<211> LENGTH: 410
<212> TYPE: DNA
<213> ORGANISM: Zea mays
<220> FEATURE:
<221> NAME/KEY: misc_feature
<222> LOCATION: (352)..(352)
<223> OTHER INFORMATION: n is a, c, g, or t

<400> SEQUENCE: 26
tcgttaacaa ggagaggaga gaacgggttt cgtggaccgg gccggtcttc cactatgggc    60
ttgttaggac atacaaagac acagccgaaa tttgctgttg gtctcgagca aggccacggc    120
ccacaggtct gcttgggttt gggtctagga aaggaaaaga actactctca ctaaaatgag    180
agaaaggtgc ggtaaaaaat gagagaaagg tgcggtaaaa aaaaccaaaa agagagaaag    240
atgaaaaaga agacttcaaa cgcactggca tagacgccac ggcagtccag tggcaaccgc    300
atcagtgcgt atttacggag caaaacagat ctccccgtcg acctggtaca cngccgcagt    360
tggtatcagg acgtcgcacg gcaggtcacg agtcttcaga gttcagagag               410
```

```
<210> SEQ ID NO 27
<211> LENGTH: 359
<212> TYPE: DNA
<213> ORGANISM: Zea mays
<220> FEATURE:
<221> NAME/KEY: misc_feature
<222> LOCATION: (162)..(162)
<223> OTHER INFORMATION: n is a, c, g, or t

<400> SEQUENCE: 27
gcagctcaaa gcattcgtca agcaggatca acaagggacc ttgttattct tgttgatgac    60
accattagtg accaccaccg caaggggctg gaatctgctg ggtggaaggt tagaataata    120
cagaggatcc ggaatcccaa agcggaacgt gatgcctaca angaatggaa ctacagcaaa    180
ttccggctgt ggcagcttac agattacgac aaggtcattt tcattgatgc tgatctgctc    240
atcctgagga acattgattt cttgtttgca atgccggaaa tcaccgcaac tgggaacaat    300
gctacactct tcaactctgg ggtgatggtc attgagcctt caaactgcac gttccagtt    359
```

```
<210> SEQ ID NO 28
<211> LENGTH: 384
<212> TYPE: DNA
<213> ORGANISM: Zea mays
<220> FEATURE:
<221> NAME/KEY: misc_feature
<222> LOCATION: (106)..(106)
<223> OTHER INFORMATION: n is a, c, g, or t

<400> SEQUENCE: 28
```

```
atcattcctt tatctattgg aaatctcaaa gggttaaatg tctttgatgc acatcattgc      60
aacttggggg ggccaattcc agcaagcata ggcaacatgt cgaatntgtt gacacttgat     120
ttatcaaaga actccctcga tggttcaatt tccaatgaga ttttcaaact gtcatccctt     180 gaccettatc tatttaaagt tttaaactta tcatacaatt cgctatcggg acatcttcct     240
tctgagatga gtagtttggg gaacctgaac caactagttc tgtctgggaa ccgattgtct     300
ggcgagatac ctgagagtat tggggaatgc actgtgctgc aataccttat attggatata     360
taactcaatc gatggaagca tacc                                           384
```

```
<210> SEQ ID NO 29
<211> LENGTH: 788
<212> TYPE: DNA
<213> ORGANISM: Zea mays
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (736)..(741)
<223> OTHER INFORMATION: n is a, c, g, or t
<220> FEATURE:
<221> NAME/KEY: misc_feature
<222> LOCATION: (746)..(757)
<223> OTHER INFORMATION: n is a, c, g, or t
<220> FEATURE:
<221> NAME/KEY: misc_feature
<222> LOCATION: (768)..(773)
<223> OTHER INFORMATION: n is a, c, g, or t

<400> SEQUENCE: 29
gtttgcttcg cagctgtttg taggacatgg agagaaatgt gtaaagagat tgtgttgagc      60
ccggagtttt gtggcaagct caccttccct gtgtctctaa aacaggtaag ggaaagaaca     120
atcaacctcc ttcagttcga gcaatcttga accggatgtt gagaattgcc tccaaacctt     180
gagcagcgga tatctatatc tccctctggt ccttgatata ttgcttgttt cttttgacag     240
cctggtcctc gagatggaaa tacaatggtc cagtgtttta taaagaggaa taagtcaaaa     300
tccacttacc atctctacnt gtgccttagc aatggtacgt cacatgattt gcacattttc     360
aagattcaat agcaatgttc ataagtttat actgttttat tggagcatat gggattattg     420
ttagccagat atgtttctcc tttttgagtg tttgattttg tgattatatc tcgtatcttg     480
taatcctcat aaattctgaa attgtgtggc cttttaatct catattcatg agagtattta     540
cagttaaatg atcaatggtc tgtttatctt gtttcacttt atcaaatttg ttgactcatt     600
ttcttctgtg cacagttgtt acttcagaaa gtgggaaatt cctcttatca gctaaacgac     660
accgcaaaac cacatgcacc gagtacacta tatcaatgga ttctggcaac atctcaagat     720
ngaaaagaac ctacannnnn naaatnnnnn nnnnnnnatg ttttgannn nnntgttctt     780 gtttccccc                                                             788
```

```
<210> SEQ ID NO 30
<211> LENGTH: 443
<212> TYPE: DNA
<213> ORGANISM: Zea mays
<220> FEATURE:
<221> NAME/KEY: misc_feature
<222> LOCATION: (33)..(33)
```

```
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 30
actataatct acaatgaata gcaagcaatc ggntattagc ttctatacna ttgactacca    60
tcaatccttt gtaagtgccc ctgacaactc tttgtaccct tgacagtgtc ctactactgt   120
agtgccnttt tttggagacc agttcttctg gggcgagaga gttcatgcac gaggagtggg   180
tcctgcacct atatctatng cagaacttac tgtagaagca ctatcagatg caataatatt   240
catgcttgat ccagaggtag tactatttct tatgctttca ctatatgcat ctggtcatgc   300
caacaatgtt tttgatgcag aactctgctt tggtaaggcc ccattgtgct aataactaat   360
ccatttatga tcctttgctg aaggtaaaat cacgaacaat ggaactggcg atagcaatag   420
gcaatgagga tggtgtggca gca                                           443

<210> SEQ ID NO 31
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t

<400> SEQUENCE: 31
gattttgagg agtcataggt ggtagggaga agttttgctg gggtgggcag aaggattgat    60
ggtaattacc tatgtcatgt tctacgtgct ctatgtcgaa nggtccggtg tggtacgtgg   120
acagtccaga tgcatactcg ggtagtctgc acgcatagct cganggttcg agcatgtntg   180
ttagcccttg catagggtgt g                                             201

<210> SEQ ID NO 32
<211> LENGTH: 1083
<212> TYPE: DNA
<213> ORGANISM: Zea mays
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (294)..(297)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
```

<222> LOCATION: (615)..(620)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (896)..(897)
<223> OTHER INFORMATION: n is a, c, g, or t

<400> SEQUENCE: 32

```
gtgatgtcag attgtttgga ataaccagat aaacatctat cgggttgact gattcatatc      60
ctttcagtgt tgctgannac taactgaatg aaagtaggca gacttctgaa ttaattgcaa     120
ttttgggaag tgtaacatac aaaaattatc ttgtgtccga ggaaatggat tgattgattc     180
agaaaaccaa ccaccctggt tgtgcaaacc aaaaaaagaa caatatagag cagtaaaggt     240
tgattataac cagcattcca gcaatgaagc caacagtacc attacaaaag caannnngtc     300
aacatgagac atacctgaag gataaggcac gtatgtcaaa tcacttgcag cccactgaat     360
atggaatcat tagtgataga aactgatatt caanttctat tgcatagagg gtggttacat     420
atatagaccc aggggaaccc taaccctaat gggctagcag cccatttaca catacatgga     480
taatatagga gcatacactc taacaatcag tctggtggag aagctggaaa tacacagtac     540
aaaagtagca gaaatagaga aagtacttaa aaatgaaat ataaaaggtc aaatagttta      600
gagttgccat acttnnnnnn gtgaagaata tgttcctagt caggaaagca atttacggtt     660
gccaacgcta gtgaaaaata tgaaagatat gaatcaagta cagtactatt tgacgaccaa     720
atataacctt gatgaatgtc tcccaacaac cagccaacta ggataaggat ttntaatgtc     780
aacccactga aaactaaaga ttcattagca ttctacaaag cagatgttac aatctaaaat     840
atgttcaatc agcagggaaa tggtgataaa acctcaaagc taatttaaaa cagttnnctg     900
cctataaact gctggttctc actaacacat acatgtacag ttaaatcact ccagtcaacc     960
cacttattca gaagaataga ctgctatgga gctgtgagct atatacgaga gagatcgcca    1020
tttatatttg atcaagtatc tggctttctc tttgaaaggg ggctaaatgc agctgcaggc    1080
atg                                                                 1083
```

<210> SEQ ID NO 33
<211> LENGTH: 693
<212> TYPE: DNA
<213> ORGANISM: Zea mays
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (618)..(620)
<223> OTHER INFORMATION: n is a, c, g, or t
<220> FEATURE:
<221> NAME/KEY: misc_feature
<222> LOCATION: (625)..(627)

```
<223> OTHER INFORMATION: n is a, c, g, or t
<220> FEATURE:
<221> NAME/KEY: misc_feature
<222> LOCATION: (630)..(632)
<223> OTHER INFORMATION: n is a, c, g, or t
<220> FEATURE:
<221> NAME/KEY: misc_feature
<222> LOCATION: (637)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (647)..(657)
<223> OTHER INFORMATION: n is a, c, g, or t
<220> FEATURE:
<221> NAME/KEY: misc_feature
<222> LOCATION: (665)..(672)
<223> OTHER INFORMATION: n is a, c, g, or t
<220> FEATURE:
<221> NAME/KEY: misc_feature
<222> LOCATION: (675)..(677)
<223> OTHER INFORMATION: n is a, c, g, or t
<220> FEATURE:
<221> NAME/KEY: misc_feature
<222> LOCATION: (688)..(689)
<223> OTHER INFORMATION: n is a, c, g, or t

<400> SEQUENCE: 33
cctgcagacc atatatgttt atggcatgcc aatatctagt aggaacttag taatagaaac      60
gaataaattg ccttcttagt tttaagaata aaagttggtg catnacatgc agccgctgga     120
acaaagtttt ggctcaaagt catatggtat tgtgaaagca tcactaatat ctagggaaat     180
acttcttgaa gaagtgaaga agatcagtaa tgctgttggt agcactcttg aggatttgga     240
tcgcactgac ttaacccttg gtaaatatga gacagttcaa ccatcaaagt cagcttcgcc     300
cagttacagt tatgggcang gtacgcccac aaagtgtagt ccccagatga ctggcatctt     360
acgtgatttt cttgaggtat acttcacttt ttttnctgaa aaacgttttc tatctttttg     420
aatatctgta ttggttgatg catctcaaac ttgtttcaga gttctggggt tgtggttgga     480
agcactgatg atatcttgct gtatactcta tctgaggaag aattgtttga actatttcaa     540
attgtcagca gccaactctc atttatatgg aatgagttct tgaaattcca taggttagtt     600
atcttnncat gcatctcnnn ttagnnnatn nntgtannnn nngantnnnn nnnnnnnatt     660
cttannnnnn nntannnata aacatatnnt gac                                 693

<210> SEQ ID NO 34
<211> LENGTH: 201
<212> TYPE: DNA
<213> ORGANISM: Zea mays
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
```

```
<222> LOCATION: (155)..(155)
<223> OTHER INFORMATION: n is a, c, g, or t

<400> SEQUENCE: 34
aggtaatgag gcaatngtnt cagcagcaag gcctttgctt tccgtaccga caacttcacc    60
cagcgcaatt agctcctgag gtcaccacgt tcatgaatca nctttgcacg gtagcagaaa   120
acaaatgcac agaanatcct aatctcttca acaanaataa cttgcctcgt aagagtattc   180
gtctgggtca acatcttccc a                                             201

<210> SEQ ID NO 35
<211> LENGTH: 201
<212> TYPE: DNA
<213> ORGANISM: Zea mays
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t

<400> SEQUENCE: 35
tgcccttgtt gacgaaggtc caacgatcag tttcaaaaga aacgnttcca aatgttaaga    60
atcagctaga tctaagtgtc gatgaagatg tcgaatactt nggtgtgttt ggttggagag   120
tcaattagaa tagagtggtt ccattctant ttttgagaat ggagccgttc tattctccgt   180
ttggcaagca aaacagagtc a                                             201

<210> SEQ ID NO 36
<211> LENGTH: 1549
<212> TYPE: DNA
<213> ORGANISM: Zea mays
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t

<400> SEQUENCE: 36
ggctaaaaga attatatatn tgggacagag gggntacgtt ggaagcatct ttatagccag    60
cagtcggctg tacttgctca gtcaagaaaa cgcgacatag gcctccctca ccaacactat   120
ctgctataaa taaaaggatc ccgccagtac attccctcta cgtggtcatt gaaccaaatc   180
gcagttccta tgtcgacaca tcactgtcaa tttccacgga agttccagct gcaatccgat   240
gcatagatta cacagaatgc atatacttcc aatagtaggc tatgccatct ccatatcact   300
gtgactcatg agtacagtgt aaacatgaag gcaacgttct gttcgtaagg atttcagaac   360
attttccgag tanctcattt atatgatccg ttattcgatc ttcagatatg gtcctgttat   420
tcgatcttca gacttactaa agcaaagcca tgtggagaag aacttcgccc tctacttggc   480
cttcttggaa gcctcgtaca agtagccagc gataactacg gctgcagcaa ctgctacccc   540
```

| | |
|---|---|
| aaaggcactc tgtgcaagca cggcggcggt tggaagatct gatttggatg gtgctgtgct | 600 |
| gcgaggcgtg aagccaagct cagagagttt cttgtgtgat tcagcataat ctttgaagaa | 660 |
| cgcatcttca tcctttgcat agagctccac atagcgccta aattcaggat ctgataacag | 720 |
| tgccttgtca gttgggagct ttaaaagtcc ctcagattcc tcattcaaca gctcaagaaa | 780 |
| gtatgagtta tcaaacttaa gaggctcctt tgtccaggca ccatcgaatc cagacctctc | 840 |
| agggtgagcc cttcccagag tatgtccccc tgatagagct acaatatctt tgtccgataa | 900 |
| gcccatccga taaagatgt ccctcagatg tggtgcacct ttcttagcat ctggcagacg | 960 |
| cccttcacgg gggcacaccg acgaatcacg tctgccagga ataaattcaa cagttggccc | 1020 |
| cccagtcact tcgactgcaa ccactccagc aagctgatac aggtctgcat atgttatctt | 1080 |
| tggattcttt gctttgatag gctcaaggag atcgatagca atctttaaac cagcatttga | 1140 |
| accatgagtg tactcttctt catatctaat cgaaccattt gcaccaccag tttttgtctt | 1200 |
| caggtcataa gttccagcat catgccatgc gaggcggagc atgatcgggg cgcatcccctt | 1260 |
| gttggagatg agggcgcgga ggtggcgcg cgccctgtcg acctggcgca ggtattcggc | 1320 |
| gtcgaccatg ggagccgcca tcgccggcgc ctcagccgcg gattcctgga gatcggagag | 1380 |
| ttggagtgga accgtgggcg gagcggaggc gtgtgggtgg cgagtgctga ctgactgctg | 1440 |
| agcagtgggg gatgggaagg gaggaaacga caactgacga gccgaacaag ataacgcaag | 1500 |
| cgagcgattc tattggcctc cagttgccgg cgcctggcaa cccccggcc | 1549 |

```
<210> SEQ ID NO 37
<211> LENGTH: 669
<212> TYPE: DNA
<213> ORGANISM: Zea mays
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
```

<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (643)..(644)
<223> OTHER INFORMATION: n is a, c, g, or t
<220> FEATURE:
<221> NAME/KEY: misc_feature
<222> LOCATION: (646)..(647)
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (664)..(666)
<223> OTHER INFORMATION: n is a, c, g, or t

<400> SEQUENCE: 37

```
acaaatcact cgctactctt gcctacaccc tcacaatcat ntacgaatac tagtgactgc    60
tttcctctcc tcagcatttt tggcaagtgt tgtgctggcg tgccgtgtgt ggagnggaac   120
gctatataaa gcaacgtcta aaaagaaaa aaaatactat atattagcat actagtatat   180
aaatataaga gtaactccaa tagttttcta aaagactctc taaattaata atttaagtaa   240
ctaaactaaa agctcctctc caacggttct ctaaatgaac ttcataaatt tagctactnc   300
tcatctaacc ttatttctc tctacattta gnaacnattt accaactncn taaacaaaaa   360
aaaattgacn gtaattttg tatttcgctg ccttttcac tttatagtaa cgatatatta   420
acatagccca tgcgtcgaac aacgacagtc agctagagat taaataattg ccaatacaat   480
agccgcacgt ncacntgtcg gaaataaata aataaacaat tgcaacngta aatnaaaaga   540
tcaacacaac tcaccaagtt gaatatgcca tcgatnatgg tcccactcag atgagtgaca   600
tgttaaattt taacatattt agaaagtaat atatatataa ctnntnnann agatgcgttt   660 tttnnntat                                                           669
```

<210> SEQ ID NO 38
<211> LENGTH: 684
<212> TYPE: DNA
<213> ORGANISM: Zea mays
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (599)..(601)

<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (622)..(626)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (649)..(659)
<223> OTHER INFORMATION: n is a, c, g, or t
<220> FEATURE:
<221> NAME/KEY: misc_feature
<222> LOCATION: (661)..(669)
<223> OTHER INFORMATION: n is a, c, g, or t
<220> FEATURE:
<221> NAME/KEY: misc_feature
<222> LOCATION: (673)..(679)
<223> OTHER INFORMATION: n is a, c, g, or t

<400> SEQUENCE: 38

```
tcgaagctgg gaggctacct ggcgatattt ttgatgagat accaagcaag tactataatg        60
gatcagttgt ttgtgaggta agttgtttta tcacacataa gaaaggctat gcatgcaatg       120
ctattgaact gcaacatgct gaaaccnttc tgaaatttat tctcttataa nttgtggttg       180
gtttctctga tacatggttc aaaaagcatg ctggtacaat ttctgtactg aggatttatg       240
ctatatggga gaaatccttc tttaaaagaa aaactagaag tttggtgagc tttactgncg       300
acatgttcta taatatgcca acctaccagt actgtaccaa ccttttttcta acacttattt     360
cagaaacaac cgttatgcat tatcatgaag catcatgttg tgtcatgtgc tcatggtcat       420
gtgctactgt accttattga taagagacca ttgagtcttt agcagtactt cattgtctta      480
catcgacata agtaatgagt tctctttcta gatacatgac taccgaaagc atgtgnccaa      540
ccaagcgcct gcatcatctg ctgagctagg atcaccaatt gtgaataaag tacgactgnn      600
natgacctnt gaaaatgttg tnnnnnacat tacccctncna nctgatgann nnnnnnnna      660
nnnnnnnnnt atnnnnnnna tgct                                             684
```

<210> SEQ ID NO 39
<211> LENGTH: 738
<212> TYPE: DNA
<213> ORGANISM: Zea mays
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (623)..(625)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (689)..(690)
<223> OTHER INFORMATION: n is a, c, g, or t
<220> FEATURE:
<221> NAME/KEY: misc_feature
<222> LOCATION: (692)..(698)
<223> OTHER INFORMATION: n is a, c, g, or t
<220> FEATURE:
<221> NAME/KEY: misc_feature
<222> LOCATION: (702)..(706)
<223> OTHER INFORMATION: n is a, c, g, or t
<220> FEATURE:
<221> NAME/KEY: misc_feature
<222> LOCATION: (710)..(715)
<223> OTHER INFORMATION: n is a, c, g, or t
<220> FEATURE:
<221> NAME/KEY: misc_feature
<222> LOCATION: (717)..(720)
<223> OTHER INFORMATION: n is a, c, g, or t
<220> FEATURE:
<221> NAME/KEY: misc_feature
<222> LOCATION: (727)..(735)
<223> OTHER INFORMATION: n is a, c, g, or t

<400> SEQUENCE: 39

| | | | | | |
|---|---|---|---|---|---|
| agttggattt | ccttctgtag | cttccagtcc | tagtgantcc | atgcaccgaa | tacaacagcc | 60 |
| tgctgttgct | tcctcaaaga | ggaaaacaaa | ttctgtcccc | aaaactcaac | cgcctgtgag | 120 |
| tgctgttggg | tctccagcca | gtgtttcaaa | catgcatgcg | ctgctgaatg | caagcagtcc | 180 |
| atcgattggg | accacaccta | tgggagacca | agcaatcctt | gataaatttg | tgaaaattga | 240 |
| taacatttcc | catcggtata | gcataattc | tacatctgct | ccctcccttc | acgaattttt | 300 |
| gttgtcactt | tcctttctat | tcttagtttc | tttggaagtc | tgtcatggga | gacttttaa | 360 |
| ggaagttttg | ggttgcacgg | tgtgaatttg | atgtctaggc | tatttaaag | ctgagattca | 420 |
| gccctattac | tttggatggt | cacacaaaaa | aatgtcaggc | tataatgtgc | aaatgaactg | 480 |
| tttcaattct | ttatcaaagt | taatcaacat | tttaacctaa | ataactagtc | cctccagttc | 540 |
| aaattgtaag | ttgttttggt | tttttnagat | acctggtttt | cactgtgtat | atagacatag | 600 |
| cacacatcta | nntgcatagc | agnnnctatg | tacctagaaa | agtcaaaaca | acttacaatt | 660 |
| tgaaattgag | ggaatgccta | acanaatann | annnnnnnga | gnnnnnacan | nnnnntnnnn | 720 |
| accggannnn | nnnnnaaa | | | | | 738 |

<210> SEQ ID NO 40
<211> LENGTH: 201
<212> TYPE: DNA
<213> ORGANISM: Zea mays
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t

<400> SEQUENCE: 40

```
gtgacacagg tggtgaggtg ccagccttcg cctttgatgg acgctgtacc tgtacgcgcg    60
cgtgttgcng tctgtagagt agcaggataa ttggacgctc ngatgacacg actgcacatt   120
ctcgtacacc aggctgctat ctgctttcat atatttgacg cgtatgcata cgtncgtgct   180
tggactcgta tactactact t                                             201
```

<210> SEQ ID NO 41
<211> LENGTH: 201
<212> TYPE: DNA
<213> ORGANISM: Zea mays
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t

<400> SEQUENCE: 41

```
tgaattagga cttctgtttt ctcactaaac taggtctnta ttttaatctc ttaaacaaac    60
ctatgcaaat aaccaaacac gcttgtgcaa ctaaggtttt nctaagtgt tgctacctct   120 actgnaaaag gagttttgta acctaagttc caatcctacc aactagtctt tattctaaac   180
taagaatggt aacgataaca a                                             201
```

<210> SEQ ID NO 42
<211> LENGTH: 201
<212> TYPE: DNA
<213> ORGANISM: Zea mays
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t

<400> SEQUENCE: 42

```
aggactcgtc ngagctggta aacagcgacc attcgcttga cgtggcctcc gagaagtccg    60
cgctnaccga gtctgcgaag gcatcgtcgg cgcgatggaa ntccctggat ctcaactctg   120
cttgctgatc ttgcgtgtag ccctcgccat cnggtctaaa gtcataaaca ccgtatgctg   180
gatcgttcgc cgagaggagt a                                             201
```

<210> SEQ ID NO 43
<211> LENGTH: 201
<212> TYPE: DNA
<213> ORGANISM: Zea mays
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature

```
<222> LOCATION: (24)..(24)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 43
cctacggttg tttgtctttg tncnttgctt gttcacgatc ganttcacc gaaaacgttt      60 ccgatgctgt aacaanatac tcgtttccgt cctagataga nacaacgtga ttttgttttc    120
actaatctcg atgcaaacga gcaacaacaa aaaaaatcac caaaatgagc acacccagga   180
acttgatcgt atctcttcat t                                              201

<210> SEQ ID NO 44
<211> LENGTH: 2607
<212> TYPE: DNA
<213> ORGANISM: Zea mays
<220> FEATURE:
<221> NAME/KEY: misc_feature
<222> LOCATION: (2239)..(2239)
<223> OTHER INFORMATION: n is a, c, g, or t

<400> SEQUENCE: 44
caggaaaaaa acccggtgtt ctagccgcac gcatctcaaa ggtgatactg ggcggggcga     60
tttggagatg atgttctagc actagcagca cgcacgcatc tcaaaggtga tactgggcgg   120
ggcgatttgg agatgatgtt ctagcactag cagcacgcac gcatctcaag gtcatactgg   180
gcggggcgat ttgcgagtcc tgtggcctcg tgggccacgt gcacgcagca gaccgcagga   240
atttgcacga gaccagtacc tagaacaccc tactccagcg aaatccgcca cttcgtcgtc   300
gtcgtcgcac ggattggcat tggctgcccc ccggccctgt tcctcgtcct cctcatcaat   360
tcccgtctct cagtcctccc aataatggtg gcgtggtgag aaatccttcc gtccggccgt   420
cgtcttagaa gatgaactgt tcctcttgct gcgccgctgc cactccatct tctccggcgc   480
ttctcgccag gccgcggggg ggtttagctg ctagctgctc cacgacgaca gcaaatcaga   540
aggtgctttt cctgggctca aaacagtttc cacggatcac gtatagccgt gcgtcgtcac   600
ggttgtcgcg gagagaggta atagcttttg ccgggcaaca accttgggac atcggcagat   660
ttgtcaagac gctgtatttc ttcaacgggc ctccaaacct tctcaagatt gtagaatcta   720
tcatcagcag tttcactgga cctgcttcta gtgaagtgcc aaagaaaatg gaaacgtcgg   780
atgtggtgct ggttactgga gccaccggtg gtgttgggcg acgggtggtg gacgtcctgc   840
agaagaaggg agtacctgtt cgagtattgg ctagaaatgt agacaaggca aggagcatgt   900
tggggccgga tgtacctctg atcataggag atgttacgaa ggaagataca cttgatccta   960
agctattcaa agggataaaa aaagtagtca atgcagtctc tgtcatagtg gggccaaagg   1020
aaggtgatac gccagacagg cagaagtaca acaaggcat caaattttc gaacctgaga   1080 tcaagggacc ttcacctgaa atggttgagt acatcggaat gcaaaacttg attaatgcca   1140
taaagagtag tgttggactg agtgaaggga aactgctatt tggtttcaaa ggcaacttat   1200
ctggagagat tgtgtgggga gctcttgatg acgttgtgat gggtggtgtt agtgaaagta   1260
```

-continued

```
cattccaaat cttgccaaca ggaagtgaaa gtagtggacc aactgggttg ttcaaaggga      1320
ctgtatctac ttcaaataat ggtgggttta ctagtataag gacaaagaat tttactgtgc      1380
cagaggacct gtcagcatat gatggtattg agttacgagt taatggtgat gggcgacggt      1440
ataaactcat tatacggact agctatgaat gggatactgt tggctataca gcaagtttta      1500
acacaactaa gggggatgg caaagtgtta aagtaccttt ctcttctctg aaacctgtat       1560
tccgtgctcg tactgtgact gatgctccac ccttcgatgc aagcaacatt acttcactac      1620
aactcatgtt tagcaaattt gaatacgatg gaatactcaa cccaacattt actgaaggtc      1680
cgtttgagct tcctttttcg agtattagag catacatcaa tgagccgatc actccaaggt      1740
tcgttcatgt gagttctgcg ggagttacaa gacctgaaag accggggtta gatttaagca      1800
agcagccacc tgctgttcga ttgaacaaag agcttggctc cattttaact tttaagttga      1860
agggagagga tttaattcgg gaaagcggta ttccgtacac tattgtaagg ccatgtgcat      1920
taactgagga accagctgga gccgatctca tgtttgacca gggggacaac atcacaggaa      1980
agatatcaag ggaagaagtt gcccgtattt gtgtagcagc tctggcaagc ccagatgctg      2040
tgggcaaaac tttcgaggtc aagagcactg ttccattcag cgaaccgtat gtgattgacc      2100
ctgcaaatcc tcctcctgaa aaggactatg aagtatattt caaagaactc aaagaaggca      2160
tcacgggtaa agaggcgtta gaggcaacac ctgctcaagt ttgaagatgt cgttgaatta      2220
agaatttcgt ctgttttcnt aaattctgac acagtaaccc ccactctgaa tgtctaaagt      2280
catctagaaa catagatgac actaatgcta aattttgtag ctgaagatca gaccaataaa      2340
tattcccaag aacacattac tgttaggttg ggggatcatt aaactcgagc taagacacaa      2400
atatgtagat gaaattagtg ctgctgttca tgccttcgtt ggagttagcc attacaggac      2460
acaagaattt agtaagaggt ttggcaaaaa aaaaaaaaaa aaggagcagc tgcctgatga      2520
gttggtagag tggttgcttt cagtcaattc tctagggtgc ctatctctat ttaacttgat      2580
gctgcacact gggggctccc ttcagtc                                          2607
```

<210> SEQ ID NO 45
<211> LENGTH: 608
<212> TYPE: DNA
<213> ORGANISM: Zea mays
<220> FEATURE:
<221> NAME/KEY: misc_feature
<222> LOCATION: (115)..(124)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (350)..(351)
<223> OTHER INFORMATION: n is a, c, g, or t
<220> FEATURE:
<221> NAME/KEY: misc_feature
<222> LOCATION: (358)..(360)
<223> OTHER INFORMATION: n is a, c, g, or t
<220> FEATURE:
<221> NAME/KEY: misc_feature
<222> LOCATION: (562)..(563)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t

<400> SEQUENCE: 45

```
ttatgctagt tagattttgc aaagaaaagt tcaattaccc cagttatctt gtttccctga    60
atccttggta cacttgtagt ttcttcttaa ttatgtaact ttaggttata taatnnnnnn   120
nnnngctaca tcttgattgc tgctgttcct ataataatat tccatgattt ggcattttg    180 gcttcattta gctgaaccaa ctgtaatctn acttcttatc accccgggc nttaatgatg    240 cttctgtagc caagggtggg ctgagggagg cttttgcagc tccagggtta ggttacgttg    300
atattccaaa tgcacagata agaaaggtaa attttgatgg ccagaaacan nttttttnnn    360
catattagat gttagtaact tgagcatgtg ttgatttctg ttgtcttcag gttaccgcaa    420
accgcttgct agcatctaaa cagaccattc ctcattacta cttgacagta gatgcacgtg    480
ttgacaaact tgtcaagtat gtttctaacc taatatatga tttacagagc tcttttcgtt    540
ggtgggacag cacttctaac tnngagttnt gtcattctaa tccacaggtt gcgaggtgaa    600
ctgaatcc                                                              608
```

<210> SEQ ID NO 46
<211> LENGTH: 201
<212> TYPE: DNA
<213> ORGANISM: Zea mays
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t

<400> SEQUENCE: 46

```
ttggagtgat acttgttcga ggaagagccg tggtggtggc gaaaacntcc atgttctctc    60
gtcttgtcaa ttgtcacaag ctaggacatc gatcgccgat ngagctagct aggggtcgtc   120
gacggcgagg ccgccccagc tagctagcta ctctcgatca ggggaanctg cttggtcngg   180
acccgcgccc agacgacgac g                                              201
```

<210> SEQ ID NO 47
<211> LENGTH: 1294
<212> TYPE: DNA
<213> ORGANISM: Zea mays
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:

-continued

```
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (558)..(559)
<223> OTHER INFORMATION: n is a, c, g, or t
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (576)..(580)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (620)..(622)
<223> OTHER INFORMATION: n is a, c, g, or t
<220> FEATURE:
<221> NAME/KEY: misc_feature
<222> LOCATION: (625)..(627)
<223> OTHER INFORMATION: n is a, c, g, or t
<220> FEATURE:
<221> NAME/KEY: misc_feature
<222> LOCATION: (634)..(644)
<223> OTHER INFORMATION: n is a, c, g, or t
<220> FEATURE:
<221> NAME/KEY: misc_feature
<222> LOCATION: (647)..(650)
<223> OTHER INFORMATION: n is a, c, g, or t
```

```
<220> FEATURE:
<221> NAME/KEY: misc_feature
<222> LOCATION: (652)..(681)
<223> OTHER INFORMATION: n is a, c, g, or t
<220> FEATURE:
<221> NAME/KEY: misc_feature
<222> LOCATION: (687)..(702)
<223> OTHER INFORMATION: n is a, c, g, or t
<220> FEATURE:
<221> NAME/KEY: misc_feature
<222> LOCATION: (704)..(720)
<223> OTHER INFORMATION: n is a, c, g, or t
<220> FEATURE:
<221> NAME/KEY: misc_feature
<222> LOCATION: (722)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (729)..(730)
<223> OTHER INFORMATION: n is a, c, g, or t
<220> FEATURE:
<221> NAME/KEY: misc_feature
<222> LOCATION: (734)..(745)
<223> OTHER INFORMATION: n is a, c, g, or t
<220> FEATURE:
<221> NAME/KEY: misc_feature
<222> LOCATION: (747)..(755)
<223> OTHER INFORMATION: n is a, c, g, or t
<220> FEATURE:
<221> NAME/KEY: misc_feature
<222> LOCATION: (757)..(765)
<223> OTHER INFORMATION: n is a, c, g, or t
<220> FEATURE:
<221> NAME/KEY: misc_feature
<222> LOCATION: (770)..(771)
<223> OTHER INFORMATION: n is a, c, g, or t
<220> FEATURE:
<221> NAME/KEY: misc_feature
<222> LOCATION: (779)..(782)
<223> OTHER INFORMATION: n is a, c, g, or t
<220> FEATURE:
<221> NAME/KEY: misc_feature
<222> LOCATION: (784)..(791)
<223> OTHER INFORMATION: n is a, c, g, or t
<220> FEATURE:
<221> NAME/KEY: misc_feature
<222> LOCATION: (798)..(799)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (805)..(812)
<223> OTHER INFORMATION: n is a, c, g, or t
<220> FEATURE:
<221> NAME/KEY: misc_feature
<222> LOCATION: (816)..(824)
<223> OTHER INFORMATION: n is a, c, g, or t
<220> FEATURE:
<221> NAME/KEY: misc_feature
<222> LOCATION: (831)..(836)
<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t

<400> SEQUENCE: 47
ttgttgacag cggagcgcaa tcgactatca tatcaaaaag ttgcgctgaa cgttgcgggt    60
atgattataa tttagttgat ttgagctgct tagatttat atttgcagca ccatggtttt   120
```

```
tgtgattttc agcatggaga acataatatt angtagcaat cagccaatca tagggggtgt      180
ttgctatagc tctgcttcac tantgaagta gctttgctgg aggagctgtt ctggaatagn      240
tctgctggtg catttgaagc tgtttttcta gaccatttgg taaaacagct tctcatgata      300
gataaataag gcaaaanggc ctctatccga gttggttagg tggtntgggt agcactcctt      360
aggtcctgag ttcgaatccc agtggaagcg aattttaggc tnaggnttaa aaaatgtnac      420
tcgttggttc ccctggtcgt gtgcacacaa gatggactga cctatggggg ncngatcctc      480 gtntagggc tgngagggct taaatcacga gtaaagatct ggtcnatagg ggatgnaccc       540
tcatgttgca cgngggganna actttcgtga cctntnnnnn tcaggnctnc gattgagctt      600
cttcttaata taataccgtn nnagnnntct tttnnnnnnn nnnngannnn tnnnnnnnnn      660
nnnnnnnnnn nnnnnnnnnn nactacnnnn nnnnnnnnnn nntnnnnnnn nnnnnnnnnn      720
cnncntctnn atcnnnnnnn nnnnntnnnn nnnnncnnnn nnnncgctn nattccgann       780 nngnnnnnnn ntgtgtcnng ncatnnnnnn nnaccnnnnn nnnntacgcc nnnnnncnct      840
gcgctaggag ctccagcgac cccacgccag cacaacttct tcacgttgcc acgcctcccc      900
tcgctgtcac cgcgcgcgcc cctggggcaa attcgactat gctcacatga ggccccacgg      960
agacaagtga gagcagggtg aaggtgcctt tttcagctcc acctcacacc tttgacttgt     1020
gtgagcagaa aaaacgggga cttcacatgt ggagctgcaa cctccctaac cgtttggctg     1080
ttgttcttgt gagactgctt cgggagttgt cccaggagcg gtaacaaacg gcctcttagt     1140
ttataaagta cttcctccgg cccaaaataa atcaattcct agaatcaccc ttagccaaac     1200
tattaagttt gaccaacttc ataggaatgg gtatgtgcac caaataagta cattacgagg     1260
ctgttgcttt gaattaaagc tagttgttcg gact                                 1294

<210> SEQ ID NO 48
<211> LENGTH: 332
<212> TYPE: DNA
<213> ORGANISM: Zea mays
<220> FEATURE:
<221> NAME/KEY: misc_feature
<222> LOCATION: (247)..(247)
<223> OTHER INFORMATION: n is a, c, g, or t

<400> SEQUENCE: 48
gtcaagtccg gcgcctccaa ggtggccgtc aacgacgtcg tcttcaagaa catccacggc       60
acctccaaca cgccggaggc catcacgctc aactgcgcca caacctgcc ctgccagggc      120 gtgcagctca tcaacgtcga catcaagtac aacaggtccg acaacaagac catgtccgtc      180
tgcaagaacg ccatcggcaa gtccattggc atggcgaagg agctcgcctg cgtctgaacc      240
tacttgnatc catcactcac tcttcgtcac ctctctcttt ctcactctcg ccagtctttt      300
tttaggcctc tggcaatctg cgaactttct ta                                   332

<210> SEQ ID NO 49
<211> LENGTH: 776
<212> TYPE: DNA
<213> ORGANISM: Zea mays
<220> FEATURE:
<221> NAME/KEY: misc_feature
<222> LOCATION: (719)..(719)
<223> OTHER INFORMATION: n is a, c, g, or t

<400> SEQUENCE: 49
gcgggcacga cgtgtccaaa ctcaaccacg cgctcgctca aggcacacgc caatccctcc       60
cagcgcaccg ctctcgtcga agcccgcaag tacgttgcct tctacaccct ttcgcccagc      120
```

-continued

| | |
|---|---|
| gctcaggcct tgaagggtcc ctttctgtgt gtagcttgcc ttgaagggtg tccaaacttg | 180 |
| tgttttgttt gctctggatt tctttacctc tctctgggga ggagacaagt tgctgcaata | 240 |
| acgttatgct ctggattctg aatcatgtgc cttcatcgtt aggttgattt tcctgattca | 300 |
| gaaagatgat cgaggcaatc tacgagtacc gaggcgagga tccgctccaa ccgtggctgg | 360 |
| agtaagcgat tctcgatgcc tctctttagc tcgcctcttt cgatttgttc gttcgtggtt | 420 |
| gctaccctag ccgaaagatt gcttatctct tctctgcttc gtccgcgcgc agctgcatca | 480 |
| agtgggtcca ggagtcattc ccgaccggcg gcgacagtgc gtgcggacct tatggcacga | 540 |
| cgagcgctac aaggacgaca tccgctttct caaagtgtgg ctggaatacg tgagtcgtgc | 600 |
| gatggcagct tgattttttt tcctgtagtt ttagtctgtg cagtgaaggc atctcacata | 660 |
| tcattccgct gccgatcttg ttctctttgt aggctgggaa ctgtgctgat gccgaggtna | 720 |
| catacaggtt cctggaggcc aaccagattg gcagggcca tgccatctac tacatg | 776 |

<210> SEQ ID NO 50
<211> LENGTH: 612
<212> TYPE: DNA
<213> ORGANISM: Zea mays
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (593)..(594)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (602)..(606)
<223> OTHER INFORMATION: n is a, c, g, or t

<400> SEQUENCE: 50

| | |
|---|---|
| nnatctctga ttctgttcgc tccaaattaa ttacatgctc ttttctcttt tcaggaggct | 60 |
| tctcaatggc aactgccaac agttcgtgat tagtatacac aagcattatg gtaacaaaga | 120 |
| atcgattagt cagatttgca acagcatata tacctggtac agctaaattt atttcacggg | 180 |
| gtttctttct ttcaggaacn tcagataaac ctgttagtga aacttgaaaa tcatgtatca | 240 |
| tganatgaaa acaacanaag aaaacacata aatacattac acaatggtca atgaaagtta | 300 |
| accttttttg gcatcatgtc tagactgcac cgaagcttgc ttgcttttg gctcctcagc | 360 |

```
cctctgatgc ctacctaatt gagccatgga ataatcacgt ctagtctgtc tttcttgata    420
cttggacang caaaatacta ccagtagcgc nagaactatg aatagcacaa tagcaagaag    480
aacatatcca acagttctga gggttgaagg cttcttcttc ttggatgacg tagaattgct    540
atttcgagca gtagatccac tagaagagtt tgatgctgca ttagatggtg aannagatnc    600
tnnnnnggat ga                                                       612
```

```
<210> SEQ ID NO 51
<211> LENGTH: 755
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (248)..(252)
<223> OTHER INFORMATION: n is a, c, g, or t
<220> FEATURE:
<221> NAME/KEY: misc_feature
<222> LOCATION: (320)..(331)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (388)..(390)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (665)..(671)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (712)..(713)
<223> OTHER INFORMATION: n is a, c, g, or t
<220> FEATURE:
<221> NAME/KEY: misc_feature
<222> LOCATION: (726)..(727)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (740)..(747)
<223> OTHER INFORMATION: n is a, c, g, or t
```

<400> SEQUENCE: 51

```
ngcctgcagn tgcttaaact caccgaaaca aatatatcgg tcccagctgg tatttcatat      60
ccctcttttg ctccattgca cccgcctggg taaatagacg ntcacggcgg cagagttaga     120
aggcatgtac cagcgaaggc aacgcaccct gcttgtcact aaactaattc attgaaaaat     180
agttgtgtgt gctgatcgaa ggatacaatt tgcnaacatc catccacaag tatagaaagg     240
ctgtcatnnn nncaccaagg tctcgataaa catattacca gtaacaagaa cagcgacttc     300
aaccaaacta gtctaaatgn nnnnnnnnnn naccactaca caccntttgt attgctcagg     360
aaagaactta cgacattaca gagaagannn tggtacctgg caacttgtct ggccggagag     420
aacgcctgat taacaatggt ggctgaggat acaagcgaag agcttcaaga ataatcagtt     480
ttatgtacct agaggncaac acaaaggttt catgagagat gcaaattcat ttcaaatgta     540
tagatatagc tagtaatttc agagaagtcg gataccatgg atatgctact gttaataatc     600
tgataatatt ttttatgaaa caataatcct tattgataat atttttatga aacaataatc     660
cttannnnnn ngcaccatac acctatccct caataaatgg aaaatannng anncaattct     720
agatgnntna aaaatnatgn nnnnnnngac atact                                755
```

<210> SEQ ID NO 52
<211> LENGTH: 399
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:

```
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t

<400> SEQUENCE: 52
gatcnggcca ggcactggct acaccgcntt gattggggtc ctggggctcg aaggaatacc      60
accaaacctg ttgaccagga ncttgaaaca ngggaacgaa acggcgtaca gcacgaccag     120
tacaattggt gcagcaataa gccaacccag catctgttgt cgacaatngc agtagtcttn     180
tgtcaatgtc ccagcaaagc aagagtanaa cagngctcct ancatangaa ngagcaggac     240
tgatttgngg aaaggntgtt cactcaccgc atggacgatg ctcatnagca catcctttga     300
ggcatgaccn gtgagaacat tcttcaatgc gtcggcngtc aaggggaagt gcccgctgcc     360
ngtgacggct tcacccaaac gcaagaaagg gacgatcaa                            399

<210> SEQ ID NO 53
<211> LENGTH: 448
<212> TYPE: DNA
<213> ORGANISM: Zea mays
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t

<400> SEQUENCE: 53
agtacaaccc tgacggcgcc atctggggca acaagatcgc gtggggccac gccgtgtccc      60
gngacctgat ccactggcgc cacctcccgc tggccatggt gcccgaccag tggtacgaca     120
ccaacggcgt gtggacgggg tccgccacca cgctccccga cggccgcctc gccatgctct     180
acacgggctc caccaacgcc tccgtccagg tgcagtgcct ggccgtgccc gccgacgacg     240
ccgacccgct gctcaccaac tggaccaagt acgagggcaa cccggtgctg tacccgcccc     300
cgggcatcgg gcccanggac ttccgcgacc ccaccacggc ctggatcgac ccctcggacg     360
gcgcatggcg cgtcgtcatc ggctccaagg acgacgacgg ccacgcgggc atcgccgtcg     420
tctaccgcac cacggacctg gtgcactt                                        448

<210> SEQ ID NO 54
<211> LENGTH: 226
<212> TYPE: DNA
<213> ORGANISM: Zea mays
<220> FEATURE:
<221> NAME/KEY: misc_feature
```

<222> LOCATION: (167)..(167)
<223> OTHER INFORMATION: n is a, c, g, or t

<400> SEQUENCE: 54

```
ggcttgttga agttcttgta ccoctgggca acaatggcgc acgccatgga tgagaagcaa      60
gcatcaagca gcagcgagca gcaatagacg gatggtgatg gagatggaga ctcgggacac     120
ggaccacgcc ggagacgtca aggatggtgg tgctctggtc gacgtgnttc ttggcggaga     180
tggagcaggc ggggaacttg acggcgaagg cgcgctcgaa ctccct                    226
```

<210> SEQ ID NO 55
<211> LENGTH: 398
<212> TYPE: DNA
<213> ORGANISM: Zea mays
<220> FEATURE:
<221> NAME/KEY: misc_feature
<222> LOCATION: (99)..(99)
<223> OTHER INFORMATION: n is a, c, g, or t

<400> SEQUENCE: 55

```
ttttgagtca tcgggtcgat ctgacgattt gctatgggtg ctctgagtac tcgacctggg      60
aactgtgggg cgcttgtagg cggcgcagag ttgggtctng tcgttgtaat gattccatcg     120
gctcgttgcg tagggtttga tctgcctgtc gttttctttt cttttaatta aatttctgat     180
gcacagtcat gtattgatct ggtttggtgt tccttagatgc gtgtaataaa tggggaaaaa    240
accatgtcgt aataaaatca atttattttt aataaaaaaa atctgaattc tggctctagt     300
gaataaatgg atagagcctg gctctaattc tggtaaaata aaaagacaac gagcttaact     360
tcttaattgg tcaattggaa gggttctccg atctaatt                            398
```

<210> SEQ ID NO 56
<211> LENGTH: 521
<212> TYPE: DNA
<213> ORGANISM: Zea mays
<220> FEATURE:
<221> NAME/KEY: misc_feature
<222> LOCATION: (390)..(390)
<223> OTHER INFORMATION: n is a, c, g, or t

<400> SEQUENCE: 56

```
cgtctgcgcg gtcctgcatt gaaaaaaata aacgcatggt tcacataaaa atacgggacc      60
gtaatgctga ctactgtcga atataaaaaa aaagatgtat aggaccatac cggcctaaac     120
atgtccacga caatgtcatc cagaccacca ctaagtcccc tttgcagcct acctgtcccc     180
atgagttcgt tgttgtagtt tagatgactg ctgacagctt ggtgatcaat cctgccatct     240
tgcagagggg ggacaacaca accacctgaa ttgctaccac ccagtgtctg ccctggaaca     300
acagaaccgt ctatgcgaag gttcggcaat gtagagttga cgcctgaatt actaagcgca     360
aggttgttat tcagcatctc tctcgagttn gtgctgcttc cataagcgaa gggcactgct     420
tcctgagtga acggcatcgg aagaccgttg ctggctagtg atgctacttg gtggctctgc     480
atttcatttc ccagcaaagg gatctgactg gatgcttctg t                         521
```

<210> SEQ ID NO 57
<211> LENGTH: 783
<212> TYPE: DNA
<213> ORGANISM: Zea mays
<220> FEATURE:
<221> NAME/KEY: misc_feature
<222> LOCATION: (279)..(279)
<223> OTHER INFORMATION: n is a, c, g, or t

<400> SEQUENCE: 57

```
cgctcagcgc gggcgcgacg tgtccaaact caaccacgcg ctcaaggcac acgccgatcc    60
cgcccagcgc gccactcttc tcgaagcccg aaagtacgtt tccttctcca gtctttcgcc   120
cagcaatggg ggaaaaggag ttgtggtttt gtaactttg tttgctctgg atttcttttt    180
cttgggcctg ggtctgtggg gaggagacaa gttgctgcag taatgcaaat atatatcatg   240
tgtgttcatc gttcggttca tttgcttgat ccaggaagnt gattgaggca atctacgagt   300
accaaggcga ggatccgctc caaccgtggc tggagtaagt ttttctcata gccccttaa    360
ctcgcctttt tcgatttctt ggttcgtgcc aggactggta gctgttctag cagatagatt   420
gttcatttct tctctgattc gtccgcgtgc agctgcatca agtgggtgca ggagtatttt   480
ccgaccggcg gcgagtgctc agggttggtg gtgttgtacg agcagtgcgt gcggaccta    540
ttggacgacg agcgctacaa ggacgacctc cgcttcctca aagtgtggct ggaatacgtg   600
agtgatgctt tgccagcttg attgttttc tctgtagttt gtgtcagtgc agtggaggca    660
cctcatatat cattccgctg ccgatcttgt ccttttttgca ggcggggaac tgtgctgatg   720
ctgaggtaat atacaggttc ctggaggcca accagattgg gcagggccat gcgatctact   780
act                                                                 783
```

<210> SEQ ID NO 58
<211> LENGTH: 201
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t

<400> SEQUENCE: 58

```
aaacngacat ccccaagcaa accgagtgca atacgataca agtagagatg tagaacatca    60
ccttggttag gccggatctt ggtagcgaac actaacaacc ngatttgtca ccctgatctg   120
aaggccatgt atcaaacaca aatcattaga acaattgcaa cncnttcgna ttactcatgc   180
atataaggaa acaatcacgg a                                             201
```

<210> SEQ ID NO 59
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t

<400> SEQUENCE: 59
gtacaattaa tgctcgtaag aaattgcaat aaataaaata aaaaagagaa atttactatg       60
nttcattgtt cttgtaccga aatggcctgg tcggccctcn tggcctagcc caatagtctg      120
t                                                                     121

<210> SEQ ID NO 60
<211> LENGTH: 669
<212> TYPE: DNA
<213> ORGANISM: Zea mays
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (81)..(82)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (601)..(602)
<223> OTHER INFORMATION: n is a, c, g, or t
<220> FEATURE:
<221> NAME/KEY: misc_feature
<222> LOCATION: (621)..(624)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (630)..(634)
<223> OTHER INFORMATION: n is a, c, g, or t
<220> FEATURE:

<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (643)..(655)
<223> OTHER INFORMATION: n is a, c, g, or t
<220> FEATURE:
<221> NAME/KEY: misc_feature
<222> LOCATION: (657)..(658)
<223> OTHER INFORMATION: n is a, c, g, or t
<220> FEATURE:
<221> NAME/KEY: misc_feature
<222> LOCATION: (661)..(666)
<223> OTHER INFORMATION: n is a, c, g, or t

<400> SEQUENCE: 60
ttgcttcatc gacggccggg acggcgcgtc gtccccggtg cacatgaccc cgagcttgaa     60
canggccacg gcgtcgtcga nntanacggc cctgtcctgg atggtctcgt ccacgacgtc    120
gtggagaggg nnccccgcct tgtacctccg ccacgccac tccaccaggc agcagtcagc    180
ggcgtccttg ctgctgtcgt tggctaccct cccggtcgcc agctccagca gcaccacgcc    240
gaagctgtac acgtctacct tctggttcac cttggcnccg cgtccgtact ctgcatccaa    300
ttccaaccat agcagatcag cagagtgtcg attcatttna gcctcctgag aagaccagaa    360
gggttggccn gctggtgnct gncgnacggc ngattaagaa cgcacctgga gccatgtatc    420
cgaaggtgcc acngacggcg gacacggact cgggctcgcc ggacttgagc aggatccggg    480
cgagcccgaa gtcggcgatc ttggcacgga accccgggtc gagcaggatg ttgctggact    540
tgacgtcccg gtgcatgatg ggctgcgcgc actcgtcgtg catgtagctg agcccctcg    600 nngcgtcgat ggcgatgccc nnnngngtcn nnnngtncag cgnnnnnnnn nnnnngnngt    660 nnnnnnggt                                                            669

<210> SEQ ID NO 61
<211> LENGTH: 393
<212> TYPE: DNA
<213> ORGANISM: Zea mays
<220> FEATURE:
<221> NAME/KEY: misc_feature
<222> LOCATION: (125)..(125)
<223> OTHER INFORMATION: n is a, c, g, or t

<400> SEQUENCE: 61
tcagattaac atatgtgctt tacaaaattt tctatcttgt ttatttccta gtaggaactc     60
caaagcatga gtagaaaagg aattgatttg gttttgtta gttattattg aaagagaaat    120
caacngtttg ctagtaatgt tgtgactcaa tcatttctgt cggtgtacaa tcatattgca    180
caaaattatt tacagccttt gtaaatgcaa gcatattagt tctgtttgac taccttgatg    240
ggttctacac ttgtactctg ttgttatttt acctttgatg gaagtttctt tgtaaggaaa    300
tttctatagt aacttctagc ctatatgtca tagaacctct gttgcaataa tacctttctt    360
tcatcagtta caaacccaaa tgcgttctaa aga                                 393

<210> SEQ ID NO 62
<211> LENGTH: 201
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 62
agtgagagcc aaggaacata agacanagtg atcaaccata ggtttagcaa agcaatatgt      60
tcatggtgat cnactagacc cttgattttg gcgtacatat ngatatattg actctagttc     120
ttagtggtgg ccttgtcaac tatcttgtgg gtgcanctcg naagggtgaa catagggcat     180
ggggaantga tatcnagccc a                                               201

<210> SEQ ID NO 63
<211> LENGTH: 467
<212> TYPE: DNA
<213> ORGANISM: Zea mays
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t

<400> SEQUENCE: 63
ttctattgat tgcagtttta tattgtgatg ttgtggaggc atatgagtac cattttttt      60 tcttcttaat atagcactag tgttctgata ggcgcaggaa atcaacagct cgtgcagatg     120
ggtttcttcg agcaccctct cttgtcgaca accttgttat attttagaag ttatttgttt     180
gacatccatc catccatctt ctctccaaat ttaggtcgga tgtacgagct ctatcgacgt     240
tatanttgtg cctccgcgag tccgagctga cccagcagcg agtcaggtac cagcagtaga     300
gttgtttgtt ttgtcgtccc atactgaaaa tntatcatct atgcacatct cttgcctgat     360
ccccctttng ccttctgtat cgtggttcag aatccagcag ttgttgccag gaggatggtt     420
ctgaagtcac cacgcctaag gatcaaaagg cntgtcgtag tggcaca                  467

<210> SEQ ID NO 64
<211> LENGTH: 201
<212> TYPE: DNA
<213> ORGANISM: Zea mays
<220> FEATURE:

```
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t

<400> SEQUENCE: 64
agtgactata agaataatgg aataaacgat gacccagtgt gtgtatgatt tccgttctga    60
agaacaacac atcccttgca ggattgttgt tcagtagatt ntacttgtac cgcggctttg   120
gagttccnca aaggacttta cttgttcaag aacttcttct ctnacaggaa ataacatgtg   180
agtgcagtcc ntgcttttat c                                            201

<210> SEQ ID NO 65
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 65
cgccgcgtcg gcgcgccttt ccgctggata tcccttgcca ccgccgcaaa ctgcttgcag    60
cgtctttttg cattattgcc tacacaaggc agaagacacg ntgattagaa tgcagcacgt   120
acgtgatatc agagtacaac cacctacaca atggacacgc agagatctct tccgtttctg   180
ggcacagngc tttccatggg c                                            201

<210> SEQ ID NO 66
<211> LENGTH: 201
<212> TYPE: DNA
<213> ORGANISM: Zea mays
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t

<400> SEQUENCE: 66
agaattgcta ccatgcatnt tggggtcctg ctatgtattg ggttcantct atggagaata    60
gaatcaagga actgagttgg gaagcgcttt gtgccaccct naacactaga tagatcagca   120
taacctgctc attagacatt tttatcacat ccatcaaacc aacttagtaa ccnaatatgt   180
```
ggaacaattt gaccaactta t                                                   201

<210> SEQ ID NO 67
<211> LENGTH: 201
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 67 ctgnttttc atatctngac attgtgattt agtaagttgc tcatatattc tactacattc          60
tttagcacgc tttccncaag gggggcagtt ttaggcattc ntactgtggt tctgaatgaa        120
gagataaatg atactccctc attcctgaag tctctgaccg aatttataga aattagtacc        180
aacatttctc tctncaaata a                                                  201

<210> SEQ ID NO 68
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t

<400> SEQUENCE: 68
ttagagacta atctttaacc cctctaacca aacaccatct aaattaaatt aggtcgcaat         60
acatgattta ggactccttg gagttgctct aacgttccca nttgtcggac gccttcagta       120
tcnggttggn catttaaca aagcaagtgc attcgagaga cccatttta caagttcgat         180 gagagtcggc ctattttaga g                                                  201

<210> SEQ ID NO 69
<211> LENGTH: 201
<212> TYPE: DNA
<213> ORGANISM: Zea mays
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (101)..(101)

```
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 69
aaagctacat ccgaattgct gaattcatga tatgttcagc agttgcaact tcttcgcctc    60
atattcagna gggcactctg tccaattata caagctagat nttcaaattt tgtcacgata   120
ccactcattt gttgcaaaca ctacactaat gtcaccctgt tgatncaaaa gtctccaaca   180
tgagnaacat tttgcagtcc a                                             201

<210> SEQ ID NO 70
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 70
atgccatcta gttgctcctt ctccacaagt ctgaaaaaca atgaacttat tcctatatga    60
attcttaata gaggtccttc tatatgacaa acagctctcc nttgtcgtag agggagggac   120
tgtagcatac ctgtattgaa gaactgcatg ttgcttgctg caggagggat gatctgtggg   180
gacatctgca actttccttt c                                             201

<210> SEQ ID NO 71
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 71
gaagtttgaa acaatggaat ctacatttag atttccgcta aagcttttgt cttccctatc    60
agagcttaag tttcttatta ataatgatag ggtaattcta ntagcacgat caccaaggtt   120
gtgtttggat tggggactta gaggatggga tggttccatt cctgttttg aggatgcctt    180 tagtttggtt gagagggtct g                                             201

<210> SEQ ID NO 72
<211> LENGTH: 854
<212> TYPE: DNA
<213> ORGANISM: Zea mays
<220> FEATURE:
<221> NAME/KEY: misc_feature
<222> LOCATION: (5)..(12)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t

<400> SEQUENCE: 72
```

-continued

```
tgcannnnnn nngctgttaa tctcacatcc tgctctgtcc agaaccctc ctcagccatg      60 gcataactca aatcaagaat cttctcaaag agtgtcctct tgtttgacct ccactcattc    120
aggaacttga tcaaccgacc aacattcaca tgaagatcct tctcttctgc aaatgggtat    180
gcctgaatat agtccttcct gtaaatagta ggtggataga aagccacata tccaccaatc    240
tcccacaaga tccgttgcgc ccagtaccca cggatcacnt ctgctgccat tgagctcaca    300
gacactggca tcatnagccc ccagaaagca ggtgactgga acaatgtatt gaacgagttc    360
actggtgcca tcatgccctg aggtagtgcc accttcgggg cttccgaatc aaacctcaga    420
tcgaacgccg aagttggtgg ttttctagtg aagtagaaca ccgcatctac atctggcaac    480
ccgtccgaca gcccctgctg aatgaattgc cggccactga agacctcggt gtagaacacc    540
tcatgggcga cctccccaac cttatcgagc ggcagccccc ttggccagac cgaccgctgg    600
ccgaagtgca cgtaggggtt caccactgtg cgattgggat ccgcgtggct gtactggagc    660
agcactgggt ggttggtgac tccagatccc aaatccacgt cgaaatgctt ccccagatcg    720
ttcccgggca cctcggcgcg gtcgtcggcg tcgaagatca ccttggcccc gtgctggatg    780
gcgaagaggt agcccgccgt cttgcggacg tgggagccgt agggcaggaa gtcgacggag    840
cggtatccga gctg                                                      854
```

<210> SEQ ID NO 73
<211> LENGTH: 440
<212> TYPE: DNA
<213> ORGANISM: Zea mays
<220> FEATURE:
<221> NAME/KEY: misc_feature
<222> LOCATION: (265)..(265)
<223> OTHER INFORMATION: n is a, c, g, or t

<400> SEQUENCE: 73

```
tacactggta tatgatacac tgaaacccaa aaaggtgtca ggaggcataa ttatacatgt     60
aaaccaaaga agaaaaaact aggtgatggt taccagctct acactatcgt tgtcttctca   120
ttccccggtt atcaacatga aatacaccct ggcatgccga tgcgatgata gttatgtgca   180
acttgcaagt ccactgcagg ttaagatttt gctaaatttg aaatgctgca aaatggatgg   240
gtgcaatata tcagatatgg tatcnaaaga ataccacaag cctatgaaca aaaagccaag   300
ccattagaag cctccgtcaa taagtggaca tcatcaagaa caatatcagc agggtcccca   360
atccaaagtc tatccctcca ccgaaacttt atcctcagct cacatactgc acaagtcccg   420
tgccagattc tcgacaacta                                                440
```

<210> SEQ ID NO 74
<211> LENGTH: 201
<212> TYPE: DNA
<213> ORGANISM: Zea mays
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (164)..(164)

<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t

<400> SEQUENCE: 74
gcggcagcat gcggacgatg gatttgagct cctccacccg atgcaccgtc gatacacgcc    60
anaggttcgg ctcgccggag tcggaaaggt ctcccgtcgt nagtacagcc gctcggtcca   120
agaaccttca cgtgggagga caataaacaa gtaacnacct ctgnaatgca catganacca   180
acgtctgaag taataagcaa g                                             201

<210> SEQ ID NO 75
<211> LENGTH: 201
<212> TYPE: DNA
<213> ORGANISM: Zea mays
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t

<400> SEQUENCE: 75
gtatgccttg gtaaggaatc ctacatcngt gagtgattca agagtacaat tttaggaata    60
aaggcgatct atatggtttc ttttgaaaat ccattgaaag ntccgattac taaagatgtg   120
aaaatggggg agaaaagttt gtttcaagaa ttgttcaact tttactcacc cgattttaaa   180
atgtaagana ttttagcttt t                                             201

<210> SEQ ID NO 76
<211> LENGTH: 760
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (587)..(589)
<223> OTHER INFORMATION: n is a, c, g, or t
<220> FEATURE:
<221> NAME/KEY: misc_feature
<222> LOCATION: (614)..(620)
<223> OTHER INFORMATION: n is a, c, g, or t
<220> FEATURE:
<221> NAME/KEY: misc_feature
<222> LOCATION: (622)..(625)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (641)..(644)
<223> OTHER INFORMATION: n is a, c, g, or t
<220> FEATURE:
<221> NAME/KEY: misc_feature
<222> LOCATION: (648)..(650)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (655)..(659)
<223> OTHER INFORMATION: n is a, c, g, or t
<220> FEATURE:
<221> NAME/KEY: misc_feature
<222> LOCATION: (668)..(670)
<223> OTHER INFORMATION: n is a, c, g, or t
<220> FEATURE:
<221> NAME/KEY: misc_feature
<222> LOCATION: (672)..(673)
<223> OTHER INFORMATION: n is a, c, g, or t
<220> FEATURE:
<221> NAME/KEY: misc_feature
<222> LOCATION: (677)..(687)
<223> OTHER INFORMATION: n is a, c, g, or t
<220> FEATURE:
<221> NAME/KEY: misc_feature
<222> LOCATION: (690)..(691)
<223> OTHER INFORMATION: n is a, c, g, or t
<220> FEATURE:
<221> NAME/KEY: misc_feature
<222> LOCATION: (693)..(700)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (707)..(711)
<223> OTHER INFORMATION: n is a, c, g, or t
<220> FEATURE:
<221> NAME/KEY: misc_feature
<222> LOCATION: (716)..(726)
<223> OTHER INFORMATION: n is a, c, g, or t
<220> FEATURE:
<221> NAME/KEY: misc_feature
<222> LOCATION: (729)..(738)
<223> OTHER INFORMATION: n is a, c, g, or t
<220> FEATURE:
<221> NAME/KEY: misc_feature
<222> LOCATION: (740)..(758)
<223> OTHER INFORMATION: n is a, c, g, or t

<400> SEQUENCE: 76

```
ggccngactg ctcctgcgaa gacgangctg acatcgagta cgacagcagc cgtatctggg      60
ttctggacnc gcccaacata ccaaagcctc caccagagac ggagaggcta gtgattatgg     120
gcggtgacta caccagaatg gacacgtatt acgtcatgcc caatgggaag cgtgcgaggt     180
gtgctggtga cgtggacaag tttctggang caaatccagc gtacaaaagc cgcatatctg     240
cttcggattt cgactttgca ccgcccgagg ttgttgagga gactgttgtt tctcacaatt     300
```

```
ttctgcctct gcaaggttgc caaggccaag aaacaggaga aggcagagag gcacacaaaa    360
taggtgaaag cagagaggca tcgatgctct gaactgtgcc tgtgccctgt gctatgtagg    420
tgatagtccg ctcaagatca cgtcacgtct cgttcctatc tagtacggtt gtctatctcg    480
gctgaagtta atgtagtagg tcttcttgcg tgttaattcc tngggaatat atgagatgtt    540
taataattag ttgcttaggc cttaaaactg tgcttcctta acttttnnnc ttcagtcatc    600
tcgtatatgc acgnnnnnnn cnnnngctag cagcntagnc nnnnactnnn cancnnnnna    660
tcatagcnnn anntctnnnn nnnnnnngcn ngnnnnnnnn ctnacannnn ntacannnnn    720
nnnnnngann nnnnnnnnan nnnnnnnnnn nnnnnnnnat                          760

<210> SEQ ID NO 77
<211> LENGTH: 553
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (73)..(78)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (345)..(347)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 77
tgaatgtgtc gagggcctgc aaaatttant tttggtaaag cttaggacag aagcaaaatg     60
catagatatc cannnnnnaa atagcaaatg tttttatacg atntaancat taagtaaatc    120
catttctctt gacacaacta caggttattg tatatgagca tagcgttgat catanattct    180
taccttgttt agatagttca tctgtgttac natgcacaag attacaacaa atgagaacac    240
ccatgtttgt gaatanacaa gctggttcat ccctgaaaat gtcaccttca aggctatccc    300
aagagctttg acactcatga cctggcaaan caaagacaat acagnnngag agtatttatg    360
tcctagcntt cttgagaata gttatgtgaa ttcactgga aagaactgtt aatcatgaga    420
agcataccga taaagatcca acaagagaac atatgccaat atataccatg atatgtgtct    480
```

```
gcccatactg agggacaaaa tggcatatga gcacaaaagc tgctgcaaat acaacagctg    540
catagaatag gaa                                                      553

<210> SEQ ID NO 78
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 78
cagtttggta cttacttcca ctattgctga tactaagggg atgttttgta ctcttactaa     60
agtttagttc gtatcacatc gattgtttaa atgtcagcta ngaatattaa atatagttta    120
attataaaac taattacaca tatgtaaaat taactagcat caccacgtta ttcagatatt    180
cctttcaatg atatcaagga t                                             201

<210> SEQ ID NO 79
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 79
ctttcacatt aagagtagaa ccgaaacata aacttcact tttatagaaa ttaattttca      60
agcccgacat ttgttcaaaa aacagcaata taaatttaag nttttagct ccagttagat     120 catcttggag gagaaacacc gtgtcatcag catattgaag acatgctacc catctttcca    180
taatgtgagc gataagacca a                                             201

<210> SEQ ID NO 80
<211> LENGTH: 608
<212> TYPE: DNA
<213> ORGANISM: Zea mays
<220> FEATURE:
<221> NAME/KEY: misc_feature
<222> LOCATION: (91)..(91)
<223> OTHER INFORMATION: n is a, c, g, or t

<400> SEQUENCE: 80
tgtccgtcag ctccgccgcc tcatccagcg tcaggttgtg gttgcacccg gtgaaggcca     60
gcatgtcctt ctcgtatctg acgacgatca nggcaaacca atgcaagttc atccattgat    120
tgatctgcag ataatagccg gccaccgaac gctgtgaact ctcagctacc tcaggtgaag    180
cgcgatgtaa tgctgggact cgtttctcag ccgatcaacc agcgtgttgc cgagctcttc    240
gatctccttc ctgtactgga gcgcctcgta gttcgcgcgg caccgaagct tttgcagcga    300
aggagcgagg ccgttgttca cgatccgtga atccgtgtgt gtaaacctca ccactttgaa    360
cttcctcagg attttcgcaa agtctctgta gaaggaagcc tggaaaacgg agctggcgat    420
gcatcagcct attcagtacg tattcggtta tcctctaagc tgctgcaact gcaatgcaat    480
ccagtagagc aaacaagttg ttgactcgta ccctggacca ggaggtgggc gctctcacgt    540
acggtttcac ccttctgtaa tgtggtggga gggaatccac gatcacaatg tcttccttca    600
acgactcc                                                            608
```

<210> SEQ ID NO 81
<211> LENGTH: 602
<212> TYPE: DNA
<213> ORGANISM: Zea mays
<220> FEATURE:
<221> NAME/KEY: misc_feature
<222> LOCATION: (8)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t

<400> SEQUENCE: 81
aggatccnnn nnngnagcaa tttcgaccag ggaagctcat taacagnaaa tgatgccaca      60
gccagtgaaa ttgaatgtca cagactccaa atggctgcaa taaatgatta tggatttggt    120
aaacctgaga ttccttctag ttcctcaatg ccattttttct tggctgttga tcctcaacaa   180
ctgaaattga gaaatgagac aaatgtttct tcaacatctt ccaacattcc ttcagattct    240
gcatcaccaa acttgaaaaa tggcacggat cctcttttga tgccatttaa ttcctacatg    300
gcagattgga gcagcgataa gataacttac accactctga acactccaaa aataagcaca    360
gaacttccag gtcagtatgc atcnctttct tctattatta gctaaatcaa tttagctgac    420
aacaaaaact taaccatgca gtcaagttac accatgacaa agtagtagc tttgaagcac     480 caaacctgaa ggagcatgaa tcagtctttg caacacatga aatgacggta gaagcaacaa   540
gaaaagaaga cgaacacaca tcaaaatcta gttttacttc ctacaatgga gtaccagata   600
ca                                                                  602

<210> SEQ ID NO 82
<211> LENGTH: 591
<212> TYPE: DNA
<213> ORGANISM: Zea mays
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t
<220> FEATURE:
<221> NAME/KEY: misc_feature
<222> LOCATION: (44)..(47)
<223> OTHER INFORMATION: n is a, c, g, or t
<220> FEATURE:
<221> NAME/KEY: misc_feature
<222> LOCATION: (77)..(79)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t -continued

```
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (348)..(349)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (522)..(524)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (552)..(554)
<223> OTHER INFORMATION: n is a, c, g, or t
<220> FEATURE:
<221> NAME/KEY: misc_feature
<222> LOCATION: (556)..(560)
<223> OTHER INFORMATION: n is a, c, g, or t
<220> FEATURE:
<221> NAME/KEY: misc_feature
<222> LOCATION: (562)..(566)
<223> OTHER INFORMATION: n is a, c, g, or t
<220> FEATURE:
<221> NAME/KEY: misc_feature
<222> LOCATION: (570)..(575)
<223> OTHER INFORMATION: n is a, c, g, or t
<220> FEATURE:
<221> NAME/KEY: misc_feature
<222> LOCATION: (583)..(589)
<223> OTHER INFORMATION: n is a, c, g, or t

<400> SEQUENCE: 82
```

```
cnngcgcctn nnnttctaga acaaggcgag tagcacgcct ttannnnccc ggctcgcctt      60
actacctaag cgtctcnnng gcgacgcttg aatactatgt atatactttg tttcaatagt     120
taacctggta gtttggattt tttttnaaat tctagctaac aatttgttta atacatatgc     180
tgaactcttg ttaaggtgcc nttaaactgg aaggattaga nanggcaaaa gctagtggtg     240
cntgccagct tgttgtgaag natctgaaag aataatttgt tggtgaatat acatacccct     300
gcttgngtgc tggtgcaatt natgaaagaa agtatttgct ggggantnna atggctaggc     360
ctgttattgc taaggtaaag ttgctctggt aattacattt tttnacatat aatnaccaaa     420
aatgcatcct attttcttaa aagtagatac tacttatttt cttgagatct aatngacatt     480
atngcttaca gtatngttta gtagtgtgca catgcgcatg tnnnaacaca ttattagtat     540
tataattana annncnnnnn annnnntgan nnnnntgatg tgnnnnnnng a              591

<210> SEQ ID NO 83
<211> LENGTH: 201
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t

<400> SEQUENCE: 83
aganacgcaa acgtnnacat accttcatag ttcttaaggc tatatcccat gctttgatga      60
cagcgccttg tccaatttca aatgagaaaa tagagttatc ntcatgggtg gtatcgaaaa     120
cttcaccagt ctcagcaagt gtaccttcgt aatgaactat agacaaggta aaatggtaan     180
tattcatatt tncatgactt t                                               201

<210> SEQ ID NO 84
<211> LENGTH: 561
<212> TYPE: DNA
<213> ORGANISM: Zea mays
<220> FEATURE:
<221> NAME/KEY: misc_feature
<222> LOCATION: (140)..(144)
<223> OTHER INFORMATION: n is a, c, g, or t
<220> FEATURE:
<221> NAME/KEY: misc_feature
<222> LOCATION: (147)..(148)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
```

```
<222> LOCATION: (335)..(335)
<223> OTHER INFORMATION: n is a, c, g, or t
<220> FEATURE:
<221> NAME/KEY: misc_feature
<222> LOCATION: (437)..(438)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t

<400> SEQUENCE: 84
acagaaaatt aagttataga tatactgaca gttataccgt acaaagaagg atcttttcta      60
ttaagtcaac ataaaattca aaaatattac taaatgtcaa cataaaattc aaaaatatta    120
ctaaatgtca acataaaatn nnnnatnnta aaattcatta ctattagaag tataacaaat    180
ggtgcaagga tagtgtcaat ttaaactagg caaagtatat aattgatcag atagtagaaa    240
ttcaagacgt gtntacatat gcagatcaga caanattcgg atagtatacc acagtatgta    300
cagtcaatat gcgctagtct ctacacaaac tcaantggca gaatcaatat gcagaacttt    360
gattgatgtg cattaatgaa aaaatcattt ggctaacaat taatcataat tatgcaacaa    420
attagcagag gcaatgnntt aaccatgcca aagcatttga angacaagct accnagcaat    480
atttttgttt tatcacaata aagttccaca tttacaaacc tcatcttcct gaggacgccc    540
gccatctcct ctctcttctt c                                              561

<210> SEQ ID NO 85
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 85
actcaccatg atttttaggg catatatagg cactatatat acctatgcat ttcacatgac      60
catccactag ctaatatatt aattggtgac cgtccttgtt nccttacgtg ttcaagatgt    120
tcctcaacat ttgcaggaaa atgtaggcac gtaggacacc gtacctttgg agggacgacg    180
gcattgcaat ttgcatgtgt a                                              201

<210> SEQ ID NO 86
<211> LENGTH: 201
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
```

<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 86
aacntctngg atganatctt tatgagacaa naggaatcga tcaaattagg gaattattaa      60
tcttgtaaag aatacaacaa acacggatat cattctaaca ncgtgccgcc agcacaacgt     120
atctaaaggt gatgccaaag gattgagaac caaaatgatt cnagacganc ccttgtggtg     180
ttagangctg ntgnattagt t                                                201

<210> SEQ ID NO 87
<211> LENGTH: 201
<212> TYPE: DNA
<213> ORGANISM: Zea mays
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t

<400> SEQUENCE: 87 gtcccngta ggatccgcaa tcctatcaac ccaccagatc ctgatcccca acaacaggta      60
ctacgattct cacacgagga tccatcttat ttggcccttt ntttgtaacg gtcgtagaca    120
attatgagaa actcaaacta cntgaccagg caggtagctg caataatgaa aaagtaaatt    180
aaagatttaa taggtttgtt t                                                201

<210> SEQ ID NO 88
<211> LENGTH: 804
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t

<400> SEQUENCE: 88
tttgcatgcc tgcagccgcc tccttgagca catgcgagtt cacttcccng accttggcgt      60
cacccaatcg gactgcgagg agataagctg gatccagtcc accgtgtact tcgccttcta    120
ctcgagctcc aagccactgg agctgctcct ggacaggagc ggcgagacgc ccagatacgt    180

```
caaggccaag tccgactacg tgcaagaacc catcccacgg cacgtgtggg agagaacatg      240
gtcatggctg gagaagcccg aggccgggct gctcatcctg daccccctacg gcggccggat     300 gggcagcatc tctccgtcag cgacgccgtt cccgcaccgg aaggggaacc tgtacaacct      360
ccagtactac tcgtattggt tcgagaatgg cactgcggca ttggagaagc ggatgagctg      420 ggtcagggg ctgtacgagg agatggagcc gtatgtgtcc aagaacccaa gaactggata       480
tgtcaactac agggacctgg atcttgggac gaacgagttg gaggacaatg tgactagcta      540
cgccagggcg aggatctggg gggagaagta tttcaaaggc aattttgaga ggctggcagc      600
tgtgaaggcc atggcggatc ctgatgactt cttcaggaat gagcagagca tccctcctct      660
tcccgctgca aaaggatggg gcttcatttg agtggtcgtt tgtttcgtag ctttgtggtg      720
gtggatttct tggctacatt tgtgaattgt gaacaccggt gaggaattgc atgggtgaag      780
tgtaaaatca cttttggatt tcgg                                             804
```

```
<210> SEQ ID NO 89
<211> LENGTH: 434
<212> TYPE: DNA
<213> ORGANISM: Zea mays
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t

<400> SEQUENCE: 89
```

```
aaagttgttt tctttgttcg atgaactaaa taatgagtaa atttcagtga actatgtgac       60
tggtcctaaa gataattta gcttaaccca tatccaaaac cacacgtgtg tccatattac       120
cacgaactac gctttgtaac tagaataaca acattgattt ggatgtggac tgacatactg      180
ggtccattgt aaaacagttg cagctcacag actaacagtg tcntatactc atatatgtct      240
aggcccaata tgtcattgac atttgaacta acagtgttag ctaacacgtt cattttntct      300
atcatatgaa atgaacaaat attatgtagc attgagcctt tgagaaattt gttcatattt      360
ttttgataat ctagactata tatatatcgt ttagttatta ccagtaatta ctgaagatcg      420
ttcagtaatt acca                                                        434
```

```
<210> SEQ ID NO 90
<211> LENGTH: 25
<212> TYPE: DNA
<213> ORGANISM: Zea mays

<400> SEQUENCE: 90
ccaacagttg ttaagaccgt tatcg                                             25

<210> SEQ ID NO 91
<211> LENGTH: 25
<212> TYPE: DNA
<213> ORGANISM: Zea mays

<400> SEQUENCE: 91
actggaaatg agtccgtgtg ttatt                                             25

<210> SEQ ID NO 92
<211> LENGTH: 25
<212> TYPE: DNA
```

```
<213> ORGANISM: Zea mays

<400> SEQUENCE: 92
gggtcgaaaa gttttggttc ttgtg                                    25

<210> SEQ ID NO 93
<211> LENGTH: 35
<212> TYPE: DNA
<213> ORGANISM: Zea mays

<400> SEQUENCE: 93
gcgtgattct aggtaaaagt ttatgtttac ataat                         35

<210> SEQ ID NO 94
<211> LENGTH: 25
<212> TYPE: DNA
<213> ORGANISM: Zea mays

<400> SEQUENCE: 94
gcaacactag ataagcaact gcaat                                    25

<210> SEQ ID NO 95
<211> LENGTH: 23
<212> TYPE: DNA
<213> ORGANISM: Zea mays

<400> SEQUENCE: 95
caatacggtg ggtctggata tgg                                      23

<210> SEQ ID NO 96
<211> LENGTH: 24
<212> TYPE: DNA
<213> ORGANISM: Zea mays

<400> SEQUENCE: 96
cctctaaggt gaagaccgtt gtta                                     24

<210> SEQ ID NO 97
<211> LENGTH: 22
<212> TYPE: DNA
<213> ORGANISM: Zea mays

<400> SEQUENCE: 97
gcaagaaggt gatccgatca ac                                       22

<210> SEQ ID NO 98
<211> LENGTH: 32
<212> TYPE: DNA
<213> ORGANISM: Zea mays

<400> SEQUENCE: 98
actactgtag aagtacaaac caattttgtg at                            32

<210> SEQ ID NO 99
<211> LENGTH: 25
<212> TYPE: DNA
<213> ORGANISM: Zea mays

<400> SEQUENCE: 99
cgcatggcag aaacaaatac ataga                                    25

<210> SEQ ID NO 100
<211> LENGTH: 24
```

```
<212> TYPE: DNA
<213> ORGANISM: Zea mays

<400> SEQUENCE: 100
gcagcacgca gatcaaattt acac                                           24

<210> SEQ ID NO 101
<211> LENGTH: 25
<212> TYPE: DNA
<213> ORGANISM: Zea mays

<400> SEQUENCE: 101
tcttctgagt catttcatgg tgtgg                                          25

<210> SEQ ID NO 102
<211> LENGTH: 22
<212> TYPE: DNA
<213> ORGANISM: Zea mays

<400> SEQUENCE: 102
aaatcttgtg actcgtcctg ca                                             22

<210> SEQ ID NO 103
<211> LENGTH: 23
<212> TYPE: DNA
<213> ORGANISM: Zea mays

<400> SEQUENCE: 103
tagcagggta tgttacgcag tga                                            23

<210> SEQ ID NO 104
<211> LENGTH: 25
<212> TYPE: DNA
<213> ORGANISM: Zea mays

<400> SEQUENCE: 104
agtcttccaa ctctccttct caact                                          25

<210> SEQ ID NO 105
<211> LENGTH: 15
<212> TYPE: DNA
<213> ORGANISM: Zea mays

<400> SEQUENCE: 105
gggcgcggag gttct                                                     15

<210> SEQ ID NO 106
<211> LENGTH: 21
<212> TYPE: DNA
<213> ORGANISM: Zea mays

<400> SEQUENCE: 106
cacgggtcat tggcaatctc t                                              21

<210> SEQ ID NO 107
<211> LENGTH: 25
<212> TYPE: DNA
<213> ORGANISM: Zea mays

<400> SEQUENCE: 107
gggaggaaaa caaatgcttg aaagg                                          25

<210> SEQ ID NO 108
```

-continued

```
<210> SEQ ID NO 109
<211> LENGTH: 22
<212> TYPE: DNA
<213> ORGANISM: Zea mays

<400> SEQUENCE: 108
aaaggaagct ggagctcaag ag                                              22

<210> SEQ ID NO 109
<211> LENGTH: 21
<212> TYPE: DNA
<213> ORGANISM: Zea mays

<400> SEQUENCE: 109
tggagtatgg caacggatga c                                               21

<210> SEQ ID NO 110
<211> LENGTH: 19
<212> TYPE: DNA
<213> ORGANISM: Zea mays

<400> SEQUENCE: 110
gcgcaggact acctttgca                                                  19

<210> SEQ ID NO 111
<211> LENGTH: 29
<212> TYPE: DNA
<213> ORGANISM: Zea mays

<400> SEQUENCE: 111
ggtagtatat gtgcattcat cgtttttca                                       29

<210> SEQ ID NO 112
<211> LENGTH: 26
<212> TYPE: DNA
<213> ORGANISM: Zea mays

<400> SEQUENCE: 112
ggtttggtaa gttctgcagc taaaat                                          26

<210> SEQ ID NO 113
<211> LENGTH: 20
<212> TYPE: DNA
<213> ORGANISM: Zea mays

<400> SEQUENCE: 113
ccttgagggc accaaagaca                                                 20

<210> SEQ ID NO 114
<211> LENGTH: 18
<212> TYPE: DNA
<213> ORGANISM: Zea mays

<400> SEQUENCE: 114
cggctgtgcc caaacaac                                                   18

<210> SEQ ID NO 115
<211> LENGTH: 21
<212> TYPE: DNA
<213> ORGANISM: Zea mays

<400> SEQUENCE: 115
ccgcatcagt gcgtatttac g                                               21
```

```
<210> SEQ ID NO 116
<211> LENGTH: 19
<212> TYPE: DNA
<213> ORGANISM: Zea mays

<400> SEQUENCE: 116
cccaaagcgg aacgtgatg                                                19

<210> SEQ ID NO 117
<211> LENGTH: 21
<212> TYPE: DNA
<213> ORGANISM: Zea mays

<400> SEQUENCE: 117
tccagcaagc ataggcaaca t                                             21

<210> SEQ ID NO 118
<211> LENGTH: 31
<212> TYPE: DNA
<213> ORGANISM: Zea mays

<400> SEQUENCE: 118
ggtccagtgt tttataaaga ggaataagtc a                                  31

<210> SEQ ID NO 119
<211> LENGTH: 26
<212> TYPE: DNA
<213> ORGANISM: Zea mays

<400> SEQUENCE: 119
ctctttgtac ccttgacagt gtccta                                        26

<210> SEQ ID NO 120
<211> LENGTH: 26
<212> TYPE: DNA
<213> ORGANISM: Zea mays

<400> SEQUENCE: 120
acctatgtca tgttctacgt gctcta                                        26

<210> SEQ ID NO 121
<211> LENGTH: 25
<212> TYPE: DNA
<213> ORGANISM: Zea mays

<400> SEQUENCE: 121
agcccactga atatggaatc attag                                         25

<210> SEQ ID NO 122
<211> LENGTH: 21
<212> TYPE: DNA
<213> ORGANISM: Zea mays

<400> SEQUENCE: 122
cagcttcgcc cagttacagt t                                             21

<210> SEQ ID NO 123
<211> LENGTH: 19
<212> TYPE: DNA
<213> ORGANISM: Zea mays

<400> SEQUENCE: 123
ctcctgaggt caccacgtt                                                19
```

<210> SEQ ID NO 124
<211> LENGTH: 27
<212> TYPE: DNA
<213> ORGANISM: Zea mays

<400> SEQUENCE: 124
tcagctagat ctaagtgtcg atgaaga                              27

<210> SEQ ID NO 125
<211> LENGTH: 25
<212> TYPE: DNA
<213> ORGANISM: Zea mays

<400> SEQUENCE: 125
caacgttctg ttcgtaagga tttca                                25

<210> SEQ ID NO 126
<211> LENGTH: 21
<212> TYPE: DNA
<213> ORGANISM: Zea mays

<400> SEQUENCE: 126
cctcagcatt tttggcaagt g                                    21

<210> SEQ ID NO 127
<211> LENGTH: 22
<212> TYPE: DNA
<213> ORGANISM: Zea mays

<400> SEQUENCE: 127
tgaactgcaa catgctgaaa cc                                   22

<210> SEQ ID NO 128
<211> LENGTH: 24
<212> TYPE: DNA
<213> ORGANISM: Zea mays

<400> SEQUENCE: 128
gcagttggat ttccttctgt agct                                 24

<210> SEQ ID NO 129
<211> LENGTH: 14
<212> TYPE: DNA
<213> ORGANISM: Zea mays

<400> SEQUENCE: 129
acgcgcgcgt gttg                                            14

<210> SEQ ID NO 130
<211> LENGTH: 22
<212> TYPE: DNA
<213> ORGANISM: Zea mays

<400> SEQUENCE: 130
ccaaacacgc ttgtgcaact aa                                   22

<210> SEQ ID NO 131
<211> LENGTH: 19
<212> TYPE: DNA
<213> ORGANISM: Zea mays

<400> SEQUENCE: 131
gagtctgcga aggcatcgt                                       19

```
<210> SEQ ID NO 132
<211> LENGTH: 25
<212> TYPE: DNA
<213> ORGANISM: Zea mays

<400> SEQUENCE: 132
gaaaacgttt ccgatgctgt aacaa                                             25

<210> SEQ ID NO 133
<211> LENGTH: 24
<212> TYPE: DNA
<213> ORGANISM: Zea mays

<400> SEQUENCE: 133
ctgctcaagt ttgaagatgt cgtt                                              24

<210> SEQ ID NO 134
<211> LENGTH: 23
<212> TYPE: DNA
<213> ORGANISM: Zea mays

<400> SEQUENCE: 134
ttggtgggac agcacttcta act                                               23

<210> SEQ ID NO 135
<211> LENGTH: 25
<212> TYPE: DNA
<213> ORGANISM: Zea mays

<400> SEQUENCE: 135
ttctctcgtc ttgtcaattg tcaca                                             25

<210> SEQ ID NO 136
<211> LENGTH: 25
<212> TYPE: DNA
<213> ORGANISM: Zea mays

<400> SEQUENCE: 136
ggtgtttgct atagctctgc ttcac                                             25

<210> SEQ ID NO 137
<211> LENGTH: 19
<212> TYPE: DNA
<213> ORGANISM: Zea mays

<400> SEQUENCE: 137
ccattggcat ggcgaagga                                                    19

<210> SEQ ID NO 138
<211> LENGTH: 19
<212> TYPE: DNA
<213> ORGANISM: Zea mays

<400> SEQUENCE: 138
gctgggaact gtgctgatg                                                    19

<210> SEQ ID NO 139
<211> LENGTH: 28
<212> TYPE: DNA
<213> ORGANISM: Zea mays

<400> SEQUENCE: 139
```

```
catggaataa tcacgtctag tctgtctt                                28

<210> SEQ ID NO 140
<211> LENGTH: 20
<212> TYPE: DNA
<213> ORGANISM: Zea mays

<400> SEQUENCE: 140
ccctcttttg ctccattgca                                         20

<210> SEQ ID NO 141
<211> LENGTH: 21
<212> TYPE: DNA
<213> ORGANISM: Zea mays

<400> SEQUENCE: 141
ggctcgaagg aataccacca a                                       21

<210> SEQ ID NO 142
<211> LENGTH: 16
<212> TYPE: DNA
<213> ORGANISM: Zea mays

<400> SEQUENCE: 142
cctgacggcg ccatct                                             16

<210> SEQ ID NO 143
<211> LENGTH: 19
<212> TYPE: DNA
<213> ORGANISM: Zea mays

<400> SEQUENCE: 143
cggagacgtc aaggatggt                                          19

<210> SEQ ID NO 144
<211> LENGTH: 17
<212> TYPE: DNA
<213> ORGANISM: Zea mays

<400> SEQUENCE: 144
gtaggcggcg cagagtt                                            17

<210> SEQ ID NO 145
<211> LENGTH: 25
<212> TYPE: DNA
<213> ORGANISM: Zea mays

<400> SEQUENCE: 145
cgcaaggttg ttattcagca tctct                                   25

<210> SEQ ID NO 146
<211> LENGTH: 23
<212> TYPE: DNA
<213> ORGANISM: Zea mays

<400> SEQUENCE: 146
catcgttcgg ttcatttgct tga                                     23

<210> SEQ ID NO 147
<211> LENGTH: 21
<212> TYPE: DNA
<213> ORGANISM: Zea mays

<400> SEQUENCE: 147
```

```
tggttaggcc ggatcttggt a                                              21
```

<210> SEQ ID NO 148
<211> LENGTH: 35
<212> TYPE: DNA
<213> ORGANISM: Zea mays

<400> SEQUENCE: 148

```
tgctcgtaag aaattgcaat aaataaaata aaaaa                               35
```

<210> SEQ ID NO 149
<211> LENGTH: 24
<212> TYPE: DNA
<213> ORGANISM: Zea mays

<400> SEQUENCE: 149

```
aaccatagca gatcagcaga gtgt                                           24
```

<210> SEQ ID NO 150
<211> LENGTH: 26
<212> TYPE: DNA
<213> ORGANISM: Zea mays

<400> SEQUENCE: 150

```
gaactccaaa gcatgagtag aaaagg                                         26
```

<210> SEQ ID NO 151
<211> LENGTH: 27
<212> TYPE: DNA
<213> ORGANISM: Zea mays

<400> SEQUENCE: 151

```
ggtttagcaa agcaatatgt tcatggt                                        27
```

<210> SEQ ID NO 152
<211> LENGTH: 24
<212> TYPE: DNA
<213> ORGANISM: Zea mays

<400> SEQUENCE: 152

```
tctatgcaca tctcttgcct gatc                                           24
```

<210> SEQ ID NO 153
<211> LENGTH: 22
<212> TYPE: DNA
<213> ORGANISM: Zea mays

<400> SEQUENCE: 153

```
cccttgcagg attgttgttc ag                                             22
```

<210> SEQ ID NO 154
<211> LENGTH: 25
<212> TYPE: DNA
<213> ORGANISM: Zea mays

<400> SEQUENCE: 154

```
gcgtcttttt gcattattgc ctaca                                          25
```

<210> SEQ ID NO 155
<211> LENGTH: 20
<212> TYPE: DNA
<213> ORGANISM: Zea mays

<400> SEQUENCE: 155
ctgagttggg aagcgctttg                                               20

<210> SEQ ID NO 156
<211> LENGTH: 27
<212> TYPE: DNA
<213> ORGANISM: Zea mays

<400> SEQUENCE: 156
tctactacat tctttagcac gctttcc                                       27

<210> SEQ ID NO 157
<211> LENGTH: 27
<212> TYPE: DNA
<213> ORGANISM: Zea mays

<400> SEQUENCE: 157
gcaatacatg atttaggact ccttgga                                       27

<210> SEQ ID NO 158
<211> LENGTH: 24
<212> TYPE: DNA
<213> ORGANISM: Zea mays

<400> SEQUENCE: 158
gcaacttctt cgcctcatat tcag                                          24

<210> SEQ ID NO 159
<211> LENGTH: 38
<212> TYPE: DNA
<213> ORGANISM: Zea mays

<400> SEQUENCE: 159
tgaacttatt cctatatgaa ttcttaatag aggtccctt                          38

<210> SEQ ID NO 160
<211> LENGTH: 28
<212> TYPE: DNA
<213> ORGANISM: Zea mays

<400> SEQUENCE: 160
gtcttcccta tcagagctta agtttctt                                      28

<210> SEQ ID NO 161
<211> LENGTH: 18
<212> TYPE: DNA
<213> ORGANISM: Zea mays

<400> SEQUENCE: 161
atccgttgcg cccagtac                                                 18

<210> SEQ ID NO 162
<211> LENGTH: 25
<212> TYPE: DNA
<213> ORGANISM: Zea mays

<400> SEQUENCE: 162
aatggatggg tgcaatatat cagat                                         25

<210> SEQ ID NO 163
<211> LENGTH: 17
<212> TYPE: DNA
<213> ORGANISM: Zea mays

```
<400> SEQUENCE: 163
gccggagtcg gaaaggt                                              17

<210> SEQ ID NO 164
<211> LENGTH: 30
<212> TYPE: DNA
<213> ORGANISM: Zea mays

<400> SEQUENCE: 164
gcgatctata tggtttcttt tgaaaatcca                                30

<210> SEQ ID NO 165
<211> LENGTH: 20
<212> TYPE: DNA
<213> ORGANISM: Zea mays

<400> SEQUENCE: 165
tgctggtgac gtggacaagt                                           20

<210> SEQ ID NO 166
<211> LENGTH: 26
<212> TYPE: DNA
<213> ORGANISM: Zea mays

<400> SEQUENCE: 166
attacaacaa atgagaacac ccatgt                                    26

<210> SEQ ID NO 167
<211> LENGTH: 32
<212> TYPE: DNA
<213> ORGANISM: Zea mays

<400> SEQUENCE: 167
ctcttactaa agtttagttc gtatcacatc ga                             32

<210> SEQ ID NO 168
<211> LENGTH: 25
<212> TYPE: DNA
<213> ORGANISM: Zea mays

<400> SEQUENCE: 168
tttcaagccc gacatttgtt caaaa                                     25

<210> SEQ ID NO 169
<211> LENGTH: 23
<212> TYPE: DNA
<213> ORGANISM: Zea mays

<400> SEQUENCE: 169
cagcatgtcc ttctcgtatc tga                                       23

<210> SEQ ID NO 170
<211> LENGTH: 19
<212> TYPE: DNA
<213> ORGANISM: Zea mays

<400> SEQUENCE: 170
ccctgggaag caatttcga                                            19

<210> SEQ ID NO 171
<211> LENGTH: 25
<212> TYPE: DNA
```

<213> ORGANISM: Zea mays

<400> SEQUENCE: 171
ttggtgaata tacataccccc tgctt                                25

<210> SEQ ID NO 172
<211> LENGTH: 25
<212> TYPE: DNA
<213> ORGANISM: Zea mays

<400> SEQUENCE: 172
cgccttgtcc aatttcaaat gagaa                                25

<210> SEQ ID NO 173
<211> LENGTH: 23
<212> TYPE: DNA
<213> ORGANISM: Zea mays

<400> SEQUENCE: 173
gcaacaaatt agcagaggca atg                                  23

<210> SEQ ID NO 174
<211> LENGTH: 26
<212> TYPE: DNA
<213> ORGANISM: Zea mays

<400> SEQUENCE: 174
catttcacat gaccatccac tagcta                               26

<210> SEQ ID NO 175
<211> LENGTH: 32
<212> TYPE: DNA
<213> ORGANISM: Zea mays

<400> SEQUENCE: 175
tcttgtaaag aatacaacaa acacggatat ca                        32

<210> SEQ ID NO 176
<211> LENGTH: 25
<212> TYPE: DNA
<213> ORGANISM: Zea mays

<400> SEQUENCE: 176
ggtactacga ttctcacacg aggat                                25

<210> SEQ ID NO 177
<211> LENGTH: 18
<212> TYPE: DNA
<213> ORGANISM: Zea mays

<400> SEQUENCE: 177
ccgcctcctt gagcacat                                        18

<210> SEQ ID NO 178
<211> LENGTH: 23
<212> TYPE: DNA
<213> ORGANISM: Zea mays

<400> SEQUENCE: 178
gggtccattg taaaacagtt gca                                  23

<210> SEQ ID NO 179
<211> LENGTH: 23

<212> TYPE: DNA
<213> ORGANISM: Zea mays

<400> SEQUENCE: 179
cggccatcgg aaataagcta tgt					23

<210> SEQ ID NO 180
<211> LENGTH: 21
<212> TYPE: DNA
<213> ORGANISM: Zea mays

<400> SEQUENCE: 180
ccagcaaagt cagacggtac t						21

<210> SEQ ID NO 181
<211> LENGTH: 19
<212> TYPE: DNA
<213> ORGANISM: Zea mays

<400> SEQUENCE: 181
ggccatggca tctctgaca						19

<210> SEQ ID NO 182
<211> LENGTH: 29
<212> TYPE: DNA
<213> ORGANISM: Zea mays

<400> SEQUENCE: 182
agtttacaaa gctagtttcc aagaaagga					29

<210> SEQ ID NO 183
<211> LENGTH: 25
<212> TYPE: DNA
<213> ORGANISM: Zea mays

<400> SEQUENCE: 183
caaaaaggct gaagacggat acaaa					25

<210> SEQ ID NO 184
<211> LENGTH: 26
<212> TYPE: DNA
<213> ORGANISM: Zea mays

<400> SEQUENCE: 184
acccgaataa taccctcctt gactat					26

<210> SEQ ID NO 185
<211> LENGTH: 30
<212> TYPE: DNA
<213> ORGANISM: Zea mays

<400> SEQUENCE: 185
ttatttgagc tattctctgt tgacactgaa				30

<210> SEQ ID NO 186
<211> LENGTH: 23
<212> TYPE: DNA
<213> ORGANISM: Zea mays

<400> SEQUENCE: 186
agtagagacc gtggctagat cga					23

<210> SEQ ID NO 187

```
<211> LENGTH: 25
<212> TYPE: DNA
<213> ORGANISM: Zea mays

<400> SEQUENCE: 187
gtactttaca ggagcaagca ggaat                                              25

<210> SEQ ID NO 188
<211> LENGTH: 23
<212> TYPE: DNA
<213> ORGANISM: Zea mays

<400> SEQUENCE: 188
cgctgtcacc agtatcttca gat                                                23

<210> SEQ ID NO 189
<211> LENGTH: 19
<212> TYPE: DNA
<213> ORGANISM: Zea mays

<400> SEQUENCE: 189
tgggtgcatg tgtgtgctt                                                     19

<210> SEQ ID NO 190
<211> LENGTH: 19
<212> TYPE: DNA
<213> ORGANISM: Zea mays

<400> SEQUENCE: 190
ccgccgttca agaccaaac                                                     19

<210> SEQ ID NO 191
<211> LENGTH: 22
<212> TYPE: DNA
<213> ORGANISM: Zea mays

<400> SEQUENCE: 191
ggcacacctt gagtccagat ct                                                 22

<210> SEQ ID NO 192
<211> LENGTH: 24
<212> TYPE: DNA
<213> ORGANISM: Zea mays

<400> SEQUENCE: 192
catatgcgct actgttccac acta                                               24

<210> SEQ ID NO 193
<211> LENGTH: 31
<212> TYPE: DNA
<213> ORGANISM: Zea mays

<400> SEQUENCE: 193
ccataacaag tgttaagtat gagtaggact a                                       31

<210> SEQ ID NO 194
<211> LENGTH: 16
<212> TYPE: DNA
<213> ORGANISM: Zea mays

<400> SEQUENCE: 194
gctcgccgac gcagaa                                                        16
```

```
<210> SEQ ID NO 195
<211> LENGTH: 18
<212> TYPE: DNA
<213> ORGANISM: Zea mays

<400> SEQUENCE: 195
ctccagtcgc gtgaggtt                                                   18

<210> SEQ ID NO 196
<211> LENGTH: 19
<212> TYPE: DNA
<213> ORGANISM: Zea mays

<400> SEQUENCE: 196
cccgcgctaa gaactggaa                                                  19

<210> SEQ ID NO 197
<211> LENGTH: 23
<212> TYPE: DNA
<213> ORGANISM: Zea mays

<400> SEQUENCE: 197
gcccgcaacc ttactgtaat ttt                                             23

<210> SEQ ID NO 198
<211> LENGTH: 25
<212> TYPE: DNA
<213> ORGANISM: Zea mays

<400> SEQUENCE: 198
tgctgtttgg tgatgttaag gtatg                                           25

<210> SEQ ID NO 199
<211> LENGTH: 17
<212> TYPE: DNA
<213> ORGANISM: Zea mays

<400> SEQUENCE: 199
gccctctcct ccagcct                                                    17

<210> SEQ ID NO 200
<211> LENGTH: 25
<212> TYPE: DNA
<213> ORGANISM: Zea mays

<400> SEQUENCE: 200
ccaaactctc gatgaccaag cataa                                           25

<210> SEQ ID NO 201
<211> LENGTH: 25
<212> TYPE: DNA
<213> ORGANISM: Zea mays

<400> SEQUENCE: 201
gcggaagttt gaaatactgc tgatt                                           25

<210> SEQ ID NO 202
<211> LENGTH: 23
<212> TYPE: DNA
<213> ORGANISM: Zea mays

<400> SEQUENCE: 202
gctctcttgg atgttggcct tat                                             23
```

<210> SEQ ID NO 203
<211> LENGTH: 23
<212> TYPE: DNA
<213> ORGANISM: Zea mays

<400> SEQUENCE: 203
gattttgctc catgctagtt tcg                                          23

<210> SEQ ID NO 204
<211> LENGTH: 19
<212> TYPE: DNA
<213> ORGANISM: Zea mays

<400> SEQUENCE: 204
cgtgcgacgt cctgatacc                                               19

<210> SEQ ID NO 205
<211> LENGTH: 19
<212> TYPE: DNA
<213> ORGANISM: Zea mays

<400> SEQUENCE: 205
ctgccacagc cggaatttg                                               19

<210> SEQ ID NO 206
<211> LENGTH: 25
<212> TYPE: DNA
<213> ORGANISM: Zea mays

<400> SEQUENCE: 206
gaagatgtcc cgatagcgaa ttgta                                        25

<210> SEQ ID NO 207
<211> LENGTH: 24
<212> TYPE: DNA
<213> ORGANISM: Zea mays

<400> SEQUENCE: 207
tgcaaatcat gtgacgtacc attg                                         24

<210> SEQ ID NO 208
<211> LENGTH: 21
<212> TYPE: DNA
<213> ORGANISM: Zea mays

<400> SEQUENCE: 208
ctctctcgcc ccagaagaac t                                            21

<210> SEQ ID NO 209
<211> LENGTH: 21
<212> TYPE: DNA
<213> ORGANISM: Zea mays

<400> SEQUENCE: 209
ccgagtatgc atctggactg t                                            21

<210> SEQ ID NO 210
<211> LENGTH: 29
<212> TYPE: DNA
<213> ORGANISM: Zea mays

<400> SEQUENCE: 210
gtctatatat gtaaccaccc tctatgcaa                                    29

<210> SEQ ID NO 211
<211> LENGTH: 24
<212> TYPE: DNA
<213> ORGANISM: Zea mays

<400> SEQUENCE: 211
gtcatctggg gactacactt tgtg                                              24

<210> SEQ ID NO 212
<211> LENGTH: 25
<212> TYPE: DNA
<213> ORGANISM: Zea mays

<400> SEQUENCE: 212
gacgaatact cttacgaggc aagtt                                             25

<210> SEQ ID NO 213
<211> LENGTH: 29
<212> TYPE: DNA
<213> ORGANISM: Zea mays

<400> SEQUENCE: 213
gaaccactct attctaattg actctccaa                                         29

<210> SEQ ID NO 214
<211> LENGTH: 28
<212> TYPE: DNA
<213> ORGANISM: Zea mays

<400> SEQUENCE: 214
gaataacagg accatatctg aagatcga                                          28

<210> SEQ ID NO 215
<211> LENGTH: 30
<212> TYPE: DNA
<213> ORGANISM: Zea mays

<400> SEQUENCE: 215
gtattttttt tcttttttag acgttgcttt                                        30

<210> SEQ ID NO 216
<211> LENGTH: 26
<212> TYPE: DNA
<213> ORGANISM: Zea mays

<400> SEQUENCE: 216 gcttttgaa ccatgtatca gagaaa                                             26

<210> SEQ ID NO 217
<211> LENGTH: 20
<212> TYPE: DNA
<213> ORGANISM: Zea mays

<400> SEQUENCE: 217
ggaagcaaca gcaggctgtt                                                   20

<210> SEQ ID NO 218
<211> LENGTH: 21
<212> TYPE: DNA
<213> ORGANISM: Zea mays

<400> SEQUENCE: 218

```
agcctggtgt acgagaatgt g                                           21

<210> SEQ ID NO 219
<211> LENGTH: 27
<212> TYPE: DNA
<213> ORGANISM: Zea mays

<400> SEQUENCE: 219
gttggtagga ttggaactta ggttaca                                     27

<210> SEQ ID NO 220
<211> LENGTH: 24
<212> TYPE: DNA
<213> ORGANISM: Zea mays

<400> SEQUENCE: 220
aagatcagca agcagagttg agat                                        24

<210> SEQ ID NO 221
<211> LENGTH: 21
<212> TYPE: DNA
<213> ORGANISM: Zea mays

<400> SEQUENCE: 221
gttgttgctc gtttgcatcg a                                           21

<210> SEQ ID NO 222
<211> LENGTH: 31
<212> TYPE: DNA
<213> ORGANISM: Zea mays

<400> SEQUENCE: 222
gtttctagat gactttagac attcagagtg g                                31

<210> SEQ ID NO 223
<211> LENGTH: 22
<212> TYPE: DNA
<213> ORGANISM: Zea mays

<400> SEQUENCE: 223
gattcagttc acctcgcaac ct                                          22

<210> SEQ ID NO 224
<211> LENGTH: 22
<212> TYPE: DNA
<213> ORGANISM: Zea mays

<400> SEQUENCE: 224
ttcccctgat cgagagtagc ta                                          22

<210> SEQ ID NO 225
<211> LENGTH: 25
<212> TYPE: DNA
<213> ORGANISM: Zea mays

<400> SEQUENCE: 225
ggtctagaaa aacagcttca aatgc                                       25

<210> SEQ ID NO 226
<211> LENGTH: 22
<212> TYPE: DNA
<213> ORGANISM: Zea mays

<400> SEQUENCE: 226
```
agaaagttcg cagattgcca ga					22

<210> SEQ ID NO 227
<211> LENGTH: 18
<212> TYPE: DNA
<213> ORGANISM: Zea mays

<400> SEQUENCE: 227
gttggcctcc aggaacct						18

<210> SEQ ID NO 228
<211> LENGTH: 29
<212> TYPE: DNA
<213> ORGANISM: Zea mays

<400> SEQUENCE: 228
atatgttctt cttgctattg tgctattca				29

<210> SEQ ID NO 229
<211> LENGTH: 21
<212> TYPE: DNA
<213> ORGANISM: Zea mays

<400> SEQUENCE: 229
cttcgctggt acatgccttc t						21

<210> SEQ ID NO 230
<211> LENGTH: 19
<212> TYPE: DNA
<213> ORGANISM: Zea mays

<400> SEQUENCE: 230
tgctgtacgc cgtttcgtt						19

<210> SEQ ID NO 231
<211> LENGTH: 16
<212> TYPE: DNA
<213> ORGANISM: Zea mays

<400> SEQUENCE: 231
aggtggcgcc agtgga							16

<210> SEQ ID NO 232
<211> LENGTH: 17
<212> TYPE: DNA
<213> ORGANISM: Zea mays

<400> SEQUENCE: 232
cccgcctgct ccatctc							17

<210> SEQ ID NO 233
<211> LENGTH: 19
<212> TYPE: DNA
<213> ORGANISM: Zea mays

<400> SEQUENCE: 233
gcaacgagcc gatggaatc						19

<210> SEQ ID NO 234
<211> LENGTH: 20
<212> TYPE: DNA
<213> ORGANISM: Zea mays

<400> SEQUENCE: 234
cgatgccgtt cactcaggaa                                              20

<210> SEQ ID NO 235
<211> LENGTH: 22
<212> TYPE: DNA
<213> ORGANISM: Zea mays

<400> SEQUENCE: 235
cgccttggta ctcgtagatt gc                                           22

<210> SEQ ID NO 236
<211> LENGTH: 25
<212> TYPE: DNA
<213> ORGANISM: Zea mays

<400> SEQUENCE: 236
tgtgtttgat acatggcctt cagat                                        25

<210> SEQ ID NO 237
<211> LENGTH: 17
<212> TYPE: DNA
<213> ORGANISM: Zea mays

<400> SEQUENCE: 237
gccgaccagg ccatttc                                                 17

<210> SEQ ID NO 238
<211> LENGTH: 21
<212> TYPE: DNA
<213> ORGANISM: Zea mays

<400> SEQUENCE: 238
gccaacccTt ctggtcttct c                                            21

<210> SEQ ID NO 239
<211> LENGTH: 25
<212> TYPE: DNA
<213> ORGANISM: Zea mays

<400> SEQUENCE: 239
cgacagaaat gattgagtca caaca                                        25

<210> SEQ ID NO 240
<211> LENGTH: 24
<212> TYPE: DNA
<213> ORGANISM: Zea mays

<400> SEQUENCE: 240
gccaccacta agaactagag tcaa                                         24

<210> SEQ ID NO 241
<211> LENGTH: 21
<212> TYPE: DNA
<213> ORGANISM: Zea mays

<400> SEQUENCE: 241
tgctggattc tgaaccacga t                                            21

<210> SEQ ID NO 242
<211> LENGTH: 25
<212> TYPE: DNA
<213> ORGANISM: Zea mays

```
<400> SEQUENCE: 242
ggactgcact cacatgttat ttcct                                              25

<210> SEQ ID NO 243
<211> LENGTH: 23
<212> TYPE: DNA
<213> ORGANISM: Zea mays

<400> SEQUENCE: 243
gatatcacgt acgtgctgca ttc                                                23

<210> SEQ ID NO 244
<211> LENGTH: 26
<212> TYPE: DNA
<213> ORGANISM: Zea mays

<400> SEQUENCE: 244
gtctaatgag caggttatgc tgatct                                             26

<210> SEQ ID NO 245
<211> LENGTH: 25
<212> TYPE: DNA
<213> ORGANISM: Zea mays

<400> SEQUENCE: 245
agacttcagg aatgagggag tatca                                              25

<210> SEQ ID NO 246
<211> LENGTH: 25
<212> TYPE: DNA
<213> ORGANISM: Zea mays

<400> SEQUENCE: 246
ctctcgaatg cacttgcttt gttaa                                              25

<210> SEQ ID NO 247
<211> LENGTH: 26
<212> TYPE: DNA
<213> ORGANISM: Zea mays

<400> SEQUENCE: 247
acagggtgac attagtgtag tgtttg                                             26

<210> SEQ ID NO 248
<211> LENGTH: 23
<212> TYPE: DNA
<213> ORGANISM: Zea mays

<400> SEQUENCE: 248
gtatgctaca gtccctccct cta                                                23

<210> SEQ ID NO 249
<211> LENGTH: 22
<212> TYPE: DNA
<213> ORGANISM: Zea mays

<400> SEQUENCE: 249
tccccaatcc aaacacaacc tt                                                 22

<210> SEQ ID NO 250
<211> LENGTH: 21
<212> TYPE: DNA
```

<213> ORGANISM: Zea mays

<400> SEQUENCE: 250
tgccagtgtc tgtgagctca a                                              21

<210> SEQ ID NO 251
<211> LENGTH: 22
<212> TYPE: DNA
<213> ORGANISM: Zea mays

<400> SEQUENCE: 251
ggcttctaat ggcttggctt tt                                             22

<210> SEQ ID NO 252
<211> LENGTH: 20
<212> TYPE: DNA
<213> ORGANISM: Zea mays

<400> SEQUENCE: 252
cccacgtgaa ggttcttgga                                                20

<210> SEQ ID NO 253
<211> LENGTH: 25
<212> TYPE: DNA
<213> ORGANISM: Zea mays

<400> SEQUENCE: 253 caaactttc tcccccattt tcaca                                           25

<210> SEQ ID NO 254
<211> LENGTH: 20
<212> TYPE: DNA
<213> ORGANISM: Zea mays

<400> SEQUENCE: 254
cgaagcagat atgcggcttt                                                20

<210> SEQ ID NO 255
<211> LENGTH: 23
<212> TYPE: DNA
<213> ORGANISM: Zea mays

<400> SEQUENCE: 255
gaaggtgaca ttttcaggga tga                                            23

<210> SEQ ID NO 256
<211> LENGTH: 34
<212> TYPE: DNA
<213> ORGANISM: Zea mays

<400> SEQUENCE: 256
gtggtgatgc tagttaattt tacatatgtg taat                                34

<210> SEQ ID NO 257
<211> LENGTH: 24
<212> TYPE: DNA
<213> ORGANISM: Zea mays

<400> SEQUENCE: 257
ggtgtttctc ctccaagatg atct                                           24

<210> SEQ ID NO 258
<211> LENGTH: 19

<212> TYPE: DNA
<213> ORGANISM: Zea mays

<400> SEQUENCE: 258
cgcttcacct gaggtagct                                          19

<210> SEQ ID NO 259
<211> LENGTH: 25
<212> TYPE: DNA
<213> ORGANISM: Zea mays

<400> SEQUENCE: 259
ttggagtctg tgacattcaa tttca                                   25

<210> SEQ ID NO 260
<211> LENGTH: 24
<212> TYPE: DNA
<213> ORGANISM: Zea mays

<400> SEQUENCE: 260
ttagcaataa caggcctagc catt                                    24

<210> SEQ ID NO 261
<211> LENGTH: 25
<212> TYPE: DNA
<213> ORGANISM: Zea mays

<400> SEQUENCE: 261
gctgagactg gtgaagtttt cgata                                   25

<210> SEQ ID NO 262
<211> LENGTH: 27
<212> TYPE: DNA
<213> ORGANISM: Zea mays

<400> SEQUENCE: 262
agatgaggtt tgtaaatgtg gaacttt                                 27

<210> SEQ ID NO 263
<211> LENGTH: 22
<212> TYPE: DNA
<213> ORGANISM: Zea mays

<400> SEQUENCE: 263
cgtgcctaca ttttcctgca aa                                      22

<210> SEQ ID NO 264
<211> LENGTH: 25
<212> TYPE: DNA
<213> ORGANISM: Zea mays

<400> SEQUENCE: 264
tggcatcacc tttagatacg ttgtg                                   25

<210> SEQ ID NO 265
<211> LENGTH: 18
<212> TYPE: DNA
<213> ORGANISM: Zea mays

<400> SEQUENCE: 265
cagctacctg cctggtca                                           18

<210> SEQ ID NO 266

-continued

```
<210> SEQ ID NO 266
<211> LENGTH: 18
<212> TYPE: DNA
<213> ORGANISM: Zea mays

<400> SEQUENCE: 266
tcctcgcagt ccgattgg                                                 18

<210> SEQ ID NO 267
<211> LENGTH: 24
<212> TYPE: DNA
<213> ORGANISM: Zea mays

<400> SEQUENCE: 267
tcaatgacat attgggccta gaca                                          24

<210> SEQ ID NO 268
<211> LENGTH: 16
<212> TYPE: DNA
<213> ORGANISM: Zea mays

<400> SEQUENCE: 268
tcgacaacca aaaggt                                                   16

<210> SEQ ID NO 269
<211> LENGTH: 14
<212> TYPE: DNA
<213> ORGANISM: Zea mays

<400> SEQUENCE: 269
caaggcggca acgc                                                     14

<210> SEQ ID NO 270
<211> LENGTH: 20
<212> TYPE: DNA
<213> ORGANISM: Zea mays

<400> SEQUENCE: 270
ctaatttaga cgtcacccgc                                               20

<210> SEQ ID NO 271
<211> LENGTH: 24
<212> TYPE: DNA
<213> ORGANISM: Zea mays

<400> SEQUENCE: 271
aactgaatta ttgtatatac cttc                                          24

<210> SEQ ID NO 272
<211> LENGTH: 20
<212> TYPE: DNA
<213> ORGANISM: Zea mays

<400> SEQUENCE: 272
agtgagcttg ttacttctta                                               20

<210> SEQ ID NO 273
<211> LENGTH: 17
<212> TYPE: DNA
<213> ORGANISM: Zea mays

<400> SEQUENCE: 273
cagaccctga tcctgaa                                                  17
```

```
<210> SEQ ID NO 274
<211> LENGTH: 20
<212> TYPE: DNA
<213> ORGANISM: Zea mays

<400> SEQUENCE: 274
ttcaaataag aagaaagttc                                               20

<210> SEQ ID NO 275
<211> LENGTH: 13
<212> TYPE: DNA
<213> ORGANISM: Zea mays

<400> SEQUENCE: 275
cagaggcatg gcc                                                      13

<210> SEQ ID NO 276
<211> LENGTH: 20
<212> TYPE: DNA
<213> ORGANISM: Zea mays

<400> SEQUENCE: 276
tttgttctta tgaatttcgt                                               20

<210> SEQ ID NO 277
<211> LENGTH: 20
<212> TYPE: DNA
<213> ORGANISM: Zea mays

<400> SEQUENCE: 277
ccttccagta tcttttagt                                                20

<210> SEQ ID NO 278
<211> LENGTH: 16
<212> TYPE: DNA
<213> ORGANISM: Zea mays

<400> SEQUENCE: 278
tcaaaacgca ggccaa                                                   16

<210> SEQ ID NO 279
<211> LENGTH: 20
<212> TYPE: DNA
<213> ORGANISM: Zea mays

<400> SEQUENCE: 279
cagttgattc atttaatctg                                               20

<210> SEQ ID NO 280
<211> LENGTH: 16
<212> TYPE: DNA
<213> ORGANISM: Zea mays

<400> SEQUENCE: 280
tcgaaggaca acacaa                                                   16

<210> SEQ ID NO 281
<211> LENGTH: 16
<212> TYPE: DNA
<213> ORGANISM: Zea mays

<400> SEQUENCE: 281
tgggaggatt ctaatg                                                   16
```

```
<210> SEQ ID NO 282
<211> LENGTH: 20
<212> TYPE: DNA
<213> ORGANISM: Zea mays

<400> SEQUENCE: 282
catagtacac agtacactcg                                                   20

<210> SEQ ID NO 283
<211> LENGTH: 16
<212> TYPE: DNA
<213> ORGANISM: Zea mays

<400> SEQUENCE: 283
atctcgacgc cggtct                                                       16

<210> SEQ ID NO 284
<211> LENGTH: 18
<212> TYPE: DNA
<213> ORGANISM: Zea mays

<400> SEQUENCE: 284
caatctctgg acagatac                                                     18

<210> SEQ ID NO 285
<211> LENGTH: 18
<212> TYPE: DNA
<213> ORGANISM: Zea mays

<400> SEQUENCE: 285
cagtttcgtc gccgtcag                                                     18

<210> SEQ ID NO 286
<211> LENGTH: 17
<212> TYPE: DNA
<213> ORGANISM: Zea mays

<400> SEQUENCE: 286
atcatcgatc gacatcg                                                      17

<210> SEQ ID NO 287
<211> LENGTH: 15
<212> TYPE: DNA
<213> ORGANISM: Zea mays

<400> SEQUENCE: 287
accttgctgg ataat                                                        15

<210> SEQ ID NO 288
<211> LENGTH: 15
<212> TYPE: DNA
<213> ORGANISM: Zea mays

<400> SEQUENCE: 288
tgcttcaaga atcag                                                        15

<210> SEQ ID NO 289
<211> LENGTH: 18
<212> TYPE: DNA
<213> ORGANISM: Zea mays

<400> SEQUENCE: 289
cttgattaga ccaaagtg                                                     18
```

```
<210> SEQ ID NO 290
<211> LENGTH: 17
<212> TYPE: DNA
<213> ORGANISM: Zea mays

<400> SEQUENCE: 290
caggtcaatg aaggagt                                                  17

<210> SEQ ID NO 291
<211> LENGTH: 14
<212> TYPE: DNA
<213> ORGANISM: Zea mays

<400> SEQUENCE: 291
cccagtcgta gtcc                                                     14

<210> SEQ ID NO 292
<211> LENGTH: 17
<212> TYPE: DNA
<213> ORGANISM: Zea mays

<400> SEQUENCE: 292
cttctctgtt gaataga                                                  17

<210> SEQ ID NO 293
<211> LENGTH: 16
<212> TYPE: DNA
<213> ORGANISM: Zea mays

<400> SEQUENCE: 293
aactgcggct gtgtac                                                   16

<210> SEQ ID NO 294
<211> LENGTH: 20
<212> TYPE: DNA
<213> ORGANISM: Zea mays

<400> SEQUENCE: 294
ctgtagttcc attcgttgta                                               20

<210> SEQ ID NO 295
<211> LENGTH: 16
<212> TYPE: DNA
<213> ORGANISM: Zea mays

<400> SEQUENCE: 295
tgtcaacaga ttcgac                                                   16

<210> SEQ ID NO 296
<211> LENGTH: 17
<212> TYPE: DNA
<213> ORGANISM: Zea mays

<400> SEQUENCE: 296
ctaaggcaca ggtagag                                                  17

<210> SEQ ID NO 297
<211> LENGTH: 16
<212> TYPE: DNA
<213> ORGANISM: Zea mays

<400> SEQUENCE: 297
```
actgtagtgc catttt                                                  16

<210> SEQ ID NO 298
<211> LENGTH: 14
<212> TYPE: DNA
<213> ORGANISM: Zea mays

<400> SEQUENCE: 298
ccggaccatt cgac                                                    14

<210> SEQ ID NO 299
<211> LENGTH: 16
<212> TYPE: DNA
<213> ORGANISM: Zea mays

<400> SEQUENCE: 299
actgatattc aaattc                                                  16

<210> SEQ ID NO 300
<211> LENGTH: 14
<212> TYPE: DNA
<213> ORGANISM: Zea mays

<400> SEQUENCE: 300
tgggcaaggt acgc                                                    14

<210> SEQ ID NO 301
<211> LENGTH: 16
<212> TYPE: DNA
<213> ORGANISM: Zea mays

<400> SEQUENCE: 301
catgaatcag ctttgc                                                  16

<210> SEQ ID NO 302
<211> LENGTH: 18
<212> TYPE: DNA
<213> ORGANISM: Zea mays

<400> SEQUENCE: 302
ccaaacacac ctaagtat                                                18

<210> SEQ ID NO 303
<211> LENGTH: 20
<212> TYPE: DNA
<213> ORGANISM: Zea mays

<400> SEQUENCE: 303
cattttccga gtaactcatt                                              20

<210> SEQ ID NO 304
<211> LENGTH: 14
<212> TYPE: DNA
<213> ORGANISM: Zea mays

<400> SEQUENCE: 304
tgtggagagg aacg                                                    14

<210> SEQ ID NO 305
<211> LENGTH: 14
<212> TYPE: DNA
<213> ORGANISM: Zea mays

<400> SEQUENCE: 305
ccaaccacaa ttta     14

<210> SEQ ID NO 306
<211> LENGTH: 16
<212> TYPE: DNA
<213> ORGANISM: Zea mays

<400> SEQUENCE: 306
catggagtca ctagga     16

<210> SEQ ID NO 307
<211> LENGTH: 17
<212> TYPE: DNA
<213> ORGANISM: Zea mays

<400> SEQUENCE: 307
tcgtgtcatc ggagcgt     17

<210> SEQ ID NO 308
<211> LENGTH: 18
<212> TYPE: DNA
<213> ORGANISM: Zea mays

<400> SEQUENCE: 308
caacacttag ataaaacc     18

<210> SEQ ID NO 309
<211> LENGTH: 15
<212> TYPE: DNA
<213> ORGANISM: Zea mays

<400> SEQUENCE: 309
cgatggaaat ccctg     15

<210> SEQ ID NO 310
<211> LENGTH: 19
<212> TYPE: DNA
<213> ORGANISM: Zea mays

<400> SEQUENCE: 310
aaatcacgtt gtatctatc     19

<210> SEQ ID NO 311
<211> LENGTH: 16
<212> TYPE: DNA
<213> ORGANISM: Zea mays

<400> SEQUENCE: 311
ctgttttcgt aaattc     16

<210> SEQ ID NO 312
<211> LENGTH: 18
<212> TYPE: DNA
<213> ORGANISM: Zea mays

<400> SEQUENCE: 312
attagaatga cataactc     18

<210> SEQ ID NO 313
<211> LENGTH: 16
<212> TYPE: DNA
<213> ORGANISM: Zea mays

```
<400> SEQUENCE: 313
atcgccgatg gagcta                                                    16

<210> SEQ ID NO 314
<211> LENGTH: 15
<212> TYPE: DNA
<213> ORGANISM: Zea mays

<400> SEQUENCE: 314
ctggaataga tctgc                                                     15

<210> SEQ ID NO 315
<211> LENGTH: 16
<212> TYPE: DNA
<213> ORGANISM: Zea mays

<400> SEQUENCE: 315
cctacttgca tccatc                                                    16

<210> SEQ ID NO 316
<211> LENGTH: 14
<212> TYPE: DNA
<213> ORGANISM: Zea mays

<400> SEQUENCE: 316
ccgaggtaac atac                                                      14

<210> SEQ ID NO 317
<211> LENGTH: 15
<212> TYPE: DNA
<213> ORGANISM: Zea mays

<400> SEQUENCE: 317
cttggacaag caaaa                                                     15

<210> SEQ ID NO 318
<211> LENGTH: 15
<212> TYPE: DNA
<213> ORGANISM: Zea mays

<400> SEQUENCE: 318
agacgatcac ggcgg                                                     15

<210> SEQ ID NO 319
<211> LENGTH: 15
<212> TYPE: DNA
<213> ORGANISM: Zea mays

<400> SEQUENCE: 319
accaggacct tgaaa                                                     15

<210> SEQ ID NO 320
<211> LENGTH: 14
<212> TYPE: DNA
<213> ORGANISM: Zea mays

<400> SEQUENCE: 320
tgtcccgaga cctg                                                      14

<210> SEQ ID NO 321
<211> LENGTH: 17
<212> TYPE: DNA
<213> ORGANISM: Zea mays
```

```
<400> SEQUENCE: 321
ccaagaagca cgtcgac                                                17

<210> SEQ ID NO 322
<211> LENGTH: 14
<212> TYPE: DNA
<213> ORGANISM: Zea mays

<400> SEQUENCE: 322
caacgacgag accc                                                   14

<210> SEQ ID NO 323
<211> LENGTH: 14
<212> TYPE: DNA
<213> ORGANISM: Zea mays

<400> SEQUENCE: 323
cagcacgaac tcga                                                   14

<210> SEQ ID NO 324
<211> LENGTH: 16
<212> TYPE: DNA
<213> ORGANISM: Zea mays

<400> SEQUENCE: 324
tccaggaaga tgattg                                                 16

<210> SEQ ID NO 325
<211> LENGTH: 18
<212> TYPE: DNA
<213> ORGANISM: Zea mays

<400> SEQUENCE: 325
cactaacaac cagatttg                                               18

<210> SEQ ID NO 326
<211> LENGTH: 20
<212> TYPE: DNA
<213> ORGANISM: Zea mays

<400> SEQUENCE: 326
caagaacaat gaagcatagt                                             20

<210> SEQ ID NO 327
<211> LENGTH: 15
<212> TYPE: DNA
<213> ORGANISM: Zea mays

<400> SEQUENCE: 327
aggaggctta aatga                                                  15

<210> SEQ ID NO 328
<211> LENGTH: 20
<212> TYPE: DNA
<213> ORGANISM: Zea mays

<400> SEQUENCE: 328
aaagagaaat caacagtttg                                             20

<210> SEQ ID NO 329
<211> LENGTH: 21
<212> TYPE: DNA
```

```
<213> ORGANISM: Zea mays

<400> SEQUENCE: 329
tttggcgtac atattgatat a                                       21

<210> SEQ ID NO 330
<211> LENGTH: 14
<212> TYPE: DNA
<213> ORGANISM: Zea mays

<400> SEQUENCE: 330
cctttcgcct tctg                                               14

<210> SEQ ID NO 331
<211> LENGTH: 18
<212> TYPE: DNA
<213> ORGANISM: Zea mays

<400> SEQUENCE: 331
cggtacaagt agaatcta                                           18

<210> SEQ ID NO 332
<211> LENGTH: 18
<212> TYPE: DNA
<213> ORGANISM: Zea mays

<400> SEQUENCE: 332
cagaagacac ggtgatta                                           18

<210> SEQ ID NO 333
<211> LENGTH: 17
<212> TYPE: DNA
<213> ORGANISM: Zea mays

<400> SEQUENCE: 333
tgccaccctg aacacta                                            17

<210> SEQ ID NO 334
<211> LENGTH: 16
<212> TYPE: DNA
<213> ORGANISM: Zea mays

<400> SEQUENCE: 334
accacagtag gaatgc                                             16

<210> SEQ ID NO 335
<211> LENGTH: 16
<212> TYPE: DNA
<213> ORGANISM: Zea mays

<400> SEQUENCE: 335
tccgacaagt gggaac                                             16

<210> SEQ ID NO 336
<211> LENGTH: 22
<212> TYPE: DNA
<213> ORGANISM: Zea mays

<400> SEQUENCE: 336
tgacaaaatt tgaaaatcta gc                                      22

<210> SEQ ID NO 337
<211> LENGTH: 16
```

```
<212> TYPE: DNA
<213> ORGANISM: Zea mays

<400> SEQUENCE: 337
cagctctcct ttgtcg                                                   16

<210> SEQ ID NO 338
<211> LENGTH: 19
<212> TYPE: DNA
<213> ORGANISM: Zea mays

<400> SEQUENCE: 338
tgatcgtgct aatagaatt                                                19

<210> SEQ ID NO 339
<211> LENGTH: 15
<212> TYPE: DNA
<213> ORGANISM: Zea mays

<400> SEQUENCE: 339
agcagatgtg atccg                                                    15

<210> SEQ ID NO 340
<211> LENGTH: 17
<212> TYPE: DNA
<213> ORGANISM: Zea mays

<400> SEQUENCE: 340
tggtatcaaa agaatac                                                  17

<210> SEQ ID NO 341
<211> LENGTH: 16
<212> TYPE: DNA
<213> ORGANISM: Zea mays

<400> SEQUENCE: 341
cccgtcgtca gtacag                                                   16

<210> SEQ ID NO 342
<211> LENGTH: 19
<212> TYPE: DNA
<213> ORGANISM: Zea mays

<400> SEQUENCE: 342
ttagtaatcg gaactttca                                                19

<210> SEQ ID NO 343
<211> LENGTH: 13
<212> TYPE: DNA
<213> ORGANISM: Zea mays

<400> SEQUENCE: 343
ctggacgcaa atc                                                      13

<210> SEQ ID NO 344
<211> LENGTH: 15
<212> TYPE: DNA
<213> ORGANISM: Zea mays

<400> SEQUENCE: 344
ccagcttgtt tattc                                                    15

<210> SEQ ID NO 345
```

-continued

```
<211> LENGTH: 18
<212> TYPE: DNA
<213> ORGANISM: Zea mays

<400> SEQUENCE: 345
atgtcagcta tgaatatt                                                 18

<210> SEQ ID NO 346
<211> LENGTH: 20
<212> TYPE: DNA
<213> ORGANISM: Zea mays

<400> SEQUENCE: 346
ctggagctaa aaaacttaaa                                               20

<210> SEQ ID NO 347
<211> LENGTH: 15
<212> TYPE: DNA
<213> ORGANISM: Zea mays

<400> SEQUENCE: 347
acgatcaagg caaac                                                    15

<210> SEQ ID NO 348
<211> LENGTH: 16
<212> TYPE: DNA
<213> ORGANISM: Zea mays

<400> SEQUENCE: 348
ctcattaaca gaaaat                                                   16

<210> SEQ ID NO 349
<211> LENGTH: 17
<212> TYPE: DNA
<213> ORGANISM: Zea mays

<400> SEQUENCE: 349
tctttcatga attgcac                                                  17

<210> SEQ ID NO 350
<211> LENGTH: 16
<212> TYPE: DNA
<213> ORGANISM: Zea mays

<400> SEQUENCE: 350
cacccatgaa gataac                                                   16

<210> SEQ ID NO 351
<211> LENGTH: 15
<212> TYPE: DNA
<213> ORGANISM: Zea mays

<400> SEQUENCE: 351
ctaccaagca atatt                                                    15

<210> SEQ ID NO 352
<211> LENGTH: 16
<212> TYPE: DNA
<213> ORGANISM: Zea mays

<400> SEQUENCE: 352
cacgtaaggg aacaag                                                   16
```

```
<210> SEQ ID NO 353
<211> LENGTH: 15
<212> TYPE: DNA
<213> ORGANISM: Zea mays

<400> SEQUENCE: 353
cggcacggtg ttaga                                                    15

<210> SEQ ID NO 354
<211> LENGTH: 19
<212> TYPE: DNA
<213> ORGANISM: Zea mays

<400> SEQUENCE: 354
atttggccct tttttttgta                                               19

<210> SEQ ID NO 355
<211> LENGTH: 14
<212> TYPE: DNA
<213> ORGANISM: Zea mays

<400> SEQUENCE: 355
ttccccgacc ttgg                                                     14

<210> SEQ ID NO 356
<211> LENGTH: 18
<212> TYPE: DNA
<213> ORGANISM: Zea mays

<400> SEQUENCE: 356
ctaacagtgt catatact                                                 18

<210> SEQ ID NO 357
<211> LENGTH: 15
<212> TYPE: DNA
<213> ORGANISM: Zea mays

<400> SEQUENCE: 357
cgacaaccga aaggt                                                    15

<210> SEQ ID NO 358
<211> LENGTH: 14
<212> TYPE: DNA
<213> ORGANISM: Zea mays

<400> SEQUENCE: 358
caaggccgca acgc                                                     14

<210> SEQ ID NO 359
<211> LENGTH: 16
<212> TYPE: DNA
<213> ORGANISM: Zea mays

<400> SEQUENCE: 359
tttagacgcc acccgc                                                   16

<210> SEQ ID NO 360
<211> LENGTH: 22
<212> TYPE: DNA
<213> ORGANISM: Zea mays

<400> SEQUENCE: 360
ctgaattatt gtatatgcct tc                                            22
```

```
<210> SEQ ID NO 361
<211> LENGTH: 18
<212> TYPE: DNA
<213> ORGANISM: Zea mays

<400> SEQUENCE: 361
tgagcttgtt gcttctta                                                       18

<210> SEQ ID NO 362
<211> LENGTH: 17
<212> TYPE: DNA
<213> ORGANISM: Zea mays

<400> SEQUENCE: 362
cagaccctga ccctgaa                                                        17

<210> SEQ ID NO 363
<211> LENGTH: 21
<212> TYPE: DNA
<213> ORGANISM: Zea mays

<400> SEQUENCE: 363
cttcaaataa gaataaagtt c                                                   21

<210> SEQ ID NO 364
<211> LENGTH: 14
<212> TYPE: DNA
<213> ORGANISM: Zea mays

<400> SEQUENCE: 364
aggcagagac atgg                                                           14

<210> SEQ ID NO 365
<211> LENGTH: 20
<212> TYPE: DNA
<213> ORGANISM: Zea mays

<400> SEQUENCE: 365
tttgttctta tgattttcgt                                                     20

<210> SEQ ID NO 366
<211> LENGTH: 20
<212> TYPE: DNA
<213> ORGANISM: Zea mays

<400> SEQUENCE: 366
ccttccagta tctctttagt                                                     20

<210> SEQ ID NO 367
<211> LENGTH: 15
<212> TYPE: DNA
<213> ORGANISM: Zea mays

<400> SEQUENCE: 367
caaaacgccg gccaa                                                          15

<210> SEQ ID NO 368
<211> LENGTH: 20
<212> TYPE: DNA
<213> ORGANISM: Zea mays

<400> SEQUENCE: 368
cagttgattc atttgatctg                                                     20
```

```
<210> SEQ ID NO 369
<211> LENGTH: 14
<212> TYPE: DNA
<213> ORGANISM: Zea mays

<400> SEQUENCE: 369
cgaagggcaa caca                                                    14

<210> SEQ ID NO 370
<211> LENGTH: 15
<212> TYPE: DNA
<213> ORGANISM: Zea mays

<400> SEQUENCE: 370
tgggagggtt ctaat                                                   15

<210> SEQ ID NO 371
<211> LENGTH: 18
<212> TYPE: DNA
<213> ORGANISM: Zea mays

<400> SEQUENCE: 371
tagtacacag tgcactcg                                                18

<210> SEQ ID NO 372
<211> LENGTH: 17
<212> TYPE: DNA
<213> ORGANISM: Zea mays

<400> SEQUENCE: 372
catctcgaca ccggtct                                                 17

<210> SEQ ID NO 373
<211> LENGTH: 16
<212> TYPE: DNA
<213> ORGANISM: Zea mays

<400> SEQUENCE: 373
atctctggcc agatac                                                  16

<210> SEQ ID NO 374
<211> LENGTH: 18
<212> TYPE: DNA
<213> ORGANISM: Zea mays

<400> SEQUENCE: 374
cagtttcgtc accgtcag                                                18

<210> SEQ ID NO 375
<211> LENGTH: 15
<212> TYPE: DNA
<213> ORGANISM: Zea mays

<400> SEQUENCE: 375
catcgatcaa catcg                                                   15

<210> SEQ ID NO 376
<211> LENGTH: 15
<212> TYPE: DNA
<213> ORGANISM: Zea mays

<400> SEQUENCE: 376
```

```
ttgctgtata atttc                                              15

<210> SEQ ID NO 377
<211> LENGTH: 16
<212> TYPE: DNA
<213> ORGANISM: Zea mays

<400> SEQUENCE: 377
ttgcttcaag gatcag                                             16

<210> SEQ ID NO 378
<211> LENGTH: 16
<212> TYPE: DNA
<213> ORGANISM: Zea mays

<400> SEQUENCE: 378
tgattaggcc aaagtg                                             16

<210> SEQ ID NO 379
<211> LENGTH: 17
<212> TYPE: DNA
<213> ORGANISM: Zea mays

<400> SEQUENCE: 379
caggtcaatg gaggagt                                            17

<210> SEQ ID NO 380
<211> LENGTH: 16
<212> TYPE: DNA
<213> ORGANISM: Zea mays

<400> SEQUENCE: 380
cccagttgta gtccta                                             16

<210> SEQ ID NO 381
<211> LENGTH: 18
<212> TYPE: DNA
<213> ORGANISM: Zea mays

<400> SEQUENCE: 381
atgcttctct gttaaata                                           18

<210> SEQ ID NO 382
<211> LENGTH: 14
<212> TYPE: DNA
<213> ORGANISM: Zea mays

<400> SEQUENCE: 382
ctgcggcagt gtac                                               14

<210> SEQ ID NO 383
<211> LENGTH: 20
<212> TYPE: DNA
<213> ORGANISM: Zea mays

<400> SEQUENCE: 383
ctgtagttcc attcattgta                                         20

<210> SEQ ID NO 384
<211> LENGTH: 16
<212> TYPE: DNA
<213> ORGANISM: Zea mays

<400> SEQUENCE: 384
```
tgtcaacaaa ttcgac                                                       16

<210> SEQ ID NO 385
<211> LENGTH: 17
<212> TYPE: DNA
<213> ORGANISM: Zea mays

<400> SEQUENCE: 385
ctaaggcaca agtagag                                                      17

<210> SEQ ID NO 386
<211> LENGTH: 16
<212> TYPE: DNA
<213> ORGANISM: Zea mays

<400> SEQUENCE: 386
actgtagtgc cgtttt                                                       16

<210> SEQ ID NO 387
<211> LENGTH: 14
<212> TYPE: DNA
<213> ORGANISM: Zea mays

<400> SEQUENCE: 387
ccggaccgtt cgac                                                         14

<210> SEQ ID NO 388
<211> LENGTH: 17
<212> TYPE: DNA
<213> ORGANISM: Zea mays

<400> SEQUENCE: 388
aactgatatt caacttc                                                      17

<210> SEQ ID NO 389
<211> LENGTH: 13
<212> TYPE: DNA
<213> ORGANISM: Zea mays

<400> SEQUENCE: 389
tgggcagggt acg                                                          13

<210> SEQ ID NO 390
<211> LENGTH: 16
<212> TYPE: DNA
<213> ORGANISM: Zea mays

<400> SEQUENCE: 390
catgaatcaa ctttgc                                                       16

<210> SEQ ID NO 391
<211> LENGTH: 17
<212> TYPE: DNA
<213> ORGANISM: Zea mays

<400> SEQUENCE: 391
caaacacacc caagtat                                                      17

<210> SEQ ID NO 392
<211> LENGTH: 20
<212> TYPE: DNA
<213> ORGANISM: Zea mays

```
<400> SEQUENCE: 392
cattttccga gtacctcatt                                              20

<210> SEQ ID NO 393
<211> LENGTH: 14
<212> TYPE: DNA
<213> ORGANISM: Zea mays

<400> SEQUENCE: 393
tggagtggaa cgct                                                    14

<210> SEQ ID NO 394
<211> LENGTH: 14
<212> TYPE: DNA
<213> ORGANISM: Zea mays

<400> SEQUENCE: 394
ccaaccacaa ctta                                                    14

<210> SEQ ID NO 395
<211> LENGTH: 14
<212> TYPE: DNA
<213> ORGANISM: Zea mays

<400> SEQUENCE: 395
tgcatggaat cact                                                    14

<210> SEQ ID NO 396
<211> LENGTH: 16
<212> TYPE: DNA
<213> ORGANISM: Zea mays

<400> SEQUENCE: 396
cgtgtcatca gagcgt                                                  16

<210> SEQ ID NO 397
<211> LENGTH: 16
<212> TYPE: DNA
<213> ORGANISM: Zea mays

<400> SEQUENCE: 397
acacttagac aaaacc                                                  16

<210> SEQ ID NO 398
<211> LENGTH: 15
<212> TYPE: DNA
<213> ORGANISM: Zea mays

<400> SEQUENCE: 398
cgatggaatt ccctg                                                   15

<210> SEQ ID NO 399
<211> LENGTH: 18
<212> TYPE: DNA
<213> ORGANISM: Zea mays

<400> SEQUENCE: 399
aatcacgttg tttctatc                                                18

<210> SEQ ID NO 400
<211> LENGTH: 17
<212> TYPE: DNA
<213> ORGANISM: Zea mays
```

-continued

<400> SEQUENCE: 400
tctgttttct taaattc                                                  17

<210> SEQ ID NO 401
<211> LENGTH: 17
<212> TYPE: DNA
<213> ORGANISM: Zea mays

<400> SEQUENCE: 401
ttagaatgac acaactc                                                  17

<210> SEQ ID NO 402
<211> LENGTH: 16
<212> TYPE: DNA
<213> ORGANISM: Zea mays

<400> SEQUENCE: 402
atcgccgatt gagcta                                                   16

<210> SEQ ID NO 403
<211> LENGTH: 15
<212> TYPE: DNA
<213> ORGANISM: Zea mays

<400> SEQUENCE: 403
ctggaatagc tctgc                                                    15

<210> SEQ ID NO 404
<211> LENGTH: 18
<212> TYPE: DNA
<213> ORGANISM: Zea mays

<400> SEQUENCE: 404
aacctacttg tatccatc                                                 18

<210> SEQ ID NO 405
<211> LENGTH: 14
<212> TYPE: DNA
<213> ORGANISM: Zea mays

<400> SEQUENCE: 405
ccgaggtgac atac                                                     14

<210> SEQ ID NO 406
<211> LENGTH: 15
<212> TYPE: DNA
<213> ORGANISM: Zea mays

<400> SEQUENCE: 406
cttggacatg caaaa                                                    15

<210> SEQ ID NO 407
<211> LENGTH: 14
<212> TYPE: DNA
<213> ORGANISM: Zea mays

<400> SEQUENCE: 407
agacggtcac ggcg                                                     14

<210> SEQ ID NO 408
<211> LENGTH: 16
<212> TYPE: DNA

```
<213> ORGANISM: Zea mays

<400> SEQUENCE: 408
ccaggatctt gaaaca                                              16

<210> SEQ ID NO 409
<211> LENGTH: 13
<212> TYPE: DNA
<213> ORGANISM: Zea mays

<400> SEQUENCE: 409
tcccgcgacc tga                                                 13

<210> SEQ ID NO 410
<211> LENGTH: 17
<212> TYPE: DNA
<213> ORGANISM: Zea mays

<400> SEQUENCE: 410
ccaagaaaca cgtcgac                                             17

<210> SEQ ID NO 411
<211> LENGTH: 14
<212> TYPE: DNA
<213> ORGANISM: Zea mays

<400> SEQUENCE: 411
caacgaccag accc                                                14

<210> SEQ ID NO 412
<211> LENGTH: 14
<212> TYPE: DNA
<213> ORGANISM: Zea mays

<400> SEQUENCE: 412
cagcacaaac tcga                                                14

<210> SEQ ID NO 413
<211> LENGTH: 16
<212> TYPE: DNA
<213> ORGANISM: Zea mays

<400> SEQUENCE: 413
tccaggaagc tgattg                                              16

<210> SEQ ID NO 414
<211> LENGTH: 17
<212> TYPE: DNA
<213> ORGANISM: Zea mays

<400> SEQUENCE: 414
actaacaacc ggatttg                                             17

<210> SEQ ID NO 415
<211> LENGTH: 20
<212> TYPE: DNA
<213> ORGANISM: Zea mays

<400> SEQUENCE: 415
caagaacaat gaaacatagt                                          20

<210> SEQ ID NO 416
<211> LENGTH: 14
```

```
<212> TYPE: DNA
<213> ORGANISM: Zea mays

<400> SEQUENCE: 416
aggctgaaat gaat                                                       14

<210> SEQ ID NO 417
<211> LENGTH: 19
<212> TYPE: DNA
<213> ORGANISM: Zea mays

<400> SEQUENCE: 417
aagagaaatc aacggtttg                                                  19

<210> SEQ ID NO 418
<211> LENGTH: 19
<212> TYPE: DNA
<213> ORGANISM: Zea mays

<400> SEQUENCE: 418
tggcgtacat atcgatata                                                  19

<210> SEQ ID NO 419
<211> LENGTH: 14
<212> TYPE: DNA
<213> ORGANISM: Zea mays

<400> SEQUENCE: 419 cccctttgc cttc                                                        14

<210> SEQ ID NO 420
<211> LENGTH: 18
<212> TYPE: DNA
<213> ORGANISM: Zea mays

<400> SEQUENCE: 420
cggtacaagt aaaatcta                                                   18

<210> SEQ ID NO 421
<211> LENGTH: 18
<212> TYPE: DNA
<213> ORGANISM: Zea mays

<400> SEQUENCE: 421
cagaagacac gttgatta                                                   18

<210> SEQ ID NO 422
<211> LENGTH: 17
<212> TYPE: DNA
<213> ORGANISM: Zea mays

<400> SEQUENCE: 422 tgccaccta aacacta                                                     17

<210> SEQ ID NO 423
<211> LENGTH: 15
<212> TYPE: DNA
<213> ORGANISM: Zea mays

<400> SEQUENCE: 423
ccacagtaag aatgc                                                      15

<210> SEQ ID NO 424
```

```
<211> LENGTH: 16
<212> TYPE: DNA
<213> ORGANISM: Zea mays

<400> SEQUENCE: 424
tccgacaaat gggaac                                                        16

<210> SEQ ID NO 425
<211> LENGTH: 20
<212> TYPE: DNA
<213> ORGANISM: Zea mays

<400> SEQUENCE: 425
acaaaatttg aacatctagc                                                    20

<210> SEQ ID NO 426
<211> LENGTH: 15
<212> TYPE: DNA
<213> ORGANISM: Zea mays

<400> SEQUENCE: 426
agctctccgt tgtcg                                                         15

<210> SEQ ID NO 427
<211> LENGTH: 19
<212> TYPE: DNA
<213> ORGANISM: Zea mays

<400> SEQUENCE: 427
tgatcgtgct attagaatt                                                     19

<210> SEQ ID NO 428
<211> LENGTH: 14
<212> TYPE: DNA
<213> ORGANISM: Zea mays

<400> SEQUENCE: 428
agcagacgtg atcc                                                          14

<210> SEQ ID NO 429
<211> LENGTH: 16
<212> TYPE: DNA
<213> ORGANISM: Zea mays

<400> SEQUENCE: 429
atggtatcga aagaat                                                        16

<210> SEQ ID NO 430
<211> LENGTH: 17
<212> TYPE: DNA
<213> ORGANISM: Zea mays

<400> SEQUENCE: 430
tcccgtcgtt agtacag                                                       17

<210> SEQ ID NO 431
<211> LENGTH: 14
<212> TYPE: DNA
<213> ORGANISM: Zea mays

<400> SEQUENCE: 431
aatcggagct ttca                                                          14
```

-continued

```
<210> SEQ ID NO 432
<211> LENGTH: 13
<212> TYPE: DNA
<213> ORGANISM: Zea mays

<400> SEQUENCE: 432
ctggaggcaa atc                                                       13

<210> SEQ ID NO 433
<211> LENGTH: 16
<212> TYPE: DNA
<213> ORGANISM: Zea mays

<400> SEQUENCE: 433
cagcttgtct attcac                                                    16

<210> SEQ ID NO 434
<211> LENGTH: 15
<212> TYPE: DNA
<213> ORGANISM: Zea mays

<400> SEQUENCE: 434
tcagctacga atatt                                                     15

<210> SEQ ID NO 435
<211> LENGTH: 20
<212> TYPE: DNA
<213> ORGANISM: Zea mays

<400> SEQUENCE: 435
ctggagctaa aaatcttaaa                                                20

<210> SEQ ID NO 436
<211> LENGTH: 14
<212> TYPE: DNA
<213> ORGANISM: Zea mays

<400> SEQUENCE: 436
cgatcagggc aaac                                                      14

<210> SEQ ID NO 437
<211> LENGTH: 18
<212> TYPE: DNA
<213> ORGANISM: Zea mays

<400> SEQUENCE: 437
attaacagga aatgatgc                                                  18

<210> SEQ ID NO 438
<211> LENGTH: 17
<212> TYPE: DNA
<213> ORGANISM: Zea mays

<400> SEQUENCE: 438
ctttctttca taaattg                                                   17

<210> SEQ ID NO 439
<211> LENGTH: 15
<212> TYPE: DNA
<213> ORGANISM: Zea mays

<400> SEQUENCE: 439
acccatgagg ataac                                                     15
```

<210> SEQ ID NO 440
<211> LENGTH: 15
<212> TYPE: DNA
<213> ORGANISM: Zea mays

<400> SEQUENCE: 440
agctaccgag caata                                                    15

<210> SEQ ID NO 441
<211> LENGTH: 15
<212> TYPE: DNA
<213> ORGANISM: Zea mays

<400> SEQUENCE: 441
acgtaaggaa acaag                                                    15

<210> SEQ ID NO 442
<211> LENGTH: 15
<212> TYPE: DNA
<213> ORGANISM: Zea mays

<400> SEQUENCE: 442
cggcacgatg ttaga                                                    15

<210> SEQ ID NO 443
<211> LENGTH: 18
<212> TYPE: DNA
<213> ORGANISM: Zea mays

<400> SEQUENCE: 443
tttggccctt tctttgta                                                 18

<210> SEQ ID NO 444
<211> LENGTH: 14
<212> TYPE: DNA
<213> ORGANISM: Zea mays

<400> SEQUENCE: 444
ttcccggacc ttgg                                                     14

<210> SEQ ID NO 445
<211> LENGTH: 16
<212> TYPE: DNA
<213> ORGANISM: Zea mays

<400> SEQUENCE: 445
acagtgtcgt atactc                                                   16

<210> SEQ ID NO 446
<211> LENGTH: 201
<212> TYPE: DNA
<213> ORGANISM: Zea mays
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 446
cactagaagt ngggtatatg attggaacta aagacactng tccngtcata atatgggatc    60
atatcatcca caaaaaatga acaagaagtg tccagataaa ncaaagctca aaggtttaat   120
ccattagact atgtgcttgc catggagaat gagttgcatg atgaatccaa cagtganagt   180
gatggggagc ttcatttgtt g                                             201

<210> SEQ ID NO 447
<211> LENGTH: 201
<212> TYPE: DNA
<213> ORGANISM: Zea mays
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 447
ttgatacaca aatatgatnt ttcatatttg cgtagaatat agtgcctttg attgagcctc    60
actatantan cccatggatg atcggatgat gttagaattt ntgtagtggt atttagatgg   120
acatacttga catttggatg gatgaatgca ctagatatat atttggattg atggaataga   180
tggtattaga acttgaatta t                                             201

<210> SEQ ID NO 448
<211> LENGTH: 675
<212> TYPE: DNA
<213> ORGANISM: Zea mays
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (72)..(76)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (532)..(534)
<223> OTHER INFORMATION: n is a, c, g, or t
<220> FEATURE:

<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (575)..(575)
<223> OTHER INFORMATION: n is a, c, g, or t
<220> FEATURE:
<221> NAME/KEY: misc_feature
<222> LOCATION: (578)..(580)
<223> OTHER INFORMATION: n is a, c, g, or t
<220> FEATURE:
<221> NAME/KEY: misc_feature
<222> LOCATION: (597)..(602)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (607)..(623)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (646)..(674)
<223> OTHER INFORMATION: n is a, c, g, or t

<400> SEQUENCE: 448

```
tggttcangt caaatcnnna aactngtttt gtgacaattg gacaacgagt gcttgccaat      60
ccactgaggt annnnncttg gttcatattt cattttacat tcatgttgtg gttatgcatt    120
atctattggt tctagtattt caatctttag gttgtgtgaa tcgtcctctt atttgttttg    180
ttcttcgggg tgttactatc ctaagatgtt tgcttngtaa tttttttcct gaaccttctt    240
tattcagggt tcggtttcat tatggccatc ctgatgtctt cgatcgtctt ttccacgtta    300
cgaggggcgg tgtcagtaaa gcatccaaaa ttatcaatct tagtgaggac atctttgcag    360
gtacttttct tttgctgtta ctgctcaaca tttgtaaatg tggaaccact aagataatat    420
tttggcttct tatggttcag gattcaattc cacattgcgc gaaggcaatg ttactcacca    480
tgaatacatg caagttggca aaggaaggga tgtaggtctc aatcaaatat cnnngtttga    540
ggcaaanata gcaaatggca atggcgaaca aangntgnnn cgtgacatct accggcnnnn    600
nnatngnnnn nnnnnnnnnn nnntgctgtn ttgttactac acaacnnnnn nnnnnnnnnn    660
nnnnnnnnnn nnnnt                                                    675
```

<210> SEQ ID NO 449
<211> LENGTH: 667
<212> TYPE: DNA
<213> ORGANISM: Zea mays
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (566)..(573)
<223> OTHER INFORMATION: n is a, c, g, or t
<220> FEATURE:
<221> NAME/KEY: misc_feature
<222> LOCATION: (622)..(624)
<223> OTHER INFORMATION: n is a, c, g, or t

```
<220> FEATURE:
<221> NAME/KEY: misc_feature
<222> LOCATION: (641)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (655)..(661)
<223> OTHER INFORMATION: n is a, c, g, or t

<400> SEQUENCE: 449
tccacacgtt cacgacctgt accttgacac ctttcccatt ctatctacga gtaaacaggg      60
cttcttatgg atgctggagc aacccaagga tagcagcatc aatggcgcta gcccagggat     120
cagagacagg aagctcctcg tcgaggtttt ccctgtaaaa atgtctgcta cgcttcaagg     180
acantccctc accttgtctg gacccgatga tgcctcgcag ctaaccattg acctgctcgg     240
ttgcacagtt gctgctgttt ctgcatccaa tctgccctca cgtaaatggt tagtgcaaat     300
cgtagctggc ctcttcaaca ttcatctctc tctacttatt gttgttgttt tcttgccatc     360
agctacaaag cgtgacttac tcggtgtatg cattattatg cttttagcag ctatctggat     420
ccttgactta ctacataata caatacccag atttgataca ctcctactat ataagaaatc     480
agagtcaaat aactgtagca ggctcctaaa gttgattata cagtttggct aaaactaccg     540
tcagtacctg ttttttttc agggcnnnnn nnnatccgat aaaactggaa agcaaggaat     600
ctggtatttg caggggagc annntatgct atgtttatgc nnnnccnct tgggnnnnnn     660 natcatg                                                               667

<210> SEQ ID NO 450
<211> LENGTH: 201
<212> TYPE: DNA
<213> ORGANISM: Zea mays
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t

<400> SEQUENCE: 450
tntgcacctg caggcacctg agcggctcnt accatggctt gtgcgacacc tcctacaccc      60
cctgcctaga tacatgcaaa ggggaagaca gcaacaacgt nggcggcgct tgctttgact     120
ccccncctcg ttgctggtgn ttcaccaact gctagctgag ctcgccgtga tgtcgtcgat     180
cccatcctct tactcggcct c                                               201

<210> SEQ ID NO 451
<211> LENGTH: 201
<212> TYPE: DNA
```

<213> ORGANISM: Zea mays
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t

<400> SEQUENCE: 451
tgtaattgca gttgtctctc tcttttggc tcaatttgcc cttttgtttt gttgctttgc     60
cctcatgtaa tcgtanatga tatttgttgg atgttctaac nactggcata gattgaagtg    120
tgctgaaata aattcctgct ggtgagaaac agcncncttc gtgtcagtta actcngagat    180
ttatcataga tgagatgaat t                                              201

<210> SEQ ID NO 452
<211> LENGTH: 492
<212> TYPE: DNA
<213> ORGANISM: Zea mays
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t

<400> SEQUENCE: 452
ttggaattga catcagagaa gacgattgag gaactttctc aatggtgacc ttgcaatgct     60
cgttcctgcc aatgattggg tatgccaaat gatttccggt ggctgtagaa ggtgatgttg    120
agcaagaagg aatttcctcc gttagtacag attgtgtagc acctggagtc atcagttggg    180
ttccagcttt ggacaaaacg ttggttgatg aaatntgtgg atagacaaca tctgacacat    240
ctgcaagcac aaattgtttc tgtgnaggct tctgctgttc ttgcttcatt ggtggtggcg    300
cctgtgatgc ttgcagcgaa acatcgctat cttgttgagg caggatccgc tgctgggcaa    360
gtgaatgaga gcttgatagc tgctgcatgt ccaaaagtaa cttctgttgt tcctgtatta    420
cctgtaacgg cgagagtgta actgttggct gtgatacaag tgactgctgc tgtagtttct    480
gtaatagctg ca                                                        492

<210> SEQ ID NO 453
<211> LENGTH: 201
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

```
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t

<400> SEQUENCE: 453
ncaattattt nggacctcta ggcctcacta tacatggatg agatgttcaa cattgacctt      60
tccaacaatt ctattgatgg agctttctca acacttaggg ntagtttgtg aactctattt     120
tcccaaagga ttctcatttt cccaagagaa aatgaactaa tttcccttgn aaaaataggg     180
ttgccaaact agcccntaca a                                               201

<210> SEQ ID NO 454
<211> LENGTH: 789
<212> TYPE: DNA
<213> ORGANISM: Zea mays
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (367)..(368)
```

```
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (461)..(487)
<223> OTHER INFORMATION: n is a, c, g, or t
<220> FEATURE:
<221> NAME/KEY: misc_feature
<222> LOCATION: (492)..(500)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (537)..(539)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (686)..(690)
<223> OTHER INFORMATION: n is a, c, g, or t
<220> FEATURE:
<221> NAME/KEY: misc_feature
<222> LOCATION: (726)..(727)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (747)..(753)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (757)..(782)
<223> OTHER INFORMATION: n is a, c, g, or t
<220> FEATURE:
<221> NAME/KEY: misc_feature
<222> LOCATION: (784)..(788)
<223> OTHER INFORMATION: n is a, c, g, or t

<400> SEQUENCE: 454
```

```
cttnnnnnnt caggttcgtt cttctcttcc tccttgtaga atctaacatt ctctaggagc      60
agaactccac cttctggcaa agcggcagcc aanttctcna cttcntcacc aatgcaatca     120
ttggccatca cgacctattt atgcacacat attagcnctt ngaataactg aaagatagca     180
ggtactaaaa taagctaatg tcaaatctta gcatacttca actccaagga gctcagacaa     240
gcgtggaaca agaggcttca agctgtactt tggggtgaca ccntttggac gaccctgnaa     300
atggcatcaa caaattgcat tattacaaaa ntaaanantta ttgttgctac              360 actcaanncn aaaaaggttg acttgttact nttagtaacc aaaaagattg attcacaaag     420
cacaagcaca tacaggttaa gcaaccacag anaatcagtt nnnnnnnnnn nnnnnnnnnn    480 nnnnnntga annnnnnnnn tatttccaaa aacagtacac ttngctataa attatcnnng     540
tgcgaantgc cgattgccaa ggggcacaaa atctctcacn aatatgntgt ttaagagcat     600
cagctatcag gttctagata taaatcatt tcatatcatg gaaaaaaacg ctagtattat     660
tttcatactn tcaaacaaaa tgaaannnnn gttgcagcag acgataggat ctgacttgga     720
aatgannatg atagnctgaa ctgantnnnn nnntngnnnn nnnnnnnnnn nnnnnnnnnn    780 nntnnnnnc                                                           789
```

```
<210> SEQ ID NO 455
<211> LENGTH: 759
<212> TYPE: DNA
<213> ORGANISM: Zea mays
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
```

```
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (595)..(605)
<223> OTHER INFORMATION: n is a, c, g, or t
<220> FEATURE:
<221> NAME/KEY: misc_feature
<222> LOCATION: (608)..(612)
<223> OTHER INFORMATION: n is a, c, g, or t
<220> FEATURE:
<221> NAME/KEY: misc_feature
<222> LOCATION: (615)..(624)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (755)..(756)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t

<400> SEQUENCE: 455
ctgctgttgc cggcttcnnc atgcagaagg taataaaatg tcacccatgc tcatgatctt      60
ttaagtgtat ttaggtactg ttaagtagga tggggtaaat attttntacc tttcaaaaga     120
gaccaataaa tcttttaac atttcagttt tttcataaat naaaaaagga aagntttgac     180
aaatgacttt attatctcag gaacttgact accttgttgg agctgttgcc aacccaagaa     240
agccatttgc cgcnattgtt ggtggatcca aggtctcaan taagattggt gtcattgagt     300
cnttgctggc gaaggtcgat atcctcatcc ttggtggtgg tatgatctac acattttaca     360
aggcacangg atattctgtt ggaaaatctc tcgtggaaga ggataaactn gagctcgcaa     420
cttctcttat tgagaaggcg aaggcaaagg gggtttctct tttgcttccc actgatattg     480
tagtagcgga caagtttgca gcngatgctg agagcaaggt ttgtttattt acacataaac     540
acctcagatg gnacttcaga attntttctt tcttccctt taatgaatcg tgaannnnnn     600
nnnnnagnnn nnctnnnnnn nnnnattcac tagtaattct gccgcataag tcgtgcagca     660
gantagaatt aggcatgaat agttcagtgt taatagtgat aagacatgtt attttgtatg     720
ataggttttc cacagtgcag naccggaaac aaatnngnc                             759

<210> SEQ ID NO 456
<211> LENGTH: 577
<212> TYPE: DNA
<213> ORGANISM: Zea mays
<220> FEATURE:
<221> NAME/KEY: misc_feature
<222> LOCATION: (322)..(322)
<223> OTHER INFORMATION: n is a, c, g, or t

<400> SEQUENCE: 456
tgctaagatt tgacattagc ttattttagt acctgctatc tttcagttat tccaagtgct      60
aatatgtgtg cataaatagg tcgtgatggc caatgattgc attggtgaag aagttgagaa     120
gttggctgcc gctttgccag aaggtggagt tctgctccta gagaatgtta gattctacaa     180
ggaggaagag aagaacgaac ctgagtttgc taagaagcta gcatctgttg ctgacctta     240
```

```
tgtcaatgat gcttttggca cggcacacag agctcatgct tcaaccgaag gagttaccaa    300
gtatttgaag cctgctgttg cnggcttcct catgcagaag gtaataaaat gtcacccatg    360
ctcatgatct tttaagtgta tttaggtact gttaagtagg atggggtaaa tattttgta     420 cctttcaaaa gagaccaata aatcttttta acatttcagt ttttcataa ataaaaaaag     480 gaaaggtttg acaaatgact ttattatctc aggaacttga ctaccttgtt ggagctgttg    540
ccaacccaaa gaagccattt gccgctattg ttggtgg                             577
```

```
<210> SEQ ID NO 457
<211> LENGTH: 500
<212> TYPE: DNA
<213> ORGANISM: Zea mays
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t

<400> SEQUENCE: 457
ttccaaattc ttttccaggg ctcaaaggat ccgctccaa tgaaaaaagc tctgtaggca     60
tctactagac agaatactca aaacagtctt gcgtttcctt atatcgacat ctatcttact   120
aatgtttaca gggagctatc cttgatattt tagaacagtt ttactgtaat ttgaaagcag   180
caattacctt attcatttat accaaactgc caataaggtc cattgtcaac tgatggatag   240
agtatttaag gctttactta tttctggaca aagtgttttg ttactataac aaaagtaacc   300
agtgaggaat ttgcatttaa ttttctgtcc aacgcttatt atgcntgcaa ctctatgttt   360
atatagcacc aaaccaccaa tgttaattga agaattaata tcgattctaa gtggatgcct   420
gtttcctcat ttactttatt cattacaaac gttgattgaa gaatttctgt aaatactgan   480
tttttattcc cttttctgtg                                               500
```

```
<210> SEQ ID NO 458
<211> LENGTH: 412
<212> TYPE: DNA
<213> ORGANISM: Zea mays
<220> FEATURE:
<221> NAME/KEY: misc_feature
<222> LOCATION: (58)..(58)
<223> OTHER INFORMATION: n is a, c, g, or t

<400> SEQUENCE: 458
ccaaggactg acggaacgga tcggatggat tgggcgattg gcatcgcagg agattctnga    60
tcagattgtc ttcgagcgca cgccgcaatg gtcaactgcg cagcgctggc ttggctgctg   120
cctccgttca ctcttcgctg tcagagcgaa acagcggtaa cagagcaaga cacgaggggt   180
ctgcactctg cagttgtgca ggaggaggaa cagacacagg gagaggaggg cgcgcggccg   240
gacatggcgt ggaacagaga tcgtcgtcac cgccggcggg ggtgtggtcg acgacgcgac   300
atgcgaaaca ctacgtgcta gctagcatag gaaaaaacaa catgaaatcg tacaaccaac   360
caatccctcg cactgtttta gttgttagct gtaggcgaaa ctgttcatcc aa            412
```

```
<210> SEQ ID NO 459
<211> LENGTH: 664
<212> TYPE: DNA
<213> ORGANISM: Zea mays
<220> FEATURE:
```

```
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (609)..(613)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (642)..(656)
<223> OTHER INFORMATION: n is a, c, g, or t
<220> FEATURE:
<221> NAME/KEY: misc_feature
<222> LOCATION: (662)..(663)
<223> OTHER INFORMATION: n is a, c, g, or t

<400> SEQUENCE: 459
tgtggcacag ccggtctgga aggagaccgc agcaatagtc gatttgaggg catatagcag      60
tgaagaaaaa gcaggaggga gaagttttgg gtggtggcca tgcatctgga taatgggaga     120
agcaaggtgc gccaagggag agagcattca cacaagagac agaggacgag cagtggcgct     180
gggaatctgg gtccccatta aatgtatcca tgtaggttac ccaggggagg gtacatgggc     240
tggctgatgg gctgggccag ctccttctta ctcctccctt ctccttttt cttttttccc      300 tttttcctca gccacatgtt agaatttgta tggcactatg gngtagcctt tcctcgcctt     360
atcaccgcct aggcatcaca tagacatttg ctaagtgttt ggttcgccga aatgtaatgt     420
aaatggatta cacgaggtaa tggataccga tacttatgtt tggttgagtt ctttctagta     480
atactaggta ctaatatcca atccaattat aactagtgac cattaccgcc ggtaagggat     540
cccattacca ttcccttaac aatatatgaa ccaaacatca ccttggaaga agctggctcg     600
ctacaactnn nnnatagcac cttaagnacc atgattaaaa tnnnnnnnnn nnnnncaca     660 tnnc                                                                  664

<210> SEQ ID NO 460
<211> LENGTH: 1203
<212> TYPE: DNA
<213> ORGANISM: Zea mays
<220> FEATURE:
<221> NAME/KEY: misc_feature
<222> LOCATION: (234)..(258)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t

<400> SEQUENCE: 460
ggccgggatg tcagagaaag gaaaacccac accggccaaa ccacgactgc aaagagaaag      60
gaaaggctct ctcccagccc caagaaaaaa ggcagcacac caactcacca agaaagtgtg     120
gagctgctcc tgcctgcagc ctcctgctca tcgaccctt cgccccacaa gctcgattcc      180
tcgctcggcc atggctgcac ccgcggagga gacgcttgcc gccgaggata cggnnnnnnn     240
nnnnnnnnnn nnnnnnnntg cggggttctg gttccttggc gaggataagt ctgtccacaa     300
ggctctcggc gggggtaaaa ctgctgatgt acttttgtgg aaagacaaga agacctctgc     360
tgcggtagtt ggtggtgcaa ctgtcctatg ggttctgttc gaaattgtag aataccatct     420
cctgaccctg gtttctcatg tgctgatcgc tgcactgacc atcttgttcc tgtggtccaa     480
tgcgactgtc tttatcaaaa agagtcctcc tgatgttcct gaagtgcaga tatctgaaga     540
```

```
cnttgctgta aacattgcgc tagcattgcg tgctgacatc aacaaggcac ttgccctgct      600
tcgggagatt gctctgggcc ataacctgat gaagttccta ggcgtggtcg tcgcccttg      660 gattctttca gagatcgggg agctatgtga tctcctgaga ttgatgtaca ttgtggtctt      720
gatcctccac acagtgccga tactgtacca caagtatcag gaccaggtgg acaatttcgc      780
tgcaaaggcg cacagggagc tctgcaagca atacgcggtc ctggatgcca aagttctgag      840
caagattcca agagctccac caaaagataa gaaacagaac tagaacgtgg aggatgacaa      900
gcgccttgtt ttcggcttgg gcgacgagag tttgtagcca atggtctgat gtggttcgtg      960
ggctttgtgt aggtgcacag tttcacgtat atgttctggt cgtgtaatct atatgtttat     1020
ataaacctgt aggggtgttg atgaccatcg aaagtgtcgt aaatattcag tagtatatgt     1080
agcttagggc ttaacggttg tgtttataag gtcattgtcg ttgtcgatgg gaagtattat     1140
catgttattt tcaggactca ggagtataaa atgaaataaa atgtgaattc atctgaaaaa     1200
aaa                                                                   1203

<210> SEQ ID NO 461
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t

<400> SEQUENCE: 461
cttgtcatga tatattttt tcttcaaatg tgtttgagtt ttttctctag aatatttact       60
attacaatga ctcaacccat cttttctctgt agttggtgac ncttttgtta ctgaggacac     120
tacaaatgtg angtttcctc gggaagtaac agttccaggc tatacacacc cattggttgc     180
agttggcaca ggtattttc a                                                201

<210> SEQ ID NO 462
<211> LENGTH: 262
<212> TYPE: DNA
<213> ORGANISM: Zea mays
<220> FEATURE:
<221> NAME/KEY: misc_feature
<222> LOCATION: (73)..(73)
<223> OTHER INFORMATION: n is a, c, g, or t

<400> SEQUENCE: 462
tcgactcgct cgtgcgcctc tacggcacca acgccgacgc cttctcgtcg gacttcgccg      60
cgtccatggt cangctcggc aacatcggcc cgctcacggg ttccgcgggg gaggtcaggc     120
tcaactgcag gacggtgaat tcgaattcgt gacttcagga cggtgaatgc caccattttg     180
aattggtact gctctttttc ccccacaagg agttgtagaa tttgcattcc ttcaacgatt     240
tcgaatttcg aatttgctgt ga                                              262

<210> SEQ ID NO 463
<211> LENGTH: 267
<212> TYPE: DNA
<213> ORGANISM: Zea mays
<220> FEATURE:
<221> NAME/KEY: misc_feature
<222> LOCATION: (129)..(129)
```

<223> OTHER INFORMATION: n is a, c, g, or t

<400> SEQUENCE: 463

```
ccaccgacgg cggcgagagt atatatacac acacacctga cgcctctgct gctgctggga      60
tcaacgcggc agcttagtga cgacgacgac tcttctgtct ctgcgttgat taatggacag     120
taacagatnc atggcgacga gcggcgtggc tccgttcgtg gccaagacgt accgcatggt     180
ggatgacccg gcgaccgacg gcgtggtcgc gtggggcagg gacaacaaca gcttcgtcgt     240
ggccgacccc ttcgccttct cgcagac                                         267
```

<210> SEQ ID NO 464
<211> LENGTH: 201
<212> TYPE: DNA
<213> ORGANISM: Zea mays
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 464

```
gaaaaggtta aaccctattt ccntttcagt tagcataaaa aatctctatg atatgatatt      60
caagagatga tgaggcaaac tacgatgcta agtggcatga ncaagtcgtg ctctagtatc     120
cnanaagata ggaanggggtg taaaccanct ngaccatatt tgtaaaatgc ttgagaagac    180
ttccattatt ttccaacnag a                                               201
```

<210> SEQ ID NO 465
<211> LENGTH: 201
<212> TYPE: DNA
<213> ORGANISM: Zea mays
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

```
<220> FEATURE:
<221> NAME/KEY: misc_feature
<222> LOCATION: (101)..(101)
<223> OTHER INFORMATION: n is a, c, g, or t

<400> SEQUENCE: 465
actttagacc ctaggccctt ggtcacccta taaatacccc cactngacag tggatggggc    60
ccgcttcnca agacatccnt gctcccctac caaccatttt ntcatgcatt gtttgtctca   120
catgctcccg agttcttggg ccagtgtgta aggacccaac acacatatat ggcaaatatc   180
ttaataaaat caaatataag c                                             201

<210> SEQ ID NO 466
<211> LENGTH: 371
<212> TYPE: DNA
<213> ORGANISM: Zea mays
<220> FEATURE:
<221> NAME/KEY: misc_feature
<222> LOCATION: (234)..(234)
<223> OTHER INFORMATION: n is a, c, g, or t

<400> SEQUENCE: 466
tatgaagcgg actaggacat cgccggaggg gaagaagaac gggacatcgc cggaggggaa    60
gaagaacgag agcctcttct gatgcttgac ttcgtgtaca agttgtagct gaatgttcct   120
caaaatatag gattaactag ttctgtaaca ctaacacccc ggcttggtta tgacttagaa   180
actgttaggc catgtttggt tcacatctcc taaagtttag tcacttgttt aaanatgtta   240
aaggaggtaa ctaaaaaaaa aacctcttaa ataggacatt ataggacta atgtttagtt    300 cctaaaattt aggagatgac taaaggaacc aaacatagtt tactaagcct tagtaaacgt   360
gtgaataaat g                                                        371

<210> SEQ ID NO 467
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (198)..(199)
<223> OTHER INFORMATION: n is a, c, g, or t

<400> SEQUENCE: 467
acatgctacc gtgcagaatt cgagcaccaa gaacaaacta aattcagttc ccattatcac    60
catcgctaac accagagcag ttccttactc tacaaaccaa nttcattgac aattcagctt   120
ctaactagaa agtcttctgt tctatttcta gaactaaccc gccatgaata tcagttgtcc   180
acaacataaa taagcaanng t                                             201

<210> SEQ ID NO 468
<211> LENGTH: 698
<212> TYPE: DNA
<213> ORGANISM: Zea mays
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
```

<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: misc_feature
<222> LOCATION: (619)..(620)
<223> OTHER INFORMATION: n is a, c, g, or t
<220> FEATURE:
<221> NAME/KEY: misc_feature
<222> LOCATION: (628)..(631)
<223> OTHER INFORMATION: n is a, c, g, or t
<220> FEATURE:
<221> NAME/KEY: misc_feature
<222> LOCATION: (640)..(646)
<223> OTHER INFORMATION: n is a, c, g, or t
<220> FEATURE:
<221> NAME/KEY: misc_feature
<222> LOCATION: (652)..(655)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (680)..(681)
<223> OTHER INFORMATION: n is a, c, g, or t
<220> FEATURE:
<221> NAME/KEY: misc_feature
<222> LOCATION: (691)..(693)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t

<400> SEQUENCE: 468

```
taagatagaa agcaggagtc aattctgaat aacactagga gctaagtctg acaatgtata    60
tattttgaag gtaaaagatt tattaaatat gagtagcttc gtagctggga gagtgatcat   120
tctcataatg aaacatggaa ctagtattgt atcatgataa gcaataagat tagaataatt   180
gaagaaagat catacaaatg ctccaggagc ccattctcga tatgtgatac cttccgcgct   240
acattggaan ataagataca aagttatttg ctagtatata ggataaaaga taaacacttc   300
atgttaaaga atacctgcga ttaaatccaa acttctcata actacgggag aaggcttcca   360
agcctccttc atgttcatca atgtctgaac ggattcttct atagaggctg tacctgttct   420
tttattcaag gaagttgaaa gcacagtgag atggatagtg gtgttcgcat gggttatata   480
taggantcct tataagaaga atacagaagg gatggaaatg aaggttgcca aagaattaga   540
acccgctgtt gcctctatat tgtctgncta acatttctgt aaatatcctc tgaangagna   600
catatcttgt ncgttcaann gtaatgcnnn ntgaaaccan nnnnnntact tnnnncatca   660
aagcagtatg naagatttcn ngtgaaaacg nnnctgnc                          698
```

<210> SEQ ID NO 469
<211> LENGTH: 708
<212> TYPE: DNA
<213> ORGANISM: Zea mays

-continued

```
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (309)..(310)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (565)..(566)
<223> OTHER INFORMATION: n is a, c, g, or t
<220> FEATURE:
<221> NAME/KEY: misc_feature
<222> LOCATION: (578)..(580)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (650)..(652)
<223> OTHER INFORMATION: n is a, c, g, or t
<220> FEATURE:
<221> NAME/KEY: misc_feature
<222> LOCATION: (659)..(662)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (668)..(682)
```

<223> OTHER INFORMATION: n is a, c, g, or t
<220> FEATURE:
<221> NAME/KEY: misc_feature
<222> LOCATION: (685)..(696)
<223> OTHER INFORMATION: n is a, c, g, or t
<220> FEATURE:
<221> NAME/KEY: misc_feature
<222> LOCATION: (698)..(699)
<223> OTHER INFORMATION: n is a, c, g, or t
<220> FEATURE:
<221> NAME/KEY: misc_feature
<222> LOCATION: (703)..(704)
<223> OTHER INFORMATION: n is a, c, g, or t

<400> SEQUENCE: 469

```
tctgatgaca gaagctgaaa gaaaactgaa ataaacagtg tctttacagg tggcaaatgt      60
gatggatcat ttctttaccc gtcattcagc ttctaacaca atcgctacag taaaagaacc     120
ttatcggttt gtctcatcgc ttttgaaaca attaagctcc cgtccactca aatgggtca      180
ttcgttgtgc nctagcgcct gccattctcc accaccgcca ccccacatca gattagantt     240
gcatctaatc tgtggtttgt gtctttaatc tcactttctg atggcgtagc agcctatcgt     300
ctaaaggann ttcatatttg aaacanagta aaaatagaa tatgtagaac taaaaataaa     360
taaagntaga aaatatagg attgaaaaac aaggaaatt ttanaggagt nagtgttagt      420
gtttggaaca cntgaatata agaatatgtn tattcctcta ttctagtgaa taaaggcttg     480
ctcntcattc tatcatgtat agaatatttt taaggaatga gaacttgatt aggtgtacaa    540
atttttacttt ctctatatca cgaannaaaa cgagcctnnn actggaaaaa taaaacttaa    600
ntcnttcatt ctaaacanta catgatgtaa aagtagaaat tggatttttn nnaaatgtnn    660
nngnancnnn nnnnnnnnnn nnctnnnnnn nnnnnngnnc tannactc                 708
```

<210> SEQ ID NO 470
<211> LENGTH: 692
<212> TYPE: DNA
<213> ORGANISM: Zea mays
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (557)..(558)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t
<220> FEATURE:
<221> NAME/KEY: misc_feature
<222> LOCATION: (638)..(640)
<223> OTHER INFORMATION: n is a, c, g, or t
<220> FEATURE:
<221> NAME/KEY: misc_feature
<222> LOCATION: (648)..(649)
<223> OTHER INFORMATION: n is a, c, g, or t
<220> FEATURE:
<221> NAME/KEY: misc_feature

```
<222> LOCATION: (651)..(651)
<223> OTHER INFORMATION: n is a, c, g, or t
<220> FEATURE:
<221> NAME/KEY: misc_feature
<222> LOCATION: (659)..(660)
<223> OTHER INFORMATION: n is a, c, g, or t
<220> FEATURE:
<221> NAME/KEY: misc_feature
<222> LOCATION: (667)..(667)
<223> OTHER INFORMATION: n is a, c, g, or t
<220> FEATURE:
<221> NAME/KEY: misc_feature
<222> LOCATION: (669)..(672)
<223> OTHER INFORMATION: n is a, c, g, or t
<220> FEATURE:
<221> NAME/KEY: misc_feature
<222> LOCATION: (679)..(684)
<223> OTHER INFORMATION: n is a, c, g, or t
<220> FEATURE:
<221> NAME/KEY: misc_feature
<222> LOCATION: (686)..(691)
<223> OTHER INFORMATION: n is a, c, g, or t

<400> SEQUENCE: 470 cnnccccga cgaccgcctt gccgatcgcc gccccgatcg cgccgacgtt cacggcgatc      60
accgctattg tggggatcag cagtggcgtc cactgcacca cgtacatctc agcgtacttc     120
tcgttcacgg cgctcgtagc ctgcttcgcc gtcagcttga acgaaacgcc gttcccgcgn     180
aggactagct tcagcacgat gtgcagcgtc gctaacgggt acacggctgt cgccccgatg     240
atgtagaact gctcgttgcg gatccagtcc agcagcgtga ggcctgccca cttgatctcc     300
accatgccga tcagctctgt cattgctatg atgacgacga ggtacagcac gtatgtcggg     360
aacggcttct ggatgtagaa ctcgccacgg aagatccata tgacggggaa gaggaggtag     420
aacacnagga agaccgatga gattgggtag gctgtcatgt tggtgtaggc gatccgttgc     480
atcaagttca gtcgacggcc agcaaggagc gggcagtgtg agaagaacat ttcaagggag     540
ccgcccgacc agcgcannat ctggcagagg cgctccgtga ggttgattgn tgcagtgcca     600
cggaaggcat ccggctccat gcggcagtac atnnatcnnn acctgtnng ntgtactcnn     660 aagccgntnn nnacgtccnn nnnngnnnnn nt                                   692

<210> SEQ ID NO 471
<211> LENGTH: 395
<212> TYPE: DNA
<213> ORGANISM: Zea mays
<220> FEATURE:
<221> NAME/KEY: misc_feature
<222> LOCATION: (173)..(173)
<223> OTHER INFORMATION: n is a, c, g, or t

<400> SEQUENCE: 471
cgcggccgtg gctgggaaac ggtggccggc gccatccttg aggtggtgtg acgatcgacg      60
acgtgcatgg cgtggcgcac agagctagta ataaaagggt agtgtacgct taccgcgtac     120
gtacgtgtca ccgggcgtgg cactctccag tctccaggga cccatccacc aantgctact     180
gctccttcgt agggagacgt gggaataaag agtggtagct gcatgcacgt acggcggcca     240
tggctctccg atgagagagc tagctgtgta cgtgtgttcg tgatgttgtt ccatgcatga     300
catgtatacg tcttgcctaa gtacgcttgt actagttgag agactgtgta agtgaaatgt     360
gctataataa taaataagta aagggcgcct tctcc                                395

<210> SEQ ID NO 472
<211> LENGTH: 201
<212> TYPE: DNA
```

<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 472
tatggctaga ctataggtta attcaaagtg atagaatatt tatgaaaggg agaataaaag    60
tgaaacccta atgaatagtt tagtggttaa ctttgtgaaa ntaatcccat ttaatatatg   120
atcccatctc tgaaatgact ttaggtaagt aagtaattca ttaaggtaga tgtagttaag   180
taatgtaatc tactgagata g                                             201

<210> SEQ ID NO 473
<211> LENGTH: 201
<212> TYPE: DNA
<213> ORGANISM: Zea mays
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t

<400> SEQUENCE: 473
ataaggaatt aaggagacac aaattagtct gaacgagtag gagnngtgga atttcattgg    60
ataagaagga tccaattagt ctgcaacgtg tgtggccacc naaaaagatt ctgcagttct   120
ctanatctgc atatagtcca taggatcgga tatgctcctt ccatgttctt tcgtttcaca   180
aggtcaaagc tggtaccacg c                                             201

<210> SEQ ID NO 474
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 474
gtaatcgagg ttcagatcaa gcatctatca tttactcggc aattgacaaa gcttataaag    60
cttacggtcc aaactcgttg aaggtatgtg aagaaccttg ngcacagtaa gggcacacgc   120
atccatatga tgaaatagca tgaatggctg aactttgtgt gtgagatcaa acttataata   180
ttaagggcta gtttagaaac c                                             201

<210> SEQ ID NO 475
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 475
ctaggtctca tgtggaggca tggagaacct gcttctcttc ctgacacatt ccaagcttta    60
aaaaaactca cacatgcccc gcatggcgct cgggatattc ngtacaagcg acgcgggtgc   120
ctgcagcacc actaacaatc ctacaagaca acatactgac aataacaagg cttccattaa    180
tatagtatgg ggcttccata a                                              201

<210> SEQ ID NO 476
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t

<400> SEQUENCE: 476
tccccaaacc tgaaccagc gaccaggcgg gggcaaaaaa aaaggctcac tgtaactgct     60
tacaatgggg tggtaattgc gtatcgagtg atcagatctc ntctcaccct ctccaggaac   120
agtgggtggt caacgaacac gcggtccact ccgcgcttgt agcagtggaa gaacctgacc   180
gtctcgtacc ngtctcccat c                                              201

<210> SEQ ID NO 477
<211> LENGTH: 201
<212> TYPE: DNA
<213> ORGANISM: Zea mays
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t

<400> SEQUENCE: 477
ttattttagg aaatgaggat tagggttagc gagtgagnat tttgcatttt tatatggggg    60
cagngtgaga ngatttgttg gaatcgaact tcataggccg ngcgagggga atgtatgact   120
cctaatttgg gtcttcattg gatccccatg gnagaaattt catccccacc ctgccatcct   180 cgcagggaa atttcatccc c                                               201

<210> SEQ ID NO 478
<211> LENGTH: 707
<212> TYPE: DNA
<213> ORGANISM: Zea mays
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:

```
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (619)..(623)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (648)..(654)
<223> OTHER INFORMATION: n is a, c, g, or t
<220> FEATURE:
<221> NAME/KEY: misc_feature
<222> LOCATION: (663)..(664)
<223> OTHER INFORMATION: n is a, c, g, or t
<220> FEATURE:
<221> NAME/KEY: misc_feature
<222> LOCATION: (666)..(669)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (679)..(680)
<223> OTHER INFORMATION: n is a, c, g, or t
<220> FEATURE:
<221> NAME/KEY: misc_feature
<222> LOCATION: (682)..(685)
<223> OTHER INFORMATION: n is a, c, g, or t
<220> FEATURE:
<221> NAME/KEY: misc_feature
<222> LOCATION: (690)..(691)
<223> OTHER INFORMATION: n is a, c, g, or t
<220> FEATURE:
<221> NAME/KEY: misc_feature
<222> LOCATION: (697)..(699)
<223> OTHER INFORMATION: n is a, c, g, or t
<220> FEATURE:
<221> NAME/KEY: misc_feature
<222> LOCATION: (701)..(704)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t

<400> SEQUENCE: 478
nncaatgctt gtcctgtttt ctttgcctca gtaagtngta tctttgtata ttttgctttg      60
ccagatacag gctgtaaaat gtaggcatgc ttttcgaag cagatctgga accatcctgc     120
tcctgaaact caaaaacctg aaatgtagt ttacaaacca ataatatttt gttaggttgc     180
tggatgcaag caacagaaga ataaaagatc ccaacaaaac ctcattacag cactgcgtct     240
attcacactc taccacatgt tttttcaaac agaaattgac aaaggtaatt gtctccatgc     300
caatttattc tctcaaaccc agggtattta tttgcgcaca aacaaaattg ggaggcacct     360
gactccactc tgatggaagt aaatcctccc agggtttatc cacaatccaa gnactgctat     420
cagagtcaaa atacaccgcc agactctcaa gttcaacaga ctgcaaaatg ccaagttaaa     480
gaagtcacgc aaattgatca aaagtaaaaa aggtcaaact aaaacaaata agcacaccaa     540
```

| | |
|---|---|
| atgtgaaaaa tgcttgatgt gtgaagcgaa aagaattcat tactanntcc tgaaaacttt | 600 |
| aaatcaaatt aattgatcnn nnnaattaga aantnaaaaa tgagctannn nnnnttttta | 660 |
| ctnncnnnnc tantattcnn cnnnntagan natgagnnnt nnnnant | 707 |

<210> SEQ ID NO 479
<211> LENGTH: 764
<212> TYPE: DNA
<213> ORGANISM: Zea mays
<220> FEATURE:
<221> NAME/KEY: misc_feature
<222> LOCATION: (108)..(129)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t

<400> SEQUENCE: 479

| | |
|---|---|
| tgggtacctc gcctcgagcc ggaattcggc acgaggatcc aatcgaacca ccagtccacc | 60 |
| acctgattga ctagagcaaa agcacaagcc gcccacgcat ctcgattnnn nnnnnnnnnn | 120 |
| nnnnnnnnng gcgcgcagag ctcgtgacga gagcaacctt ccttccgttc ctcgatcgcc | 180 |
| atggacaagg tgctggcctt ctcgatcctg agcgcgtcgc cggccgacct ctcctccacg | 240 |
| ggcgccggct tcggcgggag ctgggcgcgg ctgtcgtggc ggcggggcgc ggacgaccag | 300 |
| cgtgcgccgt ggtggtagca ctataatcag caccaggagg aggacaggga gaagcgagac | 360 |
| ttgcgctccc gcgacggcgg agcgcacgcg agcggagggg gagcggcggc ggcgccaccg | 420 |
| cggttcgcgc cggagtttga cggnatcgac tggttcggaa ccatcgtgtc gcgctgatca | 480 |
| acaatccggg ctcggccgac gcgcccccg agttaaccac gtgaccaatc ctgtctacta | 540 |
| tgttttttt accttatggt ggattaattg tcccaacaca gataattggg actccgcgtg | 600 |
| ttgtacatac agggaactgc tcaattacca ggtgggatgg ggaacattta tttgttcctg | 660 |
| tcctctgcat tttttttctg taccgaaatg gatggatggt ctccaacttg aaattgagtc | 720 |
| cctcagcccc aggtaatctg gcggtggatg aacccaagcc gaac | 764 |

<210> SEQ ID NO 480
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 480

| | |
|---|---|
| atgagaagca tgcatgcatg ggattgtccg attcctttct tcatgtagat atatacgatt | 60 |
| gtatatgtat gcatccattg ttcttgtctt ctttaataaa natgtaagtt atgcttgctt | 120 |
| catgctttca acggagacga tgctggctca taagtacgtt gacagaaagg cacaaaccca | 180 |
| ctatatgtat atggcatggg n | 201 |

<210> SEQ ID NO 481
<211> LENGTH: 201
<212> TYPE: DNA
<213> ORGANISM: Zea mays
<220> FEATURE:

```
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 481
ncgatcgatt taatgttgag ctggtgatat gggtgctgtt tctttgatat ggcgtgtaga      60
ttgggtcaaa actatgttaa taggcattga taaatggata nggctattat tcttgccttt     120
tcagttgcta gaattagggg attgaggttc ggaatcaggc aattgcatag ttttgatgat     180
tattcagcta gcaaatgaat t                                               201

<210> SEQ ID NO 482
<211> LENGTH: 201
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 482
ctcctctggn ccttcaagtg atgaaattgt tgggtgatct ggagagagat tcctttagga      60
gaatattacc ctgctttttc ccattattgg ctgatctgat ncgctgtgaa catagctctg     120
gagaagttca acatgcactg tacaatatct tccaatcagc cattctcccc atgatanggg     180
tttaataaca gattgtgacc c                                               201

<210> SEQ ID NO 483
<211> LENGTH: 27
<212> TYPE: DNA
<213> ORGANISM: Zea mays

<400> SEQUENCE: 483
ccacaaaaaa tgaacaagaa gtgtcca                                          27

<210> SEQ ID NO 484
<211> LENGTH: 24
<212> TYPE: DNA
<213> ORGANISM: Zea mays

<400> SEQUENCE: 484
cccatggatg atcggatgat gtta                                             24

<210> SEQ ID NO 485
<211> LENGTH: 24
<212> TYPE: DNA
<213> ORGANISM: Zea mays

<400> SEQUENCE: 485
tgttcttcgg ggtgttacta tcct                                             24

<210> SEQ ID NO 486
<211> LENGTH: 25
```

```
<212> TYPE: DNA
<213> ORGANISM: Zea mays

<400> SEQUENCE: 486
ctgtaaaaat gtctgctacg cttca                                          25

<210> SEQ ID NO 487
<211> LENGTH: 23
<212> TYPE: DNA
<213> ORGANISM: Zea mays

<400> SEQUENCE: 487
ccctgcctag atacatgcaa agg                                            23

<210> SEQ ID NO 488
<211> LENGTH: 24
<212> TYPE: DNA
<213> ORGANISM: Zea mays

<400> SEQUENCE: 488
ttgctttgcc ctcatgtaat cgta                                           24

<210> SEQ ID NO 489
<211> LENGTH: 23
<212> TYPE: DNA
<213> ORGANISM: Zea mays

<400> SEQUENCE: 489
tgacacatct gcaagcacaa att                                            23

<210> SEQ ID NO 490
<211> LENGTH: 28
<212> TYPE: DNA
<213> ORGANISM: Zea mays

<400> SEQUENCE: 490
gttcaacatt gacctttcca acaattct                                       28

<210> SEQ ID NO 491
<211> LENGTH: 21
<212> TYPE: DNA
<213> ORGANISM: Zea mays

<400> SEQUENCE: 491
aactccacct tctggcaaag c                                              21

<210> SEQ ID NO 492
<211> LENGTH: 20
<212> TYPE: DNA
<213> ORGANISM: Zea mays

<400> SEQUENCE: 492
gctgttgcca acccaaagaa                                                20

<210> SEQ ID NO 493
<211> LENGTH: 27
<212> TYPE: DNA
<213> ORGANISM: Zea mays

<400> SEQUENCE: 493
accgaaggag ttaccaagta tttgaag                                        27

<210> SEQ ID NO 494
```

-continued

```
<210> SEQ ID NO 494
<211> LENGTH: 23
<212> TYPE: DNA
<213> ORGANISM: Zea mays

<400> SEQUENCE: 494
gcatttaatt ttctgtccaa cgc                                              23

<210> SEQ ID NO 495
<211> LENGTH: 21
<212> TYPE: DNA
<213> ORGANISM: Zea mays

<400> SEQUENCE: 495
ggaacggatc ggatggattg g                                                21

<210> SEQ ID NO 496
<211> LENGTH: 25
<212> TYPE: DNA
<213> ORGANISM: Zea mays

<400> SEQUENCE: 496
cctcagccac atgttagaat ttgta                                            25

<210> SEQ ID NO 497
<211> LENGTH: 25
<212> TYPE: DNA
<213> ORGANISM: Zea mays

<400> SEQUENCE: 497
cctgatgttc ctgaagtgca gatat                                            25

<210> SEQ ID NO 498
<211> LENGTH: 30
<212> TYPE: DNA
<213> ORGANISM: Zea mays

<400> SEQUENCE: 498
ctattacaat gactcaaccc atctttctct                                       30

<210> SEQ ID NO 499
<211> LENGTH: 19
<212> TYPE: DNA
<213> ORGANISM: Zea mays

<400> SEQUENCE: 499
cgccttctcg tcggacttc                                                   19

<210> SEQ ID NO 500
<211> LENGTH: 25
<212> TYPE: DNA
<213> ORGANISM: Zea mays

<400> SEQUENCE: 500
gactcttctg tctctgcgtt gatta                                            25

<210> SEQ ID NO 501
<211> LENGTH: 24
<212> TYPE: DNA
<213> ORGANISM: Zea mays

<400> SEQUENCE: 501
tgaggcaaac tacgatgcta agtg                                             24
```

```
<210> SEQ ID NO 502
<211> LENGTH: 24
<212> TYPE: DNA
<213> ORGANISM: Zea mays

<400> SEQUENCE: 502
gcccttggtc accctataaa tacc                                            24

<210> SEQ ID NO 503
<211> LENGTH: 25
<212> TYPE: DNA
<213> ORGANISM: Zea mays

<400> SEQUENCE: 503
gccatgtttg gttcacatct cctaa                                           25

<210> SEQ ID NO 504
<211> LENGTH: 24
<212> TYPE: DNA
<213> ORGANISM: Zea mays

<400> SEQUENCE: 504
ctaacaccag agcagttcct tact                                            24

<210> SEQ ID NO 505
<211> LENGTH: 25
<212> TYPE: DNA
<213> ORGANISM: Zea mays

<400> SEQUENCE: 505
cacagtgaga tggatagtgg tgttc                                           25

<210> SEQ ID NO 506
<211> LENGTH: 20
<212> TYPE: DNA
<213> ORGANISM: Zea mays

<400> SEQUENCE: 506
agctcccgtc cactcaaatg                                                 20

<210> SEQ ID NO 507
<211> LENGTH: 20
<212> TYPE: DNA
<213> ORGANISM: Zea mays

<400> SEQUENCE: 507
cgccacggaa gatccatatg                                                 20

<210> SEQ ID NO 508
<211> LENGTH: 18
<212> TYPE: DNA
<213> ORGANISM: Zea mays

<400> SEQUENCE: 508
cgtggcactc tccagtct                                                   18

<210> SEQ ID NO 509
<211> LENGTH: 32
<212> TYPE: DNA
<213> ORGANISM: Zea mays

<400> SEQUENCE: 509
gggagaataa aagtgaaacc ctaatgaata gt                                   32
```

```
<210> SEQ ID NO 510
<211> LENGTH: 24
<212> TYPE: DNA
<213> ORGANISM: Zea mays

<400> SEQUENCE: 510
aaggatccaa ttagtctgca acgt                                           24

<210> SEQ ID NO 511
<211> LENGTH: 23
<212> TYPE: DNA
<213> ORGANISM: Zea mays

<400> SEQUENCE: 511
cggtccaaac tcgttgaagg tat                                            23

<210> SEQ ID NO 512
<211> LENGTH: 17
<212> TYPE: DNA
<213> ORGANISM: Zea mays

<400> SEQUENCE: 512
tcacacatgc cccgcat                                                   17

<210> SEQ ID NO 513
<211> LENGTH: 25
<212> TYPE: DNA
<213> ORGANISM: Zea mays

<400> SEQUENCE: 513
gtggtaattg cgtatcgagt gatca                                          25

<210> SEQ ID NO 514
<211> LENGTH: 23
<212> TYPE: DNA
<213> ORGANISM: Zea mays

<400> SEQUENCE: 514
tgaggattag ggttagcgag tga                                            23

<210> SEQ ID NO 515
<211> LENGTH: 22
<212> TYPE: DNA
<213> ORGANISM: Zea mays

<400> SEQUENCE: 515
aaatcctccc agggtttatc ca                                             22

<210> SEQ ID NO 516
<211> LENGTH: 16
<212> TYPE: DNA
<213> ORGANISM: Zea mays

<400> SEQUENCE: 516
ggttcgcgcc ggagtt                                                    16

<210> SEQ ID NO 517
<211> LENGTH: 27
<212> TYPE: DNA
<213> ORGANISM: Zea mays

<400> SEQUENCE: 517
tgtatgcatc cattgttctt gtcttct                                        27
```

<210> SEQ ID NO 518
<211> LENGTH: 25
<212> TYPE: DNA
<213> ORGANISM: Zea mays

<400> SEQUENCE: 518
gcgtgtagat tgggtcaaaa ctatg                                    25

<210> SEQ ID NO 519
<211> LENGTH: 23
<212> TYPE: DNA
<213> ORGANISM: Zea mays

<400> SEQUENCE: 519 cctgctttt cccattattg gct                                       23

<210> SEQ ID NO 520
<211> LENGTH: 25
<212> TYPE: DNA
<213> ORGANISM: Zea mays

<400> SEQUENCE: 520
atggcaagca catagtctaa tggat                                    25

<210> SEQ ID NO 521
<211> LENGTH: 27
<212> TYPE: DNA
<213> ORGANISM: Zea mays

<400> SEQUENCE: 521
ccatccaaat gtcaagtatg tccatct                                  27

<210> SEQ ID NO 522
<211> LENGTH: 24
<212> TYPE: DNA
<213> ORGANISM: Zea mays

<400> SEQUENCE: 522
aaccgaaccc tgaataaaga aggt                                     24

<210> SEQ ID NO 523
<211> LENGTH: 20
<212> TYPE: DNA
<213> ORGANISM: Zea mays

<400> SEQUENCE: 523
ggttagctgc gaggcatcat                                          20

<210> SEQ ID NO 524
<211> LENGTH: 21
<212> TYPE: DNA
<213> ORGANISM: Zea mays

<400> SEQUENCE: 524
gctcagctag cagttggtga a                                        21

<210> SEQ ID NO 525
<211> LENGTH: 25
<212> TYPE: DNA
<213> ORGANISM: Zea mays

<400> SEQUENCE: 525
cagcaggaat ttatttcagc acact                                          25

<210> SEQ ID NO 526
<211> LENGTH: 22
<212> TYPE: DNA
<213> ORGANISM: Zea mays

<400> SEQUENCE: 526
caccaccaat gaagcaagaa ca                                             22

<210> SEQ ID NO 527
<211> LENGTH: 26
<212> TYPE: DNA
<213> ORGANISM: Zea mays

<400> SEQUENCE: 527
tgggaaaatg agaatccttt gggaaa                                         26

<210> SEQ ID NO 528
<211> LENGTH: 20
<212> TYPE: DNA
<213> ORGANISM: Zea mays

<400> SEQUENCE: 528
gtcgtgatgg ccaatgattg                                                20

<210> SEQ ID NO 529
<211> LENGTH: 19
<212> TYPE: DNA
<213> ORGANISM: Zea mays

<400> SEQUENCE: 529
tatcgacctt cgccagcaa                                                 19

<210> SEQ ID NO 530
<211> LENGTH: 25
<212> TYPE: DNA
<213> ORGANISM: Zea mays

<400> SEQUENCE: 530
agatcatgag catgggtgac atttt                                          25

<210> SEQ ID NO 531
<211> LENGTH: 27
<212> TYPE: DNA
<213> ORGANISM: Zea mays

<400> SEQUENCE: 531
taacattggt ggtttggtgc tatataa                                        27

<210> SEQ ID NO 532
<211> LENGTH: 20
<212> TYPE: DNA
<213> ORGANISM: Zea mays

<400> SEQUENCE: 532
gctctgttac cgctgtttcg                                                20

<210> SEQ ID NO 533
<211> LENGTH: 21
<212> TYPE: DNA
<213> ORGANISM: Zea mays

<400> SEQUENCE: 533
gatgcctagg cggtgataag g                                             21

<210> SEQ ID NO 534
<211> LENGTH: 19
<212> TYPE: DNA
<213> ORGANISM: Zea mays

<400> SEQUENCE: 534
cgcaatgcta gcgcaatgt                                                19

<210> SEQ ID NO 535
<211> LENGTH: 25
<212> TYPE: DNA
<213> ORGANISM: Zea mays

<400> SEQUENCE: 535
gtgtgtatag cctggaactg ttact                                         25

<210> SEQ ID NO 536
<211> LENGTH: 17
<212> TYPE: DNA
<213> ORGANISM: Zea mays

<400> SEQUENCE: 536
tgagcgggcc gatgttg                                                  17

<210> SEQ ID NO 537
<211> LENGTH: 16
<212> TYPE: DNA
<213> ORGANISM: Zea mays

<400> SEQUENCE: 537
gccacgaacg gagcca                                                   16

<210> SEQ ID NO 538
<211> LENGTH: 28
<212> TYPE: DNA
<213> ORGANISM: Zea mays

<400> SEQUENCE: 538
tggaaaataa tggaagtctt ctcaagca                                      28

<210> SEQ ID NO 539
<211> LENGTH: 22
<212> TYPE: DNA
<213> ORGANISM: Zea mays

<400> SEQUENCE: 539
cgggagcatg tgagacaaac aa                                            22

<210> SEQ ID NO 540
<211> LENGTH: 31
<212> TYPE: DNA
<213> ORGANISM: Zea mays

<400> SEQUENCE: 540
aggaactaaa cattagtccc tataatgtcc t                                  31

<210> SEQ ID NO 541
<211> LENGTH: 30
<212> TYPE: DNA
<213> ORGANISM: Zea mays

<400> SEQUENCE: 541
gaacagaaga ctttctagtt agaagctgaa                                              30

<210> SEQ ID NO 542
<211> LENGTH: 25
<212> TYPE: DNA
<213> ORGANISM: Zea mays

<400> SEQUENCE: 542
cttcatttcc atcccttctg tattc                                                   25

<210> SEQ ID NO 543
<211> LENGTH: 25
<212> TYPE: DNA
<213> ORGANISM: Zea mays

<400> SEQUENCE: 543
gacacaaacc acagattaga tgcaa                                                   25

<210> SEQ ID NO 544
<211> LENGTH: 22
<212> TYPE: DNA
<213> ORGANISM: Zea mays

<400> SEQUENCE: 544
catgacagcc tacccaatct ca                                                      22

<210> SEQ ID NO 545
<211> LENGTH: 20
<212> TYPE: DNA
<213> ORGANISM: Zea mays

<400> SEQUENCE: 545
ccacgtctcc ctacgaagga                                                         20

<210> SEQ ID NO 546
<211> LENGTH: 27
<212> TYPE: DNA
<213> ORGANISM: Zea mays

<400> SEQUENCE: 546
cctaaagtca tttcagagat gggatca                                                 27

<210> SEQ ID NO 547
<211> LENGTH: 25
<212> TYPE: DNA
<213> ORGANISM: Zea mays

<400> SEQUENCE: 547
ggagcatatc cgatcctatg gacta                                                   25

<210> SEQ ID NO 548
<211> LENGTH: 22
<212> TYPE: DNA
<213> ORGANISM: Zea mays

<400> SEQUENCE: 548
catatggatg cgtgtgccct ta                                                      22

<210> SEQ ID NO 549
<211> LENGTH: 18
<212> TYPE: DNA
<213> ORGANISM: Zea mays

```
<400> SEQUENCE: 549
ttagtggtgc tgcaggca                                                   18

<210> SEQ ID NO 550
<211> LENGTH: 20
<212> TYPE: DNA
<213> ORGANISM: Zea mays

<400> SEQUENCE: 550
gttgaccacc cactgttcct                                                 20

<210> SEQ ID NO 551
<211> LENGTH: 26
<212> TYPE: DNA
<213> ORGANISM: Zea mays

<400> SEQUENCE: 551
ggatccaatg aagacccaaa ttagga                                          26

<210> SEQ ID NO 552
<211> LENGTH: 23
<212> TYPE: DNA
<213> ORGANISM: Zea mays

<400> SEQUENCE: 552
agagtctggc ggtgtatttt gac                                             23

<210> SEQ ID NO 553
<211> LENGTH: 17
<212> TYPE: DNA
<213> ORGANISM: Zea mays

<400> SEQUENCE: 553
cagcgcgaca cgatggt                                                    17

<210> SEQ ID NO 554
<211> LENGTH: 22
<212> TYPE: DNA
<213> ORGANISM: Zea mays

<400> SEQUENCE: 554
cgtctccgtt gaaagcatga ag                                              22

<210> SEQ ID NO 555
<211> LENGTH: 25
<212> TYPE: DNA
<213> ORGANISM: Zea mays

<400> SEQUENCE: 555
gaacctcaat cccctaattc tagca                                           25

<210> SEQ ID NO 556
<211> LENGTH: 25
<212> TYPE: DNA
<213> ORGANISM: Zea mays

<400> SEQUENCE: 556
gcatgttgaa cttctccaga gctat                                           25

<210> SEQ ID NO 557
<211> LENGTH: 17
<212> TYPE: DNA
```

```
<213> ORGANISM: Zea mays

<400> SEQUENCE: 557
ttgagctttg gtttatc                                                  17

<210> SEQ ID NO 558
<211> LENGTH: 15
<212> TYPE: DNA
<213> ORGANISM: Zea mays

<400> SEQUENCE: 558
ccactacaca aattc                                                    15

<210> SEQ ID NO 559
<211> LENGTH: 14
<212> TYPE: DNA
<213> ORGANISM: Zea mays

<400> SEQUENCE: 559
tgcttcgtaa tttt                                                     14

<210> SEQ ID NO 560
<211> LENGTH: 15
<212> TYPE: DNA
<213> ORGANISM: Zea mays

<400> SEQUENCE: 560
aggacactcc ctcac                                                    15

<210> SEQ ID NO 561
<211> LENGTH: 14
<212> TYPE: DNA
<213> ORGANISM: Zea mays

<400> SEQUENCE: 561
ccgccgacgt tgtt                                                     14

<210> SEQ ID NO 562
<211> LENGTH: 21
<212> TYPE: DNA
<213> ORGANISM: Zea mays

<400> SEQUENCE: 562
tgttggatgt tctaacgact g                                             21

<210> SEQ ID NO 563
<211> LENGTH: 15
<212> TYPE: DNA
<213> ORGANISM: Zea mays

<400> SEQUENCE: 563
aagccttcac agaaa                                                    15

<210> SEQ ID NO 564
<211> LENGTH: 18
<212> TYPE: DNA
<213> ORGANISM: Zea mays

<400> SEQUENCE: 564
acacttaggg ctagtttg                                                 18

<210> SEQ ID NO 565
<211> LENGTH: 15
```

-continued

<212> TYPE: DNA
<213> ORGANISM: Zea mays

<400> SEQUENCE: 565
cattggtgag gaagt                                                15

<210> SEQ ID NO 566
<211> LENGTH: 15
<212> TYPE: DNA
<213> ORGANISM: Zea mays

<400> SEQUENCE: 566
atttgccgcc attgt                                                15

<210> SEQ ID NO 567
<211> LENGTH: 15
<212> TYPE: DNA
<213> ORGANISM: Zea mays

<400> SEQUENCE: 567
aggaagccgg caaca                                                15

<210> SEQ ID NO 568
<211> LENGTH: 15
<212> TYPE: DNA
<213> ORGANISM: Zea mays

<400> SEQUENCE: 568
ttgcatgcat aataa                                                15

<210> SEQ ID NO 569
<211> LENGTH: 16
<212> TYPE: DNA
<213> ORGANISM: Zea mays

<400> SEQUENCE: 569
atctgatcca gaatct                                               16

<210> SEQ ID NO 570
<211> LENGTH: 15
<212> TYPE: DNA
<213> ORGANISM: Zea mays

<400> SEQUENCE: 570
ctatggcgta gcctt                                                15

<210> SEQ ID NO 571
<211> LENGTH: 14
<212> TYPE: DNA
<213> ORGANISM: Zea mays

<400> SEQUENCE: 571
cagcaaggtc ttca                                                 14

<210> SEQ ID NO 572
<211> LENGTH: 19
<212> TYPE: DNA
<213> ORGANISM: Zea mays

<400> SEQUENCE: 572
tagttggtga cacttttgt                                            19

<210> SEQ ID NO 573

<210> SEQ ID NO 573
<211> LENGTH: 14
<212> TYPE: DNA
<213> ORGANISM: Zea mays

<400> SEQUENCE: 573
catggtcaag ctcg                                                    14

<210> SEQ ID NO 574
<211> LENGTH: 14
<212> TYPE: DNA
<213> ORGANISM: Zea mays

<400> SEQUENCE: 574
tcgccatgga tctg                                                    14

<210> SEQ ID NO 575
<211> LENGTH: 16
<212> TYPE: DNA
<213> ORGANISM: Zea mays

<400> SEQUENCE: 575
cacgacttga tcatgc                                                  16

<210> SEQ ID NO 576
<211> LENGTH: 18
<212> TYPE: DNA
<213> ORGANISM: Zea mays

<400> SEQUENCE: 576
ccaaccattt tgtcatgc                                                18

<210> SEQ ID NO 577
<211> LENGTH: 19
<212> TYPE: DNA
<213> ORGANISM: Zea mays

<400> SEQUENCE: 577
cctcctttaa catttttaa                                               19

<210> SEQ ID NO 578
<211> LENGTH: 19
<212> TYPE: DNA
<213> ORGANISM: Zea mays

<400> SEQUENCE: 578
ctacaaacca aattcattg                                               19

<210> SEQ ID NO 579
<211> LENGTH: 21
<212> TYPE: DNA
<213> ORGANISM: Zea mays

<400> SEQUENCE: 579
ataaggattc ctatatataa c                                            21

<210> SEQ ID NO 580
<211> LENGTH: 14
<212> TYPE: DNA
<213> ORGANISM: Zea mays

<400> SEQUENCE: 580
ttgtgcccta gcgc                                                    14

-continued

```
<210> SEQ ID NO 581
<211> LENGTH: 15
<212> TYPE: DNA
<213> ORGANISM: Zea mays

<400> SEQUENCE: 581
aacacaagga agacc                                                      15

<210> SEQ ID NO 582
<211> LENGTH: 16
<212> TYPE: DNA
<213> ORGANISM: Zea mays

<400> SEQUENCE: 582
atccaccaaa tgctac                                                     16

<210> SEQ ID NO 583
<211> LENGTH: 18
<212> TYPE: DNA
<213> ORGANISM: Zea mays

<400> SEQUENCE: 583
aaatgggatt agtttcac                                                   18

<210> SEQ ID NO 584
<211> LENGTH: 19
<212> TYPE: DNA
<213> ORGANISM: Zea mays

<400> SEQUENCE: 584 aatcttttttg ggtggccac                                                 19

<210> SEQ ID NO 585
<211> LENGTH: 19
<212> TYPE: DNA
<213> ORGANISM: Zea mays

<400> SEQUENCE: 585
tgaagaacct tgggcacag                                                  19

<210> SEQ ID NO 586
<211> LENGTH: 20
<212> TYPE: DNA
<213> ORGANISM: Zea mays

<400> SEQUENCE: 586
ctcgggatat tcagtacaag                                                 20

<210> SEQ ID NO 587
<211> LENGTH: 18
<212> TYPE: DNA
<213> ORGANISM: Zea mays

<400> SEQUENCE: 587
agagggtgag atgagatc                                                   18

<210> SEQ ID NO 588
<211> LENGTH: 14
<212> TYPE: DNA
<213> ORGANISM: Zea mays

<400> SEQUENCE: 588
cctcgcacgg ccta                                                       14
```

```
<210> SEQ ID NO 589
<211> LENGTH: 16
<212> TYPE: DNA
<213> ORGANISM: Zea mays

<400> SEQUENCE: 589
tccaagaact gctatc                                                    16

<210> SEQ ID NO 590
<211> LENGTH: 13
<212> TYPE: DNA
<213> ORGANISM: Zea mays

<400> SEQUENCE: 590
tgacggcatc gac                                                       13

<210> SEQ ID NO 591
<211> LENGTH: 22
<212> TYPE: DNA
<213> ORGANISM: Zea mays

<400> SEQUENCE: 591
caagcataac ttacatcttt at                                             22

<210> SEQ ID NO 592
<211> LENGTH: 22
<212> TYPE: DNA
<213> ORGANISM: Zea mays

<400> SEQUENCE: 592
caagaataat agccttatcc at                                             22

<210> SEQ ID NO 593
<211> LENGTH: 16
<212> TYPE: DNA
<213> ORGANISM: Zea mays

<400> SEQUENCE: 593
tcacagcgga tcagat                                                    16

<210> SEQ ID NO 594
<211> LENGTH: 17
<212> TYPE: DNA
<213> ORGANISM: Zea mays

<400> SEQUENCE: 594
ttgagctttg atttatc                                                   17

<210> SEQ ID NO 595
<211> LENGTH: 15
<212> TYPE: DNA
<213> ORGANISM: Zea mays

<400> SEQUENCE: 595
ccactacaaa aattc                                                     15

<210> SEQ ID NO 596
<211> LENGTH: 16
<212> TYPE: DNA
<213> ORGANISM: Zea mays

<400> SEQUENCE: 596
ttgctttgta atttttt                                                   16
```

<210> SEQ ID NO 597
<211> LENGTH: 16
<212> TYPE: DNA
<213> ORGANISM: Zea mays

<400> SEQUENCE: 597
aggacattcc ctcacc                                                   16

<210> SEQ ID NO 598
<211> LENGTH: 14
<212> TYPE: DNA
<213> ORGANISM: Zea mays

<400> SEQUENCE: 598
ccgccaacgt tgtt                                                     14

<210> SEQ ID NO 599
<211> LENGTH: 19
<212> TYPE: DNA
<213> ORGANISM: Zea mays

<400> SEQUENCE: 599
ttggatgttc taacaactg                                                19

<210> SEQ ID NO 600
<211> LENGTH: 14
<212> TYPE: DNA
<213> ORGANISM: Zea mays

<400> SEQUENCE: 600
agcctccaca gaaa                                                     14

<210> SEQ ID NO 601
<211> LENGTH: 17
<212> TYPE: DNA
<213> ORGANISM: Zea mays

<400> SEQUENCE: 601
cacttaggga tagtttg                                                  17

<210> SEQ ID NO 602
<211> LENGTH: 15
<212> TYPE: DNA
<213> ORGANISM: Zea mays

<400> SEQUENCE: 602
cattggtgaa gaagt                                                    15

<210> SEQ ID NO 603
<211> LENGTH: 14
<212> TYPE: DNA
<213> ORGANISM: Zea mays

<400> SEQUENCE: 603
ttgccgctat tgtt                                                     14

<210> SEQ ID NO 604
<211> LENGTH: 15
<212> TYPE: DNA
<213> ORGANISM: Zea mays

<400> SEQUENCE: 604

```
aggaagccag caaca                                              15

<210> SEQ ID NO 605
<211> LENGTH: 14
<212> TYPE: DNA
<213> ORGANISM: Zea mays

<400> SEQUENCE: 605
ttgcacgcat aata                                               14

<210> SEQ ID NO 606
<211> LENGTH: 16
<212> TYPE: DNA
<213> ORGANISM: Zea mays

<400> SEQUENCE: 606
atctgatcaa gaatct                                             16

<210> SEQ ID NO 607
<211> LENGTH: 16
<212> TYPE: DNA
<213> ORGANISM: Zea mays

<400> SEQUENCE: 607
ctatggtgta gcctttt                                            16

<210> SEQ ID NO 608
<211> LENGTH: 13
<212> TYPE: DNA
<213> ORGANISM: Zea mays

<400> SEQUENCE: 608
cagcaacgtc ttc                                                13

<210> SEQ ID NO 609
<211> LENGTH: 16
<212> TYPE: DNA
<213> ORGANISM: Zea mays

<400> SEQUENCE: 609
ttggtgacgc ttttgt                                             16

<210> SEQ ID NO 610
<211> LENGTH: 14
<212> TYPE: DNA
<213> ORGANISM: Zea mays

<400> SEQUENCE: 610
catggtcagg ctcg                                               14

<210> SEQ ID NO 611
<211> LENGTH: 13
<212> TYPE: DNA
<213> ORGANISM: Zea mays

<400> SEQUENCE: 611
cgccatgcat ctg                                                13

<210> SEQ ID NO 612
<211> LENGTH: 16
<212> TYPE: DNA
<213> ORGANISM: Zea mays

<400> SEQUENCE: 612
```
cacgacttgg tcatgc                                              16

<210> SEQ ID NO 613
<211> LENGTH: 18
<212> TYPE: DNA
<213> ORGANISM: Zea mays

<400> SEQUENCE: 613
ccaaccattt tttcatgc                                            18

<210> SEQ ID NO 614
<211> LENGTH: 19
<212> TYPE: DNA
<213> ORGANISM: Zea mays

<400> SEQUENCE: 614
cctcctttaa catgtttaa                                           19

<210> SEQ ID NO 615
<211> LENGTH: 17
<212> TYPE: DNA
<213> ORGANISM: Zea mays

<400> SEQUENCE: 615
acaaaccaag ttcattg                                             17

<210> SEQ ID NO 616
<211> LENGTH: 21
<212> TYPE: DNA
<213> ORGANISM: Zea mays

<400> SEQUENCE: 616
ataaggagtc ctatatataa c                                        21

<210> SEQ ID NO 617
<211> LENGTH: 15
<212> TYPE: DNA
<213> ORGANISM: Zea mays

<400> SEQUENCE: 617
tgtgctctag cgcct                                               15

<210> SEQ ID NO 618
<211> LENGTH: 17
<212> TYPE: DNA
<213> ORGANISM: Zea mays

<400> SEQUENCE: 618
aggtagaaca cgaggaa                                             17

<210> SEQ ID NO 619
<211> LENGTH: 16
<212> TYPE: DNA
<213> ORGANISM: Zea mays

<400> SEQUENCE: 619
atccaccaag tgctac                                              16

<210> SEQ ID NO 620
<211> LENGTH: 16
<212> TYPE: DNA
<213> ORGANISM: Zea mays

<400> SEQUENCE: 620
atgggattaa tttcac                                                    16

<210> SEQ ID NO 621
<211> LENGTH: 17
<212> TYPE: DNA
<213> ORGANISM: Zea mays

<400> SEQUENCE: 621 tcttttcgg tggccac                                                    17

<210> SEQ ID NO 622
<211> LENGTH: 19
<212> TYPE: DNA
<213> ORGANISM: Zea mays

<400> SEQUENCE: 622
tgaagaacct tgtgcacag                                                 19

<210> SEQ ID NO 623
<211> LENGTH: 19
<212> TYPE: DNA
<213> ORGANISM: Zea mays

<400> SEQUENCE: 623
tcgggatatt cggtacaag                                                 19

<210> SEQ ID NO 624
<211> LENGTH: 16
<212> TYPE: DNA
<213> ORGANISM: Zea mays

<400> SEQUENCE: 624
agggtgagac gagatc                                                    16

<210> SEQ ID NO 625
<211> LENGTH: 13
<212> TYPE: DNA
<213> ORGANISM: Zea mays

<400> SEQUENCE: 625
ctcgcgcggc cta                                                       13

<210> SEQ ID NO 626
<211> LENGTH: 16
<212> TYPE: DNA
<213> ORGANISM: Zea mays

<400> SEQUENCE: 626
caatccaagg actgct                                                    16

<210> SEQ ID NO 627
<211> LENGTH: 14
<212> TYPE: DNA
<213> ORGANISM: Zea mays

<400> SEQUENCE: 627
tgacgggatc gact                                                      14

<210> SEQ ID NO 628
<211> LENGTH: 21
<212> TYPE: DNA
<213> ORGANISM: Zea mays

```
<400> SEQUENCE: 628
aagcataact tacatgttta t                                            21

<210> SEQ ID NO 629
<211> LENGTH: 21
<212> TYPE: DNA
<213> ORGANISM: Zea mays

<400> SEQUENCE: 629
aagaataata gccctatcca t                                            21

<210> SEQ ID NO 630
<211> LENGTH: 16
<212> TYPE: DNA
<213> ORGANISM: Zea mays

<400> SEQUENCE: 630
tcacagcgaa tcagat                                                  16
```